(12) United States Patent
Jin et al.

(10) Patent No.: US 11,964,964 B2
(45) Date of Patent: Apr. 23, 2024

(54) THYROID HORMONE RECEPTOR AGONISTS AND USES THEREOF

(71) Applicant: XIZANG HAISCO PHARMACEUTICAL CO., LTD., Tibet (CN)

(72) Inventors: Bohan Jin, San Diego, CA (US); Gene Hung, San Diego, CA (US); Qing Dong, San Diego, CA (US)

(73) Assignee: XIZANG HAISCO PHARMACEUTICAL CO., LTD., Lhoka (CN)

( * ) Notice: Subject to any disclaimer, the term of this patent is extended or adjusted under 35 U.S.C. 154(b) by 668 days.

(21) Appl. No.: 17/047,358

(22) PCT Filed: May 28, 2019

(86) PCT No.: PCT/US2019/034199
§ 371 (c)(1),
(2) Date: Oct. 13, 2020

(87) PCT Pub. No.: WO2019/240938
PCT Pub. Date: Dec. 19, 2019

(65) Prior Publication Data
US 2021/0115022 A1    Apr. 22, 2021

Related U.S. Application Data

(60) Provisional application No. 62/767,402, filed on Nov. 14, 2018, provisional application No. 62/731,364, filed on Sep. 14, 2018, provisional application No. 62/684,113, filed on Jun. 12, 2018.

(51) Int. Cl.
*C07D 403/14* (2006.01)
*A61P 5/14* (2006.01)
*C07D 413/14* (2006.01)

(52) U.S. Cl.
CPC ............. *C07D 403/14* (2013.01); *A61P 5/14* (2018.01); *C07D 413/14* (2013.01)

(58) Field of Classification Search
CPC ................................. C07D 403/14; A61P 5/14
See application file for complete search history.

(56) References Cited

U.S. PATENT DOCUMENTS 11,034,676 B2 *  6/2021  Yu .......................... A61P 35/00
11,084,802 B2 *  8/2021  Yu .......................... A61P 35/00

FOREIGN PATENT DOCUMENTS

| CN | 111320609 A | 6/2020 |
|---|---|---|
| CN | 110627773 B | 3/2021 |
| EP | 1471049 A1 | 10/2004 |
| EP | 1088819 B1 | 6/2005 |
| EP | 3725779 A1 | 10/2020 |
| WO | WO-2007009913 A1 | 1/2007 |
| WO | WO-2009037172 A1 | 3/2009 |
| WO | WO-2014043706 A1 | 3/2014 |
| WO | WO-2018075650 A1 | 4/2018 |
| WO | WO-2019144835 A1 | 8/2019 |
| WO | WO-2019240938 A1 | 12/2019 |
| WO | WO-2019242766 A1 | 12/2019 |
| WO | WO-2020073974 A1 | 4/2020 |

OTHER PUBLICATIONS

Jakobsson et al., Potential role of thyroid receptor B agonists in the treatment of hyperlipidemia. Drugs 77(15):1613-1621 (2017).
Kelly et al., Discovery of 2-[3,5-dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor B agonist in clinical trials for the treatment of dyslipidemia. Journal of Medicinal Chemistry 57(10):3912-3923 (2014).
PCT/US2019/034199 International Search Report and Written Opinion dated Sep. 19, 2019.

* cited by examiner

*Primary Examiner* — Kamal A Saeed
(74) *Attorney, Agent, or Firm* — WILSON SONSINI GOODRICH & ROSATI

(57) ABSTRACT

Described herein are methods and compositions for the treatment of conditions, diseases, or disorders associated with thyroid hormone receptor activity. The methods and compositions disclosed herein include the use of at least one thyroid hormone receptor agonist.

18 Claims, 23 Drawing Sheets

A: Naive
B: Model
C: MGL-3196: 0.3 mpk
D: MGL-3196: 1 mpk
E: MGL-3196: 3 mpk
F: Example 7: 0.3 mpk
G: Example 7: 1 mpk
H: Example 7: 3 mpk A: Naive
B: Model
C: MGL-3196: 0.3 mpk
D: MGL-3196: 1 mpk
E: MGL-3196: 3 mpk
F: Example 41: 0.3 mpk
G: Example 41. 1 mpk
H: Example 41: 3 mpk
I: Example 30: 0.3 mpk
J: Example 30: 1 mpk
K: Example 30: 3 mpk
L: Example 50: 0.3 mpk
M: Example 50: 1 mpk
N: Example 50: 3 mpk

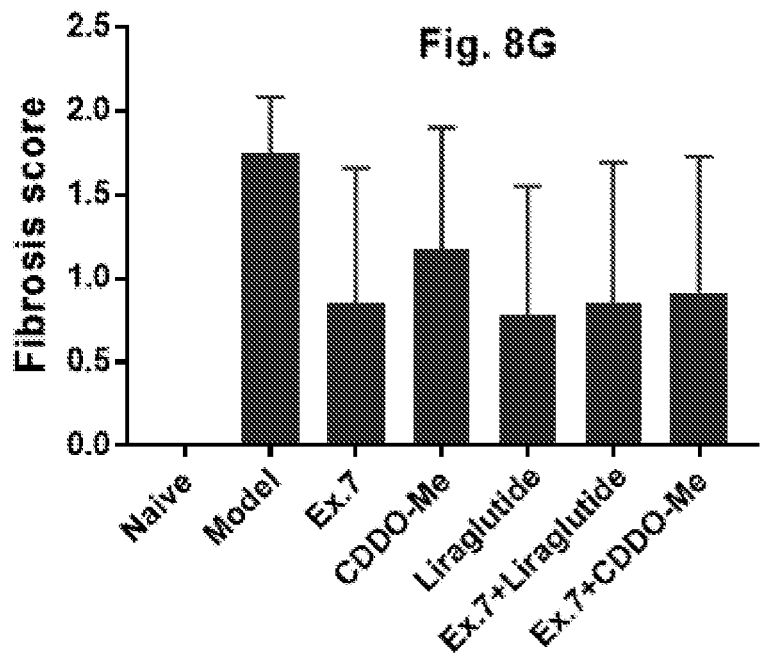
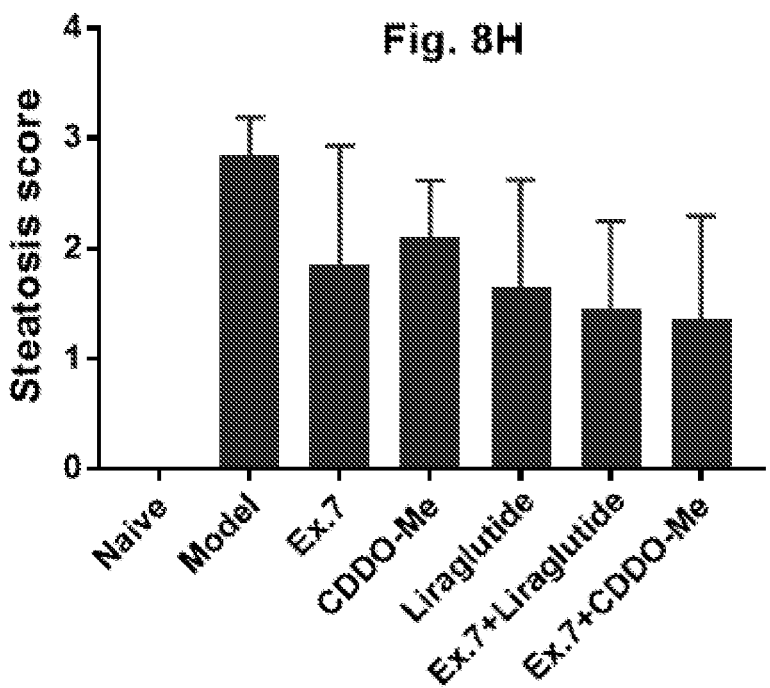

THYROID HORMONE RECEPTOR AGONISTS AND USES THEREOF

CROSS-REFERENCE

This patent application is a national stage entry of PCT/US2019/0034199, filed on May 28, 2019, which claims the benefit of U.S. Provisional Application No. 62/684,113, filed Jun. 12, 2018; U.S. Provisional Application No. 62/731,364, filed Sep. 14, 2018, and U.S. Provisional Application No. 62/767,402, filed Nov. 14, 2018; each of which are incorporated herein by reference in their entirety.

FIELD OF THE INVENTION

Described herein are methods of using thyroid hormone receptor agonists, and pharmaceutical compositions and medicaments thereof, in the treatment of conditions, diseases, or disorders associated with thyroid hormone receptor activity, such as metabolic diseases (obesity, hyperlipidemia, hypercholesterolemia and diabetes) and other disorders and diseases, such as NASH (nonalcoholic steatohepatitis), liver steatosis, atherosclerosis, cardiovascular diseases, hypothyroidism, thyroid cancer, and related disorders and diseases.

BACKGROUND OF THE INVENTION

Thyroid hormones are critical for normal growth and development and for maintaining metabolic homeostasis. Circulating levels of thyroid hormones are tightly regulated by feedback mechanisms in the hypothalamus/pituitary/thyroid (HPT) axis. Thyroid dysfunction leading to hypothyroidism or hyperthyroidism clearly demonstrates that thyroid hormones exert profound effects on cardiac function, body weight, metabolism, metabolic rate, body temperature, cholesterol, bone, muscle, and behavior.

BRIEF SUMMARY OF THE INVENTION

Disclosed herein is a compound of Formula (IV), or a pharmaceutically acceptable salt, solvate, or stereoisomer thereof:

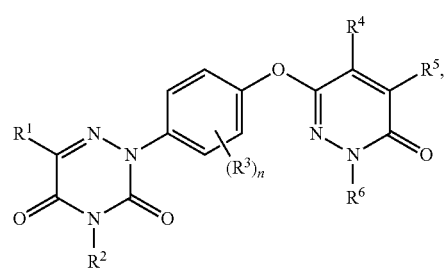

(IV)

wherein:

$R^1$ is hydrogen, deuterium, halogen, —CN, —OH, —$OR^a$, —SH, —$SR^a$, —$S(=O)R^a$, —$S(=O)_2R^a$, —$NO_2$, —$NR^bR^c$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —$NR^bR^c$, —$C(=O)R^a$, —$C(=O)OR^b$, —$C(=O)NR^bR^c$, $C_1$-$C_6$alkyl, or $C_1$-$C_6$haloalkyl;

$R^2$ is hydrogen, halogen, —CN, —OH, —$OR^a$, —$S(=O)R^a$, —$S(=O)_2R^a$, —$S(=O)_2NR^bR^c$, —$C(=O)R^a$, —$OC(=O)R^a$, —$C(=O)OR^b$, —$C(=O)NR^bR^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —$NR^bR^c$, —$C(=O)R^a$, —$C(=O)OR^b$, —$C(=O)NR^bR^c$, $C_1$-$C_6$alkyl, or $C_1$-$C_6$haloalkyl;

each $R^3$ is independently hydrogen, deuterium, halogen, —CN, —OH, —$OR^a$, —SH, —$SR^a$, —$S(=O)R^a$, —$S(=O)_2R^a$, —$NO_2$, —$NR^bR^c$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —$NR^bR^c$, —$C(=O)R^a$, —$C(=O)OR^b$, —$C(=O)NR^bR^c$, $C_1$-$C_6$alkyl, or $C_1$-$C_6$haloalkyl;

$R^4$ is hydrogen, deuterium, halogen, —CN, —OH, —$OR^a$, —SH, —$SR^a$, —$S(=O)R^a$, —$S(=O)_2R^a$, —$NO_2$, —$NR^bR^c$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —$NR^bR^c$, —$C(=O)R^a$, —$C(=O)OR^b$, —$C(=O)NR^bR^c$, $C_1$-$C_6$alkyl, or $C_1$-$C_6$haloalkyl;

$R^5$ is hydrogen, deuterium, halogen, —CN, —OH, —$OR^a$, —SH, —$SR^a$, —$S(=O)R^a$, —$S(=O)_2R^a$, —$NO_2$, —$NR^bR^c$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, $C_1$-$C_6$alkyl, $C_1$-$C_6$deuteroalkyl, $C_1$-$C_6$haloalkyl, $C_4$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —$NR^bR^c$, —$C(=O)R^a$, —$C(=O)OR^b$, —$C(=O)NR^bR^c$, $C_1$-$C_6$alkyl, or $C_1$-$C_6$haloalkyl;

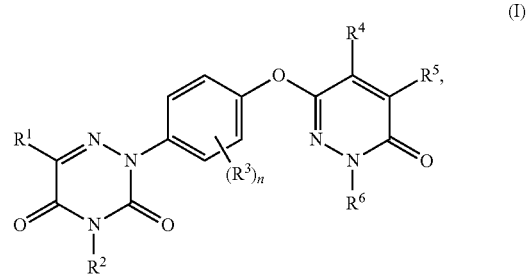

(I)

wherein:
R$^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

R$^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

each R$^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

R$^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, R$^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

n is 0-4;

each R$^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and each R$^b$ and R$^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

provided that:
(a) R$^4$ and R$^5$ are taken together to form a cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, or C$_1$-C$_6$haloalkyl; and/or (b) two R$^3$ on adjacent carbons are taken together to form a cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, or C$_1$-C$_6$haloalkyl.

Also disclosed herein is a compound of Formula (I), or a pharmaceutically acceptable salt, solvate, or stereoisomer thereof:

cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_4$-$C_6$alkyl, $C_1$-$C_6$deuteroalkyl, $C_1$-$C_6$haloalkyl, $C_4$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

n is 0-4;

each R$^a$ is independently $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl; and each R$^b$ and R$^c$ are independently hydrogen, deuterium, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

Also disclosed herein is a pharmaceutical composition comprising a therapeutically effective amount of a compound disclosed herein, and a pharmaceutically acceptable excipient.

Also disclosed herein is a method for treating a disease in a mammal comprising administering to the mammal a therapeutically effective amount of a compound or a pharmaceutical composition disclosed herein.

INCORPORATION BY REFERENCE

All publications, patents, and patent applications mentioned in this specification are herein incorporated by reference for the specific purposes identified herein.

BRIEF DESCRIPTION OF THE DRAWINGS

Included in the drawings are the following figures.

FIG. 8G shows the fibrosis score after administration of Example 7, liraglutide, elafibranor, CDDO-Me, Example 7+liraglutide, and Example 7+CDDO-Me in a NASH mouse model.

FIG. 8H shows the steatosis score after administration of Example 7, liraglutide, elafibranor, CDDO-Me, Example 7+liraglutide, and Example 7+CDDO-Me in a NASH mouse model.

DETAILED DESCRIPTION OF THE INVENTION

Figure 1A:
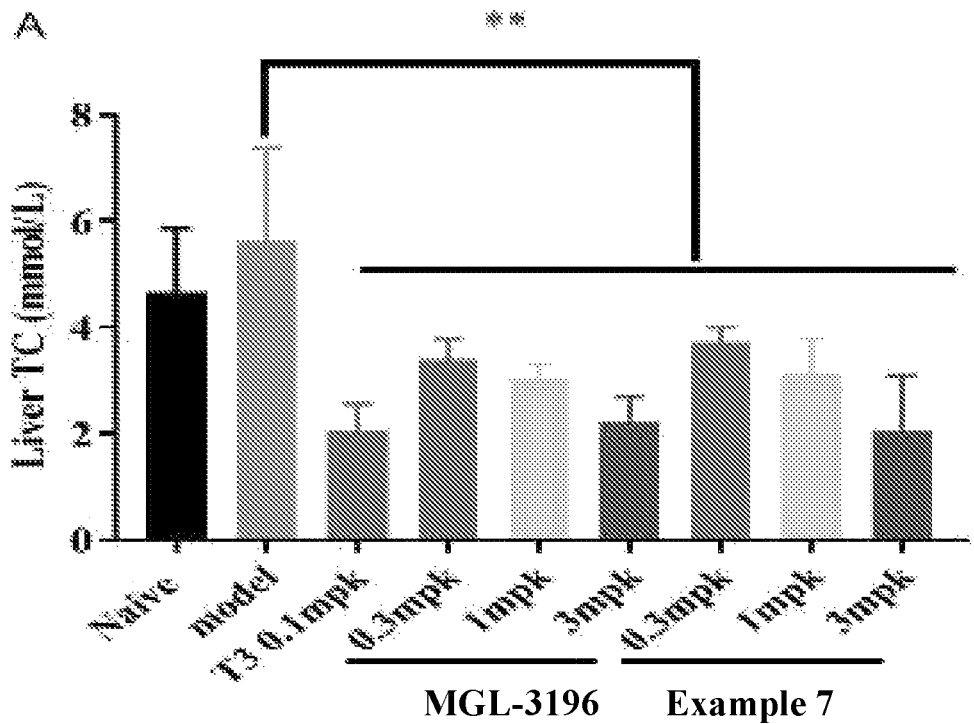
FIG. 1A shows the liver cholesterol levels after administration of MGL-3196 and Example 7 in a trans-fat AMLN diet-induced hypercholesterolemia mouse model.
Figure 1B:
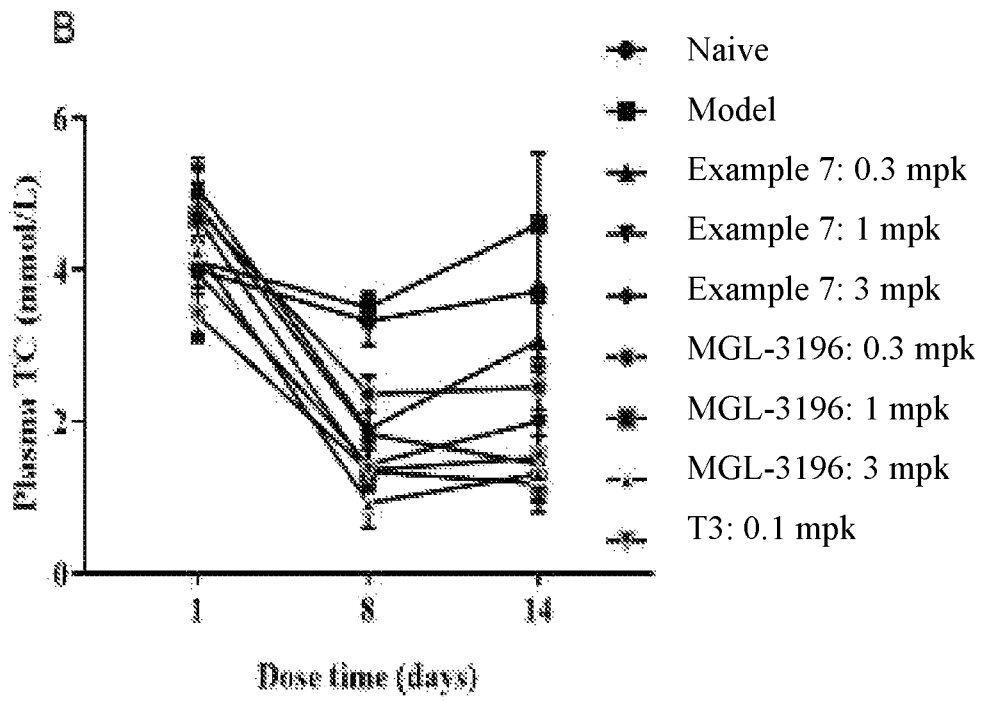
FIG. 1B shows the plasma cholesterol levels after administration of MGL-3196 and Example 7 in a trans-fat AMLN diet-induced hypercholesterolemia mouse model.
Figure 1C:
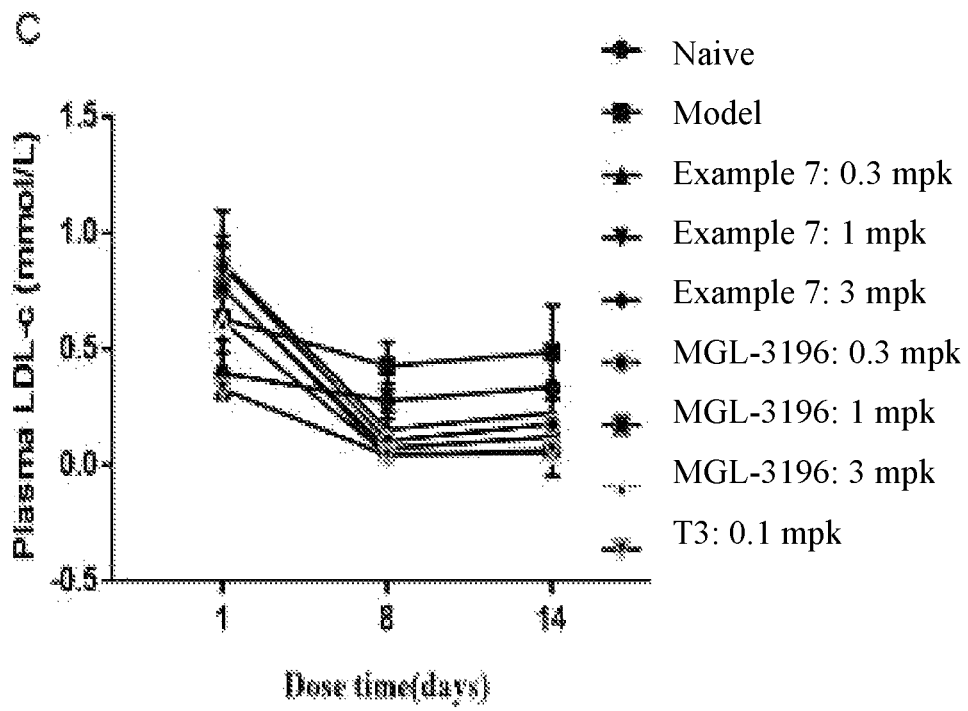
FIG. 1C shows the plasma LDL-c levels after administration of MGL-3196 and Example 7 in a trans-fat AMLN diet-induced hypercholesterolemia mouse model.

Thyroid hormones (THs) play a critical role in growth, development, metabolism, and homeostasis. They are produced by the thyroid gland as thyroxine (T4) and 3,5,3'-triiodo-L-thyronine (T3). T4 is the major secreted form in humans and is enzymatically deiodinated by deiodinases to the more active form, T3, in peripheral tissues. THs exert their action by interacting with thyroid hormone receptors (THRs), which belong to the nuclear hormone receptor superfamily, and regulate the transcription of target genes. TH's form part of the thyroid axis, also known as the Hypothalmic-Pituitary-Thyroid, or HPT axis, which comprises a complex endocrine and paracrine feedback loop linking tissues of the brain and endocrine system in order to assert global control over issues such as overall metabolic rate, lipid secretion, cardiac function, muscle and bone growth, among many others.

THRs are expressed in most tissues and exist as two isoforms (THRα and THRβ). Tissue distribution studies, mouse knockout studies, and evaluation of patients with resistance to thyroid hormone (RTH) syndrome have established that THRα is the predominant isoform in the heart and regulates most cardiac functions, while the THRβ isoform predominates in the liver and the pituitary and regulates cholesterol metabolism and thyroid stimulating hormone (TSH) production, respectively. In recognition of the potential benefits associated with modulation of THRs, numerous approaches have been pursued to identify a suitable THR agonist to lower plasma cholesterol levels. However, these benefits were offset by deleterious cardiovascular side effects, such as tachycardia, arrhythmia, elevated blood pressure, and heart failure as well as effects on the thyroid hormone axis, muscle metabolism and bone loss.

THR-mediated pathways are implicated in modulating serum lipid levels, including cholesterol, triglycerides, and associated lipoproteins. Elevated levels of serum lipids are implicated in the development of atherosclerosis and in the exacerbation of coronary artery disease. Clinical trials have demonstrated that reducing low density lipoprotein/serum cholesterol levels reduces morbidity and mortality associated with cardiovascular disease. While drugs such as statins and PCSK-9 inhibitors, along with dietary and lifestyle interventions, may help to treat hyperlipidemia in some patients, many patients fail to significantly reduce their serum cholesterol levels and many do not tolerate high doses of statins. Thus, there is an unmet medical need for additional orally administered lipid-modulating therapies.

Similarly, nonalcoholic fatty liver disease (NAFLD), a condition linked to the group of metabolic irregularities known as metabolic syndrome, is defined by excessive fat accumulation in the form of triglycerides (steatosis) in the liver. This condition can further include liver cell injury and inflammation, leading to non-alcoholic steatohepatitis (NASH). NASH generally coincides in patients with type 2 diabetes, hypercholesterolemia, hypertriglyceridemia, and obesity. Patients with NASH risk developing cirrhosis, liver failure, and hepatocellular carcinoma. Treatments for NASH are currently limited to lifestyle interventions. However, the role of thyroid hormone in regulating LDL-C and triglyceride levels makes THR-mediated pathways promising targets for treatments for NASH and NAFLD. For example, in animals, thyroid hormone mimetics have been shown to dramatically reduce liver fat content.

Selective THR agonists were developed as a means of suppressing the cardiac side effects of nonspecific THR agonists while retaining the potential beneficial effects of THR activation, such as reduction in cholesterol and serum lipid levels, and reduction in obesity due to increased cellular metabolism. However, it has been shown that even targeted THR agonists can lead to suppression of the thyroid hormone axis, which may lead to side effects ranging from depression and fatigue to muscle wasting and bone loss.

Accordingly, there is a need for compositions and methods to effect THR activation while reducing HPT axis suppression and its associated side effects.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to a straight or branched chain hydrocarbon monoradical, which may be fully saturated or unsaturated, having from one to about ten carbon atoms, or from one to six carbon atoms. Examples of saturated hydrocarbon monoradical include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. When the alkyl refers to an unsaturated straight or branched chain hydrocarbon monoradical it is known as an "alkenyl" or an "alkynyl". The alkenyl may be in either the cis or trans conformation about the double bond(s), and should be understood to include both isomers. Examples of alkenyls include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms, or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Examples of alkynyl include, but are not limited to ethynyl, 2-propynyl, 2- and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkylene" refers to a straight or branched divalent hydrocarbon chain. Whenever it appears herein, a numerical range such as "$C_1$-$C_6$ alkylene" means that the alkylene consists of 1 carbon atom, 2 carbon atoms, 3 carbon atoms, 4 carbon atoms, 5 carbon atoms, or 6 carbon atoms, although the present definition also covers the occurrence of the term "alkylene" where no numerical range is designated. In some embodiments, the alkylene is a $C_1$-$C_{10}$ alkylene, a $C_1$-$C_9$ alkylene, a $C_1$-$C_8$ alkylene, a $C_1$-$C_7$ alkylene, a $C_1$-$C_6$ alkylene, a $C_1$-$C_5$ alkylene, a $C_1$-$C_4$ alkylene, a $C_1$-$C_3$ alkylene, a $C_1$-$C_2$ alkylene, or a $C_1$ alkylene. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —$CF_3$, —OH, —OMe, —$NH_2$, or —$NO_2$. In some embodiments, an alkylene is optionally substituted with oxo, halogen, —CN, —$CF_3$, —OH, or —OMe. In some embodiments, the alkylene is optionally substituted with halogen.

"Alkoxy" refers to a radical of the formula —$OR_a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —$CF_3$, —OH, —OMe, —$NH_2$, or —$NO_2$. In some embodiments, an alkoxy is optionally substituted with oxo, halogen, —CN, —$CF_3$, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —$CF_3$, —OH, —OMe, —$NH_2$, or —$NO_2$. In some embodiments, an aryl is optionally substituted with halogen, methyl, ethyl, —CN, —$CF_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —$CF_3$, —OH, —OMe, —$NH_2$, or —$NO_2$. In some embodiments, a cycloalkyl is optionally substituted with oxo, halogen, methyl, ethyl, —CN, —$CF_3$, —OH, or —OMe. In some embodiments, the cycloalkyl is optionally substituted with halogen.

"Halo" or "halogen" refers to bromo, chloro, fluoro, or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from one to 8 heteroatoms selected from nitrogen, oxygen, phosphorous, and sulfur. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_8$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). In some embodiments, the heterocycloalkyl is a 3- to 6-membered heterocycloalkyl. In some embodiments, the heterocycloalkyl is a 5- to 6-membered heterocycloalkyl. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Partially saturated heterocycloalkyls include, for example dihydropyrrolyl or tetrahydropyridine. Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Unless stated otherwise specifically in the specification, a heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from nitrogen, oxygen, phosphorous, and sulfur, and at least one aromatic ring. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 5-membered heteroaryl. In some embodiments, the heteroaryl is a 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, about 100%, about 90%, about 80%, about 70%, about 60%, about 50%, about 40%, about 30%, about 20%, or about 10%. Furthermore, the treatment, prevention, amelioration, or inhibition provided by the methods disclosed herein can include treatment, prevention, amelioration, or inhibition of one or more conditions or symptoms of the disorder, e.g., cancer or an inflammatory disease. Also, for purposes herein, "treatment," "prevention," "amelioration," or "inhibition" encompass delaying the onset of the disorder, or a symptom or condition thereof.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

The term "Hypothalamic-Pituitary-Thyroid Axis" or "HPT Axis", as used herein refers to the set of neuroendocrine pathways, signals, and molecules responsible for the regulation of metabolism. As used herein, "HPT Axis" further refers to any molecule involved in the regulation, modification, or response to thyroid hormone. Representative components of the HPT axis include Triiodothyronine (T3), Thyroxine (T4), iodothyronines, thyrotropin-releasing hormone (TRH), and thyroid-stimulating hormone (TSH).

Compounds

Described herein are compounds of Formula (I)-(XII), or a pharmaceutically acceptable salt, solvate, or stereoisomer thereof that are thyroid hormone receptor agonists.

Disclosed herein is a compound of Formula (I), or a pharmaceutically acceptable salt, solvate, or stereoisomer thereof:

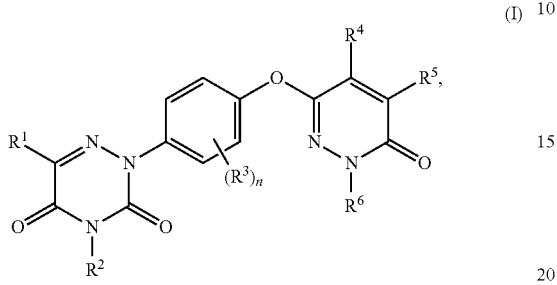

(I)

wherein:
- $R^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- $R^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- $R^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- $R^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_4$-C$_6$alkyl, C$_1$-C$_6$deuteroalkyl, C$_1$-C$_6$haloalkyl, C$_4$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- $R^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- n is 0-4;
- each $R^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and
- each $R^b$ and $R^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;
- or $R^b$ and $R^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (I), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (I), R$^1$ is hydrogen or —CN. In some embodiments of a compound of Formula (I), R$^1$ is —CN. In some embodiments of a compound of Formula (I), R$^1$ is hydrogen or deuterium.

In some embodiments of a compound of Formula (I), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (I), R$^2$ is hydrogen or C$_1$-C$_6$alkyl. In some embodiments of a compound of Formula (I), R$^2$ is hydrogen.

In some embodiments of a compound of Formula (I), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (I), each R$^3$ is independently hydrogen, halogen, C$_1$-C$_6$alkyl, or C$_1$-C$_6$haloalkyl. In some embodiments of a compound of Formula (I), each R$^3$ is independently halogen. In some embodiments of a compound of Formula (I), one of R$^3$ is deuterium. In some embodiments of a compound of Formula (I), each R$^3$ is independently hydrogen, deuterium, halogen, C$_1$-C$_6$alkyl, or C$_1$-C$_6$haloalkyl. In some embodiments of a compound of Formula (I), each R$^3$ is independently deuterium, halogen, or C$_1$-C$_6$alkyl. In some embodiments of a compound of Formula (I), each R$^3$ is independently deuterium or halogen.

In some embodiments of a compound of Formula (I), n is 1. In some embodiments of a compound of Formula (I), n is 2. In some embodiments of a compound of Formula (I), n is 3. In some embodiments of a compound of Formula (I), n is 4. In some embodiments of a compound of Formula (I), n is 1 or 2. In some embodiments of a compound of Formula (I), n is 1-3. In some embodiments of a compound of Formula (I), n is 2 or 3.

In some embodiments of a compound of Formula (I), each alkyl, alkenyl, alkynyl, cycloalkyl, heterocycloalkyl, aryl, and heteroaryl in R$^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (I), R$^4$ is hydrogen, halogen, C$_1$-C$_6$alkyl, or C$_1$-C$_6$haloalkyl. In some embodiments of a compound of Formula (I), R$^4$ is hydrogen. In some embodiments of a compound of Formula (I), R$^4$ is deuterium.

In some embodiments of a compound of Formula (I), each alkyl, alkenyl, alkynyl, cycloalkyl, heterocycloalkyl, aryl, and heteroaryl in R$^5$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (I), R$^5$ is halogen, —CN, —OH, —OR$^a$, —NR$^b$R$^c$, —C(=O)R$^a$, —C(=O)OR$^b$, —C(=O)NR$^b$R$^c$, C$_4$-C$_6$alkyl, C$_1$-C$_6$deuteroalkyl, C$_1$-C$_6$haloalkyl, C$_4$-C$_6$hydroxyalkyl, C$_1$-C$_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OR$^a$, —NR$^b$R$^c$, C$_1$-C$_6$alkyl, or C$_1$-C$_6$haloalkyl. In some embodiments of a compound of Formula (I), R$^5$ is C$_4$-C$_6$alkyl, C$_1$-C$_6$deuteroalkyl, C$_1$-C$_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —OR$^a$, —NR$^b$W, C$_1$-C$_6$alkyl, or C$_1$-C$_6$haloalkyl. In some embodiments of a compound of Formula (I), R$^5$ is C$_4$-C$_6$alkyl, C$_1$-C$_6$deuteroalkyl, C$_1$-C$_6$haloalkyl, cycloalkyl, or heterocycloalkyl; wherein each alkyl, cycloalkyl, and heterocycloalkyl is independently optionally substituted with one or more halogen. In some embodiments of a compound of Formula (I), R$^5$ is C$_1$-C$_6$deuteroalkyl.

In some embodiments of a compound of Formula (I), each alkyl, alkenyl, alkynyl, cycloalkyl, heterocycloalkyl, aryl, and heteroaryl in R$^6$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (I), R$^6$ is hydrogen or C$_1$-C$_6$alkyl. In some embodiments of a compound of Formula (I), R$^6$ is hydrogen.

Disclosed herein is a compound of Formula (II), or a pharmaceutically acceptable salt, solvate, or stereoisomer thereof:

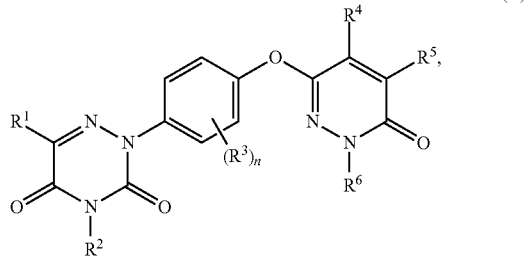

(II)

wherein:
R$^1$ is deuterium, halogen, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^a$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

R$^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

each R$^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

n is 0-4;

each R$^a$ is independently $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl; and each R$^b$ and R$^c$ are independently hydrogen, deuterium, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (II), R$^1$ is halogen, —OH, —OR$^a$, —NR$^b$R$^c$, —C(=O)R$^a$, —C(=O)OR$^a$, —C(=O)NR$^b$R$^c$, $C_1$-$C_6$haloalkyl, $C_1$-$C_6$hydroxyalkyl, $C_1$-$C_6$aminoalkyl, $C_2$-$C_6$alkynyl, cycloalkyl, or heterocycloalkyl; wherein each alkyl, alkynyl, cycloalkyl, and heterocycloalkyl is independently optionally substituted with one or more oxo, deuterium, halogen, —CN, —OH, —OR$^a$, —NR$^b$R$^c$, $C_1$-$C_6$alkyl, or $C_1$-$C_6$haloalkyl. In some embodiments of a compound of Formula (II), R$^1$ is —C(=O)R$^a$, $C_1$-$C_6$alkyl, $C_2$-$C_6$alkynyl, or cycloalkyl; wherein each alkyl, alkynyl, and cycloalkyl is independently optionally substituted with one or more oxo, deuterium, halogen, —CN, $C_1$-$C_6$alkyl, or $C_1$-$C_6$haloalkyl. In some embodiments of a compound of Formula (II), R$^1$ is deuterium.

In some embodiments of a compound of Formula (II), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (II), R$^2$ is hydrogen or $C_1$-$C_6$alkyl. In some embodiments of a compound of Formula (II), R$^2$ is hydrogen.

In some embodiments of a compound of Formula (II), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (II), each R$^3$ is independently hydrogen, halogen, $C_1$-$C_6$alkyl, or $C_1$-$C_6$haloalkyl. In some embodiments of a compound of Formula (II), each R$^3$ is independently halogen. In some embodiments of a compound of Formula (II), one of R$^3$ is deuterium.

In some embodiments of a compound of Formula (II), n is 1. In some embodiments of a compound of Formula (I), n is 2. In some embodiments of a compound of Formula (II), n is 3. In some embodiments of a compound of Formula (II), n is 4. In some embodiments of a compound of Formula (II), n is 1 or 2. In some embodiments of a compound of Formula (II), n is 1-3. In some embodiments of a compound of Formula (II), n is 2 or 3.

In some embodiments of a compound of Formula (II), each alkyl, alkenyl, alkynyl, cycloalkyl, heterocycloalkyl, aryl, and heteroaryl in $R^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (II), $R^4$ is hydrogen, halogen, $C_1$-$C_6$alkyl, or $C_1$-$C_6$haloalkyl. In some embodiments of a compound of Formula (II), $R^4$ is hydrogen. In some embodiments of a compound of Formula (II), $R^4$ is deuterium.

In some embodiments of a compound of Formula (II), each alkyl, alkenyl, alkynyl, cycloalkyl, heterocycloalkyl, aryl, and heteroaryl in $R^5$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (II), $R^5$ is halogen, $C_1$-$C_6$alkyl, or $C_1$-$C_6$haloalkyl. In some embodiments of a compound of Formula (II), $R^5$ is hydrogen or $C_1$-$C_6$alkyl. In some embodiments of a compound of Formula (II), $R^5$ is $C_1$-$C_6$alkyl. In some embodiments of a compound of Formula (II), $R^5$ is hydrogen. In some embodiments of a compound of Formula (II), $R^5$ is deuterium. In some embodiments of a compound of Formula (II), $R^5$ is $C_1$-$C_6$deuteroalkyl.

In some embodiments of a compound of Formula (II), each alkyl, alkenyl, alkynyl, cycloalkyl, heterocycloalkyl, aryl, and heteroaryl in $R^6$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (II), $R^6$ is hydrogen or $C_1$-$C_6$alkyl. In some embodiments of a compound of Formula (II), $R^6$ is hydrogen.

Disclosed herein is a compound of Formula (III), or a pharmaceutically acceptable salt, solvate, or stereoisomer thereof:

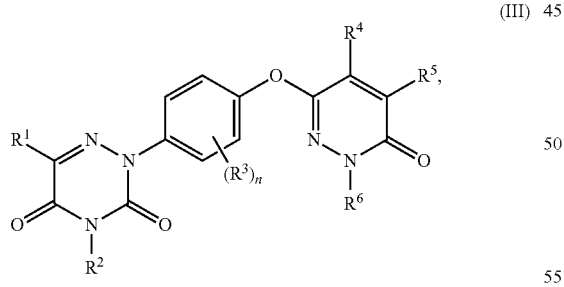

(III)

wherein:
$R^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, $C_1$-$C_6$alkyl, or $C_1$-$C_6$haloalkyl;

$R^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

$R^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

$R^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R⁶ is —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

n is 0-4;

each R$^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and each R$^b$ and R$^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (III), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (III), R$^1$ is hydrogen or —CN. In some embodiments of a compound of Formula (III), R$^1$ is —CN. In some embodiments of a compound of Formula (III), R$^1$ is deuterium.

In some embodiments of a compound of Formula (III), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (III), R$^2$ is hydrogen or C$_1$-C$_6$alkyl. In some embodiments of a compound of Formula (III), R$^2$ is hydrogen.

In some embodiments of a compound of Formula (III), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (III), each R$^3$ is independently hydrogen, halogen, C$_1$-C$_6$alkyl, or C$_1$-C$_6$haloalkyl. In some embodiments of a compound of Formula (III), each R$^3$ is independently halogen. In some embodiments of a compound of Formula (III), one of R$^3$ is deuterium.

In some embodiments of a compound of Formula (III), n is 1. In some embodiments of a compound of Formula (III), n is 2. In some embodiments of a compound of Formula (III), n is 3. In some embodiments of a compound of Formula (III), n is 4. In some embodiments of a compound of Formula (III), n is 1 or 2. In some embodiments of a compound of Formula (III), n is 1-3. In some embodiments of a compound of Formula (III), n is 2 or 3.

In some embodiments of a compound of Formula (III), each alkyl, alkenyl, alkynyl, cycloalkyl, heterocycloalkyl, aryl, and heteroaryl in R$^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (III), R$^4$ is hydrogen, halogen, C$_1$-C$_6$alkyl, or C$_1$-C$_6$haloalkyl. In some embodiments of a compound of Formula (III), R$^4$ is hydrogen. In some embodiments of a compound of Formula (III), R$^4$ is deuterium.

In some embodiments of a compound of Formula (III), each alkyl, alkenyl, alkynyl, cycloalkyl, heterocycloalkyl, aryl, and heteroaryl in R$^5$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (III), R$^5$ is halogen, C$_1$-C$_6$alkyl, or C$_1$-C$_6$haloalkyl. In some embodiments of a compound of Formula (III), R$^5$ is hydrogen or C$_1$-C$_6$alkyl. In some embodiments of a compound of Formula (III), R$^5$ is C$_1$-C$_6$alkyl. In some embodiments of a compound of Formula (III), R$^5$ is hydrogen. In some embodiments of a compound of Formula (III), R$^5$ is deuterium. In some embodiments of a compound of Formula (III), R$^5$ is C$_1$-C$_6$deuteroalkyl.

In some embodiments of a compound of Formula (III), each alkyl, alkenyl, alkynyl, cycloalkyl, heterocycloalkyl, aryl, and heteroaryl in R$^6$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (III), R$^6$ is C$_1$-C$_6$alkyl.

Disclosed herein is a compound of Formula (IV), or a pharmaceutically acceptable salt, solvate, or stereoisomer thereof:

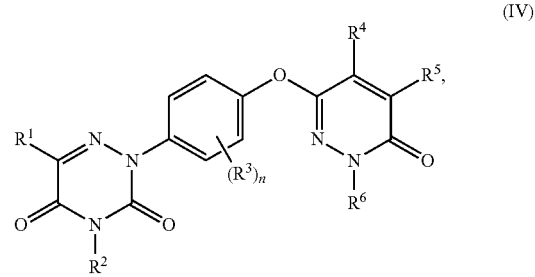

(IV)

wherein:

R$^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O) NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O) R$^a$, —C(=O)OR$^b$, —C(=O)NR$^b$R$^c$, C$_1$-C$_6$alkyl, or C$_1$-C$_6$haloalkyl;

R$^2$ is hydrogen, halogen, —CN, —OH, —OR$^a$, —S(=O) R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O) NR$^b$R$^c$, C$_1$-C$_6$alkyl, or C$_1$-C$_6$haloalkyl;

each R$^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O) NR$^b$R$^c$, C$_1$-C$_6$alkyl, or C$_1$-C$_6$haloalkyl;

R$^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O) NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O) R$^a$, —C(=O)OR$^b$, —C(=O)NR$^b$R$^c$, C$_1$-C$_6$alkyl, or C$_1$-C$_6$haloalkyl;

R$^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O) NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O) R$^a$, —C(=O)OR$^b$, —C(=O)NR$^b$R$^c$, C$_1$-C$_6$alkyl, or C$_1$-C$_6$haloalkyl;

R$^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O) NR$^b$R$^c$, C$_1$-C$_6$alkyl, or C$_1$-C$_6$haloalkyl;

n is 0-4;

each R$^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and each R$^b$ and R$^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

provided that:

(a) R$^4$ and R$^5$ are taken together to form a cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, or C$_1$-C$_6$haloalkyl; and/or (b) two R$^3$ on adjacent carbons are taken together to form a cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, or C$_1$-C$_6$haloalkyl.

Disclosed herein is a compound of Formula (IV), or a pharmaceutically acceptable salt, solvate, or stereoisomer thereof:

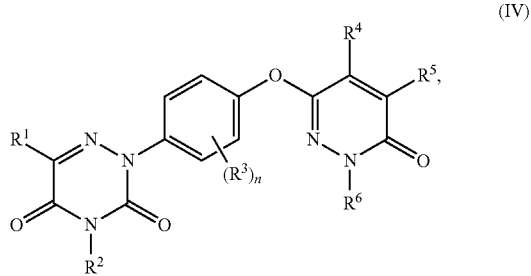

(IV)

wherein:
- R¹ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, C$_1$-C$_6$alkyl, or C$_1$-C$_6$haloalkyl;
- R² is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- each R³ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- or two R³ on adjacent carbons are taken together to form a cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, or C$_1$-C$_6$haloalkyl;
- R⁴ and R⁵ are taken together to form a cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, or C$_1$-C$_6$haloalkyl;
- R⁶ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- n is 0-4;
- each R$^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and
- each R$^b$ and R$^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;
- or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (IV), each alkyl, alkenyl, alkynyl, cycloalkyl, heterocycloalkyl, aryl, and heteroaryl in R¹ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (IV), R¹ is hydrogen or —CN. In some embodiments of a compound of Formula (IV), R¹ is —CN. In some embodiments of a compound of Formula (IV), R¹ is deuterium.

In some embodiments of a compound of Formula (IV), each alkyl, alkenyl, alkynyl, cycloalkyl, heterocycloalkyl, aryl, and heteroaryl in R² is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (IV), R² is hydrogen or C$_1$-C$_6$alkyl. In some embodiments of a compound of Formula (IV), R² is hydrogen.

In some embodiments of a compound of Formula (IV), each alkyl, alkenyl, alkynyl, cycloalkyl, heterocycloalkyl, aryl, and heteroaryl in $R^3$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (IV), each R$^3$ is independently hydrogen, halogen, C$_1$-C$_6$alkyl, or C$_1$-C$_6$haloalkyl. In some embodiments of a compound of Formula (IV), each R$^3$ is independently halogen. In some embodiments of a compound of Formula (IV), one of R$^3$ is deuterium. In some embodiments of a compound of Formula (IV), each R$^3$ is independently hydrogen, deuterium, halogen, C$_1$-C$_6$alkyl, or C$_1$-C$_6$haloalkyl. In some embodiments of a compound of Formula (IV), each R$^3$ is independently deuterium, halogen, or C$_1$-C$_6$alkyl. In some embodiments of a compound of Formula (IV), each R$^3$ is independently deuterium or halogen.

In some embodiments of a compound of Formula (IV), n is 1. In some embodiments of a compound of Formula (IV), n is 2. In some embodiments of a compound of Formula (IV), n is 3. In some embodiments of a compound of Formula (IV), n is 4. In some embodiments of a compound of Formula (IV), n is 1 or 2. In some embodiments of a compound of Formula (IV), n is 1-3. In some embodiments of a compound of Formula (IV), n is 2 or 3.

In some embodiments of a compound of Formula (IV), two R$^3$ on adjacent carbons are taken together to form a cycloalkyl optionally substituted with one or more oxo, deuterium, halogen, —CN, —OH, —OMe, —NH$_2$, C$_1$-C$_6$alkyl, C$_1$-C$_6$deuteroalkyl, r C$_1$-C$_6$haloalkyl. In some embodiments of a compound of Formula (IV), two R$^3$ on adjacent carbons are taken together to form a cycloalkyl optionally substituted with one or more oxo, deuterium, halogen, —CN, —OH, —OMe, —NH$_2$, C$_1$-C$_6$alkyl, or C$_1$-C$_6$haloalkyl. In some embodiments of a compound of Formula (IV), two R$^3$ on adjacent carbons are taken together to form a cycloalkyl.

In some embodiments of a compound of Formula (IV), each alkyl, alkenyl, alkynyl, cycloalkyl, heterocycloalkyl, aryl, and heteroaryl in R$^4$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (IV), R$^4$ is hydrogen, halogen, C$_1$-C$_6$alkyl, or C$_1$-C$_6$haloalkyl. In some embodiments of a compound of Formula (IV), R$^4$ is hydrogen. In some embodiments of a compound of Formula (IV), R$^4$ is deuterium.

In some embodiments of a compound of Formula (IV), each alkyl, alkenyl, alkynyl, cycloalkyl, heterocycloalkyl, aryl, and heteroaryl in R$^5$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (IV), R$^5$ is halogen, C$_1$-C$_6$alkyl, or C$_1$-C$_6$haloalkyl. In some embodiments of a compound of Formula (IV), R$^5$ is hydrogen or C$_1$-C$_6$alkyl. In some embodiments of a compound of Formula (IV), R$^5$ is C$_1$-C$_6$alkyl. In some embodiments of a compound of Formula (IV), R$^5$ is hydrogen. In some embodiments of a compound of Formula (IV), R$^5$ is deuterium. In some embodiments of a compound of Formula (IV), R$^5$ is C$_1$-C$_6$deuteroalkyl.

In some embodiments of a compound of Formula (IV), R$^4$ and R$^5$ are taken together to form a cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl.

In some embodiments of a compound of Formula (IV), R$^4$ and R$^5$ are taken together to form a cycloalkyl optionally substituted with one or more oxo, deuterium, halogen, —CN, —OH, —OMe, —NH$_2$, C$_1$-C$_6$alkyl, C$_1$-C$_6$deuteroalkyl, or C$_1$-C$_6$haloalkyl.

In some embodiments of a compound of Formula (IV), R$^4$ and R$^5$ are taken together to form a cycloalkyl optionally substituted with one or more oxo, deuterium, halogen, —CN, —OH, —OMe, —NH$_2$, C$_1$-C$_6$alkyl, or C$_1$-C$_6$haloalkyl. In some embodiments of a compound of Formula (IV), R$^4$ and R$^5$ are taken together to form a cycloalkyl optionally substituted with one or more C$_1$-C$_6$alkyl, C$_1$-C$_6$deuteroalkyl, or C$_1$-C$_6$haloalkyl. In some embodiments of a compound of Formula (IV), R$^4$ and R$^5$ are taken together to form a cycloalkyl optionally substituted with one or more C$_1$-C$_6$alkyl or C$_1$-C$_6$haloalkyl.

In some embodiments of a compound of Formula (IV), R$^4$ and R$^5$ are taken together to form a cycloalkyl.

In some embodiments of a compound of Formula (IV), each alkyl, alkenyl, alkynyl, cycloalkyl, heterocycloalkyl, aryl, and heteroaryl in R$^6$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (IV), R$^6$ is hydrogen or C$_1$-C$_6$alkyl. In some embodiments of a compound of Formula (IV), R$^6$ is hydrogen.

Disclosed herein is a compound of Formula (V), or a pharmaceutically acceptable salt, solvate, or stereoisomer thereof:

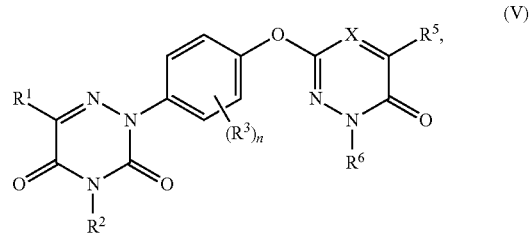

wherein:

X is CR$^4$ or N;

R$^1$ is hydrogen, deuterium, halogen, —CN, —OH, —OR$^a$, —SH, —SR$^a$, —S(═O)R$^a$, —S(═O)$_2$R$^a$, —NO$_2$, —NR$^b$R$^c$, —NHS(═O)$_2$R$^a$, —S(═O)$_2$NR$^b$R$^c$, —C(═O)R$^a$, —OC(═O)R$^a$, —C(═O)OR$^b$, —OC(═O)OR$^b$, —C(═O)NR$^b$R$^c$, —OC(═O)NR$^b$R$^c$, —NR$^b$C(═O)NR$^b$R$^c$, —NR$^b$C(═O)R$^a$, —NR$^b$C(═O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl;

R$^2$ is hydrogen, halogen, —CN, —OH, —OR$^a$, —S(═O)R$^a$, —S(═O)$_2$R$^a$, —S(═O)$_2$NR$^b$R$^c$, —C(═O)R$^a$, —OC(═O)R$^a$, —C(═O)OR$^b$, —C(═O)NR$^b$R$^c$, C$_1$-C$_6$alkyl, C$_1$-C$_6$deuteroalkyl, C$_1$-C$_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

each R$^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^4$ is deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

n is 0-4;

each R$^a$ is independently $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl; and each R$^b$ and R$^c$ are independently hydrogen, deuterium, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (V), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (V), R$^1$ is hydrogen or —CN. In some embodiments of a compound of Formula (V), R$^1$ is —CN. In some embodiments of a compound of Formula (V), R$^1$ is deuterium.

In some embodiments of a compound of Formula (V), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (V), R$^2$ is hydrogen or $C_1$-$C_6$alkyl. In some embodiments of a compound of Formula (V), R$^2$ is hydrogen.

In some embodiments of a compound of Formula (V), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (V), each R$^3$ is independently hydrogen, halogen, $C_1$-$C_6$alkyl, or $C_1$-$C_6$haloalkyl. In some embodiments of a compound of Formula (V), each R$^3$ is independently halogen. In some embodiments of a compound of Formula (V), one of R$^3$ is deuterium.

In some embodiments of a compound of Formula (V), n is 1. In some embodiments of a compound of Formula (V), n is 2. In some embodiments of a compound of Formula (V), n is 3. In some embodiments of a compound of Formula (V), n is 4. In some embodiments of a compound of Formula (V), n is 1 or 2. In some embodiments of a compound of Formula (V), n is 1-3. In some embodiments of a compound of Formula (V), n is 2 or 3.

In some embodiments of a compound of Formula (V), X is N. In some embodiments of a compound of Formula (V), X is CR⁴.

In some embodiments of a compound of Formula (V), each alkyl, alkenyl, alkynyl, cycloalkyl, heterocycloalkyl, aryl, and heteroaryl in R⁴ is independently optionally substituted with one, two, or three oxo, deuterium, halogen, —CN, —OH, —ORᵃ, —NRᵇRᶜ, —C(=O)Rᵃ, —C(=O)ORᵇ, —C(=O)NRᵇRᶜ, C₁-C₆alkyl, or C₁-C₆haloalkyl. In some embodiments of a compound of Formula (V), R⁴ is halogen, C₁-C₆alkyl, or C₁-C₆haloalkyl. In some embodiments of a compound of Formula (V), R⁴ is halogen or C₁-C₆alkyl. In some embodiments of a compound of Formula (V), R⁴ is deuterium.

In some embodiments of a compound of Formula (V), each alkyl, alkenyl, alkynyl, cycloalkyl, heterocycloalkyl, aryl, and heteroaryl in R⁵ is independently optionally substituted with one, two, or three oxo, deuterium, halogen, —CN, —OH, —ORᵃ, —NRᵇRᶜ, —C(=O)Rᵃ, —C(=O)ORᵇ, —C(=O)NRᵇRᶜ, C₁-C₆alkyl, or C₁-C₆haloalkyl. In some embodiments of a compound of Formula (V), R⁵ is halogen, C₁-C₆alkyl, or C₁-C₆haloalkyl. In some embodiments of a compound of Formula (V), R⁵ is hydrogen or C₁-C₆alkyl. In some embodiments of a compound of Formula (V), R⁵ is C₁-C₆alkyl. In some embodiments of a compound of Formula (V), R⁵ is hydrogen. In some embodiments of a compound of Formula (V), R⁵ is deuterium. In some embodiments of a compound of Formula (V), R⁵ is C₁-C₆deuteroalkyl.

In some embodiments of a compound of Formula (V), each alkyl, alkenyl, alkynyl, cycloalkyl, heterocycloalkyl, aryl, and heteroaryl in R⁶ is independently optionally substituted with one, two, or three oxo, deuterium, halogen, —CN, —OH, —ORᵃ, —NRᵇRᶜ, —C(=O)Rᵃ, —C(=O)ORᵇ, —C(=O)NRᵇRᶜ, C₁-C₆alkyl, or C₁-C₆haloalkyl. In some embodiments of a compound of Formula (V), R⁶ is hydrogen or C₁-C₆alkyl. In some embodiments of a compound of Formula (V), R⁶ is hydrogen.

Disclosed herein is a compound of Formula (VI), or a pharmaceutically acceptable salt, solvate, or stereoisomer thereof:

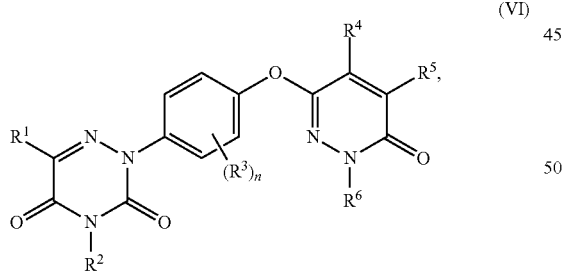

(VI)

wherein:
R¹ is hydrogen, deuterium, halogen, —CN, —OH, —ORᵃ, —SH, —SRᵃ, —S(=O)Rᵃ, —S(=O)₂Rᵃ, —NO₂, —NRᵇRᶜ, —NHS(=O)₂Rᵃ, —S(=O)₂NRᵇRᶜ, —C(=O)Rᵃ, —OC(=O)Rᵃ, —C(=O)ORᵇ, —OC(=O)ORᵇ, —C(=O)NRᵇRᶜ, —OC(=O)NRᵇRᶜ, —NRᵇC(=O)NRᵇRᶜ, —NRᵇC(=O)Rᵃ, —NRᵇC(=O)ORᵇ, C₁-C₆alkyl, C₁-C₆deuteroalkyl, C₁-C₆haloalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —ORᵃ, —C(=O)Rᵃ, —C(=O)ORᵇ, —C(=O)NRᵇRᶜ, C₁-C₆alkyl, or C₁-C₆haloalkyl;

R² is hydrogen, halogen, —CN, —OH, —ORᵃ, —S(=O)Rᵃ, —S(=O)₂Rᵃ, —S(=O)₂NRᵇRᶜ, —C(=O)Rᵃ, —OC(=O)Rᵃ, —C(=O)ORᵇ, —C(=O)NRᵇRᶜ, C₁-C₆alkyl, C₁-C₆deuteroalkyl, C₁-C₆haloalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —ORᵃ, —NRᵇRᶜ, —C(=O)Rᵃ, —C(=O)ORᵇ, —C(=O)NRᵇRᶜ, C₁-C₆alkyl, or C₁-C₆haloalkyl;

each R³ is independently hydrogen, deuterium, halogen, —CN, —OH, —ORᵃ, —SH, —SRᵃ, —S(=O)Rᵃ, —S(=O)₂Rᵃ, —NO₂, —NRᵇRᶜ, —NHS(=O)₂Rᵃ, —S(=O)₂NRᵇRᶜ, —C(=O)Rᵃ, —OC(=O)Rᵃ, —C(=O)ORᵇ, —OC(=O)ORᵇ, —C(=O)NRᵇRᶜ, —OC(=O)NRᵇRᶜ, —NRᵇC(=O)NRᵇRᶜ, —NRᵇC(=O)Rᵃ, —NRᵇC(=O)ORᵇ, C₁-C₆alkyl, C₁-C₆deuteroalkyl, C₁-C₆haloalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —ORᵃ, —NRᵇRᶜ, —C(=O)Rᵃ, —C(=O)ORᵇ, —C(=O)NRᵇRᶜ, C₁-C₆alkyl, or C₁-C₆haloalkyl;

R⁴ is hydrogen, deuterium, halogen, —CN, —OH, —ORᵃ, —SH, —SRᵃ, —S(=O)Rᵃ, —S(=O)₂Rᵃ, —NO₂, —NRᵇRᶜ, —NHS(=O)₂Rᵃ, —S(=O)₂NRᵇRᶜ, —C(=O)Rᵃ, —OC(=O)Rᵃ, —C(=O)ORᵇ, —OC(=O)ORᵇ, —C(=O)NRᵇRᶜ, —OC(=O)NRᵇRᶜ, —NRᵇC(=O)NRᵇRᶜ, —NRᵇC(=O)Rᵃ, —NRᵇC(=O)ORᵇ, C₁-C₆alkyl, C₁-C₆deuteroalkyl, C₁-C₆haloalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —ORᵃ, —NRᵇRᶜ, —C(=O)Rᵃ, —C(=O)ORᵇ, —C(=O)NRᵇRᶜ, C₁-C₆alkyl, or C₁-C₆haloalkyl;

R⁵ is hydrogen, deuterium, halogen, —CN, —OH, —ORᵃ, —SH, —SRᵃ, —S(=O)Rᵃ, —S(=O)₂Rᵃ, —NO₂, —NRᵇRᶜ, —NHS(=O)₂Rᵃ, —S(=O)₂NRᵇRᶜ, —C(=O)Rᵃ, —OC(=O)Rᵃ, —C(=O)ORᵇ, —OC(=O)ORᵇ, —C(=O)NRᵇRᶜ, —OC(=O)NRᵇRᶜ, —NRᵇC(=O)NRᵇRᶜ, —NRᵇC(=O)Rᵃ, —NRᵇC(=O)ORᵇ, C₁-C₆alkyl, C₁-C₆deuteroalkyl, C₁-C₆haloalkyl, C₁-C₆hydroxyalkyl, C₁-C₆aminoalkyl, C₂-C₆alkenyl, C₂-C₆alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —ORᵃ, —NRᵇRᶜ, —C(=O)Rᵃ, —C(=O)ORᵇ, —C(=O)NRᵇRᶜ, C₁-C₆alkyl, or C₁-C₆haloalkyl;

R⁶ is hydrogen, —CN, —OH, —ORᵃ, —S(=O)Rᵃ, —S(=O)₂Rᵃ, —S(=O)₂NRᵇRᶜ, —C(=O)Rᵃ, —OC (=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

n is 3 or 4;

each R$^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and each R$^b$ and R$^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (VI), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VI), R$^1$ is hydrogen or —CN. In some embodiments of a compound of Formula (VI), R$^1$ is —CN. In some embodiments of a compound of Formula (VI), R$^1$ is deuterium.

In some embodiments of a compound of Formula (VI), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VI), R$^2$ is hydrogen or C$_1$-C$_6$alkyl. In some embodiments of a compound of Formula (VI), R$^2$ is hydrogen.

In some embodiments of a compound of Formula (VI), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VI), each R$^3$ is independently hydrogen, halogen, C$_1$-C$_6$alkyl, or C$_1$-C$_6$haloalkyl. In some embodiments of a compound of Formula (VI), each R$^3$ is independently hydrogen, halogen, or C$_1$-C$_6$alkyl. In some embodiments of a compound of Formula (VI), each R$^3$ is independently halogen. In some embodiments of a compound of Formula (VI), one of R$^3$ is deuterium.

In some embodiments of a compound of Formula (VI), n is 3. In some embodiments of a compound of Formula (VI), n is 4.

In some embodiments of a compound of Formula (VI), each alkyl, alkenyl, alkynyl, cycloalkyl, heterocycloalkyl, aryl, and heteroaryl in R$^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VI), R$^4$ is hydrogen, halogen, C$_1$-C$_6$alkyl, or C$_1$-C$_6$haloalkyl. In some embodiments of a compound of Formula (VI), R$^4$ is hydrogen. In some embodiments of a compound of Formula (VI), R$^4$ is deuterium.

In some embodiments of a compound of Formula (VI), each alkyl, alkenyl, alkynyl, cycloalkyl, heterocycloalkyl, aryl, and heteroaryl in R$^5$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VI), R$^5$ is halogen, C$_1$-C$_6$alkyl, or C$_1$-C$_6$haloalkyl. In some embodiments of a compound of Formula (VI), R$^5$ is hydrogen or C$_1$-C$_6$alkyl. In some embodiments of a compound of Formula (VI), R$^5$ is C$_1$-C$_6$alkyl. In some embodiments of a compound of Formula (VI), R$^5$ is hydrogen. In some embodiments of a compound of Formula (VI), R$^5$ is deuterium. In some embodiments of a compound of Formula (VI), R$^5$ is C$_1$-C$_6$deuteroalkyl.

In some embodiments of a compound of Formula (VI), each alkyl, alkenyl, alkynyl, cycloalkyl, heterocycloalkyl, aryl, and heteroaryl in R$^6$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VI), R$^6$ is hydrogen or C$_1$-C$_6$alkyl. In some embodiments of a compound of Formula (VI), R$^6$ is hydrogen.

Disclosed herein is a compound of Formula (VII), or a pharmaceutically acceptable salt, solvate, or stereoisomer thereof:

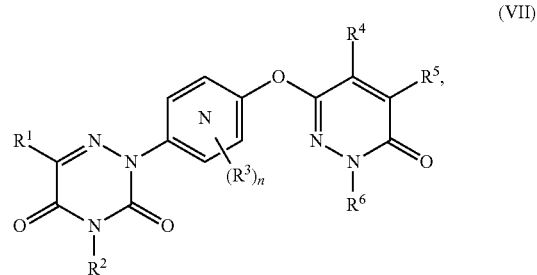

(VII)

wherein:

R$^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, $C_1$-$C_6$alkyl, or $C_1$-$C_6$haloalkyl;

$R^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

$R^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

$R^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

$R^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

n is 0-3;

each $R^a$ is independently $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl; and each $R^b$ and $R^c$ are independently hydrogen, deuterium, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or $R^b$ and $R^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (VII), each alkyl, alkenyl, alkynyl, cycloalkyl, heterocycloalkyl, aryl, and heteroaryl in $R^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (VII), $R^1$ is hydrogen or —CN. In some embodiments of a compound of Formula (VII), $R^1$ is —CN. In some embodiments of a compound of Formula (VII), $R^1$ is deuterium.

In some embodiments of a compound of Formula (VII), each alkyl, alkenyl, alkynyl, cycloalkyl, heterocycloalkyl, aryl, and heteroaryl in $R^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (VII), $R^2$ is hydrogen or $C_1$-$C_6$alkyl. In some embodiments of a compound of Formula (VII), $R^2$ is hydrogen.

In some embodiments of a compound of Formula (VII), each alkyl, alkenyl, alkynyl, cycloalkyl, heterocycloalkyl, aryl, and heteroaryl in $R^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (VII), each $R^3$ is independently hydrogen, halogen, $C_1$-$C_6$alkyl, or $C_1$-$C_6$haloalkyl. In some embodiments of a compound of Formula (VII), each $R^3$ is independently halogen. In some embodiments of a compound of Formula (VII), one of $R^3$ is deuterium.

In some embodiments of a compound of Formula (VII), n is 1. In some embodiments of a compound of Formula (VII), n is 2. In some embodiments of a compound of Formula (VII), n is 3. In some embodiments of a compound of Formula (VII), n is 4. In some embodiments of a compound of Formula (VII), n is 1 or 2. In some embodiments of a compound of Formula (VII), n is 1-3. In some embodiments of a compound of Formula (VII), n is 2 or 3.

In some embodiments of a compound of Formula (VII),

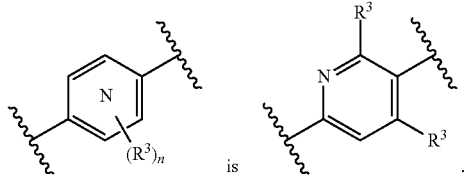

is

In some embodiments of a compound of Formula (VII), each alkyl, alkenyl, alkynyl, cycloalkyl, heterocycloalkyl, aryl, and heteroaryl in $R^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (VII), $R^4$ is hydrogen, halogen, $C_1$-$C_6$alkyl, or $C_1$-$C_6$haloalkyl. In some embodiments of a compound of Formula (VII), $R^4$ is hydrogen. In some embodiments of a compound of Formula (VII), $R^4$ is deuterium.

In some embodiments of a compound of Formula (VII), each alkyl, alkenyl, alkynyl, cycloalkyl, heterocycloalkyl, aryl, and heteroaryl in $R^5$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (VII), $R^5$ is halogen, $C_1$-$C_6$alkyl, or $C_1$-$C_6$haloalkyl. In some embodiments of a compound of Formula (VII), $R^5$ is hydrogen or $C_1$-$C_6$alkyl. In some embodiments of a compound of Formula (VII), $R^5$ is $C_1$-$C_6$alkyl. In some embodiments of a compound of Formula (VII), $R^5$ is hydrogen. In some embodiments of a compound of Formula (VII), $R^5$ is deuterium. In some embodiments of a compound of Formula (VII), $R^5$ is $C_1$-$C_6$deuteroalkyl.

In some embodiments of a compound of Formula (VII), each alkyl, alkenyl, alkynyl, cycloalkyl, heterocycloalkyl, aryl, and heteroaryl in $R^6$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (VII), $R^6$ is hydrogen or $C_1$-$C_6$alkyl. In some embodiments of a compound of Formula (VII), $R^6$ is hydrogen.

Disclosed herein is a compound of Formula (VIII), or a pharmaceutically acceptable salt, solvate, or stereoisomer thereof:

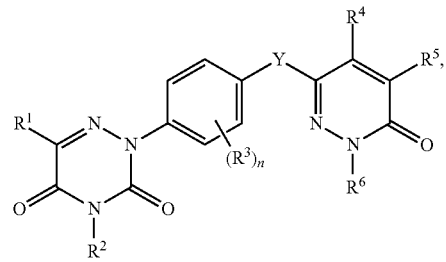

(VIII)

wherein:
Y is CR$^{11}$R$^{12}$;
$R^{11}$ and $R^{12}$ are independently hydrogen, deuterium, halogen, —CN, —OH, —OR$^a$, —NR$^b$R$^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, or heterocycloalkyl; wherein each alkyl, alkenyl, alkynyl, cycloalkyl, or heterocycloalkyl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl; provided that at least one of $R^{11}$ and $R^{12}$ is not hydrogen; or $R^{11}$ and $R^{12}$ are taken together to form a cycloalkyl or heterocycloalkyl; wherein each cycloalkyl and heterocycloalkyl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;
$R^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, $C_1$-$C_6$alkyl, or $C_1$-$C_6$haloalkyl;
$R^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;
each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

R$^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, C$_1$-C$_6$alkyl, or C$_1$-C$_6$haloalkyl;

R$^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, C$_1$-C$_6$alkyl, or C$_1$-C$_6$haloalkyl;

R$^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

n is 0-4;

each R$^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and each R$^b$ and R$^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (VIII), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VIII), R$^1$ is hydrogen or —CN. In some embodiments of a compound of Formula (VIII), R$^1$ is —CN. In some embodiments of a compound of Formula (VIII), R$^1$ is deuterium.

In some embodiments of a compound of Formula (VIII), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VIII), R$^2$ is hydrogen or C$_1$-C$_6$alkyl. In some embodiments of a compound of Formula (VIII), R$^2$ is hydrogen.

In some embodiments of a compound of Formula (VIII), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VIII), each R$^3$ is independently hydrogen, halogen, C$_1$-C$_6$alkyl, or C$_1$-C$_6$haloalkyl. In some embodiments of a compound of Formula (VIII), each R$^3$ is independently halogen. In some embodiments of a compound of Formula (VIII), one of R$^3$ is deuterium.

In some embodiments of a compound of Formula (VIII), n is 1. In some embodiments of a compound of Formula (VIII), n is 2. In some embodiments of a compound of Formula (VIII), n is 3. In some embodiments of a compound of Formula (VIII), n is 4. In some embodiments of a compound of Formula (VIII), n is 1 or 2. In some embodiments of a compound of Formula (VIII), n is 1-3. In some embodiments of a compound of Formula (VIII), n is 2 or 3.

In some embodiments of a compound of Formula (VIII), each alkyl, alkenyl, alkynyl, cycloalkyl, heterocycloalkyl, aryl, and heteroaryl in R$^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (VIII), R$^4$ is hydrogen, halogen, C$_1$-C$_6$alkyl, or C$_1$-C$_6$haloalkyl. In some embodiments of a compound of Formula (VIII), R$^4$ is hydrogen. In some embodiments of a compound of Formula (VIII), R$^4$ is deuterium.

In some embodiments of a compound of Formula (VIII), each alkyl, alkenyl, alkynyl, cycloalkyl, heterocycloalkyl, aryl, and heteroaryl in R$^5$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (VIII), R$^5$ is halogen, C$_1$-C$_6$alkyl, or C$_1$-C$_6$haloalkyl. In some embodiments of a compound of Formula (VIII), R$^5$ is hydrogen or C$_1$-C$_6$alkyl. In some embodiments of a compound of Formula (VIII), R$^5$ is C$_1$-C$_6$alkyl. In some embodiments of a compound of Formula (VIII), R$^5$ is hydrogen. In some embodiments of a compound of Formula (VIII), R$^5$ is deuterium. In some embodiments of a compound of Formula (VIII), R$^5$ is C$_1$-C$_6$deuteroalkyl.

In some embodiments of a compound of Formula (VIII), each alkyl, alkenyl, alkynyl, cycloalkyl, heterocycloalkyl, aryl, and heteroaryl in R$^6$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (VIII), R$^6$ is hydrogen or C$_1$-C$_6$alkyl. In some embodiments of a compound of Formula (VIII), R$^6$ is hydrogen.

In some embodiments of a compound of Formula (VIII), and R$^{12}$ are independently hydrogen, halogen, —CN, C$_1$-C$_6$alkyl, C$_1$-C$_6$haloalkyl, or cycloalkyl; provided that at least one of R$^{11}$ and R$^{12}$ is not hydrogen. In some embodiments of a compound of Formula (VIII), R$^{11}$ and R$^{12}$ are independently hydrogen, halogen, or C$_1$-C$_6$alkyl; provided that at least one of and R$^{12}$ is not hydrogen. In some embodiments of a compound of Formula (VIII), is deuterium and R$^{12}$ is hydrogen, halogen, —CN, C$_1$-C$_6$alkyl, C$_1$-C$_6$haloalkyl, or cycloalkyl. In some embodiments of a compound of Formula (VIII), R$^{11}$ and R$^{12}$ are deuterium.

In some embodiments of a compound of Formula (VIII), and R$^{12}$ are taken together to form a cycloalkyl.

Disclosed herein is a compound of Formula (IX), or a pharmaceutically acceptable salt, solvate, or stereoisomer thereof:

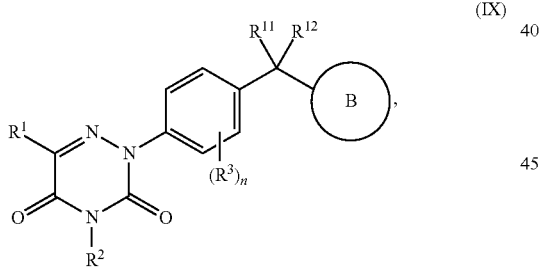

(IX)

wherein:
Ring B is an optionally substituted N-linked heterocycloalkyl;
R$^{11}$ and R$^{12}$ are independently hydrogen, deuterium, halogen, —CN, —OH, —OR$^a$, —NR$^b$W, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, or heterocycloalkyl; wherein each alkyl, alkenyl, alkynyl, cycloalkyl, and heterocycloalkyl is independently optionally substituted with one or more oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl; or R$^{11}$ and R$^{12}$ are taken together to form a cycloalkyl or heterocycloalkyl; wherein each cycloalkyl and heterocycloalkyl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

R$^1$ is hydrogen, deuterium, halogen, —CN, —OH, —OR$^a$, —SH, —SR$^a$, —S(═O)R$^a$, —S(═O)$_2$R$^a$, —NO$_2$, —NR$^b$R$^c$, —NHS(═O)$_2$R$^a$, —S(═O)$_2$NR$^b$R$^c$, —C(═O)R$^a$, —OC(═O)R$^a$, —C(═O)OR$^b$, —OC(═O)OR$^b$, —C(═O)NR$^b$R$^c$, —OC(═O)NR$^b$R$^c$, —NR$^b$C(═O)NR$^b$R$^c$, —NR$^b$C(═O)R$^a$, —NR$^b$C(═O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl;

R$^2$ is hydrogen, halogen, —CN, —OH, —OR$^a$, —S(═O)R$^a$, —S(═O)$_2$R$^a$, —S(═O)$_2$NR$^b$R$^c$, —C(═O)R$^a$, —OC(═O)R$^a$, —C(═O)OR$^b$, —C(═O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl;

each R$^3$ is independently hydrogen, deuterium, halogen, —CN, —OH, —OR$^a$, —SH, —SR$^a$, —S(═O)R$^a$, —S(═O)$_2$R$^a$, —NO$_2$, —NR$^b$R$^c$, —NHS(═O)$_2$R$^a$, —S(═O)$_2$NR$^b$R$^c$, —C(═O)R$^a$, —OC(═O)R$^a$, —C(═O)OR$^b$, —OC(═O)OR$^b$, —C(═O)NR$^b$R$^c$, —OC(═O)NR$^b$R$^c$, —NR$^b$C(═O)NR$^b$R$^c$, —NR$^b$C(═O)R$^a$, —NR$^b$C(═O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl;

n is 0-4;

each R$^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl; and each R$^b$ and R$^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(═O)Me, —C(═O)OH, —C(═O)OMe, C$_1$-C$_6$alkyl, or C$_1$-C$_6$haloalkyl.

In some embodiments of a compound of Formula (IX), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (IX), R$^1$ is hydrogen or —CN. In some embodiments of a compound of Formula (IX), R$^1$ is —CN. In some embodiments of a compound of Formula (IX), R$^1$ is deuterium.

In some embodiments of a compound of Formula (IX), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (IX), R$^2$ is hydrogen or C$_1$-C$_6$alkyl. In some embodiments of a compound of Formula (IX), R$^2$ is hydrogen.

In some embodiments of a compound of Formula (IX), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl. In some embodiments of a compound of Formula (IX), each R$^3$ is independently hydrogen, halogen, C$_1$-C$_6$alkyl, or C$_1$-C$_6$haloalkyl. In some embodiments of a compound of Formula (IX), each R$^3$ is independently hydrogen, halogen, or C$_1$-C$_6$alkyl. In some embodiments of a compound of Formula (IX), each R$^3$ is independently halogen. In some embodiments of a compound of Formula (IX), one of R$^3$ is deuterium.

In some embodiments of a compound of Formula (IX), n is 1. In some embodiments of a compound of Formula (IX), n is 2. In some embodiments of a compound of Formula (IX), n is 3. In some embodiments of a compound of Formula (IX), n is 4. In some embodiments of a compound of Formula (IX), n is 1 or 2. In some embodiments of a compound of Formula (IX), n is 1-3. In some embodiments of a compound of Formula (IX), n is 2 or 3.

In some embodiments of a compound of Formula (IX), R$^{11}$ and R$^{12}$ are independently hydrogen, halogen, —CN, C$_1$-C$_6$alkyl, C$_1$-C$_6$haloalkyl, or cycloalkyl. In some embodiments of a compound of Formula (IX), and R$^{12}$ are independently hydrogen, halogen, or C$_1$-C$_6$alkyl. In some embodiments of a compound of Formula (IX), R$^{11}$ and R$^{12}$ are hydrogen.

In some embodiments of a compound of Formula (IX), R$^{11}$ and R$^{12}$ are taken together to form a cycloalkyl.

In some embodiments of a compound of Formula (IX), the compound is of formula (IXa):

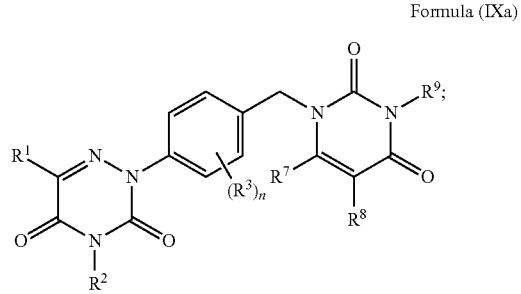

Formula (IXa)

wherein:

R$^7$ is hydrogen, deuterium, halogen, —CN, —OH, —OR$^a$, —SH, —SR$^a$, —S(═O)R$^a$, —S(═O)$_2$R$^a$, —NO$_2$, —NR$^b$R$^c$, —NHS(═O)$_2$R$^a$, —S(═O)$_2$NR$^b$R$^c$, —C(═O)R$^a$, —OC(═O)R$^a$, —C(═O)OR$^b$, —OC(═O)OR$^b$, —C(═O)NR$^b$R$^c$, —OC(═O)NR$^b$R$^c$, —NR$^b$C(═O)NR$^b$R$^c$, —NR$^b$C(═O)R$^a$, —NR$^b$C(═O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl;

R$^8$ is hydrogen, deuterium, halogen, —CN, —OH, —OR$^a$, —SH, —SR$^a$, —S(═O)R$^a$, —S(═O)$_2$R$^a$, —NO$_2$, —NR$^b$R$^c$, —NHS(═O)$_2$R$^a$, —S(═O)$_2$NR$^b$R$^c$, —C(═O)R$^a$, —OC(═O)R$^a$, —C(═O)OR$^b$, —OC(═O)OR$^b$, —C(═O)NR$^b$R$^c$, —OC(═O)NR$^b$R$^c$, —NR$^b$C(═O)NR$^b$R$^c$, —NR$^b$C(═O)R$^a$, —NR$^b$C(═O)OR$^b$, C$_1$-C$_6$alkyl, C$_1$-C$_6$deuteroalkyl, C$_1$-C$_6$haloalkyl, C$_4$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(═O)R$^a$, —C(═O)OR$^b$, —C(═O)NR$^b$R$^c$, C$_1$-C$_6$alkyl, or C$_1$-C$_6$haloalkyl; and R$^9$ is hydrogen, —CN, —OH, —OR$^a$, —S(═O)R$^a$, —S(═O)$_2$R$^a$, —S(═O)$_2$NR$^b$R$^c$, —C(═O)R$^a$, —OC(═O)R$^a$, —C(═O)OR$^b$, —C(═O)NR$^b$R$^c$, C$_1$-C$_6$alkyl, C$_1$-C$_6$deuteoalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(═O)R$^a$, —C(═O)OR$^b$, —C(═O)NR$^b$R$^c$, C$_1$-C$_6$alkyl, or C$_1$-C$_6$haloalkyl.

In some embodiments of a compound of Formula (IXa), R$^7$ is hydrogen, halogen, C$_1$-C$_6$alkyl, or C$_1$-C$_6$haloalkyl. In some embodiments of a compound of Formula (IXa), R$^7$ is hydrogen. In some embodiments of a compound of Formula (IXa), R$^7$ is deuterium.

In some embodiments of a compound of Formula (IXa), R$^8$ is hydrogen, halogen, C$_1$-C$_6$alkyl, or C$_1$-C$_6$haloalkyl. In some embodiments of a compound of Formula (IXa), $R^8$ is hydrogen. In some embodiments of a compound of Formula (IXa), $R^8$ is deuterium.

In some embodiments of a compound of Formula (IXa), $R^9$ is hydrogen or $C_1$-$C_6$alkyl. In some embodiments of a compound of Formula (IXa), $R^9$ is $C_1$-$C_6$alkyl. In some embodiments of a compound of Formula (IXa), $R^9$ is $C_1$-$C_6$deuteroalkyl.

In some embodiments of a compound of Formula (IX), the compound is of formula (IXb):

Formula (IXb)

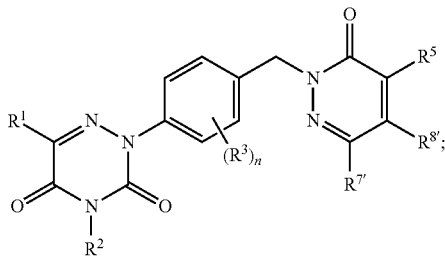

wherein:
$R^5$ is hydrogen, deuterium, halogen, —CN, —OH, —$OR^a$, —SH, —$SR^a$, —S(=O)$R^a$, —S(=O)$_2R^a$, —NO$_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC(=O)NR^bR^c$, —$NR^bC(=O)R^a$, —$NR^bC(=O)OR^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —$NR^bR^c$, —C(=O)$R^a$, —C(=O)$OR^b$, —C(=O)$NR^bR^c$, $C_1$-$C_6$alkyl, or $C_1$-$C_6$haloalkyl;

$R^{7'}$ is hydrogen, deuterium, halogen, —CN, —OH, —$OR^a$, —SH, —$SR^a$, —S(=O)$R^a$, —S(=O)$_2R^a$, —NO$_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC(=O)NR^bR^c$, —$NR^bC(=O)R^a$, —$NR^bC(=O)OR^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —$NR^bR^c$, —C(=O)$R^a$, —C(=O)$OR^b$, —C(=O)$NR^bR^c$, $C_1$-$C_6$alkyl, or $C_1$-$C_6$haloalkyl; and $R^{8'}$ is hydrogen, deuterium, halogen, —CN, —OH, —$OR^a$, —SH, —$SR^a$, —S(=O)$R^a$, —S(=O)$_2R^a$, —NO$_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC(=O)NR^bR^c$, —$NR^bC(=O)R^a$, —$NR^bC(=O)OR^b$, $C_1$-$C_6$alkyl, $C_1$-$C_6$deuteroalkyl, $C_1$-$C_6$haloalkyl, $C_4$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —$NR^bR^c$, —C(=O)$R^a$, —C(=O)$OR^b$, —C(=O)$NR^bR^c$, $C_1$-$C_6$alkyl, or $C_1$-$C_6$haloalkyl.

In some embodiments of a compound of Formula (IXb), each alkyl, alkenyl, alkynyl, cycloalkyl, heterocycloalkyl, aryl, and heteroaryl in $R^5$ is independently optionally substituted with one, two, or three oxo, deuterium, halogen, —CN, —OH, —$OR^a$, —$NR^bR^c$, —C(=O)$R^a$, —C(=O)$OR^b$, —C(=O)$NR^bR^c$, $C_1$-$C_6$alkyl, or $C_1$-$C_6$haloalkyl. In some embodiments of a compound of Formula (IXb), $R^5$ is halogen, $C_1$-$C_6$alkyl, or $C_1$-$C_6$haloalkyl. In some embodiments of a compound of Formula (IXb), $R^5$ is hydrogen or $C_1$-$C_6$alkyl. In some embodiments of a compound of Formula (IXb), $R^5$ is $C_1$-$C_6$alkyl. In some embodiments of a compound of Formula (IXb), $R^5$ is hydrogen. In some embodiments of a compound of Formula (IXb), $R^5$ is deuterium. In some embodiments of a compound of Formula (IXb), $R^5$ is $C_1$-$C_6$deuteroalkyl.

In some embodiments of a compound of Formula (IXb), $R^{7'}$ is hydrogen, halogen, $C_1$-$C_6$alkyl, or $C_1$-$C_6$haloalkyl. In some embodiments of a compound of Formula (IXb), $R^{7'}$ is hydrogen. In some embodiments of a compound of Formula (IXb), $R^{7'}$ is deuterium.

In some embodiments of a compound of Formula (IXb), $R^{8'}$ is hydrogen, halogen, $C_1$-$C_6$alkyl, or $C_1$-$C_6$haloalkyl. In some embodiments of a compound of Formula (IXb), $R^{8'}$ is hydrogen. In some embodiments of a compound of Formula (IXb), $R^{8'}$ is deuterium.

Disclosed herein is a compound of Formula (X), or a pharmaceutically acceptable salt, solvate, or stereoisomer thereof:

(X)

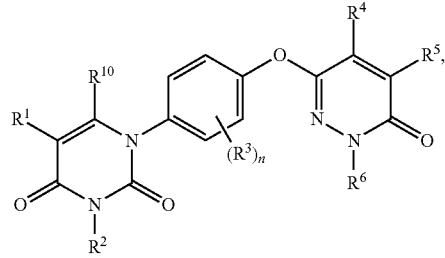

wherein:
$R^1$ is hydrogen, deuterium, halogen, —CN, —OH, —$OR^a$, —SH, —$SR^a$, —S(=O)$R^a$, —S(=O)$_2R^a$, —NO$_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC(=O)NR^bR^c$, —$NR^bC(=O)R^a$, —$NR^bC(=O)OR^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —$OR^a$, —C(=O)$R^a$, —C(=O)$OR^b$, —C(=O)$NR^bR^c$, $C_1$-$C_6$alkyl, or $C_1$-$C_6$haloalkyl;

$R^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

$R^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

$R^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

$R^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

$R^{10}$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

or $R^1$ and $R^{10}$ are taken together to form a cycloalkyl, heterocycloalkyl, aryl, or heteroaryl; wherein each cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

n is 0-4;

each $R^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and each $R^b$ and $R^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or $R^b$ and $R^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (X), each alkyl, alkenyl, alkynyl, cycloalkyl, heterocycloalkyl, aryl, and heteroaryl in $R^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (X), $R^1$ is hydrogen or —CN. In some embodiments of a compound of Formula (X), $R^1$ is —CN. In some embodiments of a compound of Formula (X), $R^1$ is deuterium.

In some embodiments of a compound of Formula (X), each alkyl, alkenyl, alkynyl, cycloalkyl, heterocycloalkyl, aryl, and heteroaryl in $R^{10}$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (X), $R^{10}$ is hydrogen, halogen, $C_1$-$C_6$alkyl, or $C_1$-$C_6$haloalkyl. In some embodiments of a compound of Formula (X), $R^{10}$ is hydrogen. In some embodiments of a compound of Formula (X), $R^{10}$ is deuterium.

In some embodiments of a compound of Formula (X), $R^1$ and $R^{10}$ are taken together to form a cycloalkyl.

In some embodiments of a compound of Formula (X), each alkyl, alkenyl, alkynyl, cycloalkyl, heterocycloalkyl, aryl, and heteroaryl in $R^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (X), $R^2$ is hydrogen or $C_1$-$C_6$alkyl. In some embodiments of a compound of Formula (X), $R^2$ is hydrogen.

In some embodiments of a compound of Formula (X), each alkyl, alkenyl, alkynyl, cycloalkyl, heterocycloalkyl, aryl, and heteroaryl in $R^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (X), each $R^3$ is independently hydrogen, halogen, $C_1$-$C_6$alkyl, or $C_1$-$C_6$haloalkyl. In some embodiments of a compound of Formula (X), each $R^3$ is independently hydrogen, halogen, or $C_1$-$C_6$alkyl. In some embodiments of a compound of Formula (X), each $R^3$ is independently halogen. In some embodiments of a compound of Formula (X), one of $R^3$ is deuterium.

In some embodiments of a compound of Formula (X), n is 1. In some embodiments of a compound of Formula (X), n is 2. In some embodiments of a compound of Formula (X), n is 3. In some embodiments of a compound of Formula (X), n is 4. In some embodiments of a compound of Formula (X), n is 1 or 2. In some embodiments of a compound of Formula (X), n is 1-3. In some embodiments of a compound of Formula (X), n is 2 or 3.

In some embodiments of a compound of Formula (X), each alkyl, alkenyl, alkynyl, cycloalkyl, heterocycloalkyl, aryl, and heteroaryl in $R^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (X), $R^4$ is hydrogen, halogen, $C_1$-$C_6$alkyl, or $C_1$-$C_6$haloalkyl. In some embodiments of a compound of Formula (X), $R^4$ is hydrogen. In some embodiments of a compound of Formula (X), $R^4$ is deuterium.

In some embodiments of a compound of Formula (X), each alkyl, alkenyl, alkynyl, cycloalkyl, heterocycloalkyl, aryl, and heteroaryl in $R^5$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (X), $R^5$ is halogen, $C_1$-$C_6$alkyl, or $C_1$-$C_6$haloalkyl. In some embodiments of a compound of Formula (X), $R^5$ is hydrogen or $C_1$-$C_6$alkyl. In some embodiments of a compound of Formula (X), $R^5$ is $C_1$-$C_6$alkyl. In some embodiments of a compound of Formula (X), $R^5$ is hydrogen. In some embodiments of a compound of Formula (X), $R^5$ is deuterium. In some embodiments of a compound of Formula (X), $R^5$ is $C_1$-$C_6$deuteroalkyl.

In some embodiments of a compound of Formula (X), each alkyl, alkenyl, alkynyl, cycloalkyl, heterocycloalkyl, aryl, and heteroaryl in $R^6$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (X), $R^6$ is hydrogen or $C_1$-$C_6$alkyl. In some embodiments of a compound of Formula (X), $R^6$ is hydrogen.

Disclosed herein is a compound of Formula (XI), or a pharmaceutically acceptable salt, solvate, or stereoisomer thereof:

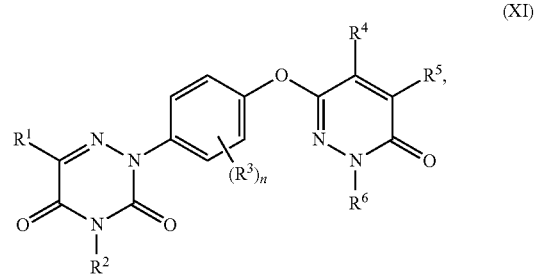

(XI)

wherein:
$R^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$W, —C(=O)R$^a$, —C(=O)OR$^b$, —C(=O)NR$^b$R$^c$, $C_1$-$C_6$alkyl, or $C_1$-$C_6$haloalkyl;

$R^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_r$$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl; provided that at least one of R$^3$ is fluoro;

R$^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

R$^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl;

n is 1-4;

each R$^a$ is independently $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl; and each R$^b$ and R$^c$ are independently hydrogen, deuterium, $C_1$-$C_6$alkyl, $C_1$-$C_6$deuteroalkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, $C_1$-$C_6$alkyl, or $C_1$-$C_6$haloalkyl.

In some embodiments of a compound of Formula (XI), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (XI), R$^1$ is hydrogen or —CN. In some embodiments of a compound of Formula (XI), R$^1$ is —CN. In some embodiments of a compound of Formula (XI), R$^1$ is deuterium.

In some embodiments of a compound of Formula (XI), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (XI), R$^2$ is hydrogen or $C_1$-$C_6$alkyl. In some embodiments of a compound of Formula (XI), R$^2$ is hydrogen.

In some embodiments of a compound of Formula (XI), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (XI), each R$^3$ is independently hydrogen, halogen, $C_1$-$C_6$alkyl, or $C_1$-$C_6$haloalkyl. In some embodiments of a compound of Formula (XI), each R$^3$ is independently hydrogen, halogen, or $C_1$-$C_6$alkyl. In some embodiments of a compound of Formula (XI), each R$^3$ is independently halogen. In some embodiments of a compound of Formula (XI), one of R$^3$ is deuterium.

In some embodiments of a compound of Formula (XI), n is 1. In some embodiments of a compound of Formula (XI), n is 2. In some embodiments of a compound of Formula (XI), n is 3. In some embodiments of a compound of Formula (XI), n is 4. In some embodiments of a compound of Formula (XI), n is 1 or 2. In some embodiments of a compound of Formula (XI), n is 1-3. In some embodiments of a compound of Formula (XI), n is 2 or 3.

In some embodiments of a compound of Formula (XI), each alkyl, alkenyl, alkynyl, cycloalkyl, heterocycloalkyl, aryl, and heteroaryl in R$^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (XI), R$^4$ is hydrogen, halogen, $C_1$-$C_6$alkyl, or $C_1$-$C_6$haloalkyl. In some embodiments of a compound of Formula (XI), R$^4$ is hydrogen. In some embodiments of a compound of Formula (XI), R$^4$ is deuterium.

In some embodiments of a compound of Formula (XI), each alkyl, alkenyl, alkynyl, cycloalkyl, heterocycloalkyl, aryl, and heteroaryl in R$^5$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XI), R$^5$ is halogen, C$_1$-C$_6$alkyl, or C$_1$-C$_6$haloalkyl. In some embodiments of a compound of Formula (XI), R$^5$ is hydrogen or C$_1$-C$_6$alkyl. In some embodiments of a compound of Formula (XI), R$^5$ is C$_1$-C$_6$alkyl. In some embodiments of a compound of Formula (XI), R$^5$ is hydrogen. In some embodiments of a compound of Formula (XI), R$^5$ is deuterium. In some embodiments of a compound of Formula (XI), R$^5$ is C$_1$-C$_6$deuteroalkyl.

In some embodiments of a compound of Formula (XI), each alkyl, alkenyl, alkynyl, cycloalkyl, heterocycloalkyl, aryl, and heteroaryl in R$^6$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XI), R$^6$ is hydrogen or C$_1$-C$_6$alkyl. In some embodiments of a compound of Formula (XI), R$^6$ is hydrogen.

Disclosed herein is a compound of Formula (XII), or a pharmaceutically acceptable salt, solvate, or stereoisomer thereof:

(XII)

wherein:

R$^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, C$_1$-C$_6$alkyl, or C$_1$-C$_6$haloalkyl;

R$^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

each R$^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

X is N or CR$^4$;

R$^4$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, C$_1$-C$_6$alkyl, or C$_1$-C$_6$haloalkyl;

R$^5$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —C(=O)R$^a$, —C(=O)OR$^b$, —C(=O)NR$^b$R$^c$, C$_1$-C$_6$alkyl, or C$_1$-C$_6$haloalkyl;

R$^6$ is hydrogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

R$^7$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

n is 0-4;

each R$^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and each R$^b$ and R$^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or R$^b$ and R$^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (XII), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XII), R$^1$ is hydrogen or —CN. In some embodiments of a compound of Formula (XII), R$^1$ is —CN. In some embodiments of a compound of Formula (XII), R$^1$ is hydrogen or deuterium.

In some embodiments of a compound of Formula (XII), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XII), R$^2$ is hydrogen or C$_1$-C$_6$alkyl. In some embodiments of a compound of Formula (XII), R$^2$ is hydrogen.

In some embodiments of a compound of Formula (XII), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XII), each R$^3$ is independently hydrogen, halogen, C$_1$-C$_6$alkyl, or C$_1$-C$_6$haloalkyl. In some embodiments of a compound of Formula (XII), each R$^3$ is independently halogen. In some embodiments of a compound of Formula (XII), one of R$^3$ is deuterium.

In some embodiments of a compound of Formula (XII), n is 1. In some embodiments of a compound of Formula (XII), n is 2. In some embodiments of a compound of Formula (XII), n is 3. In some embodiments of a compound of Formula (XII), n is 4. In some embodiments of a compound of Formula (XII), n is 1 or 2. In some embodiments of a compound of Formula (XII), n is 1-3. In some embodiments of a compound of Formula (XII), n is 2 or 3.

In some embodiments of a compound of Formula (XII), X is N. In some embodiments of a compound of Formula (XII), X is CR$^4$.

In some embodiments of a compound of Formula (XII), each alkyl, alkenyl, alkynyl, cycloalkyl, heterocycloalkyl, aryl, and heteroaryl in R$^4$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XII), R$^4$ is hydrogen, halogen, C$_1$-C$_6$alkyl, or C$_1$-C$_6$haloalkyl. In some embodiments of a compound of Formula (XII), R$^4$ is hydrogen. In some embodiments of a compound of Formula (XII), R$^4$ is deuterium.

In some embodiments of a compound of Formula (XII), each alkyl, alkenyl, alkynyl, cycloalkyl, heterocycloalkyl, aryl, and heteroaryl in R$^5$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XII), R$^5$ is halogen, C$_1$-C$_6$alkyl, or C$_1$-C$_6$haloalkyl. In some embodiments of a compound of Formula (XII), R$^5$ is hydrogen or C$_1$-C$_6$alkyl. In some embodiments of a compound of Formula (XII), R$^5$ is C$_1$-C$_6$alkyl. In some embodiments of a compound of Formula (XI), R$^5$ is hydrogen. In some embodiments of a compound of Formula (XII), R$^5$ is deuterium. In some embodiments of a compound of Formula (XII), R$^5$ is C$_1$-C$_6$deuteroalkyl.

In some embodiments of a compound of Formula (XII), each alkyl, alkenyl, alkynyl, cycloalkyl, heterocycloalkyl, aryl, and heteroaryl in R$^6$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XII), R$^6$ is hydrogen or C$_1$-C$_6$alkyl. In some embodiments of a compound of Formula (XII), R$^6$ is hydrogen.

In some embodiments of a compound of Formula (XII), R$^7$ is hydrogen, halogen, C$_1$-C$_6$alkyl, or C$_1$-C$_6$haloalkyl. In some embodiments of a compound of Formula (XII), R$^7$ is hydrogen. In some embodiments of a compound of Formula (XII), R$^7$ is deuterium.

Disclosed herein is a compound of Formula (XIII), or a pharmaceutically acceptable salt, solvate, or stereoisomer thereof:

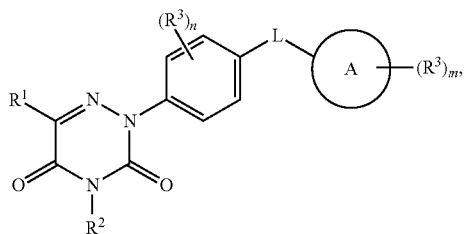

(XIII)

wherein:

Ring A is aryl or heteroaryl;

L is a bond, —O—, —S—, —NH—, or —N(CH$_3$)—;

$R^1$ is hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

$R^2$ is hydrogen, halogen, —CN, —OH, —OR$^a$, —S(=O)R$^a$, —S(=O)$_2$R$^a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;

each $R^{13}$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O) NR$^b$R$^c$, C$_1$-C$_6$alkyl, or C$_1$-C$_6$haloalkyl;

n is 0-4;

m is 0-4 each $R^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and each $R^b$ and $R^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;

or $R^b$ and $R^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

In some embodiments of a compound of Formula (XIII), L is a bond or —O—. In some embodiments of a compound of Formula (XIII), L is a bond. In some embodiments of a compound of Formula (XIII), L is a —O—.

In some embodiments of a compound of Formula (XIII), Ring A is heteroaryl. In some embodiments of a compound of Formula (XIII), Ring A is heteroaryl selected from pyridinyl, pyrimidyl, pyridazinyl, and pyrazinyl. In some embodiments of a compound of Formula (XIII), Ring A is heteroaryl selected from pyrimidyl and pyridazinyl.

In some embodiments of a compound of Formula (XIII), Ring A is a bicyclic heteroaryl. In some embodiments of a compound of Formula (XIII), Ring A is a bicyclic heteroaryl selected from pyrazolopyridazine, imidazopyridazine, triazolopyridazine, tetrazolopyridazine, oxadiazolopyridine, furopyridine, oxazolopyridine, dihydro-imidazopyridazin-3-one, dihydro-pyrrolopyridazin-3-one, dihydro-pyrazolopyridazin-5-one, and dihydro-triazolopyridazin-6-one. In some embodiments of a compound of Formula (XIII), Ring A is a bicyclic heteroaryl selected from pyrazolopyridazine, imidazopyridazine, triazolopyridazine, tetrazolopyridazine, oxadiazolopyridine, furopyridine, and oxazolopyridine. In some embodiments of a compound of Formula (XIII), Ring A is a bicyclic heteroaryl selected from dihydro-imidazopyridazin-3-one, dihydro-pyrrolopyridazin-3-one, dihydro-pyrazolopyridazin-5-one, and dihydro-triazolopyridazin-6-one.

In some embodiments of a compound of Formula (XIII),

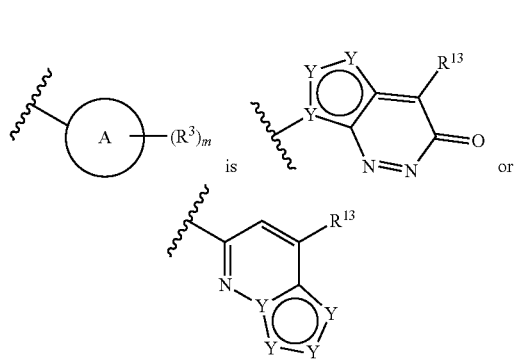

wherein Y is C, CR$^{13}$ or N.

In some embodiments of a compound of Formula (XIII),

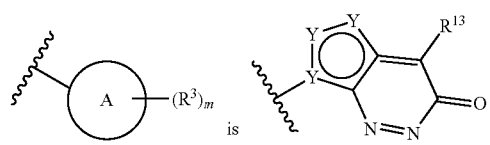

wherein Y is C, CR$^{13}$ or N. In some embodiments of a compound of Formula (XIII),

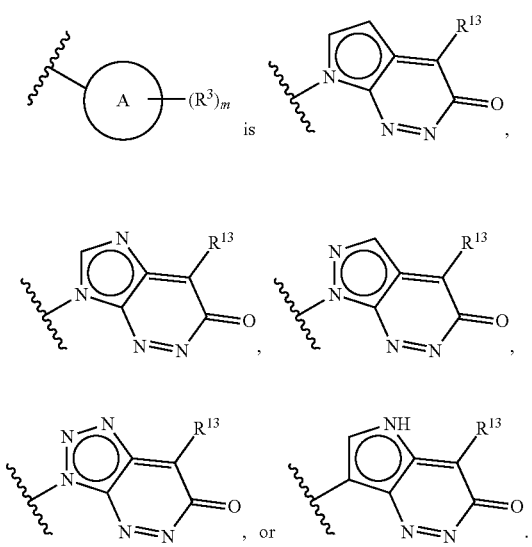

In some embodiments of a compound of Formula (XIII),

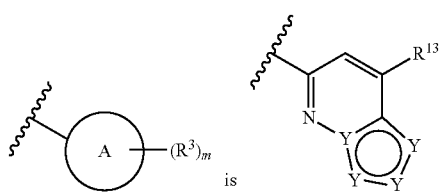

wherein Y is CR$^{13}$ or N. In some embodiments of a compound of Formula (XIII),

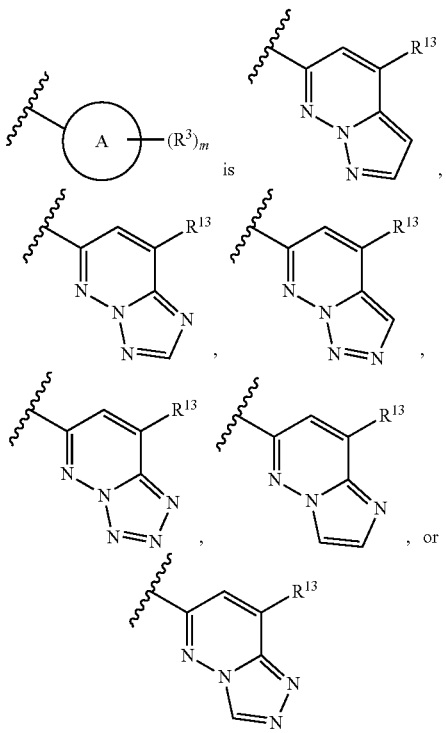

In some embodiments of a compound of Formula (XIII), each alkyl, alkenyl, alkynyl, cycloalkyl, heterocycloalkyl, aryl, and heteroaryl in R$^1$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XIII), R$^1$ is hydrogen or —CN. In some embodiments of a compound of Formula (XIII), R$^1$ is —CN. In some embodiments of a compound of Formula (XIII), R$^1$ is hydrogen or deuterium.

In some embodiments of a compound of Formula (XIII), each alkyl, alkenyl, alkynyl, cycloalkyl, heterocycloalkyl, aryl, and heteroaryl in R$^2$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XIII), R$^2$ is hydrogen or C$_1$-C$_6$alkyl. In some embodiments of a compound of Formula (XIII), R$^2$ is hydrogen.

In some embodiments of a compound of Formula (XIII), each alkyl, alkenyl, alkynyl, cycloalkyl, heterocycloalkyl, aryl, and heteroaryl in R$^3$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl. In some embodiments of a compound of Formula (XIII), each R$^3$ is independently hydrogen, halogen, C$_1$-C$_6$alkyl, or C$_1$-C$_6$haloalkyl. In some embodiments of a compound of Formula (XIII), each R$^3$ is independently halogen. In some embodiments of a compound of Formula (XIII), one of R$^3$ is deuterium.

In some embodiments of a compound of Formula (XIII), n is 1. In some embodiments of a compound of Formula (XIII), n is 2. In some embodiments of a compound of Formula (XIII), n is 3. In some embodiments of a compound of Formula (XIII), n is 4. In some embodiments of a compound of Formula (XIII), n is 1 or 2. In some embodiments of a compound of Formula (XIII), n is 1-3. In some embodiments of a compound of Formula (XIII), n is 2 or 3.

In some embodiments of a compound of Formula (XIII), m is 1. In some embodiments of a compound of Formula (XIII), m is 2. In some embodiments of a compound of Formula (XIII), m is 3. In some embodiments of a compound of Formula (XIII), m is 1 or 2. In some embodiments of a compound of Formula (XIII), m is 1-3. In some embodiments of a compound of Formula (XIII), m is 2 or 3.

In some embodiments of a compound of Formula (XIII), each alkyl, alkenyl, alkynyl, cycloalkyl, heterocycloalkyl, aryl, and heteroaryl in $R^{13}$ is independently optionally substituted with one, two, or three oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl. In some embodiments of a compound of Formula (XIII), each $R^{13}$ is independently hydrogen, halogen, $C_1$-$C_6$alkyl, $C_1$-$C_6$deuterolkyl, or $C_1$-$C_6$haloalkyl. In some embodiments of a compound of Formula (XIII), each $R^{13}$ is independently hydrogen, halogen, $C_1$-$C_6$alkyl, or $C_1$-$C_6$deuteroalkyl. In some embodiments of a compound of Formula (XIII), each $R^{13}$ is independently hydrogen, $C_1$-$C_6$alkyl, or $C_1$-$C_6$deuteroalkyl. In some embodiments of a compound of Formula (XIII), each $R^{13}$ is hydrogen. In some embodiments of a compound of Formula (XIII), each $R^{13}$ is deuterium. In some embodiments of a compound of Formula (XIII), each $R^{13}$ is $C_1$-$C_6$alkyl. In some embodiments of a compound of Formula (XIII), each $R^{13}$ is halogen. In some embodiments of a compound of Formula (XIII), each $R^{13}$ is $C_1$-$C_6$deuteroalkyl.

In some embodiments of a compound of Formula (XIII), $R^{13}$ is hydrogen, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl.

In some embodiments of a compound of Formula (XIII), $R^{11}$ is hydrogen, halogen, —CN, —OH, —OR$^a$, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl.

In some embodiments of a compound of Formula (XIII), $R^{13}$ is hydrogen, halogen, —CN, —OH, —OR$^a$, —NR$^b$R$^c$, $C_1$-$C_6$alkyl, or $C_1$-$C_6$haloalkyl; wherein each alkyl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, or $C_1$-$C_6$haloalkyl.

In some embodiments of a compound described herein, each $R^a$ is independently $C_1$-$C_6$ alkyl, cycloalkyl, or heterocycloalkyl; wherein the alkyl, cycloalkyl, and heterocycloalkyl are independently optionally substituted with one or more halogen, —OH, —NH$_2$, or $C_1$-$C_6$ alkyl. In some embodiments of a compound described herein, each $R^a$ is independently $C_1$-$C_6$ alkyl, cycloalkyl, or heterocycloalkyl; wherein the alkyl, cycloalkyl, and heterocycloalkyl are independently optionally substituted with one or more halogen or $C_1$-$C_6$ alkyl. In some embodiments of a compound described herein, each $R^a$ is independently $C_1$-$C_6$ alkyl, $C_1$-$C_6$ haloalkyl, or cycloalkyl. In some embodiments of a compound described herein, each $R^a$ is independently $C_1$-$C_6$ alkyl, or cycloalkyl. In some embodiments of a compound described herein, each $R^a$ is independently $C_1$-$C_6$ alkyl.

In some embodiments of a compound described herein, each $R^b$ and $R^c$ are independently hydrogen, $C_1$-$C_6$ alkyl, cycloalkyl, or heterocycloalkyl; wherein the alkyl, cycloalkyl, and heterocycloalkyl are independently optionally substituted with one or more halogen, —OH, —NH$_2$, or $C_1$-$C_6$ alkyl. In some embodiments of a compound described herein, each $R^b$ and $R^c$ are independently hydrogen, $C_1$-$C_6$ alkyl, cycloalkyl, or heterocycloalkyl; wherein the alkyl, cycloalkyl, and heterocycloalkyl are independently optionally substituted with one or more halogen or $C_1$-$C_6$ alkyl. In some embodiments of a compound described herein, each $R^b$ and $R^c$ are independently hydrogen, $C_1$-$C_6$ alkyl, $C_1$-$C_6$ haloalkyl, or cycloalkyl. In some embodiments of a compound described herein, each $R^b$ and are independently hydrogen, $C_1$-$C_6$ alkyl, or cycloalkyl. In some embodiments of a compound described herein, each $R^b$ and $R^c$ are independently hydrogen or $C_1$-$C_6$ alkyl.

In some embodiments of a compound described herein, $R^b$ and $R^c$ are taken together with the nitrogen atom to which they are attached to form a heterocycloalkyl optionally substituted with one or more halogen, —OH, —NH$_2$, or $C_1$-$C_6$ alkyl. In some embodiments of a compound described herein, $R^b$ and are taken together with the nitrogen atom to which they are attached to form a heterocycloalkyl optionally substituted with one or more halogen or $C_1$-$C_6$ alkyl.

In some embodiments, the compound is selected from a compound found in Table 1.

TABLE 1

| Ex. | Structure | Name |
|---|---|---|
| 1 | 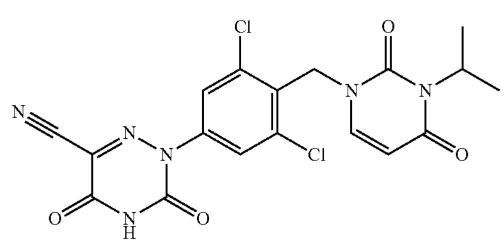 [SMILES: CC(C)n1c(=O)ccn(Cc2c(Cl)cc(-n3nc(C#N)c(=O)[nH]c3=O)cc2Cl)c1=O] | 2-(3,5-dichloro-4-((3-isopropyl-2,4-dioxo-3,4-dihydropyrimidin-1(2H)-yl)methyl)phenyl)-3,5-dioxo-2,3,4,5-tetrahydro-1,2,4-triazine-6-carbonitrile |

TABLE 1-continued

| Ex. | Structure | Name |
|---|---|---|
| 2 | 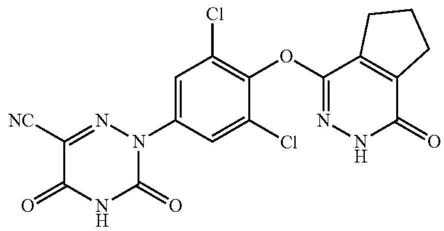 [SMILES: N#Cc1nn(-c2cc(Cl)c(Oc3n[nH]c(=O)c4c3CCC4)c(Cl)c2)c(=O)[nH]c1=O] | 2-(3,5-dichloro-4-((1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |
| 3 | 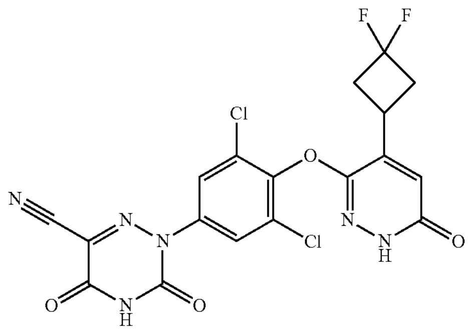 [SMILES: N#Cc1nn(-c2cc(Cl)c(Oc3n[nH]c(=O)cc3C3CC(F)(F)C3)c(Cl)c2)c(=O)[nH]c1=O] | 2-(3,5-dichloro-4-((4-(3,3-difluorocyclobutyl)-6-oxo-1,6-dihydropyridazin-3-yl)oxy)phenyl)-3,5-dioxo-2,3,4,5-tetrahydro-1,2,4-triazine-6-carbonitrile |
| 4 | 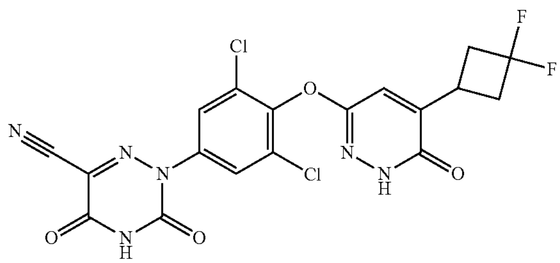 [SMILES: N#Cc1nn(-c2cc(Cl)c(Oc3cc(C4CC(F)(F)C4)c(=O)[nH]n3)c(Cl)c2)c(=O)[nH]c1=O] | 2-(3,5-dichloro-4-((5-(3,3-difluorocyclobutyl)-6-oxo-1,6-dihydropyridazin-3-yl)oxy)phenyl)-3,5-dioxo-2,3,4,5-tetrahydro-1,2,4-triazine-6-carbonitrile |
| 5 | 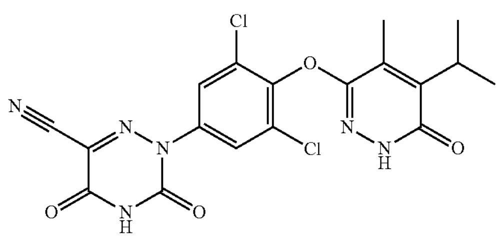 | 2-(3,5-dichloro-4-((5-isopropyl-4-methyl-6-oxo-1,6-dihydropyridazin-3-yl)oxy)phenyl)-3,5-dioxo-2,3,4,5-tetrahydro-1,2,4-triazine-6-carbonitrile |
| 6 | 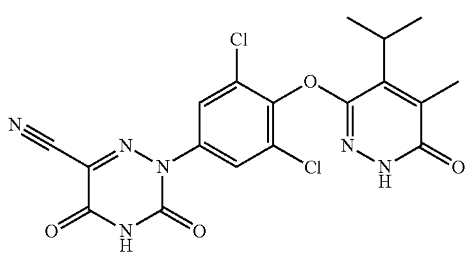 [SMILES: Cc1c(C(C)C)c(Oc2c(Cl)cc(-n3nc(C#N)c(=O)[nH]c3=O)cc2Cl)n[nH]c1=O] | 2-(3,5-dichloro-4-((4-isopropyl-5-methyl-6-oxo-1,6-dihydropyridazin-3-yl)oxy)phenyl)-3,5-dioxo-2,3,4,5-tetrahydro-1,2,4-triazine-6-carbonitrile |
| 7 | 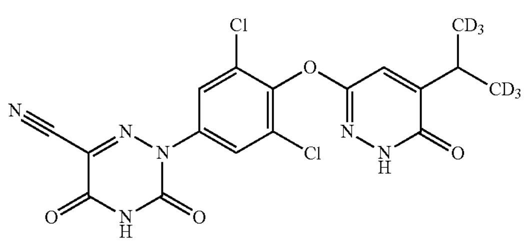 [SMILES: [2H]C([2H])([2H])C(c1cc(Oc2c(Cl)cc(-n3nc(C#N)c(=O)[nH]c3=O)cc2Cl)n[nH]c1=O)C([2H])([2H])[2H]] | 2-(3,5-dichloro-4-((6-oxo-5-(propan-2-yl-1,1,1,3,3,3-d6)-1,6-dihydropyridazin-3-yl)oxy)phenyl)-3,5-dioxo-2,3,4,5-tetrahydro-1,2,4-triazine-6-carbonitrile |

TABLE 1-continued

| Ex. | Structure | Name |
|---|---|---|
| 9 | 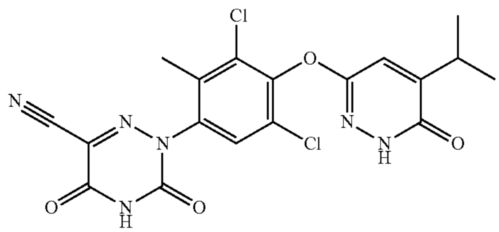 [SMILES: Cc1c(-n2nc(C#N)c(=O)[nH]c2=O)cc(Cl)c(Oc2cc(C(C)C)c(=O)[nH]n2)c1Cl] | 2-(3,5-dichloro-4-((5-isopropyl-6-oxo-1,6-dihydropyridazin-3-yl)oxy)-2-methylphenyl)-3,5-dioxo-2,3,4,5-tetrahydro-1,2,4-triazine-6-carbonitrile |
| 10 | 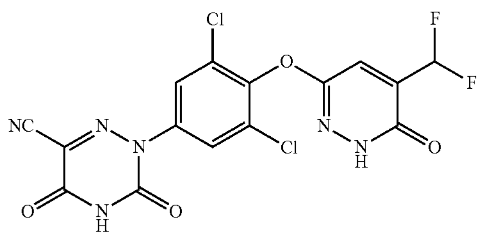 [SMILES: N#Cc1nn(-c2cc(Cl)c(Oc3cc(C(F)F)c(=O)[nH]n3)c(Cl)c2)c(=O)[nH]c1=O] | 2-(3,5-dichloro-4-((5-(difluoromethyl)-6-oxo-1,6-dihydropyridazin-3-yl)oxy)phenyl)-3,5-dioxo-2,3,4,5-tetrahydro-1,2,4-triazine-6-carbonitrile |
| 11 | 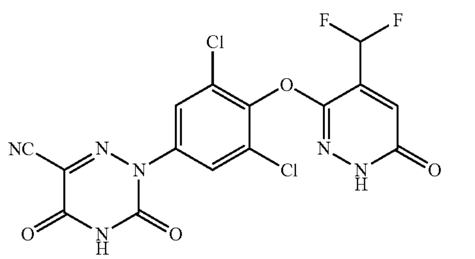 [SMILES: N#Cc1nn(-c2cc(Cl)c(Oc3n[nH]c(=O)cc3C(F)F)c(Cl)c2)c(=O)[nH]c1=O] | 2-(3,5-dichloro-4-((4-(difluoromethyl)-6-oxo-1,6-dihydropyridazin-3-yl)oxy)phenyl)-3,5-dioxo-2,3,4,5-tetrahydro-1,2,4-triazine-6-carbonitrile |
| 12 | 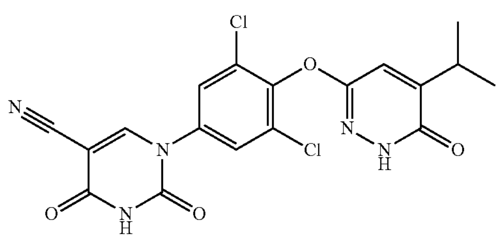 [SMILES: CC(C)c1cc(Oc2c(Cl)cc(-n3cc(C#N)c(=O)[nH]c3=O)cc2Cl)n[nH]c1=O] | 1-(3,5-dichloro-4-((5-isopropyl-6-oxo-1,6-dihydropyridazin-3-yl)oxy)phenyl)-2,4-dioxo-1,2,3,4-tetrahydropyrimidine-5-carbonitrile |
| 13 | 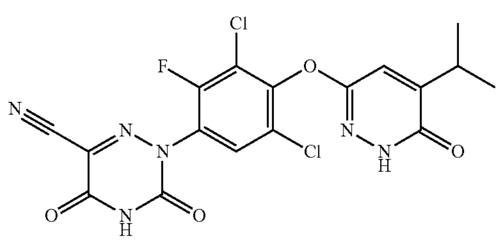 [SMILES: CC(C)c1cc(Oc2c(Cl)cc(-n3nc(C#N)c(=O)[nH]c3=O)c(F)c2Cl)n[nH]c1=O] | 2-(3,5-dichloro-2-fluoro-4-((5-isopropyl-6-oxo-1,6-dihydropyridazin-3-yl)oxy)phenyl)-3,5-dioxo-2,3,4,5-tetrahydro-1,2,4-triazine-6-carbonitrile |
| 15 | 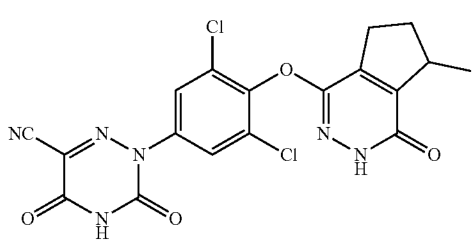 [SMILES: CC1CCc2c(Oc3c(Cl)cc(-n4nc(C#N)c(=O)[nH]c4=O)cc3Cl)n[nH]c(=O)c21] | 2-(3,5-dichloro-4-((7-methyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |

TABLE 1-continued

| Ex. | Structure | Name |
|---|---|---|
| 16 | 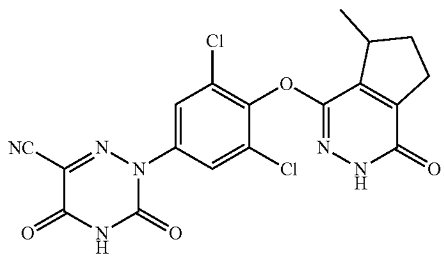 [SMILES: CC1CCc2c1c(Oc1c(Cl)cc(-n3nc(C#N)c(=O)[nH]c3=O)cc1Cl)n[nH]c2=O] | 2-(3,5-dichloro-4-((5-methyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |
| 17 | 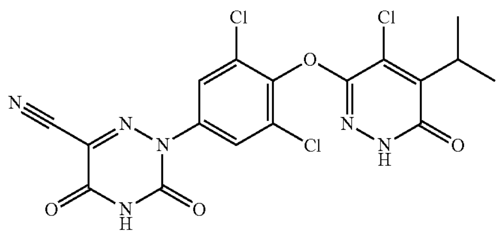 | 2-(3,5-dichloro-4-((4-chloro-5-isopropyl-6-oxo-1,6-dihydropyridazin-3-yl)oxy)phenyl)-3,5-dioxo-2,3,4,5-tetrahydro-1,2,4-triazine-6-carbonitrile |
| 19 | 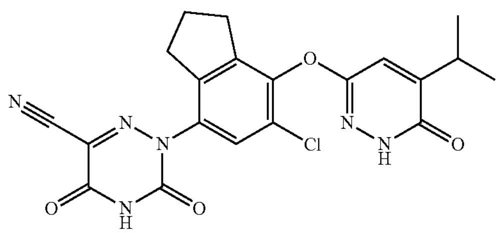 [SMILES: CC(C)c1cc(Oc2c(Cl)cc(-n3nc(C#N)c(=O)[nH]c3=O)c3c2CCC3)n[nH]c1=O] | 2-(6-chloro-7-((5-isopropyl-6-oxo-1,6-dihydropyridazin-3-yl)oxy)-2,3-dihydro-1H-inden-4-yl)-3,5-dioxo-2,3,4,5-tetrahydro-1,2,4-triazine-6-carbonitrile |
| 20 | 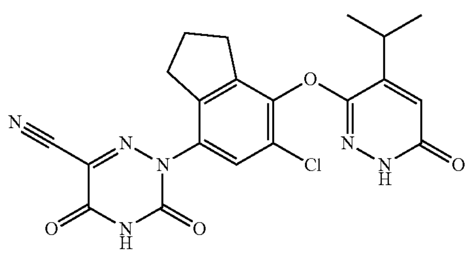 [SMILES: CC(C)c1cc(=O)[nH]nc1Oc1c(Cl)cc(-n2nc(C#N)c(=O)[nH]c2=O)c2c1CCC2] | 2-(6-chloro-7-((4-isopropyl-6-oxo-1,6-dihydropyridazin-3-yl)oxy)-2,3-dihydro-1H-inden-4-yl)-3,5-dioxo-2,3,4,5-tetrahydro-1,2,4-triazine-6-carbonitrile |
| 22 | 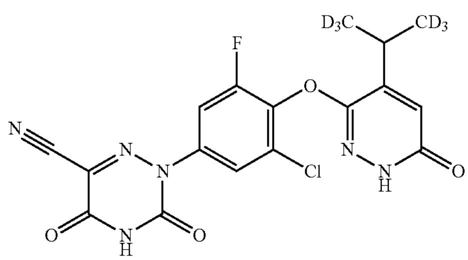 [SMILES: [2H]C([2H])([2H])C(c1cc(=O)[nH]nc1Oc1c(F)cc(-n2nc(C#N)c(=O)[nH]c2=O)cc1Cl)C([2H])([2H])[2H]] | 2-(3-chloro-5-fluoro-4-((6-oxo-4-(propan-2-yl-1,1,1,3,3,3-d6)-1,6-dihydropyridazin-3-yl)oxy)phenyl)-3,5-dioxo-2,3,4,5-tetrahydro-1,2,4-triazine-6-carbonitrile |
| 23 | 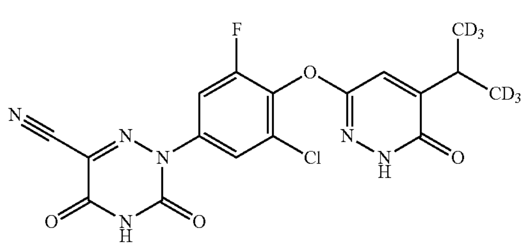 [SMILES: [2H]C([2H])([2H])C(c1cc(Oc2c(F)cc(-n3nc(C#N)c(=O)[nH]c3=O)cc2Cl)n[nH]c1=O)C([2H])([2H])[2H]] | 2-(3-chloro-5-fluoro-4-((6-oxo-5-(propan-2-yl-1,1,1,3,3,3-d6)-1,6-dihydropyridazin-3-yl)oxy)phenyl)-3,5-dioxo-2,3,4,5-tetrahydro-1,2,4-triazine-6-carbonitrile |

TABLE 1-continued

| Ex. | Structure | Name |
|---|---|---|
| 24 | 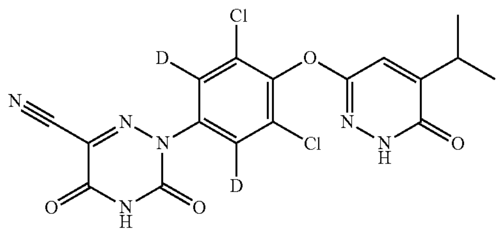 [SMILES: [2H]c1c(Cl)c(Oc2cc(C(C)C)c(=O)[nH]n2)c(Cl)c([2H])c1-n1nc(C#N)c(=O)[nH]c1=O] | 2-(3,5-dichloro-4-((5-isopropyl-6-oxo-1,6-dihydropyridazin-3-yl)oxy)phenyl-2,6-d2)-3,5-dioxo-2,3,4,5-tetrahydro-1,2,4-triazine-6-carbonitrile |
| 25 | 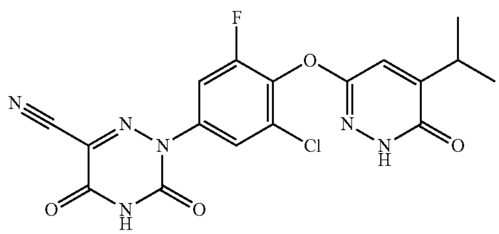 [SMILES: CC(C)c1cc(Oc2c(F)cc(-n3nc(C#N)c(=O)[nH]c3=O)cc2Cl)n[nH]c1=O] | 2-(3-chloro-5-fluoro-4-((5-isopropyl-6-oxo-1,6-dihydropyridazin-3-yl)oxy)phenyl)-3,5-dioxo-2,3,4,5-tetrahydro-1,2,4-triazine-6-carbonitrile |
| 26 | 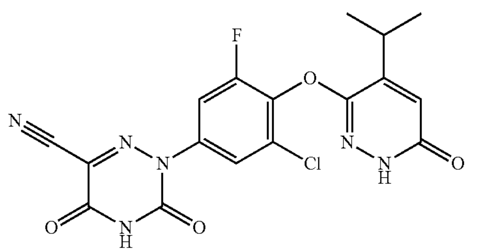 [SMILES: CC(C)c1cc(=O)[nH]nc1Oc1c(F)cc(-n2nc(C#N)c(=O)[nH]c2=O)cc1Cl] | 2-(3-chloro-5-fluoro-4-((4-isopropyl-6-oxo-1,6-dihydropyridazin-3-yl)oxy)phenyl)-3,5-dioxo-2,3,4,5-tetrahydro-1,2,4-triazine-6-carbonitrile |
| 27 | 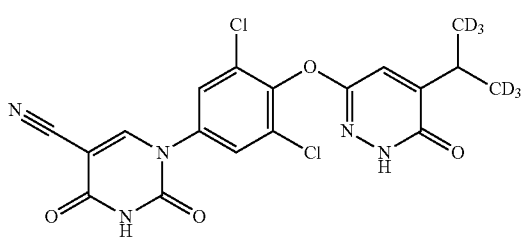 [SMILES: [2H]C([2H])([2H])C(c1cc(Oc2c(Cl)cc(-n3cc(C#N)c(=O)[nH]c3=O)cc2Cl)n[nH]c1=O)C([2H])([2H])[2H]] | 1-(3,5-dichloro-4-((6-oxo-5-(propan-2-yl-1,1,1,3,3,3-d6)-1,6-dihydropyridazin-3-yl)oxy)phenyl)-2,4-dioxo-1,2,3,4-tetrahydropyrimidine-5-carbonitrile |
| 28 | 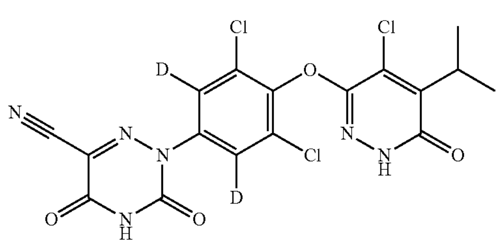 [SMILES: [2H]c1c(Cl)c(Oc2n[nH]c(=O)c(C(C)C)c2Cl)c(Cl)c([2H])c1-n1nc(C#N)c(=O)[nH]c1=O] | 2-(3,5-dichloro-4-((4-chloro-5-isopropyl-6-oxo-1,6-dihydropyridazin-3-yl)oxy)phenyl-2,6-d2)-3,5-dioxo-2,3,4,5-tetrahydro-1,2,4-triazine-6-carbonitrile |
| 29 | 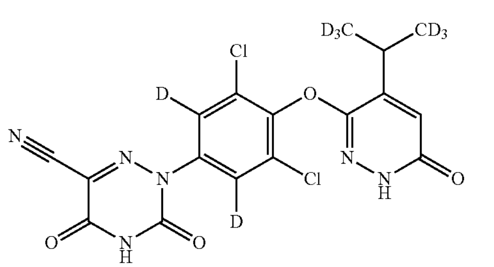 [SMILES: [2H]c1c(Cl)c(Oc2n[nH]c(=O)cc2C(C([2H])([2H])[2H])C([2H])([2H])[2H])c(Cl)c([2H])c1-n1nc(C#N)c(=O)[nH]c1=O] | 2-(3,5-dichloro-4-((6-oxo-4-(propan-2-yl-1,1,1,3,3,3-d6)-1,6-dihydropyridazin-3-yl)oxy)phenyl-2,6-d2)-3,5-dioxo-2,3,4,5-tetrahydro-1,2,4-triazine-6-carbonitrile |

TABLE 1-continued

| Ex. | Structure | Name |
|---|---|---|
| 30 | 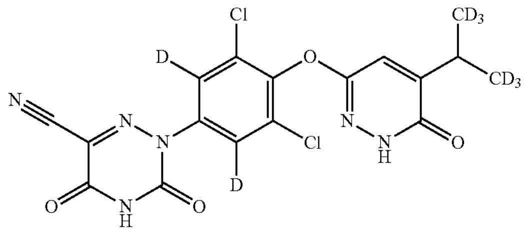 [SMILES: [2H]c1c(Cl)c(Oc2cc(C(C([2H])([2H])[2H])C([2H])([2H])[2H])c(=O)[nH]n2)c(Cl)c([2H])c1-n1nc(C#N)c(=O)[nH]c1=O] | 2-(3,5-dichloro-4-((6-oxo-5-(propan-2-yl-1,1,1,3,3,3-d6)-1,6-dihydropyridazin-3-yl)oxy)phenyl-2,6-d2)-3,5-dioxo-2,3,4,5-tetrahydro-1,2,4-triazine-6-carbonitrile |
| 31 | 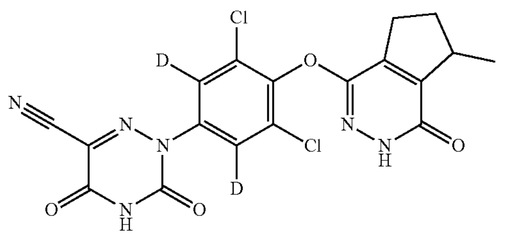 [SMILES: [2H]c1c(Cl)c(Oc2n[nH]c(=O)c3c2CCC3C)c(Cl)c([2H])c1-n1nc(C#N)c(=O)[nH]c1=O] | 2-(3,5-dichloro-4-((7-methyl-1-oxo-2,5,6,7-tetrahydro-1H-cyclopenta[d]pyridazin-4-yl)oxy)phenyl-2,6-d2)-3,5-dioxo-2,3,4,5-tetrahydro-1,2,4-triazine-6-carbonitrile |
| 32 | 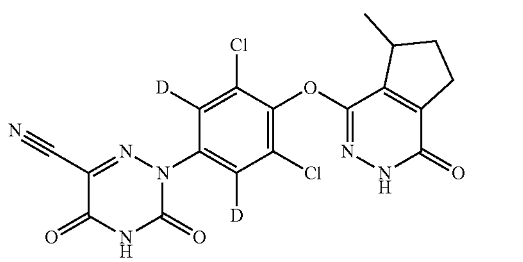 [SMILES: [2H]c1c(Cl)c(Oc2n[nH]c(=O)c3c2C(C)CC3)c(Cl)c([2H])c1-n1nc(C#N)c(=O)[nH]c1=O] | 2-(3,5-dichloro-4-((5-methyl-1-oxo-2,5,6,7-tetrahydro-1H-cyclopenta[d]pyridazin-4-yl)oxy)phenyl-2,6-d2)-3,5-dioxo-2,3,4,5-tetrahydro-1,2,4-triazine-6-carbonitrile |
| 34 | 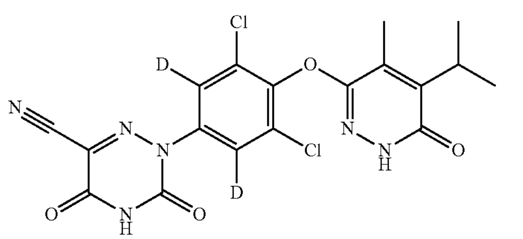 [SMILES: [2H]c1c(Cl)c(Oc2n[nH]c(=O)c(C(C)C)c2C)c(Cl)c([2H])c1-n1nc(C#N)c(=O)[nH]c1=O] | 2-(3,5-dichloro-4-((5-isopropyl-4-methyl-6-oxo-1,6-dihydropyridazin-3-yl)oxy)phenyl-2,6-d2)-3,5-dioxo-2,3,4,5-tetrahydro-1,2,4-triazine-6-carbonitrile |
| 35 | 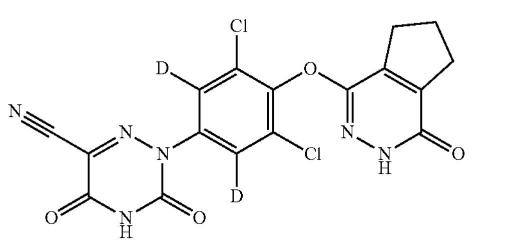 [SMILES: [2H]c1c(Cl)c(Oc2n[nH]c(=O)c3c2CCC3)c(Cl)c([2H])c1-n1nc(C#N)c(=O)[nH]c1=O] | 2-(3,5-dichloro-4-((1-oxo-2,5,6,7-tetrahydro-1H-cyclopenta[d]pyridazin-4-yl)oxy)phenyl-2,6-d2)-3,5-dioxo-2,3,4,5-tetrahydro-1,2,4-triazine-6-carbonitrile |
| 38 | 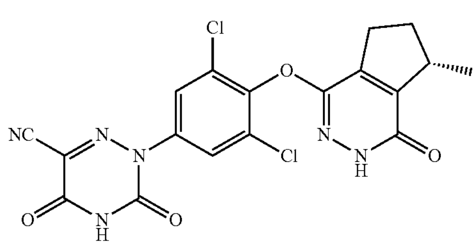 [SMILES: C[C@H]1CCc2c(Oc3c(Cl)cc(-n4nc(C#N)c(=O)[nH]c4=O)cc3Cl)n[nH]c(=O)c21] | (S)-2-(3,5-dichloro-4-((7-methyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |

TABLE 1-continued

| Ex. | Structure | Name |
|---|---|---|
| 41 | 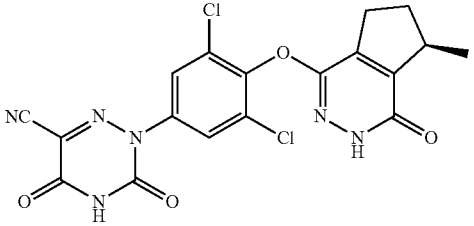 [SMILES: C[C@@H]1CCc2c(Oc3c(Cl)cc(-n4nc(C#N)c(=O)[nH]c4=O)cc3Cl)n[nH]c(=O)c21] | (R)-2-(3,5-dichloro-4-((7-methyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |
| 42 | 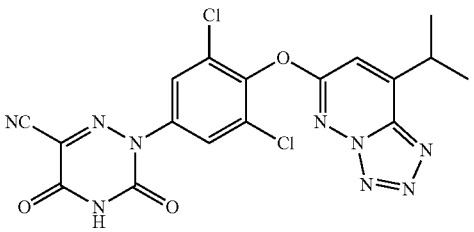 [SMILES: CC(C)c1cc(Oc2c(Cl)cc(-n3nc(C#N)c(=O)[nH]c3=O)cc2Cl)nn2nnnc12] | 2-(3,5-dichloro-4-((8-isopropyltetrazolo[1,5-b]pyridazin-6-yl)oxy)phenyl)-3,5-dioxo-2,3,4,5-tetrahydro-1,2,4-triazine-6-carbonitrile |
| 43 | 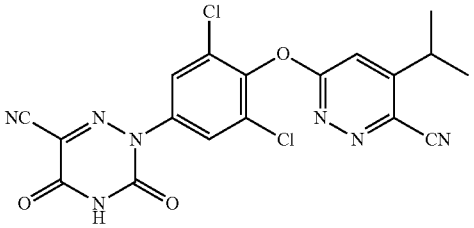 [SMILES: CC(C)c1cc(Oc2c(Cl)cc(-n3nc(C#N)c(=O)[nH]c3=O)cc2Cl)nnc1C#N] | 2-(3,5-dichloro-4-((6-cyano-5-isopropylpyridazin-3-yl)oxy)phenyl)-3,5-dioxo-2,3,4,5-tetrahydro-1,2,4-triazine-6-carbonitrile |
| 44 | 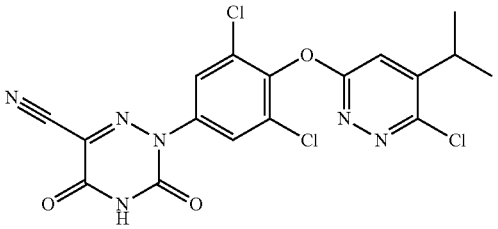 [SMILES: CC(C)c1cc(Oc2c(Cl)cc(-n3nc(C#N)c(=O)[nH]c3=O)cc2Cl)nnc1Cl] | 2-(3,5-dichloro-4-((6-chloro-5-isopropylpyridazin-3-yl)oxy)phenyl)-3,5-dioxo-2,3,4,5-tetrahydro-1,2,4-triazine-6-carbonitrile |
| 47 | 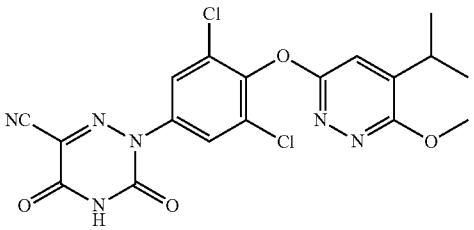 [SMILES: COc1nnc(Oc2c(Cl)cc(-n3nc(C#N)c(=O)[nH]c3=O)cc2Cl)cc1C(C)C] | 2-(3,5-dichloro-4-((5-isopropyl-6-methoxypyridazin-3-yl)oxy)phenyl)-3,5-dioxo-2,3,4,5-tetrahydro-1,2,4-triazine-6-carbonitrile |
| 48 | 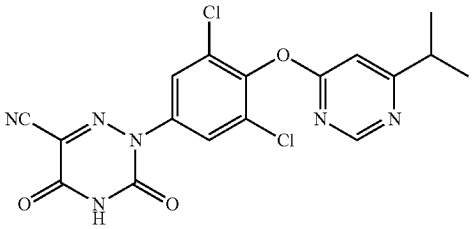 [SMILES: CC(C)c1cc(Oc2c(Cl)cc(-n3nc(C#N)c(=O)[nH]c3=O)cc2Cl)ncn1] | 2-(3,5-dichloro-4-((6-isopropylpyrimidin-4-yl)oxy)phenyl)-3,5-dioxo-2,3,4,5-tetrahydro-1,2,4-triazine-6-carbonitrile |

TABLE 1-continued

| Ex. | Structure | Name |
|---|---|---|
| 50 | 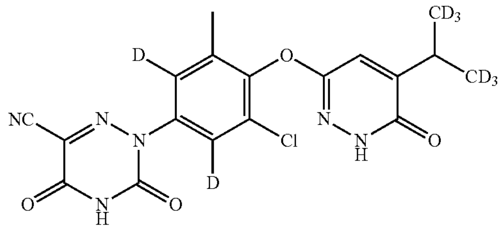 [SMILES: [2H]c1c(C)c(Oc2cc(C(C([2H])([2H])[2H])C([2H])([2H])[2H])c(=O)[nH]n2)c(Cl)c([2H])c1-n1nc(C#N)c(=O)[nH]c1=O] | 2-(3-chloro-5-methyl-4-((6-oxo-5-(propan-2-yl-1,1,1,3,3,3-d6)-1,6-dihydropyridazin-3-yl)oxy)phenyl-2,6-d2)-3,5-dioxo-2,3,4,5-tetrahydro-1,2,4-triazine-6-carbonitrile |
| 51 | 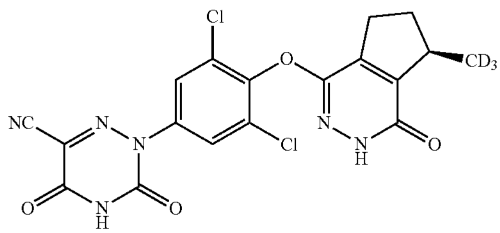 [SMILES: [2H]C([2H])([2H])[C@@H]1CCc2c(Oc3c(Cl)cc(-n4nc(C#N)c(=O)[nH]c4=O)cc3Cl)n[nH]c(=O)c21] | (R)-2-(3,5-dichloro-4-((7-(methyl-d3)-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |
| 52 | 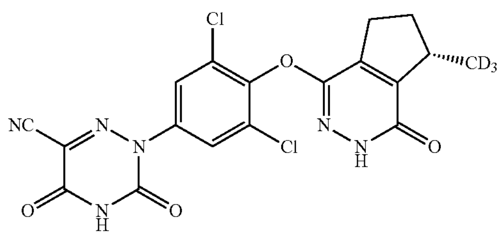 [SMILES: [2H]C([2H])([2H])[C@H]1CCc2c(Oc3c(Cl)cc(-n4nc(C#N)c(=O)[nH]c4=O)cc3Cl)n[nH]c(=O)c21] | (S)-2-(3,5-dichloro-4-((7-(methyl-d3)-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |
| 53 | 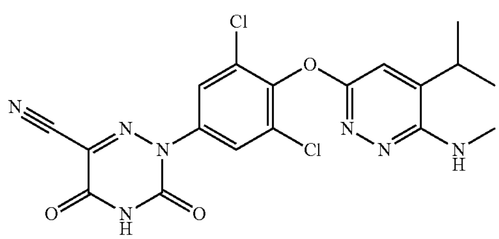 [SMILES: CNc1nnc(Oc2c(Cl)cc(-n3nc(C#N)c(=O)[nH]c3=O)cc2Cl)cc1C(C)C] | 2-(3,5-dichloro-4-((5-isopropyl-6-(methylamino)pyridazin-3-yl)oxy)phenyl)-3,5-dioxo-2,3,4,5-tetrahydro-1,2,4-triazine-6-carbonitrile |
| 56 | 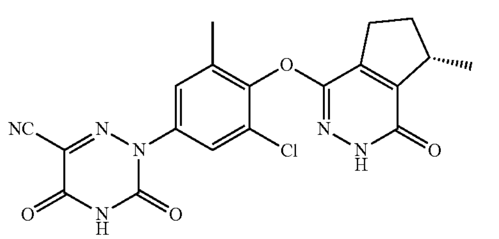 [SMILES: Cc1cc(-n2nc(C#N)c(=O)[nH]c2=O)cc(Cl)c1Oc1n[nH]c(=O)c2c1CC[C@@H]2C] | (S)-2-(3-chloro-5-methyl-4-((7-methyl-1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |
| 57 | 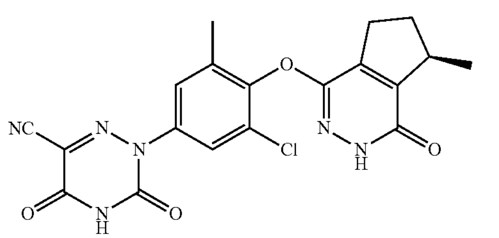 [SMILES: Cc1cc(-n2nc(C#N)c(=O)[nH]c2=O)cc(Cl)c1Oc1n[nH]c(=O)c2c1CC[C@H]2C] | (R)-2-(3-chloro-5-methyl-4-((7-methyl-1-oxo-2,5 1-oxo-2,5,6,7-tetrahydro-1H-cyclopenta[d]pyridazin-4-yl)oxy)phenyl)-3,5-dioxo-2,3,4,5-tetrahydro-1,2,4-triazine-6-carbonitrile |

TABLE 1-continued
| Ex. | Structure | Name |
|---|---|---|
| 58 | 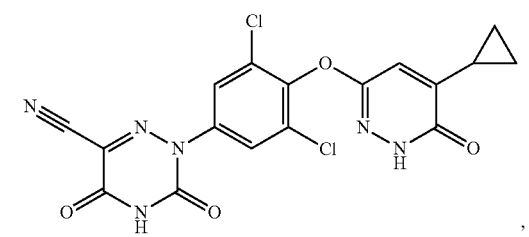 | 2-(3,5-dichloro-4-((6-oxo-5-(propan-2-yl-1,1,1,3,3,3-d6)-1,6-dihydropyridazin-3-yl)methyl)phenyl)-3,5-dioxo-2,3,4,5-tetrahydro-1,2,4-triazine-6-carbonitrile |
| 59 | 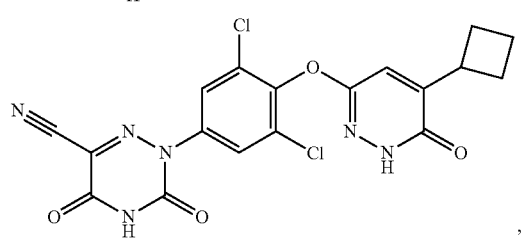 | 6-acetyl-2-(3,5-dichloro-4-((5-isopropyl-6-oxo-1,6-dihydropyridazin-3-yl)oxy)phenyl)-1,2,4-triazine-3,5(2H,4H)-dione |
In some embodiments of a compound of Formula (I)-(XIII), the compound is
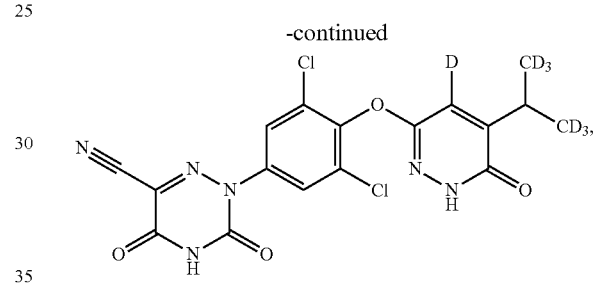
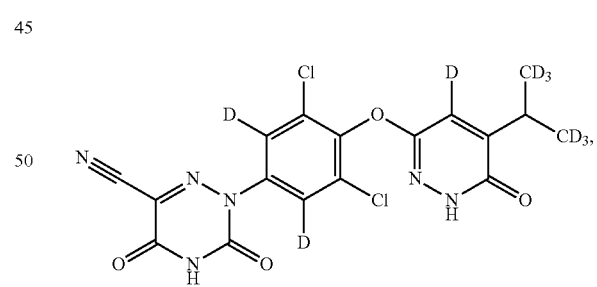
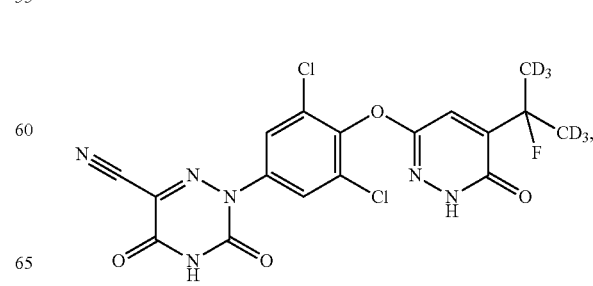

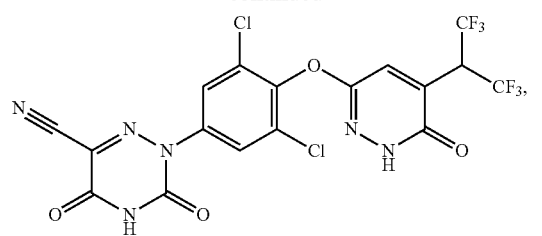
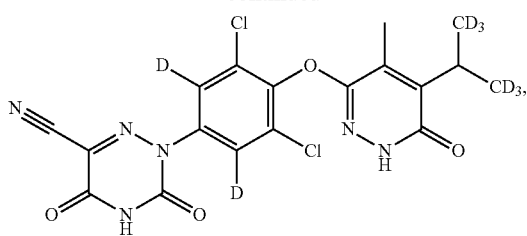
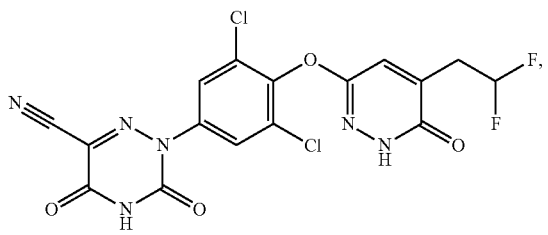
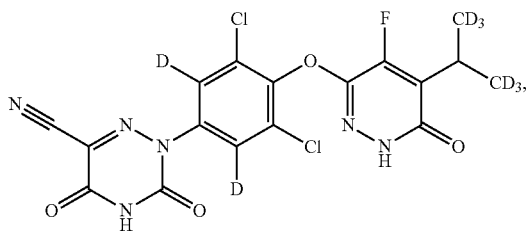
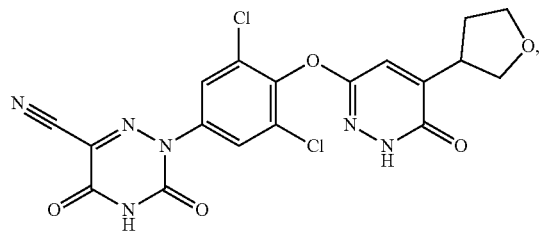
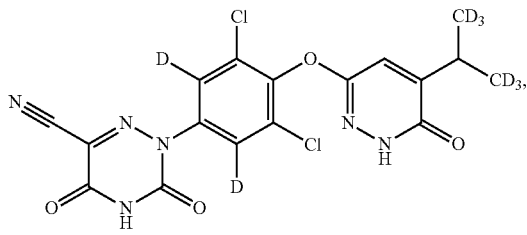
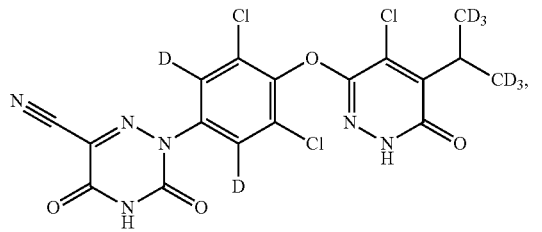
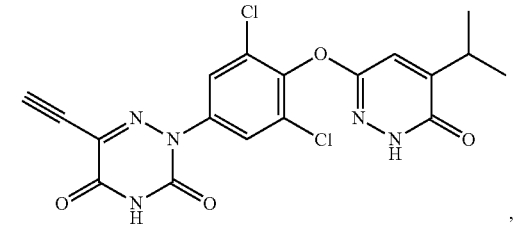
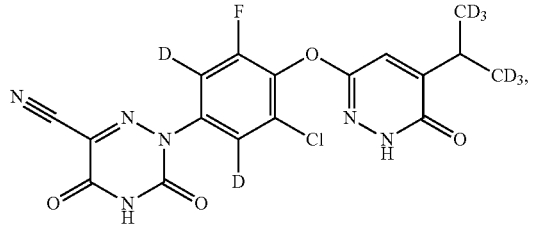
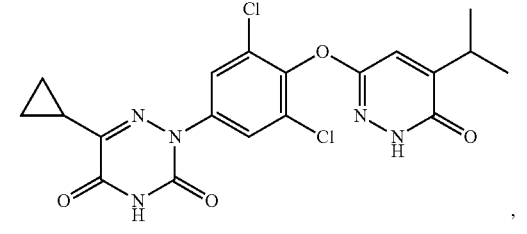
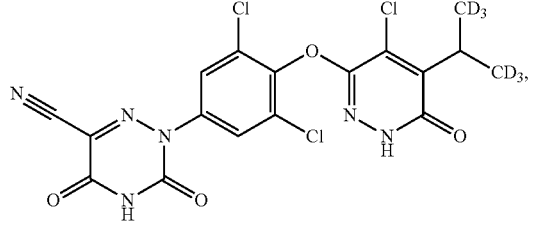
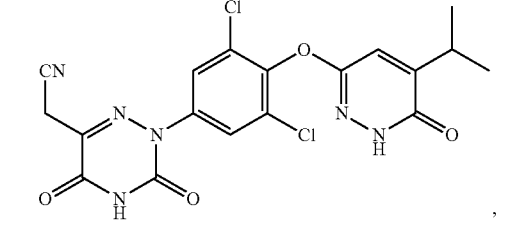
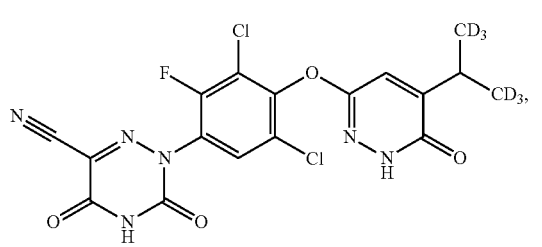
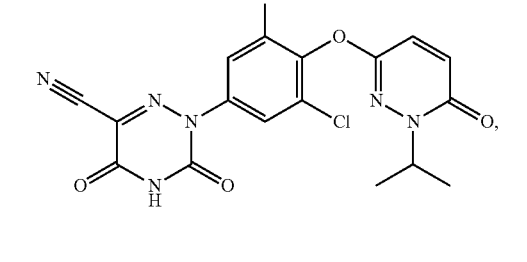

83
-continued
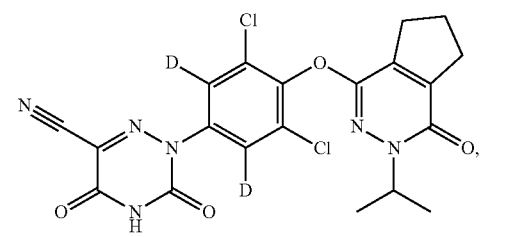
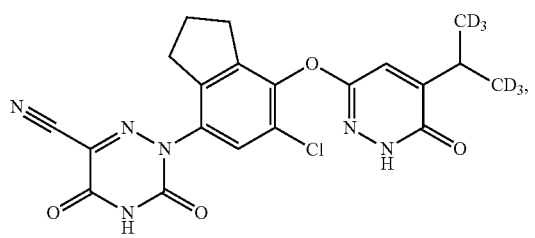
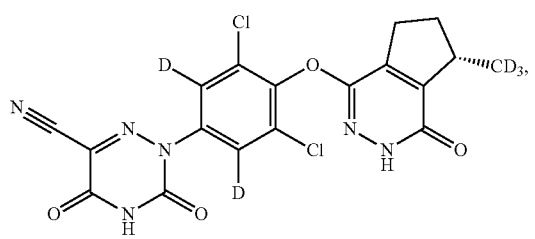
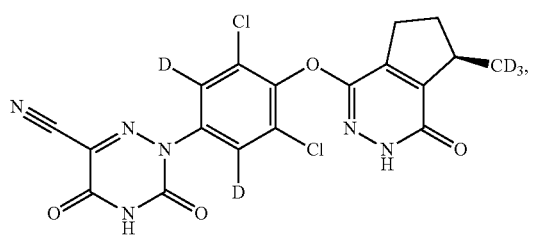
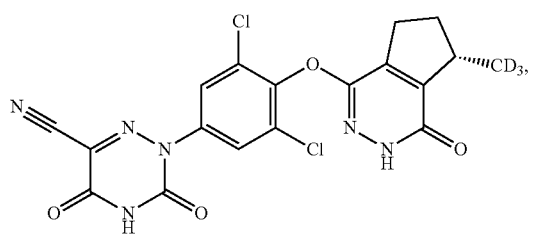
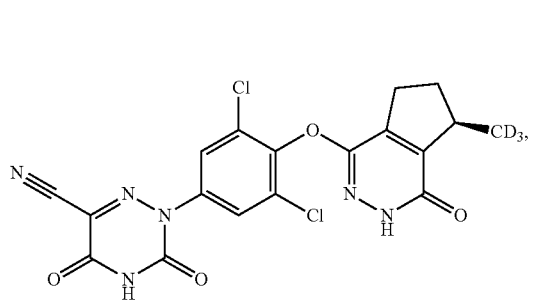
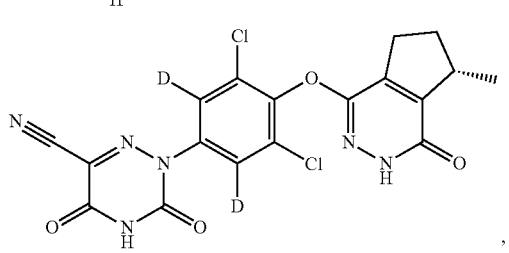
84
-continued
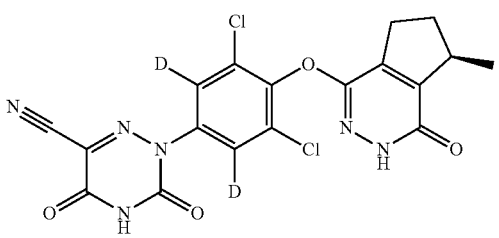
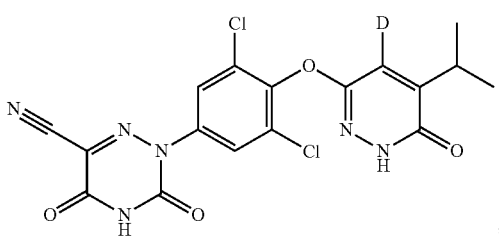
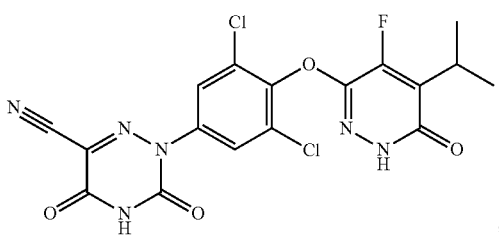
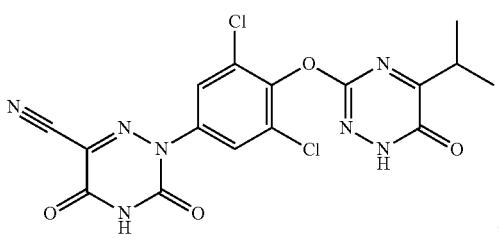
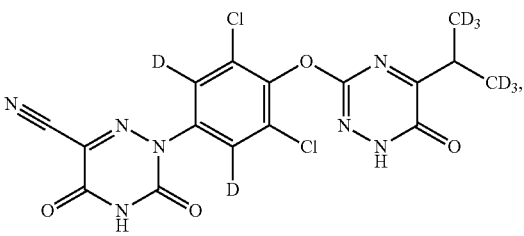
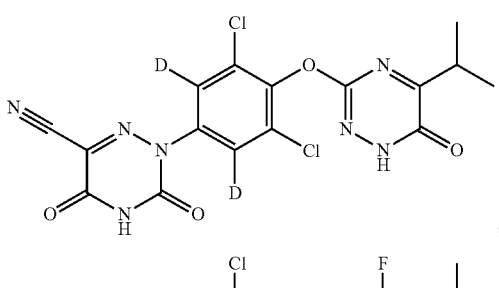
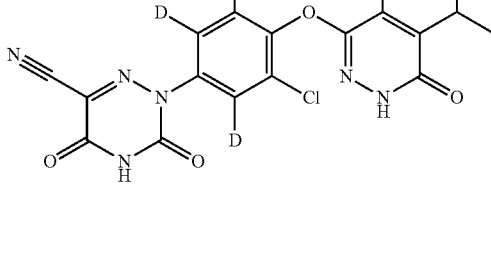

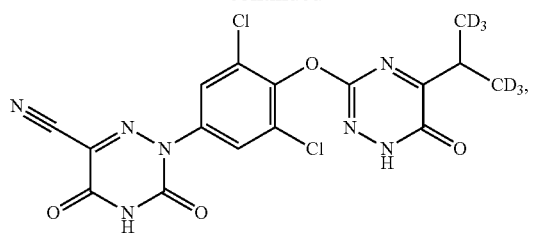
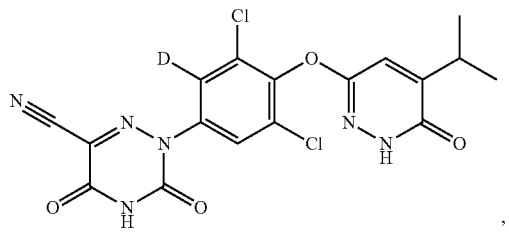
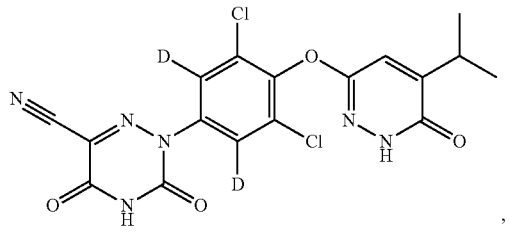
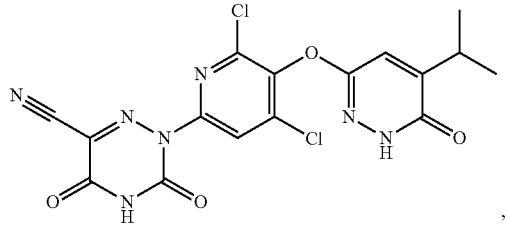
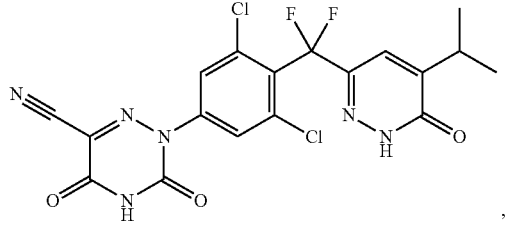
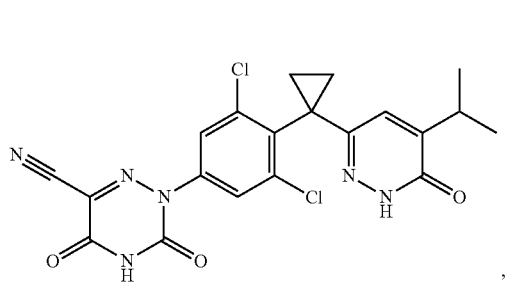
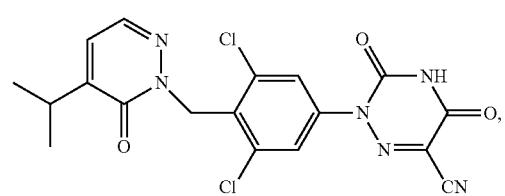
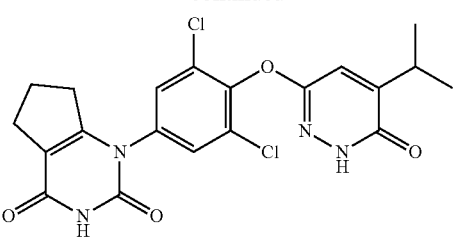
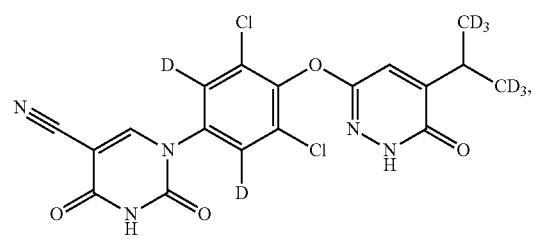
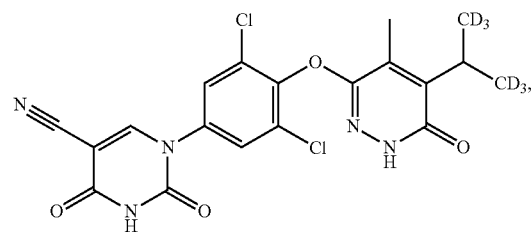
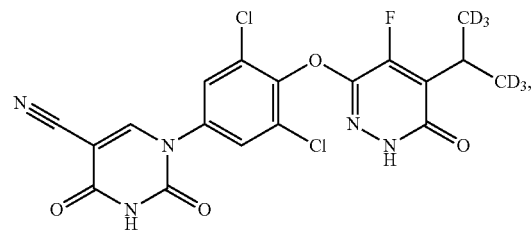
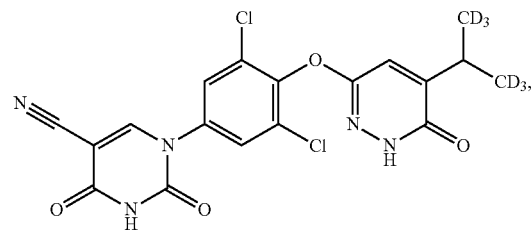
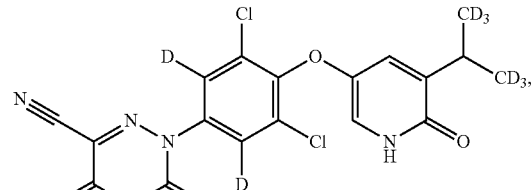
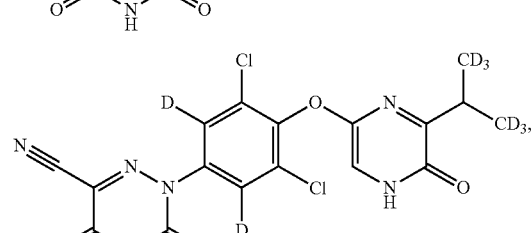

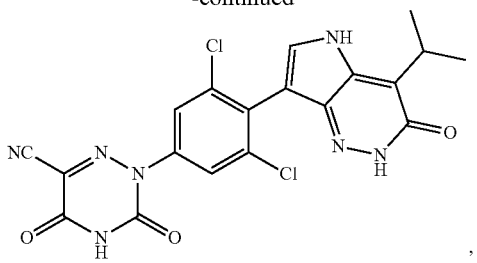

, or a pharmaceutically acceptable salt, solvate, or stereoisomer thereof.

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers, as well as, the corresponding mixtures thereof. In some situations, the compounds described herein possess one or more chiral centers and each center exists in the R configuration, or S configuration. The compounds described herein include all diastereomeric, enantiomeric, and epimeric forms, as well, as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein, or a solvate, or stereoisomer thereof, include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates, or derivatives thereof which contain the aforementioned isotopes and/or other isotopes of other atoms are within the scope of this invention. Certain isotopically-labeled compounds, for example, those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compound or a pharmaceutically acceptable salt, solvate, or stereoisomer thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefor react with any of a number of inorganic or organic bases, and inorganic and organic acids, to form a pharmaceutically acceptable salt. In some embodiments, these salts are prepared in situ during the final isolation and purification of the compounds disclosed herein, or by separately reacting a purified compound in its free form with a suitable acid or base, and isolating the salt thus formed.

Examples of pharmaceutically acceptable salts include those salts prepared by reaction of the compounds described herein with a mineral, organic acid, or inorganic base, such salts including acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\ alkyl)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. In addition, the compounds provided herein can exist in unsolvated, as well as, solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line. Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Pharmaceutical Compositions

In certain embodiments, the compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, PA (2005)).

Accordingly, provided herein is a pharmaceutical composition comprising a compound described herein, or a pharmaceutically acceptable salt, solvate, tautomer, or stereoisomer thereof, and a pharmaceutically acceptable excipient.

In certain embodiments, the compound provided herein is substantially pure, in that it contains less than about 5%, or less than about 1%, or less than about 0.1%, of other organic small molecules, such as unreacted intermediates or synthesis by-products that are created, for example, in one or more of the steps of a synthesis method.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In some embodiments, the pharmaceutical composition is formulated for oral, topical (including buccal and sublingual), rectal, vaginal, transdermal, parenteral, intrapulmonary, intradermal, intrathecal and epidural, and intranasal administration. Parenteral administration includes intramuscular, intravenous, intra-arterial, intraperitoneal, or subcutaneous administration. In some embodiments, the pharmaceutical composition is formulated for intravenous injection, oral administration, inhalation, nasal administration, topical administration, or ophthalmic administration. In some embodiments, the pharmaceutical composition is formulated for oral administration. In some embodiments, the pharmaceutical composition is formulated for intravenous injection. In some embodiments, the pharmaceutical composition is formulated as a tablet, a pill, a capsule, a liquid, an inhalant, a nasal spray solution, a suppository, a suspension, a gel, a colloid, a dispersion, a suspension, a solution, an emulsion, an ointment, a lotion, eye drop, or an ear drop. In some embodiments, the pharmaceutical composition is formulated as a tablet.

Suitable doses and dosage regimens are determined by conventional range-finding techniques known to those of ordinary skill in the art. Generally, treatment is initiated with smaller dosages that are less than the optimum dose of the compound disclosed herein. Thereafter, the dosage is increased by small increments until the optimum effect under the circumstances is reached. In some embodiments, the present method involve the administration of about 0.1 μg to about 50 mg of at least one compound of the invention per kg body weight of the subject. For a 70 kg patient, dosages of from about 10 μg to about 200 mg of the compound disclosed herein would be more commonly used, depending on a subject's physiological response.

By way of example only, the dose of the compound described herein for methods of treating a disease as described herein is about 0.001 to about 1 mg/kg body weight of the subject per day, for example, about 0.001 mg, about 0.002 mg, about 0.005 mg, about 0.010 mg, 0.015 mg, about 0.020 mg, about 0.025 mg, about 0.050 mg, about 0.075 mg, about 0.1 mg, about 0.15 mg, about 0.2 mg, about 0.25 mg, about 0.5 mg, about 0.75 mg, or about 1 mg/kg body weight per day. In some embodiments, the dose of compound described herein for the described methods is about 1 to about 1000 mg/kg body weight of the subject being treated per day, for example, about 1 mg, about 2 mg, about 5 mg, about 10 mg, about 15 mg, about 20 mg, about 25 mg, about 50 mg, about 75 mg, about 100 mg, about 150 mg, about 200 mg, about 250 mg, about 500 mg, about 750 mg, or about 1000 mg per day.

Methods of Treatment

The compounds disclosed herein, or a pharmaceutically acceptable salt, solvate, or stereoisomer thereof, are useful as thyroid hormone receptor agonists, therefore, useful in the treatment of diseases or disorders in which it is believed thyroid hormone receptor activity plays a role.

Disclosed herein are methods of treating a thyroid hormone receptor associated disease or disorder in a subject in need thereof comprising the step of administering to the subject an effective amount of a compound disclosed herein, or a pharmaceutically acceptable salt, solvate, or stereoisomer thereof.

The thyroid hormone receptor associated disease or disorder is, for example, a metabolic disease. In some embodiments, the metabolic disease is obesity, hyperlipidemia, hypercholesterolemia, diabetes, nonalcoholic steatohepatitis (NASH), atherosclerosis, a cardiovascular disease, hypothyroidism, or thyroid cancer.

In some embodiments, the compounds described herein are used to treat or prevent atherosclerosis, coronary heart disease, or heart failure because such compounds are expected to distribute to the liver and modulate the expression and production of atherogenic proteins.

Some embodiments relate to a method for the treatment of a disease associated with thyroid hormone receptor beta, comprising administering an effective amount of the compound described herein to a subject in need thereof.

In some embodiments, the disease is selected from the group consisting of obesity, hyperlipidemia, hypercholesterolemia and diabetes, and NASH (nonalcoholic steatohepatitis), atherosclerosis, cardiovascular diseases, hypothyroidism, and thyroid cancer.

Some embodiments relate to a method of agonizing thyroid hormone receptor beta, comprising contacting the thyroid hormone receptor beta with an effective amount of the compound described herein.

Some embodiments relate to a method for lowering cholesterol levels comprising administering an effective amount of the compound described herein to a subject in need thereof.

Some embodiments relate to a method for lowering triglyceride levels comprising administering an effective amount of the compound described herein to a subject in need thereof.

Also provided are methods of reducing fat content in the liver or of preventing or treating steatosis, NASH, or NAFLD in a subject in need thereof, the method comprising administering to the subject an effective amount of the compound described herein.

Some embodiments relate to a method for modulating cholesterol levels, for treating obesity, hypercholesterolemia, hyperlipidemia, hypertriglyderidemia, and other metabolic diseases. In some embodiments, the metabolic disease is obesity, NASH, hypercholesterolemia, or hyperlipidemia. Some embodiments relate to a method for treating impaired glucose tolerance, insulin resistance, arteriosclerosis, atherosclerosis, coronary heart disease, heart failure, or diabetes. Some embodiments relate to the liver specific delivery of thyroid receptor ligands and the use of these compounds for the prevention and treatment of diseases responsive to modulation of T3-responsive genes in the liver. Some embodiments relate to treatment of hypothyroidism. The method described herein for treating the various listed diseases can be achieved using the compound described herein without affecting thyroid function, thyroid production of circulating iodinated thyronines such as T3 and T4, and/or the ratio of T3 to T4.

Combination Therapy

In certain instances, the compound described herein, or a pharmaceutically acceptable salt, solvate, tautomer, or stereoisomer thereof, is administered in combination with a second therapeutic agent.

In some embodiments, the benefit experienced by a patient is increased by administering one of the compounds described herein with a second therapeutic agent (which also includes a therapeutic regimen) that also has therapeutic benefit.

In one specific embodiment, a compound described herein, or a pharmaceutically acceptable salt, solvate, tautomer, or stereoisomer thereof, is co-administered with a second therapeutic agent, wherein the compound described herein, or a pharmaceutically acceptable salt, solvate, or stereoisomer thereof, and the second therapeutic agent modulate different aspects of the disease, disorder, or condition being treated, thereby providing a greater overall benefit than administration of either therapeutic agent alone.

In any case, regardless of the disease, disorder, or condition being treated, the overall benefit experienced by the patient is simply additive of the two therapeutic agents or the patient experiences a synergistic benefit.

In certain embodiments, different therapeutically-effective dosages of the compounds disclosed herein will be utilized in formulating a pharmaceutical composition and/or in treatment regimens when the compounds disclosed herein are administered in combination with a second therapeutic agent. Therapeutically-effective dosages of drugs and other agents for use in combination treatment regimens are optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt, solvate, tautomer, or stereoisomer thereof, is initiated prior to, during, or after treatment with a second agent described herein, and continues until any time during treatment with the second agent or after termination of treatment with the second agent. It also includes treatments in which a compound described herein, or a pharmaceutically acceptable salt, solvate, or stereoisomer thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g., the disease, disorder, or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated, and so forth. In additional embodiments, when co-administered with a second therapeutic agent, the compound provided herein is administered either simultaneously with the second therapeutic agent, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt, solvate, or stereoisomer thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, the compound of described herein, or a pharmaceutically acceptable salt, solvate, or stereoisomer thereof, is administered in combination with an adjuvant. In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced).

It is also possible to combine any compound described herein with one or more other active ingredients useful in the methods described herein.

In certain aspects, the compounds described herein are combined with one or more lipid lowering agents such as statins or cholesterol absorption inhibitors to treat patients with hyperlipidemia. Preferably, such combination allows therapeutic effect at a reduced dose of one or more of the agents, improves lipid profile, or improves safety/therapeutic index of the therapy or one or more of the agents.

By way of example, the compounds described herein are administered in combination with other pharmaceutical agents that are used to lower serum cholesterol such as a cholesterol biosynthesis inhibitor or a cholesterol absorption inhibitor, especially a HMG-CoA reductase inhibitor, or a HMG-CoA synthase inhibitor, or a HMG-CoA reductase or synthase gene expression inhibitor, a cholesteryl ester transfer protein (CETP) inhibitor (e.g., torcetrapib), a bile acid sequesterant (e.g., cholestyramine (Questran®), coleseve-lam and colestipol (Colestid®)), a bile acid reabsorption inhibitor, a cholesterol absorption inhibitor (e.g., ezetimibe, tiqueside, or pamaqueside), a PPARalpha agonist, a mixed PPAR alpha/gamma agonist, a MTP inhibitor (such as, for example, implitapide), a fibrate, an ACAT inhibitor (e.g., avasimibe), an angiotensin II receptor antagonist, a squalene synthetase inhibitor, a squalene epoxidase inhibitor, a squalene cyclase inhibitor, combined squalene epoxidase/squalene cyclase inhibitor, a lipoprotein lipase inhibitor, an ATP citrate lyase inhibitor, lipoprotein(a) antagonist, an antioxidant, or niacin (e.g., slow release niacin). The compounds of the present invention may also be administered in combination with a naturally occurring compound that acts to lower plasma cholesterol levels. Such naturally occurring compounds are commonly called nutraceuticals and include, for example, garlic extract and niacin.

In one aspect, the HMG-CoA reductase inhibitor is from a class of therapeutics commonly called statins. Examples of HMG-CoA reductase inhibitors that may be used include, but are not limited to, lovastatin, simvastatin, pravastatin, lactones of pravastatin, fluvastatin, lactones of fluvastatin, atorvastatin, lactones of atorvastatin, cerivastatin, lactones of cerivastatin, rosuvastatin, lactones of rosuvastatin, itavastatin, nisvastatin, visastatin, atavastatin, bervastatin, compactin, dihydrocompactin, dalvastatin, fluindostatin, pitivastatin, mevastatin, and velostatin.

Non-limiting examples of suitable bile acid sequestrants include cholestyramine, colestipol, colesevelam hydrochloride, water soluble derivatives such as 3,3-ioene, N-(cycloalkyl)alkylamines and poliglusam, insoluble quaternized polystyrenes, saponins, and mixtures thereof. Suitable inorganic cholesterol sequestrants include bismuth salicylate plus montmorillonite clay, aluminum hydroxide and calcium carbonate antacids.

EXAMPLES

Example 1: General Procedure for Synthesis of Compound Example 1

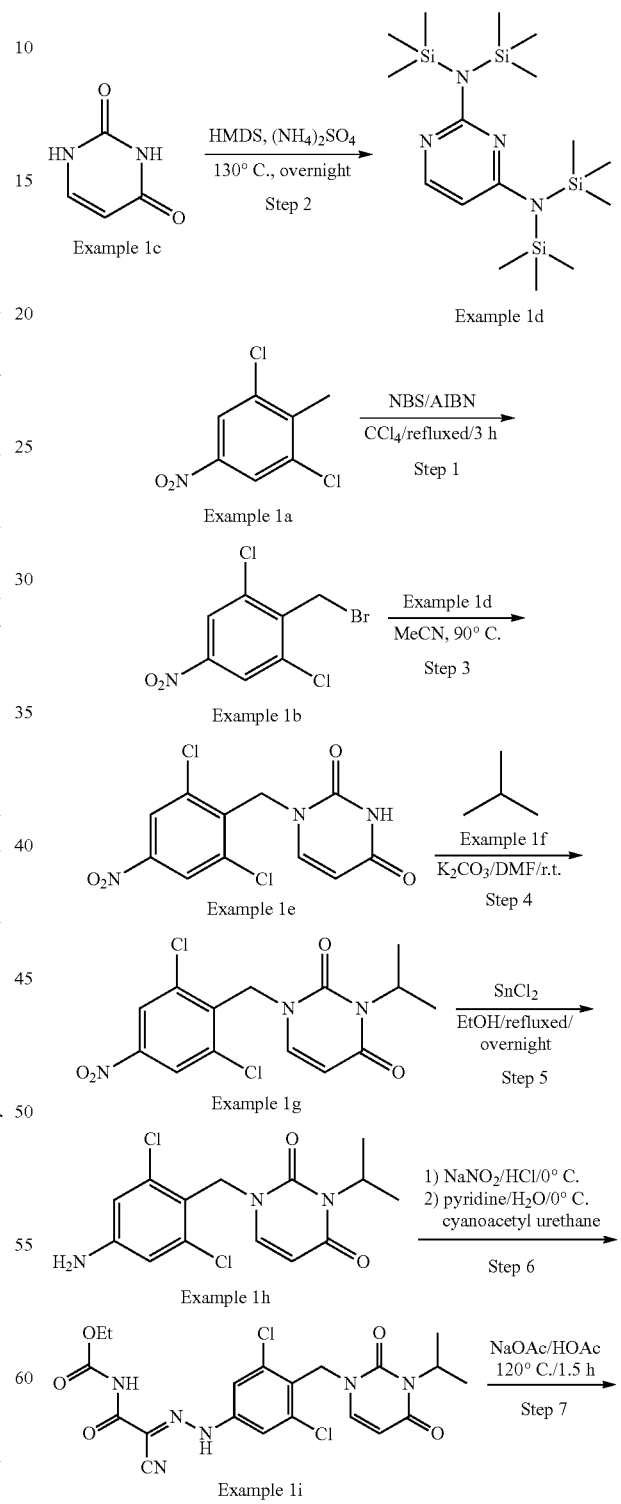

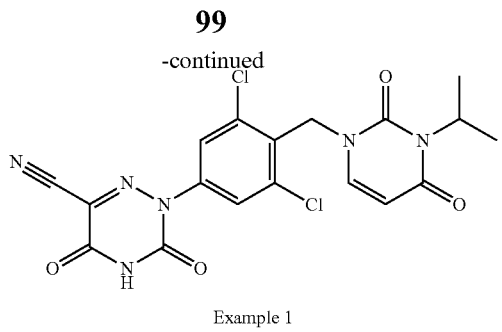

Example 1

Step 1: Example 1b

To a solution of Example 1a (2.06 g, 10.00 mmol) in CCl$_4$ (30 mL) were added NBS (1.78 g, 10.00 mmol) and AIBN (328 mg, 2.00 mmol). The mixture was heated under reflux for 3 h under N$_2$. After that, the mixture was filtered and concentrated under reduced pressure, which was purified by column chromatography (silica gel, Petroleum Ether/EtOAc=20/1~4/1) to give Example 1a (2.7 g, yield 95%) as a white solid. [M+1]$^+$=283.8/285.8.

Step 2: Example 1d

To a mixture of Example 1c (5.6 g, 50.00 mmol) in HMDS (150 mL) was added (NH$_4$)$_2$SO$_4$ (0.56 g, 10% wt of Example 1c), which was then stirred at reflux for 16 h. After that, the reaction mixture was concentrated under reduced pressure to give Example 1d (9.7 g, yield 49%) as a colourless oil, which was used for the next step without purification.

Step 3: Example 1e

To a solution of Example 1b (2.7 g, 9.47 mmol) in MeCN (50 mL) was added Example 1d (7.0 g, 17.5 mmol), which was stirred at reflux for overnight. After that, the mixture was poured into water (150 mL) and the precipitated white solid was filtered, the cake was purified by column chromatography (silica gel, DCM/MeOH=30/1 to 5/1) to give Example 1e (1.0 g, yield 33%) as a white solid. [M+1]$^+$=315.9/317.9.

Step 4: Example 1g

To a solution of Example 1e (948 mg, 3.00 mmol) in DMF (20 mL) were added K$_2$CO$_3$ (414 mg, 3.00 mmol) and Example 1f (510 mg, 3.00 mmol) at 0° C. Then the mixture was stirred at room temperature for overnight. After that, to the mixture was added water (100 mL), which was then extracted by EtOAc (50 mL*3). The combined organic layers were washed by brine (100 mL*2), dried over Na$_2$SO$_4$ and concentrated under reduced pressure. The residue was purified by column chromatography (silica gel, DCM/MeOH=50/1~20/1) to give Example 1g (280 mg, yield 30%) as yellow oil. [M+1]$^+$=358.0/360.0

Step 5: Example 1h

To a solution of Example 1g (280 mg, 0.78 mmol) in EtOH (10 mL) was added SnCl$_2$·2H$_2$O (890 mg, 4.69 mmol). Then the mixture was replaced with N$_2$ and stirred at reflux for overnight. After that, the mixture was dropped into ice-water and extracted by EtOAc (50 Ml*3). The organic layer was washed with 10% NaHCO$_3$ (aq.) for 3 times, dried over Na$_2$SO$_4$, filtered and concentrated to Example 1h (240 mg, yield 95%) as a light yellow solid. [M+1]$^+$=328.0/330.0

Step 6: Example 1i

To a solution of Example 1h (164 mg, 0.50 mmol) in HCl (4 N, 4 mL) was added NaNO$_2$ (45 mg, 0.65 mmol in 0.50 mL H$_2$O) dropwised at 0° C. Then the mixture of reaction was stirred at 0° C. for 30 min. After that, to the mixture was added pyridine (2 mL) and cyanoacetyl urethane (86 mg 0.55 mmol), which was then stirred at room temperature for 2 h. Then the reaction mixture was adjusted pH=8~9 by NaHCO$_3$ solution, the red solid was precipitated, which was filtered and dried to give Example 1i (230 mg, yield 95%) as a red solid.

Step 7: Example 1

To a mixture of Example 1i (200 mg, 0.40 mmol) in H$_2$O (20 mL) was added NaCO$_3$ (80 mg, 0.80 mmol). Then the reaction mixture was stirred at 100° C. for 30 min. After that, to the mixture was added EtOAc (30 mL), and the aqueous phase was collected. 1N HCl was added to the aqueous solution until pH=6~7, which was then extracted with EtOAc (20 mL*3). The combined organic phase was wash with brine, dried over Na$_2$SO$_4$, filtered and concentrated. The residue was purified by prep-HPLC (by Ultimate XB-C18, 50*250 mm, 10 μm, Mobile Phase: A (H$_2$O)/B (MeCN), Range of ratio:A/B (80%/20%) to A/B (54%/46%) 10 min and to A/B (34%/66%) 35 min, Rt of Peak: 25.2 min (59% of B), V=80 mL/min, wavelength 214 nm) to give Example 1 (15 mg, yield 9%) as a white solid. [M+1]$^+$=448.9/450.9.

$^1$H NMR (400 MHz, DMSO-d$_6$) δ 7.70 (s, 2H), 7.44 (d, J=7.8 Hz, 1H), 5.64 (d, J=7.8 Hz, 1H), 5.05-4.96 (m, 1H), 1.34 (d, J=6.8 Hz, 6H).

Example 2: General Procedure for Synthesis of Compound Example 2

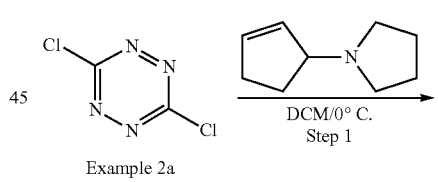

Example 2a

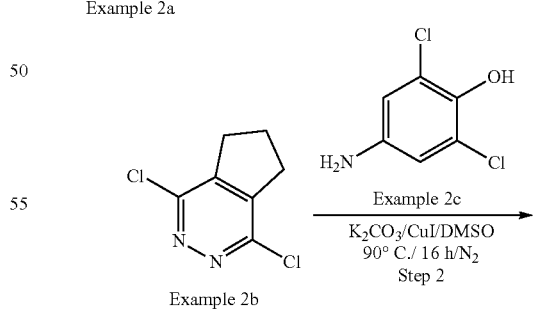

Example 2b

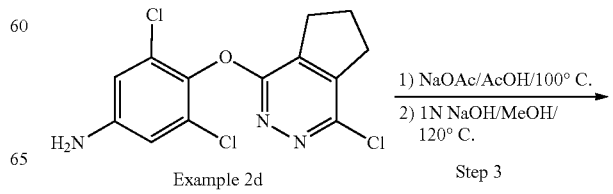

Example 2d

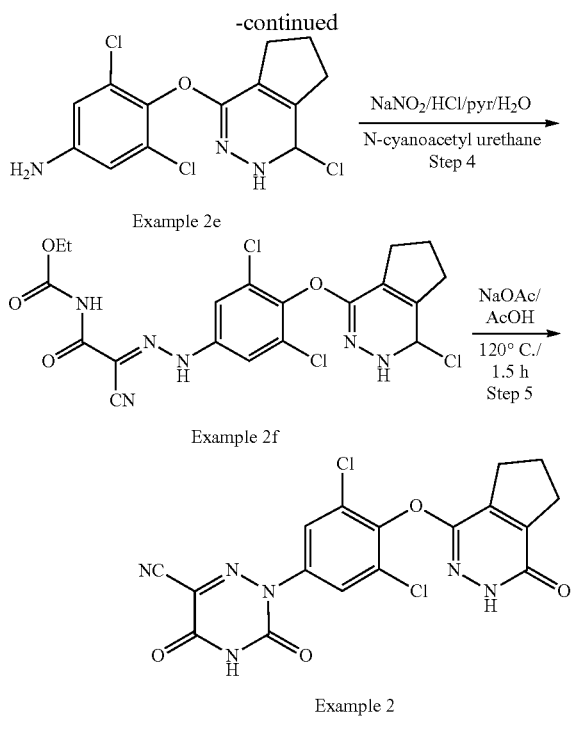

Step 1: Example 2b

A solution of Example 2a (200 mg, 1.32 mmol) in DCM (8 mL) was treated 1-(cyclopent-2-en-1-yl) pyrrolidine (181 mg, 1.32 mmol) by dropwise addition over 5 min. The reaction mixture was concentrated and purified by column chromatography (silica gel, Petroleum Ether/EtOAc=5/1) to afford Example 2b (215 mg, yield 86%) as an orange solid.

Step 2: Example 2d

To a suspension of Example 2b (349 mg, 1.85 mmol), Example 2c (219 mg, 1.23 mmol) and $K_2CO_3$ (318 mg, 2.3 mmol) in DMSO (6 mL) was added CuI (117 mg, 0.62 mmol) at room temperature under $N_2$. The reaction mixture was heated to 90° C. and stirred for 16 h under $N_2$. The reaction mixture was cooled to room temperature and diluted with EtOAc/$H_2O$ (V/V=1/2, 30 mL) and filtered. The filter cake was washed with EtOAc/$H_2O$ (V/V=1/2, 30 mL). The filtrate was separated and the aqueous layer was extracted with EtOAc (30 mL). The combined organic layer was washed with $H_2O$ (30 mL), brine (30 mL), dried over $Na_2SO_4$, filtered and the filtrate was concentrated to afford the crude product, which was purified by column chromatography (silica gel, Petroleum Ether/EtOAc=3/1) to afford Example 2d (215 mg, yield 53%) as a yellow solid. LCMS $[M+1]^+$=331.9

Step 3: Example 2e

A solution of Example 2d (215 mg, 0.65 mmol) and NaOAc (187 mg, 2.28 mmol) in AcOH (5 mL) was heated to 100° C. and stirred for 16 h. The reaction mixture was concentrated under reduced pressure and basified to pH=8 with sat. $NaHCO_3$ solution, and then extracted with EtOAc (10 mL). The aqueous layer was acidified by 2N HCl and extracted with EtOAc (10 mL). The combined organic layer was concentrated under reduced pressure and dissolved in MeOH (5 mL), which was then added 1N NaOH (5 mL) and heated to 120° C. for 16 h. The reaction mixture was cooled to room temperature and concentrated. The residue was dissolved in $H_2O$ (10 mL) and extracted with EtOAc (10 mL*3). The organic layer was washed with brine (10 mL), concentrated to afford crude Example 2e (148 mg, yield 73%), which was used for the next step without further purification. LCMS $[M+1]^+$=311.9

Step 4: Example 2f

A suspension of Example 2e (148 mg, 0.476 mmol) in $H_2O$ (5.6 mL) was treated with con. HCl (2.8 mL). The reaction mixture was cooled to 0° C. and then treated with a solution of $NaNO_2$ (41.4 mg, 0.600 mmol) in $H_2O$ (0.2 mL) followed by a $H_2O$ (0.2 mL) rinse. The reaction mixture was stirred at 0° C. for 30 min and a solution formed. In a separate flask equipped with a magnetic stirrer was added N-cyanoacetyl urethane (81.73 mg, 0.523 mmol), $H_2O$ (9.4 mL) and pyridine (2.8 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (10 mL*4) and the combined organic layer was washed with brine (10 mL), concentrated to afford crude Example 2f (220 mg, yield 97%) as an orange solid, which was used for the next step without further purification. LCMS $[M+1]^+$=478.9

Step 5: Example 2

A suspension of Example 2f (220 mg, 0.46 mmol) and NaOAc (188 mg, 2.3 mmol) in AcOH (5 mL) was heated to 120° C. and stirred for 1.5 h. The reaction mixture was cooled to room temperature and concentrated under reduced pressure, which was purified by prep-TLC (DCM/MeOH=10/1, Rf=0.1), followed by prep-HPLC (by Ultimate XB-C18, 50*250 mm, 10 μm, Mobile Phase: A ($H_2O$)/B (MeCN), Range of ratio:A/B (80%/20%) to A/B (60%/40%) 10 min and to A/B (30%/70%) 35 min, Rt of Peak: 23.1 min (58% of B), V=80 mL/min, wavelength 214 nm) to afford Example 2 (5.5 mg, yield 3%) as a white solid. LCMS $[M+1]^+$=432.8

$^1$H NMR (400 MHz, DMSO-$d_6$) δ 12.09 (s, 1H), 7.78 (s, 2H), 3.05-3.01 (t, J=8.0 Hz, 2H), 2.83-2.79 (t, J=8.0 Hz, 2H), 2.21-2.13 (q, 2H).

Example 3: General Procedure for Synthesis of Compound Example 3

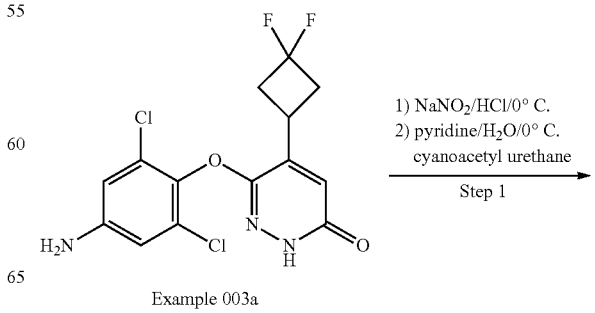

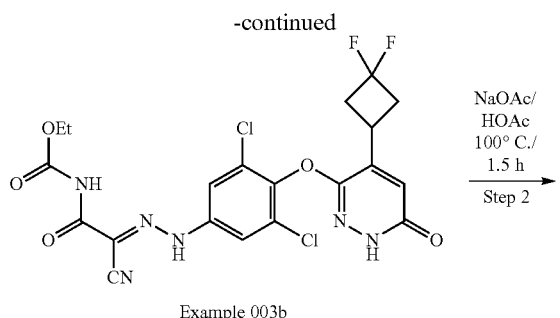

Example 003b

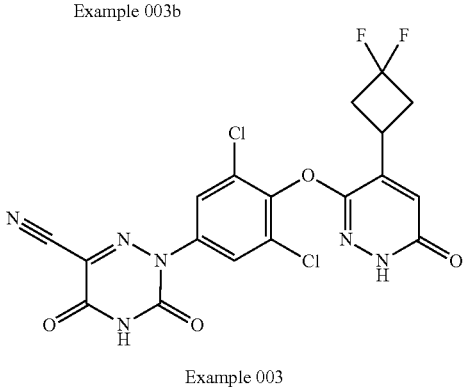

Example 003

Step 1: Example 3b

A well stirred slurry of Example 3a (120 mg, 0.3 mmol) and concentrated HCl (2.82 mL) in water (5.6 mL) was cooled to 0° C. and a cold solution of sodium nitrite (25 mg, 0.36 mmol) in water (0.2 mL) was added slowly over a period of 5 min, maintaining the reaction temperature at 0° C. for 30 min and a solution found. In a flask, equipped with a magnetic stirrer, was added cyanoacetamide (70 mg, 0.45 mmol), water (9.4 mL) and pyridine (2.8 mL). This reaction was cooled to 0° C. and the solution from the first reaction was quickly poured into the second reaction mixture. An orange precipitate formed and the suspension was stirred at 0° C. for 30 min. The resulting solution was extracted with EtOAc (100 mL*3). The combined organics were washed with brine (100 mL), dried over magnesium sulfate, filtered, rinsed with EtOAc and concentrated in vacuo to give Example 003b (270 mg, crude) as a red solid, which was used for the next step without purification. LCMS [M+1]$^+$=529.0.

Step 2: Example 3

A solution of Example 3b (270 mg, 0.5 mmol) in glacial acetic acid (5 mL) was treated with sodium acetate (240 mg, 2.5 mmol). The resulting mixture was heated to 100° C. for 1.5 h. The reaction was cooled to 25° C. and then poured onto water (25 mL). The resulting orange mixture was extracted with EtOAc (30 mL), dried with magnesium sulfate, concentrated under vacuum. The residue was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afforded Example 3 (18.9 mg, yield 8%) as a white solid. LCMS [M+1]$^+$=482.9. NMR (400 MHz, DMSO-d$_6$) δ 12.29 (s, 1H), 7.78 (s, 2H), 7.66 (s, 1H), 3.42-3.35 (m, 1H), 2.94-2.85 (m, 4H).

Example 4: General Procedure for Synthesis of Compound Example 4

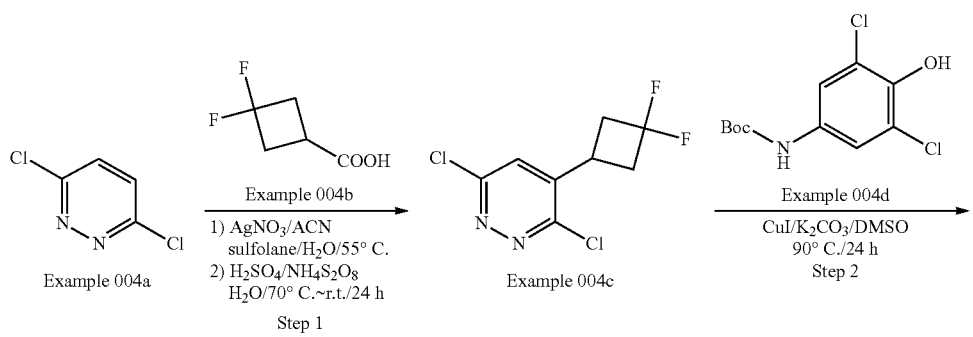

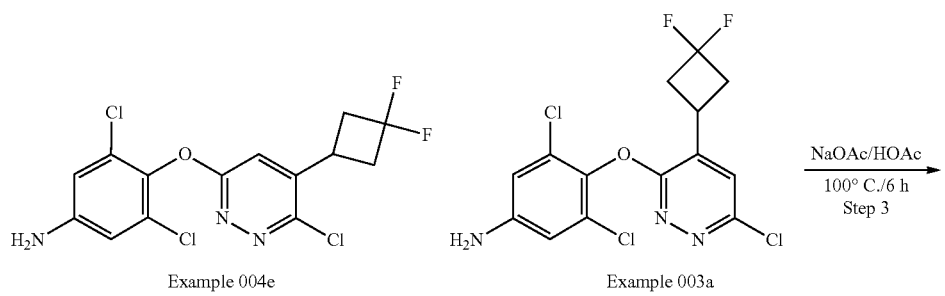

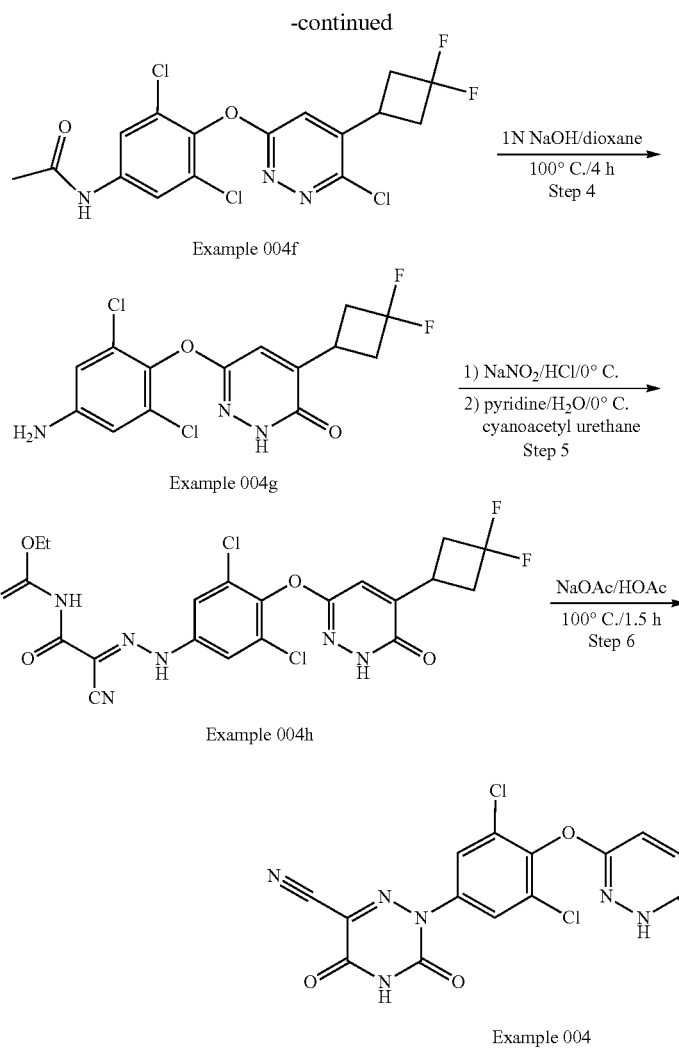

Step 1: Example 4

To a stirred suspension of Example 4a (4.45 g, 30.0 mmol) and in ACN (7 mL), sulfolone (21 mL) and H₂O (48 mL) at r.t. was treated with Example 4b (4.1 g, 30.0 mmol), followed by AgNO₃ (2.6 g, 15.0 mmol). The mixture was heated to 50° C. and then a solution of con. H₂SO₄ (4.8 mL) in H₂O (15 mL) was added in one portion, followed by dropwise addition of NH₄S₂O₈ (9.2 g, 44.0 mmol) in H₂O (15 mL) over 35 min. The mixture was stirred at 70° C. for 20 min and then cooled to r.t. for 24 h. The reaction mixture was adjusted to pH=7 with ammonium hydroxide solution (30%) in ice-bath, and then extracted with EtOAc. The extracts were washed with brine, dried (Na₂SO₄) and the solvent was removed under reduced pressure. The crude product was purified by column chromatography (silica gel, EtOAc/Petroleum Ether=1/10) to give Example 4c (4.1 g, yield 58%) as a white solid. LCMS [M+1]⁺=238.9.

¹H NMR (400 MHz, CDCl₃) δ 7.51 (s, 1H), 7.42 (d, J=1.2 Hz, 1H), 3.62-3.51 (m, 1H), 3.19-3.05 (m, 3H), 2.78-2.61 (m, 2H).

Step 2: Example 4e

A stirred suspension of Example 4c (4.1 g, 17.2 mmol), Example 4d (4.7 g, 17.2 mmol), K₂CO₃ (4.7 g, 34.4 mmol), and CuI (1.6 g, 8.6 mmol) in dry DMSO (20 mL) was heated to 90° C. for 24 h under N₂. The mixture was cooled to room temperature and transferred to a 1 L round-bottom flask with the aid of EtOAc (200 mL). Silica gel (10 g) was added and the suspension was agitated for 30 min and filtered. The reactor and cake were rinsed with EtOAc (100 mL) until the filtrate eluted colorless. The resulting filtrate was treated with 10 percent brine aqueous, and the biphasic mixture was agitated for 30 min. The upper organic layer was concentrated to dryness under reduced pressure, which was then purified by column chromatography (silica gel, EtOAc/Petroleum Ether=1/10) to give Example 4e (4.3 g, yield 66%) and Example 3a (120 mg) as a white solid. LCMS [M+1]⁺=379.9.

Step 3: Example 4f

A mixture of Example 4e (500 mg, 1.3 mmol) and sodium acetate (540 mg, 6.6 mmol) in glacial acetic acid (10 mL) was heated to 100° C. for 6 h. After this time the reaction was cooled to 25° C. and was diluted with water (450 mL). The reaction was brought to pH=5~6 by the addition of 5N aqueous sodium hydroxide solution. The resulting solution was extracted with EtOAc (100 mL*3). The combined organic was washed with brine (100 mL), dried over magnesium sulfate, and filtered. The cake was rinsed with EtOAc and the filtrate was concentrated in vacuo. The resulting yellow oil (700 mg, crude) was used for the next step without further purification. LCMS [M+1]⁺=404.0.

Step 4: Example 4g

A mixture of Example 4e (600 mg, 1.25 mmol) in dioxane (10 mL)/1N NaOH (15 mL) was heated to 100° C. for 4 h. After this time, the reaction was cooled to 25° C. and was diluted with water (50 mL). The reaction was brought to pH=7-8 by the addition of 1N HCl solution. The resulting solution was extracted with EtOAc (100 mL*3). The combined organic were washed with brine (100 mL), dried over magnesium sulfate, and filtered. The cake was rinsed with EtOAc and the filtrate was concentrated in vacuo. The residue was purified by column chromatography (silica gel, EtOAc/Petroleum Ether=1/10) to give Example 004g (130 mg, yield 58%) as a white solid. LCMS [M+1]⁺=361.9.

Step 5: Example 4h

A well stirred slurry of Example 4g (120 mg, 0.3 mmol) and concentrated HCl (2.82 mL) in water (5.6 mL) was cooled to 0° C. and a cold solution of sodium nitrite (25 mg, 0.36 mmol) in water (0.2 mL) was added slowly over a period of 5 min, maintaining the reaction temperature at 0° C. for 30 min. To another flask, equipped with a magnetic stirrer, was added cyanoacetamide (70 mg, 0.45 mmol), water (9.4 mL) and pyridine (2.8 mL). This mixture was cooled to 0° C. and the solution from previous flask was quickly poured into the second reaction mixture. An orange precipitate formed and the suspension was stirred at 0° C. for 30 min. The resulting solution was extracted with EtOAc (100 mL*3). The combined organics were washed with brine (100 mL), dried over magnesium sulfate, and filtered. The cake was rinsed with EtOAc and the filtrate was concentrated in vacuo. The residue was obtained as Example 4h (270 mg, crude yield 100%) as a red solid, which was used for the next step without purification. LCMS [M+1]⁺=529.0.

Step 6: Example 4

A solution of Example 4h (256 mg, 0.48 mmol) in glacial acetic acid (5 mL) was treated with sodium acetate (240 mg, 2.5 mmol). The resulting mixture was heated to 100° C. for 1.5 h. The reaction was cooled to 25° C. and then poured onto water (25 mL). The resulting orange mixture was extracted with EtOAc (30 mL), dried with magnesium sulfate, and concentrated under vacuum. The residue was purified by prep-HPLC (by Ultimate XB-C18, 50*250 mm, 10 μm, Mobile Phase: A (H₂O)/B (MeCN), Range of ratio: A/B (80%/20%) to A/B (60%/40%) 10 min and to A/B (30%/70%) 35 min, Rt of Peak: 23.1 min (58% of B), V=80 mL/min, wavelength 214 nm) to afford Example 4 (1.3 mg, yield 1%) as a white solid. LCMS [M+1]⁺=482.9. NMR (400 MHz, DMSO-d₆) δ 12.22 (s, 1H), 7.78 (s, 2H), 7.05 (s, 1H), 3.54-3.50 (m, 1H), 3.06-2.99 (m, 4H).

Example 5: General Procedure for Synthesis of Compound Example 005

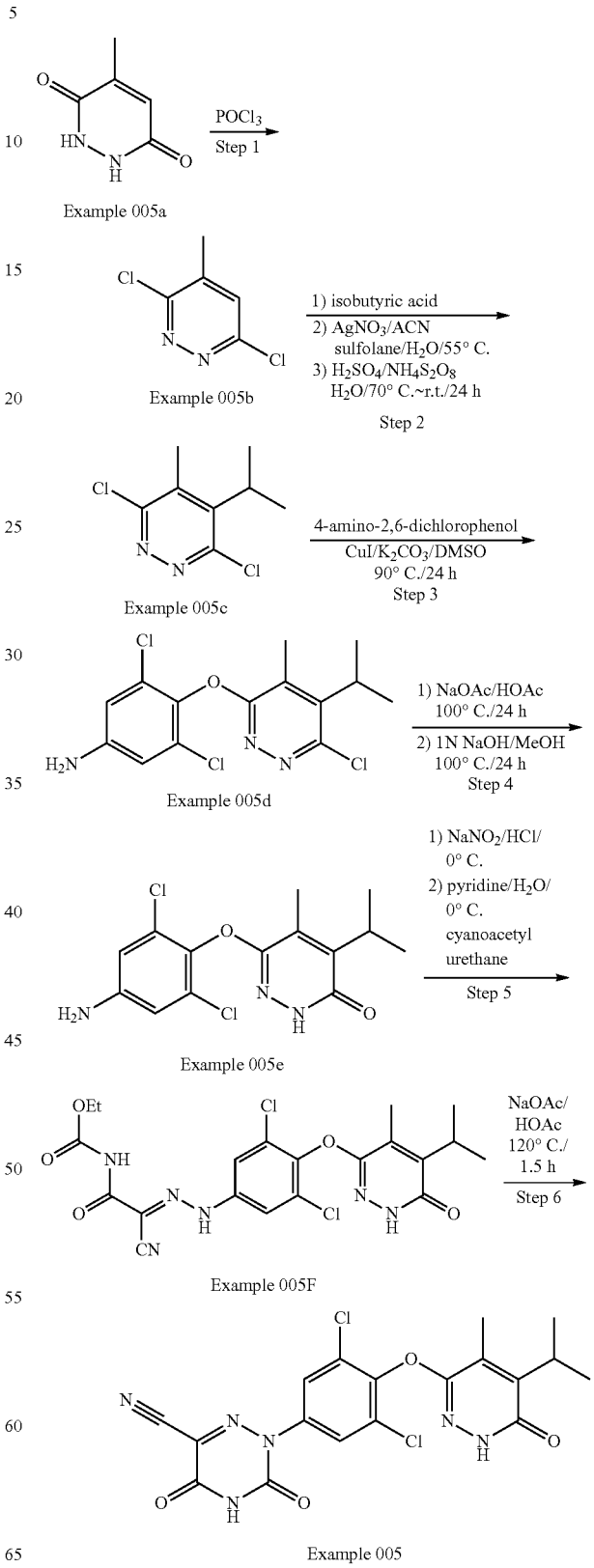

Step 1: Example 5b

Example 5a (5 g, 30.67 mmol) in POCl$_3$ (50 mL) was heated to reflux under an inert atmosphere for overnight. The reaction mixture was cooled and concentrated under reduce pressure to remove most of the POCl$_3$. Then the residue basified with aqueous NaHCO$_3$ to pH=8, and the aqueous phase was extracted with EtOAc (100 mL), dried over NaSO$_4$, concentrated and purified by column chromatography (silica gel, Petroleum Ether/EtOAc=5/1) to give Example 5b (5 g, yield 88%) as a light yellow solid.

Step 2: Example 5c

To a solution of Example 005b (5 g, 39.6 mmol), isobutyric acid (5.4 g, 61.3 mmol), AgNO$_3$ (3.7 g, 21.7 mmol), H$_2$SO$_4$ (20 g, 200 mmol) in H$_2$O (300 mL) was added drop wised a solution of ammonium persulfate (35 g, 153 mmol) in H$_2$O (200 mL) at 50° C. After addition, the mixture was heated to 70° C. for 30 min. The reaction mixture was basified with NH$_3$·H$_2$O, extracted with EtOAc, dried over Na$_2$SO$_4$, concentrated and purified by column chromatography (silica gel, Petroleum Ether/EtOAc=5/1) to give Example 005c (5.2 g, yield 84%) as a white solid. LCMS [M+1]$^+$=205.1 $^1$H NMR (400 MHz, CDCl$_3$) δ 3.60 (m, 1H), 2.49 (s, 3H), 3.03 (s, 1H), 1.4 (d, J=7.2 Hz, 6H).

Step 3: Example 5d

A mixture of Example 5c (2.0 g, 9.7 mmol), 4-amino-2,6-dichlorophenol (5.2 g, 29.2 mmol), CuI (1.95 g, 9.5 mmol), K$_2$CO$_3$ (1.5 g, 10.8 mmol) in DMSO (100 mL) was heated to 90° C. under an inert atmosphere overnight. The mixture was poured into water, filtered, and the two phases were separated. The organic layer was concentrated under vacuum, and the residue was purified by column chromatography (silica gel, Petroleum Ether/EtOAc=5/1) to give Example 5d (2.3 g, yield 90%) as a yellow solid. LCMS [M+1]$^+$=345.9/347.9.

Step 4: Example 5e

To a solution of Example 5d (2.3 g, 6.6 mmol), NaOAc (2.7 g, 32.9 mmol) in AcOH (30 mL) was heated to reflux for 4 h. The mixture was concentrated to give a yellow solid, which was dissolved in MeOH (30 mL) and 30% aqueous NaOH (20 mL). The resulting mixture was refluxed for 3 h, concentrated, neutralized with conc. HCl to pH=7, extracted with EtOAc, dried over Na$_2$SO$_4$, and concentrated to give crude Example 5e (1.4 g, yield 61%) as a yellow solid. LCMS [M+1]$^+$=327.9/329.9.

Step 5: Example 5f

To a suspension of Example 5e (430 mg, 1.31 mmol) in conc. HCl (1 mL) and water (10 mL) was added drop wised a solution of NaNO$_2$ (108 mg, 1.56 mmol) in H$_2$O (5 mL) at 0° C. After 30 min, AcONa (1.0 g, 32.9 mmol) was added, followed by addition of N-cyanoacetyl urethane (225 mg, 1.44 mmol). The reaction mixture was filtered, washed with water to give Example 5f (0.4 g, crude) as a red solid. LCMS [M+1]$^+$=495.0.

Step 6: Example 5

A mixture of Example 5f (400 mg, crude), AcONa (200 mg, 2.43 mmol) in AcOH (10 mL) was heated to reflux for 2 h. The reaction mixture was poured into H$_2$O, filtered and the solid was purified by prep-HPLC (by Ultimate XB-C18, 50*250 mm, 10 μm, Mobile Phase: A (H$_2$O)/B (MeCN); Range of ratio:A/B (80%/20%) to A/B (60%/40%) 10 min and to A/B (40%/60%) 35 min, V=80 mL/min, wavelength 214 nm) to give Example 5 (36 mg, yield 7% for two steps) as a white solid. LCMS [M+1]$^+$=449.1. $^1$H NMR (400 MHz, DMSO-d$_6$) δ 12.00 (s, 1H), 7.78 (s, 2H), 2.34 (s, 3H), 1.30 (d, J=7.2 Hz, 6H).

Example 6: General Procedure for Synthesis of Compound Example 6

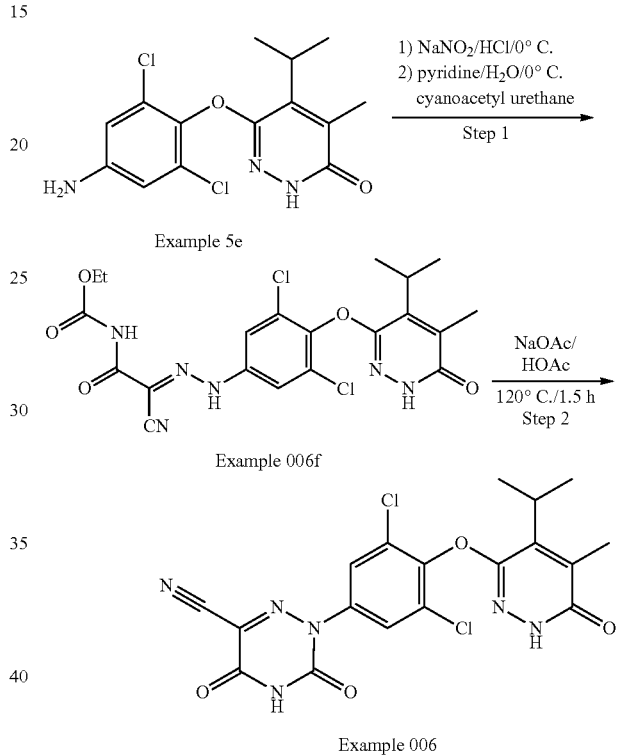

Step 1: Example 6f

To a suspension of Example 6e (430 mg, 1.31 mmol, from Example 5e) in con·HCl (1 mL) and water (10 mL) was added dropwise a solution of NaNO$_2$ (108 mg, 1.56 mmol) in H$_2$O (5 mL) at 0° C. 30 min later, NaOAc (1.0 g, 32.9 mmol) was added, followed by addition of cyanoacetyl urethane (225 mg, 1.44 mmol). The reaction mixture was filtered, washed with water to give Example 6f (400 mg, crude) as a red solid. LCMS [M+1]$^+$=495.0.

Step 2: Example 6

A mixture of Example 6f (400 mg, crude), NaOAc (200 mg, 2.43 mmol) in AcOH (10 mL) was heated to reflux for 1.5 h. The reaction mixture was poured into H$_2$O, filtered to give a brown solid, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give Example 6 (7 mg, yield 7% for 2 steps) as a white solid. LCMS [M+1]⁺=449.1. NMR (400 MHz, DMSO-d₆) δ 12.13 (s, 1H), 7.78 (s, 2H), 2.17 (s, 3H), 1.41 (d, J=7.2 Hz, 6H).

Example 7: General Procedure for Synthesis of Compound Example 7

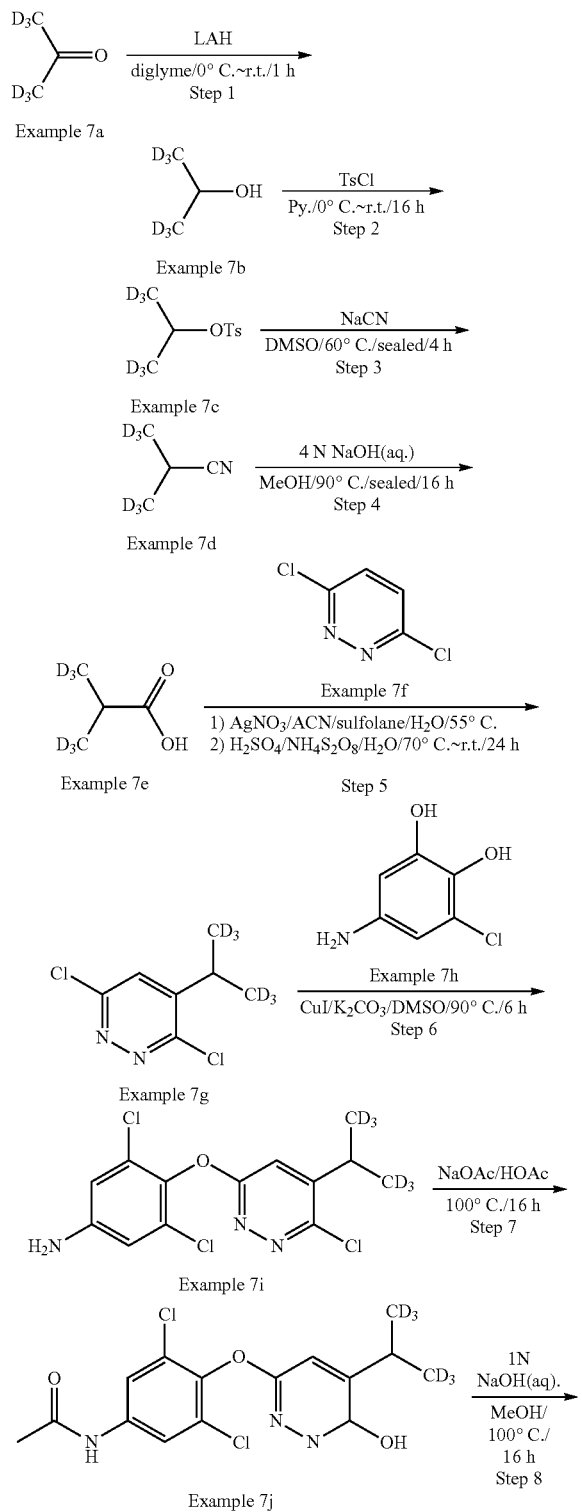

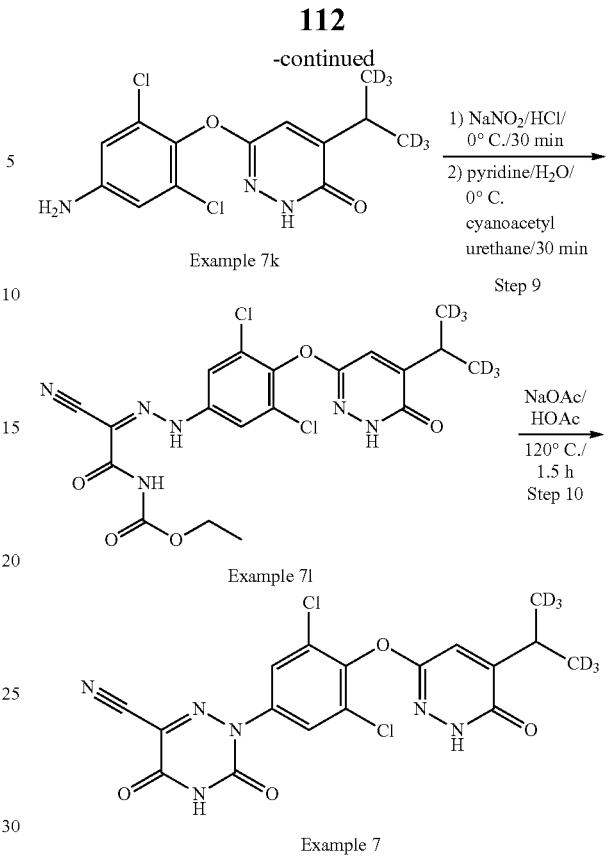

Step 1: Example 7b

To a solution of LAH (6.3 g, 165.8 mmol) in diglyme (175 mL) was slowly added Example 7a (25.0 g, 390.6 mmol) at 0° C. After addition, the mixture was allowed to stir from 0° C. to r.t. for 1 h. The reaction was quenched by adding glycol slowly at 0° C., and the resulting mixture was distilled directly (atmospheric pressure, low temperature cooling circulator) and the fraction between 79-105° C. was collected to give the desired product Example 7b (25 g, yield 100%) as colorless liquid.

Step 2: Example 7c

To a solution of Example 7b (25.0 g, 378.8 mmol) in pyridine (120 mL) was added TsCl (86.4 g, 454.5 mmol) portion wise at 0° C. The mixture was allowed to stir from 0° C. to r.t. for 16 h. Water was added into the mixture, and the reaction mixture was extracted with EtOAc (200 mL*3). The combined organic layers were dried over Na₂SO₄, filtered and concentrated in vacuo. The residue was purified by column chromatography (silica gel, Petroleum Ether/EtOAc=87/13) to give the desired product Example 7c (40 g, yield 48%) as colorless oil. LCMS [M+1]⁺=173.0
¹H NMR (400 MHz, CDCl₃) δ 7.78 (dd, J=8.4, 2.0 Hz, 2H), 7.32 (d, J=8.4 Hz, 2H), 4.69 (s, 1H), 2.43 (s, 3H).

Step 3: Example 7d

A mixture of Example 7c (39.6 g, 180.0 mmol) and NaCN (13.2 g, 270.0 mmol) in DMSO (500 mL) was sealed and stirred at 60° C. for 4 h. The reaction was cooled, distilled directly (atmospheric pressure, low temperature cooling circulator) and the fraction between 100-120° C. was collected to give the desired product Example 7d (35 g, crude) as colorless liquid. $^1$H NMR (400 MHz, CDCl$_3$) δ 2.40 (s, 1H).

Step 4: Example 7e

Example 7d (13.3 g, 177.3 mmol) in NaOH (4N, 100 mL) solution in a sealed tube was heated at 90° C. for 16 h. The reaction mixture was cooled to ambient temperature, and acidified with HCl (6N) to pH 3~4, which was then extracted by DCM/MeOH (v/v=10/1, 150 mL*3). The organic layers were combined, dried over Na$_2$SO$_4$, and filtered. The filtrate was concentrated in vacuo to give the desired product Example 7e (15.9 g, crude) as yellowish liquid, which was used for the next step directly. $^1$H NMR (400 MHz, DMSO-d$_6$) δ 11.96 (s, 1H), 2.59 (s, 1H).

Step 5: Example 7g

To a solution of Example 7f (7.1 g, 47.8 mmol) in acetonitrile (15 mL), sulfolane (45 mL) and water (105 mL) at room temperature was treated with Example 7e (4.5 g, 47.8 mmol), followed by silver nitrate (4.1 g, 23.9 mmol). The reaction mixture was heated to 55° C. A solution of sulfuric acid (conc., 7.5 mL) in water (10 mL) was added in one portion followed by dropwised addition of a solution of ammonium persulfate (14.5 g, 63.6 mmol) in water (20 mL) over 30 min. The reaction mixture was heated to 70° C. for 20 min and then cooled to room temperature, which was then stirred at ambient temperature for 16 h. At this time, the reaction mixture was cooled to 0° C. and basified with ammonium hydroxide (28-30%), which was added drop wised to bring the reaction to pH=8. The reaction mixture was diluted with water (100 mL), and extracted with EtOAc (100 mL*2). The combined organics were washed with water (100 mL*2) and brine (40 mL), dried over magnesium sulfate, filtered and the filtrate was concentrated under vacuum. The residue was purified by column chromatography (silica gel, Petroleum Ether 100%, then Petroleum Ether/EtOAc=10/1) to afford the desired product Example 7g (3.3 g, yield 35%) as colorless oil. LCMS [M+1]$^+$=197.1

Step 6: Example 7i

A solution of Example 7h (2.0 g, 11.4 mmol) in anhydrous DMSO (45 mL) at room temperature under N$_2$ were treated with Example 7g (3.3 g, 16.9 mmol), anhydrous potassium carbonate (3.1 g, 22.5 mmol) and copper (I) iodide (1.1 g, 5.65 mmol). The reaction mixture was heated to 90° C. for 6 h under nitrogen atmosphere. The reaction mixture was then cooled to room temperature and poured into water (50 mL). The solution was brought to pH=8 with hydrochloric acid (1 N). The aqueous layer was extracted with EtOAc (100 mL*3), and the combined organics were then washed with brine (50 mL), dried over magnesium sulfate, filtered and the filtrate was concentrated under vacuum. The residue was purified by column chromatography (silica gel, 27% EtOAc in Petroleum Ether) to afford the desired product Example 7i (2.9 g, yield 52%) as a yellow solid. LCMS [M+1]$^+$=338.1

Step 7&8: Example 7k

A mixture of glacial acetic acid (85 mL), sodium acetate (2.5 g, 30.0 mmol) and Example 7i (2.9 g, 8.6 mmol) was heated to 100° C. for 16 h. The reaction mixture was cooled to room temperature, and then concentrated. The residue was diluted with water (50 mL) and basified to pH=9 with NaOH (1N) solution. This suspension was extracted with EtOAc (100 mL*3). The organic layers were combined, dried with magnesium sulfate, filtered and the filtrate was concentrated under vacuum. The resulting oil was diluted with methanol (50 mL) and treated with NaOH (1 N, 50 mL). The resulting mixture was heated to 120° C. for another 16 h. The reaction mixture was cooled to room temperature and concentrated under vacuum. The residue was diluted with water (50 mL) and extracted with EtOAc (100 mL*2). The organic layer was washed with hydrochloric acid (1 N) solution to pH=5 and brine, dried over magnesium sulfate, filtered and the filtrate concentrated under vacuum to afford the desired product Example 7k (2.7 g, yield 98%) as a gray solid. LCMS [M+1]$^+$=320.1

Step 9: Example 7l

A suspension of Example 7k (500 mg, 1.56 mmol) in H$_2$O (19 mL) was treated with HCl (conc., 10 mL). The reaction mixture was cooled to 0° C. and then treated with a solution of NaNO$_2$ (136 mg, 1.97 mmol) in H$_2$O (1 mL) followed by a H$_2$O (1 mL) rinse. The reaction mixture was stirred at 0° C. for 30 min and a solution formed. In a separate flask equipped with a magnetic stirred were added N-cyanoacetyl urethane (268 mg, 1.72 mmol), H$_2$O (31 mL) and pyridine (10 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (50 mL*2) and the combined organic layer was washed with brine (10 mL), concentrated to afford the crude product Example 7l (760 mg, crude) as a brown solid, which was used for the next step without further purification. LCMS [M+1]$^+$=487.0

Step 10: Example 7

A suspension of Example 7l (760 mg, 1.56 mmol) and NaOAc (641 mg, 7.81 mmol) in AcOH (16 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (54%/46%) 10 min and to A/B (34%/66%) 35 min, Rt of Peak: 25.2 min (59% of B), V=80 mL/min, wavelength 214 nm) to afford the desired product Example 7 (132.5 mg, yield 19%) as a white solid. LCMS [M+1]$^+$=441.0. NMR (400 MHz, DMSO-d$_6$) δ 13.26 (s, 1H), 12.22 (s, 1H), 7.78 (s, 2H), 7.43 (d, J=1.2 Hz, 1H), 3.01 (s, 1H).

Example 9: General Procedure for Synthesis of Compound Example 9

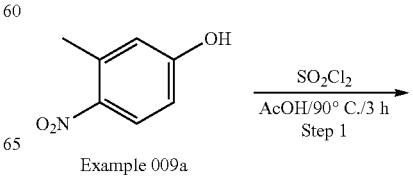

Example 009a

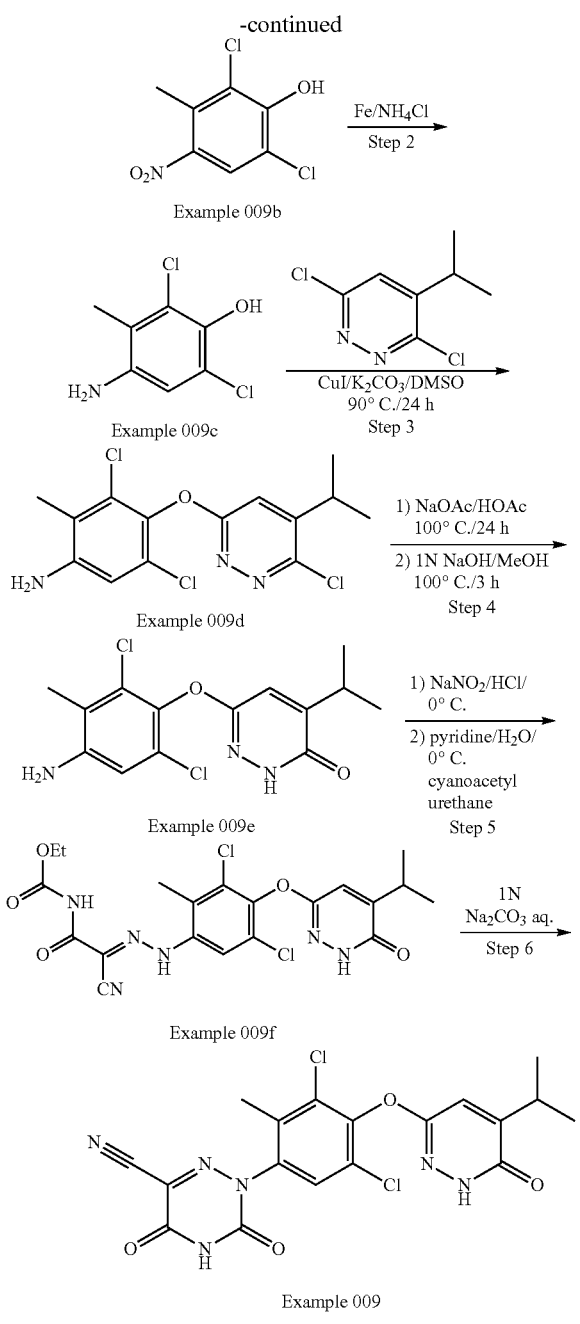

Step 1: Example 9b

A mixture of Example 9a (5.0 g, 32.6 mmol), sulfuryl dichloride (13.2 g, 97.7 mmol) in AcOH (50 mL) was heated to 90° C. for 3 h under an inert atmosphere. This mixture was poured into H$_2$O, filtered, and the filter cake was washed with H$_2$O twice, which was then dissolved in EtOAc, dried over Na$_2$SO$_4$, and concentrated to give Example 9b (6.5 g, yield 90%) as a white solid. LCMS [M−1]⁻=219.9/221.9. $^1$H NMR (400 MHz, DMSO-d$_6$) δ 8.04 (s, 1H), 2.46 (s, 3H).

Step 2: Example 9c

A mixture of Example 5b (6.5 g, 29.2 mmol), Fe (8.2 g, 146 mmol), NH$_4$Cl (8 g, 149 mmol) in EtOH (20 g, 60 mmol) and H$_2$O (60 mL) was heated to reflux for 1 h. The mixture was filtered, and the filtrate was concentrated. The residue was extracted with EtOAc, dried over Na$_2$SO$_4$, and concentrated to give Example 009c (6.0 g, yield 90%) as a green solid. LCMS [M+1]⁻=189.9/191.9.

Step 3: Example 9d

A mixture of Example 9c (2.0 g, 10.4 mmol), 3,6-dichloro-4-isopropylpyridazine (1.0 g, 5.2 mmol), CuI (1.0 g, 5.2 mmol), K$_2$CO$_3$ (0.8 g, 5.7 mmol) in DMSO (100 mL) was heated to 90° C. under an inert atmosphere for 24 h. The mixture was poured into water, filtered, and separated. The organic layer was concentrated, purified by column chromatography (silica gel, Petroleum Ether/EtOAc=5/1) to give Example 9d (1.0 g, yield 35%) as a yellow solid. LCMS [M+1]⁺=345.9/347.9.

Step 4: Example 9e

To a solution of Example 9d (1.0 g, 2.8 mmol), NaOAc (1.2 g, 14.6 mmol) in AcOH (30 mL) was heated to reflux for 4 h. The mixture was concentrated to give a yellow solid, which was dissolved in MeOH (30 mL) and 30% aqueous NaOH (20 mL). The resulting mixture was refluxed for 3 h, concentrated, acidified with con. HCl to pH=7, extracted with EtOAc, dried over Na$_2$SO$_4$, and concentrated to give Example 9e (0.6 g, yield 64%) as a yellow solid. LCMS [M+1]⁺=369.9/371.9.

Step 5: Example 9f

A well stirred slurry of Example 9g (164 mg, 0.5 mmol) and concentrated HCl (2.0 mL) in water (6.0 mL) was cooled to 0° C. and a cold solution of sodium nitrite (38 mg, 0.5 mmol) in water (0.2 mL) was added slowly over a period of 5 min, maintaining the reaction temperature at 0° C. for 30 min and a solution was formed. To another flask, equipped with a magnetic stirrer, was added cyanoacetamide (75 mg, 0.5 mmol), water (9.4 mL) and pyridine (2.8 mL). This reaction was cooled to 0° C. and the solution from the first reaction was quickly poured into the second reaction mixture. An orange precipitate formed and the suspension was stirred at 0° C. for 30 min. The resulting solution was extracted with EtOAc (100 mL*3). The combined organics were washed with brine (100 mL), dried over magnesium sulfate, and filtered. The solid was rinsed with EtOAc and the filtrate was concentrated under vacuum to give Example 9f (220 mg, crude) as a red solid, which was used for the next step without purification. LCMS [M+1]⁺=495.0

Step 6: Example 9

The mixture of Example 9f (220 mg, crude) in Na$_2$CO$_3$ (5.0 mL, 1 mol/L) was warmed to 100° C. for 15 min, and then cooled down to room temperature. The mixture was extracted with DCM twice, and the combine organic was washed with brine, dried over Na$_2$SO$_4$, filtered and concentrated to give a yellow solid, which was purified by prep-HPLC (by Ultimate XB-C18, 50*250 mm, 10 µm, Mobile Phase: A (H$_2$O)/B (MeCN), Range of ratio:A/B (80%/20%) to A/B (52%/48%) 10 min and to A/B (32%/68%) 35 min, Rt of Peak: 23.8 min (58% of B), V=80 mL/min, wavelength 214 nm) to give Example 9 (14 mg, yield 9%) as a yellow solid. LCMS [M+1]⁺=448.9. $^1$H NMR (400 MHz, DMSO-d$_6$) δ 12.19 (s, 1H), 7.74 (s, 1H), 7.44 (s, 1H), 3.10-3.01 (m, 1H), 2.21 (s, 3H), 1.20 (d, J=6.8 Hz, 6H).

Example 10: General Procedure for Synthesis of Compound Example 10

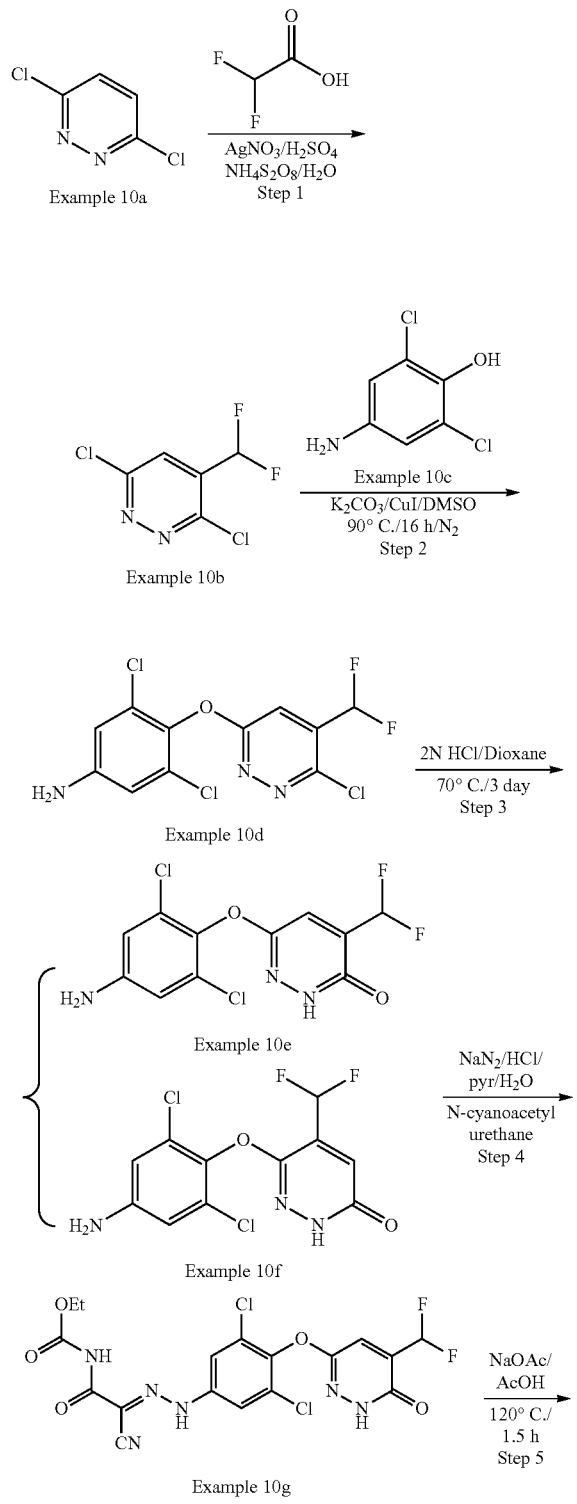

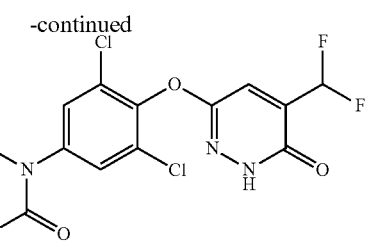

Example 10

Step 1: Example 10b

To a suspension of Example 10a (10.0 g, 67.12 mmol), 2,2-difluoroacetic acid (6.44 g, 67.12 mmol) and AgNO$_3$ (11.4 g, 67.12 mmol) in H$_2$O (200 mL) was added H$_2$SO$_4$ (conc. 19.73 g, 201.37 mmol) at 50° C. in an oil bath. After addition, the reaction mixture was heated to 60° C., to which was added a solution of NH$_4$S$_2$O$_8$ (45.95 g, 201.37 mmol) in H$_2$O (100 mL). The reaction mixture was kept at 70° C. for 30 min and cooled to room temperature, which was then basified to pH=8 with NH$_3$·H$_2$O and then extracted with EtOAc (100 mL*3). The organic layer was washed with brine (100 mL*2), dried over Na$_2$SO$_4$, filtered and concentrated to afford the crude product, which was purified by column chromatography (silica gel, Petroleum Ether/EtOAc=10/1) to afford Example 10b (2.02 g, yield 15%) as colorless oil.

Step 2: Example 10d

To a suspension of Example 10b (2.02 g, 10.15 mmol), Example 10c (1.20 g, 6.77 mmol) and K$_2$CO$_3$ (1.75 g, 12.66 mmol) in DMSO (50 mL) was added CuI (646 mg, 3.38 mmol) at room temperature under N$_2$. The reaction mixture was heated to 90° C. and stirred for 16 h under N$_2$. The reaction mixture was cooled to room temperature and diluted with EtOAc/H$_2$O (V/V=1/1, 100 mL) and filtered. The filtered cake was washed with EtOAc/H$_2$O (V/V=1/1, 50 mL*3). The filtrate was separated and the aqueous layer was extracted with EtOAc (100 mL). The combined organic layer was washed with brine (100 mL*2), dried over Na$_2$SO$_4$, filtered and concentrated to afford the crude product, which was purified by column chromatography (silica gel, Petroleum Ether/EtOAc=10/1) to afford Example 10d (649 mg, yield 28%) as a yellow solid. LCMS [M+1]$^+$=341.8

Step 3: Example 10e

To a solution of Example 10d (300 mg, 0.88 mmol) dissolved in 1,4-dioxane (5 mL) was added HCl (2N, 20 mL), which was heated to 70° C. for 16 h. Additional HCl (2N, 40 mL) was added and then the reaction mixture was heated at 70° C. for 2 days. The reaction mixture was cooled to room temperature and basified to pH=9 with NaOH (UV), and extracted with EtOAc (20 mL*3). The combined organic layer was concentrated and purified by prep-TLC (Petroleum Ether/EtOAc=2/1, Rf=0.5) to afford Example 10e (125 mg, yield 44%) and Example 10f (100 mg, yield 35%) as a white solid.
LCMS [M+1]$^+$=321.9

Step 4: Example 10g

A suspension of Example 10e (125 mg, 0.388 mmol) in H$_2$O (5.6 mL) was treated with HCl (conc., 2.8 mL). The reaction mixture was cooled to 0° C. and then added a solution of NaNO₂ (33.7 mg, 0.489 mmol) in H₂O (0.2 mL) followed by a ringsed with H₂O (0.2 mL). The reaction mixture was stirred at 0° C. for 30 min to give solution A. In a separate flask equipped with a magnetic stirrer were added N-cyanoacetyl urethane (66.6 mg, 0.427 mmol), H₂O (9.4 mL) and pyridine (2.8 mL). The reaction mixture was cooled to 0° C. and the solution A was dropped into the reaction mixture. An orange precipitate formed and the suspension was stirred at 0° C. for 30 min. The reaction mixture was extracted with EtOAc (10 mL*3), and the combined organic layer was washed with brine (10 mL), and concentrated to afford Example 10g (189 mg, crude) as an orange solid, which was used for next step without further purification. LCMS [M+1]⁺=488.9

Step 5: Example 10

A suspension of Example 10g (189 mg, 0.388 mmol) and NaOAc (159 mg, 1.94 mmol) in AcOH (3 mL) was heated to 120° C. and stirred for 1.5 h. The reaction mixture was cooled to room temperature and concentrated under reduced pressure. The residue was purified by prep-TLC (DCM/MeOH=10/1, Rf=0.1), followed by prep-HPLC (by Ultimate XB-C18, 50*250 mm, 10 μm, Mobile Phase: A (H₂O)/B (MeCN); Range of ratio:A/B (80%/20%) to A/B (60%/40%) 10 min and to A/B (40%/60%) 35 min, V=80 mL/min, wavelength 214 nm) to afford Example 10 (6.3 mg, yield 4%) as a white solid. LCMS [M+1]⁺=442.8

¹H NMR (400 MHz, DMSO-d₆) δ 12.75 (s, 1H), 7.96 (s, 1H), 7.80 (s, 2H), 7.08-6.81 (t, J=53.4 Hz, 1H).

Example 11: General Procedure for Synthesis of Compound Example 11

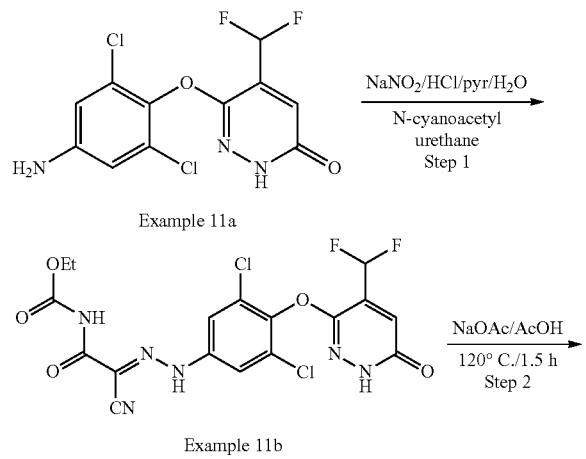

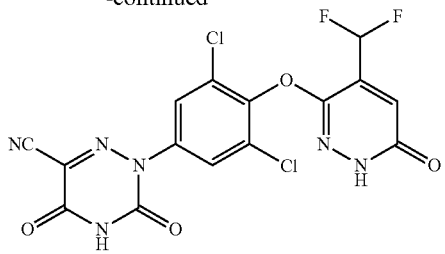

Example 11

Step 1: Example 11b

A suspension of Example 11a (100 mg, 0.310 mmol, from Example 10f) in H₂O (5.6 mL) was treated with HCl (conc. 2.8 mL). The reaction mixture was cooled to 0° C. and then treated with a solution of NaNO₂ (27 mg, 0.391 mmol) in H₂O (0.2 mL) followed by rinsed with H₂O (0.2 mL). The reaction mixture was stirred at 0° C. for 30 min to give solution A. In a separate flask equipped with a magnetic stirred were added N-cyanoacetyl urethane (53 mg, 0.342 mmol), H₂O (9.4 mL) and pyridine (2.8 mL). The reaction mixture was cooled to 0° C. and the solution A was poured into the reaction mixture. An orange precipitate formed and the suspension was stirred at 0° C. for 30 min. The reaction mixture was extracted with EtOAc (10 mL*3) and the combined organic layer was washed with brine (10 mL), concentrated to afford the crude product Example 11b (205 mg, crude) as an orange solid, which was used for the next step without further purification. LCMS [M+1]⁺=488.9

Step 2: Example 11

A suspension of Example 11b (205 mg crude, 0.42 mmol) and NaOAc (172 mg, 2.1 mmol) in AcOH (3 mL) was heated to 120° C. and stirred for 1.5 h. The reaction mixture was cooled to room temperature and concentrated under reduced pressure. The residue was purified by prep-TLC (DCM/MeOH=10/1, Rf=0.1), followed by prep-HPLC (by Ultimate XB-C18, 50*250 mm, 10 μm, Mobile Phase: A (H₂O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 11 (5.6 mg, yield 3%) as a white solid. LCMS [M+1]⁺=442.8. ¹H NMR (400 MHz, DMSO-d₆) δ 7.80 (s, 2H), 7.34 (s, 1H), 7.33-7.06 (t, J=53.4 Hz, 1H).

Example 12: General Procedure for Synthesis of Compound Example 12

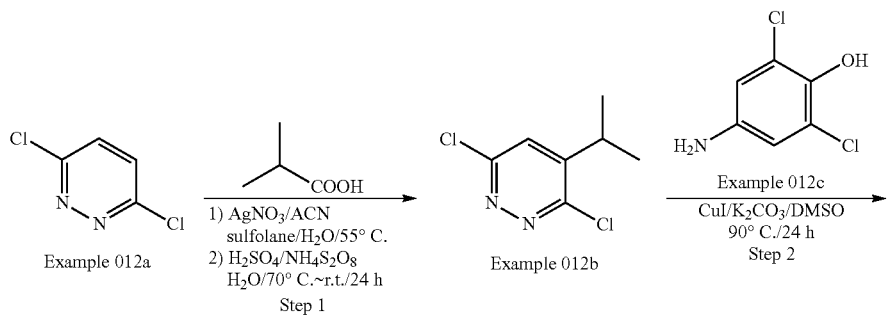

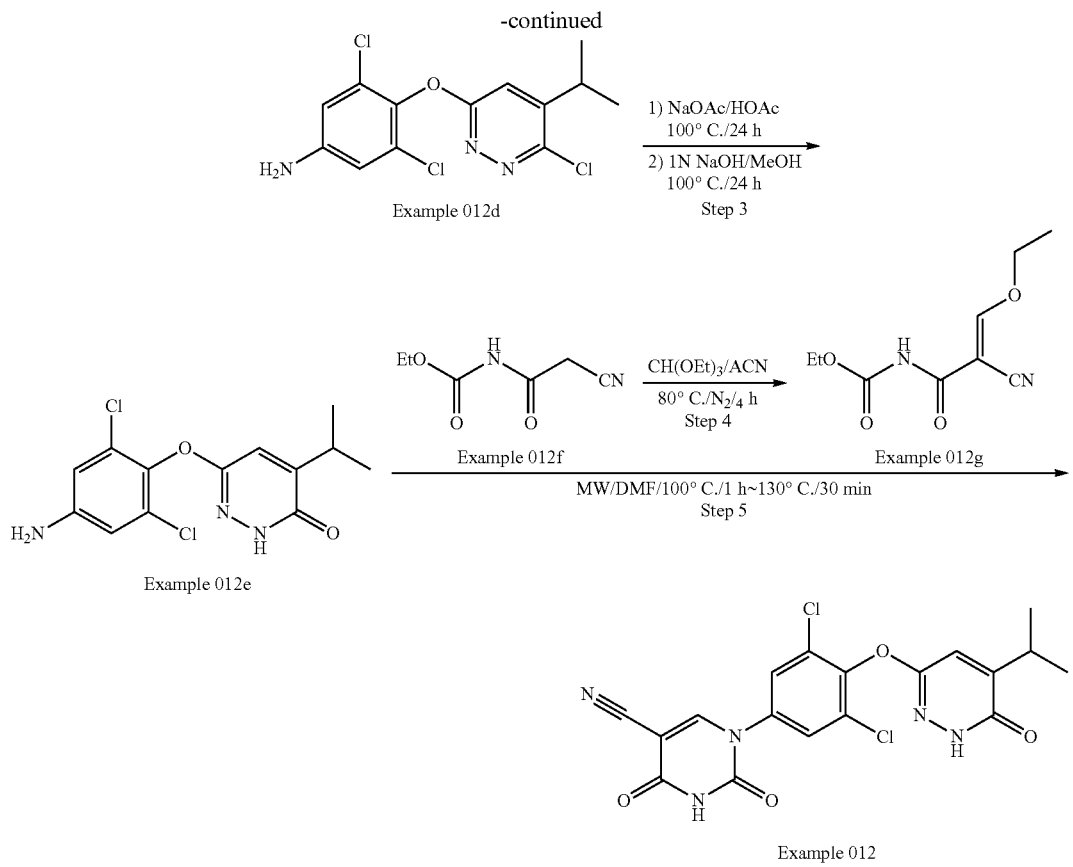

Step 1: Example 12b

A solution of Example 12a (67.5 g, 0.45 mol) in acetonitrile (105 mL), tetramethylene sulfone (321 mL) and water (735 mL) at room temperature was treated with isobutyric acid (42 mL, 0.453 mol), followed by silver nitrate (39 g, 0.225 mol). The reaction mixture was heated to 55° C., and a solution of concentrated sulfuric acid (72 mL) in water (225 mL) was added in one portion followed by dropwise addition of a solution of ammonium persulfate (154.5 g, 0.66 mol) in water (225 mL) over 35 min. The reaction mixture was heated to 70° C. for 20 min, and then cooled to room temperature and stirred for 24 h. At this time, the reaction mixture was cooled to 0° C. and basified with ammonium hydroxide (300 mL, 28-30%) to pH=8. The resulting mixture was diluted with water (1.5 L) and filtered over celite. The filtered cake was washed well with EtOAc (1.5 L). The filtrate was separated, and the aqueous layer was extracted with EtOAc (500 mL*2). The combined organic phase was washed with water, brine, dried over $Na_2SO_4$, and filtered. The filtrate was concentrated under vacuum, and the residue was purified by column chromatography (silica gel, Petroleum Ether/EtOAc=20/1~10/1) to afford Example 12b (37.5 g, yield 44%) as yellow oil. LCMS [M+1]$^+$=191.1

Step 2: Example 12d

A solution of Example 12b (855 mg, 4.5 mmol) in anhydrous dimethyl sulfoxide (15 mL) under nitrogen at room temperature was treated with Example 12c (534 mg, 3 mmol), anhydrous potassium carbonate (828 mg, 6 mmol) and copper (I) iodide (285 mg, 1.5 mmol). The reaction mixture was heated to 90° C. for 24 h. The reaction mixture was then cooled to room temperature and poured into water (50 mL). The solution was neutralized with hydrochloric acid (1N) to pH=8, and the aqueous layer was diluted with EtOAc (50 mL), which was filtered over celite. The organic layer was separated, and the aqueous layer was extracted again with EtOAc (50 mL). The combined organic layer was washed with brine (40 mL), dried over $Na_2SO_4$, and filtered. The filtrate was concentrated under vacuum, and the residue was purified by column chromatography (silica gel, Petroleum Ether/EtOAc=100/0~10/1) to afford Example 12d (580 mg, yield 58%) as a yellow solid. LCMS [M+1]$^+$=333.1

Step 3: Example 12e

A mixture of glacial acetic acid (10 mL), sodium acetate (287 mg, 3.5 mmol) and Example 12d (332 mg, 1.0 mmol) was heated to 100° C. for 24 h. The reaction mixture was cooled to room temperature, stirred for 2 days and then concentrated. The resulting residue was diluted with water (50 mL) and basified with sodium hydroxide solution (UV) to pH=9. The resulting suspension was extracted with EtOAc (50 mL), and the aqueous layer was acidified with hydrochloric acid (conc.) to pH=5. The resulting aqueous layer was extracted with EtOAc (50 mL) again, and the combined organic layer was dried over magnesium sulfate, filtered and the filtrate was concentrated under vacuum. The resulting oil was diluted with methanol (10 mL) and treated with sodium hydroxide solution (1N, 10 mL, 10 mmol). The reaction mixture was heated to 100° C. for 24 h. The reaction mixture was cooled to room temperature and the solvent was concentrated under vacuum. The residue was diluted with water (50 mL) and extracted with EtOAc (50 mL). The organic layer was washed with hydrochloric acid solution (1N) to pH=5, and then washed with brine, dried over magnesium sulfate, filtered and the filtrate was concentrated under vacuum. The residue was dissolved in DCM and purified by prep-TLC (Petroleum Ether/EtOAc=1/1) to afford Example 12 (170 mg, yield 54%) as a white solid. LCMS [M+1]$^+$=315.1

Step 4: Example 12g

To a solution of Example 12f (936 mg, 6 mmol) in acetonitrile (6 mL) was added triethyl orthoformate (2.7 g, 18 mmol) under nitrogen. The mixture was heated to 80° C. for 4 h. The reaction mixture was cooled and concentrated under reduced pressure. The crude product was purified by column chromatography (silica gel, Petroleum Ether/EtOAc=10/1) to afford Example 12g (1.1 g, yield 87%) as a yellow solid. LCMS [M+1]$^+$=213.2

Step 5: Example 12

Example 012e (313 mg, 1.0 mmol) and Example 12g (255 mg, 1.2 mmol) were dissolved in DMF (4 mL). The mixture was irradiated in a microwave reactor at 100° C. for 1 h and 130° C. for 30 min. The mixture was filtered to remove all solids and partitioned. The aqueous layer was extracted with DCM (10 mL*3) and the combined organic layer was washed with brine, and dried over sodium sulphate. The crude residue was purified by prep-HPLC (by Ultimate XB-C18, 50*250 mm, 10 μm, Mobile Phase: A (H$_2$O)/B (MeCN); Range of ratio:A/B (80%/20%) to A/B (60%/40%) 10 min and to A/B (40%/60%) 35 min, V=80 mL/min, wavelength 214 nm) to afford Example 12 (2.8 mg, yield 1%). LCMS [M+1]$^+$=435.2. NMR (400 MHz, DMSO-d$_6$) δ 12.24 (s, 1H), 8.76 (s, 1H), 7.83 (s, 2H), 7.44 (s, 1H), 3.07-3.03 (m, 1H), 1.20 (d, J=6.8 Hz, 6H).

Example 13: General Procedure for Synthesis of Compound Example 13

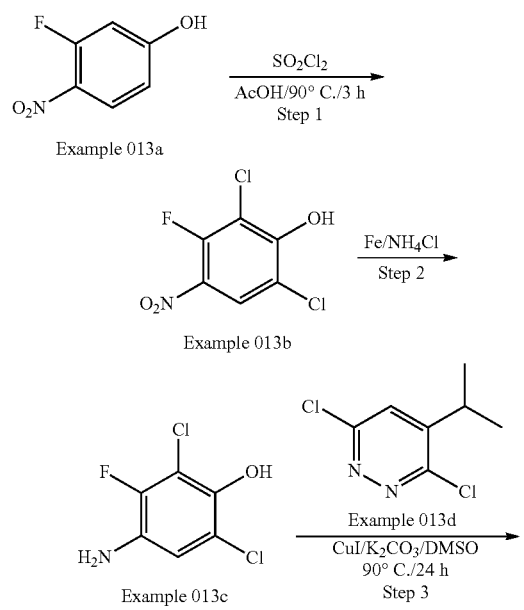

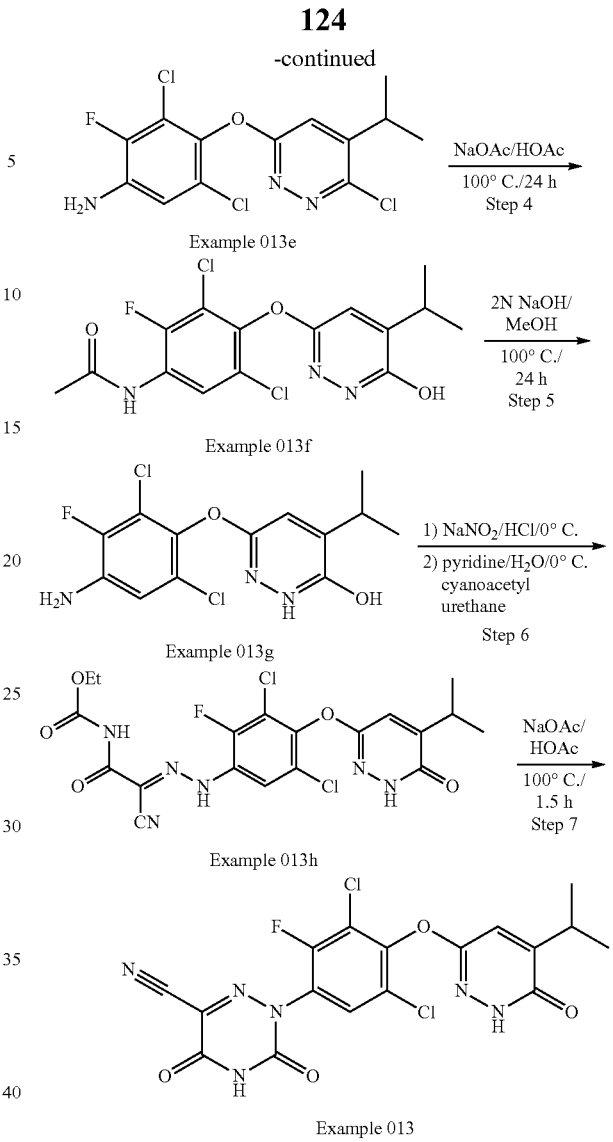

Step 1: Example 13b

A mixture of Example 13a (5.0 g, 31.8 mmol), sulfuryl dichloride (12.8 g, 95.5 mmol) in AcOH (50 mL) was heated to 90° C. for 3 h under an inert atmosphere. This mixture was poured into H$_2$O, filtered, and the filter cake was washed with H$_2$O twice, which was then dissolved in EtOAc, dried over Na$_2$SO$_4$, concentrated to give Example 13b (5.1 g, crude, 35% purity). LCMS [M-1]$^-$=219.9/221.9. $^1$H NMR (400 MHz, DMSO-d$_6$) δ 8.04 (s, 1H), 2.48 (s, 3H).

Step 2: Example 13c

A mixture of Example 13b (1.7 g, 7.6 mmol), Fe (2.12 g, 37.9 mmol), NH$_4$Cl (2.05 g, 37.9 mmol) in EtOH (30 mL) and H$_2$O (15 mL) was heated to reflux for 1 h. The mixture was filtered, and the filtrate was concentrated, which was then extracted with EtOAc, dried over Na$_2$SO$_4$, and concentrated to give Example 13c (1.0 g, yield 78%) as a green solid.

LCMS [M+1]$^-$=189.9/191.9.

Step 3: Example 13e

A mixture of Example 13c (700 mg, 4.6 mmol), Example 13d (436 mg, 2.3 mmol), CuI (435 mg, 2.3 mmol), $K_2CO_3$ (331 mg, 2.4 mmol) in DMSO (20 mL) was heated to 90° C. under an inert atmosphere for 24 h. The mixture was poured into water, filtered, and separated. The organic layer was concentrated, purified by column chromatography (silica gel, Petroleum Ether/EtOAc=5/1) to give Example 13e (130 mg, yield 17%) as a yellow solid. LCMS $[M+1]^+$=349.9.

Step 4: Example 13f

A mixture of Example 13e (760 mg, 2.28 mmol), NaOAc (380 mg, 4.5 mmol) in AcOH (10 mL) was heated to 100° C. under an inert atmosphere for 24 h. The mixture was poured into water, and extracted with EtOAc twice. The organic layer was washed with brine, dried over $Na_2SO_4$, filtered, and concentrated to give crude Example 13f (900 mg, yield 95%) as brown oil. LCMS $[M+1]^+$=374.0

Step 5: Example 13g

The Example 13f (900 mg, 2.28 mmol) in MeOH/NaOH (2 N aqueous) (10 mL/10 mL), was heated to 90'C under an inert atmosphere for 24 h. After that, the mixture was cooled down and poured in to water. 1N HCl was added to the mixture until pH=6-7, which was then extracted with EtOAc twice. The organic layer was washed with brine, dried over $Na_2SO_4$, filtered, and concentrated to give crude Example 13g (600 mg, yield 79%) as a brown solid. LCMS $[M+1]^+$=332.0. $^1H$ NMR (400 MHz, $CDCl_3$) δ 7.17 (s, 1H), 6.66 (s, 1H), 3.33-3.20 (m, 1H), 2.17 (s, 3H), 1.33 (d, J=7.2 Hz, 6H).

Step 6: Example 13h

A well stirred slurry of Example 13g (180 mg, 0.54 mmol) and concentrated HCl (2.82 mL) in water (5.6 mL) was cooled to 0° C. and a cold solution of sodium nitrite (38 mg, 0.54 mmol) in water (0.2 mL) was added slowly over a period of 5 min, maintaining the reaction temperature at 0° C. for 30 min. To another flask, equipped with a magnetic stirrer, was added cyanoacetamide (78 mg, 0.54 mmol), water (9.4 mL) and pyridine (2.8 mL). This reaction was cooled to 0° C. and the solution from the first reaction was quickly poured into the second reaction mixture. An orange precipitate formed and the suspension was stirred at 0° C. for 30 min. The resulting solution was extracted with EtOAc (100 mL*3). The combined organics were washed with brine (100 mL), dried over magnesium sulfate, and filtered. The solid was rinsed with EtOAc and the filtrate was concentrated in vacuo to give the Example 13h (270 mg, crude) as a red solid, which was used for the next step without purification. LCMS $[M+1]^+$=498.9

Step 7: Example 13

A solution of Example 13h (270 mg, 0.5 mmol) in glacial acetic acid (5 mL) was treated with sodium acetate (240 mg, 2.5 mmol). The resulting mixture was heated to 100° C. for 1.5 h. The reaction was cooled to 25° C. and then poured onto water (25 mL). The resulting orange mixture was extracted with EtOAc (30 mL), dried with magnesium sulfate, and concentrated under vacuum. The residue was purified by prep-HPLC (by Ultimate XB-C18, 50*250 mm, 10 μm, Mobile Phase: A ($H_2O$)/B (MeCN), Range of ratio: A/B (80%/20%) to A/B (54%/46%) 10 min and to A/B (34%/66%) 35 min, Rt of Peak: 25.2 min (59% of B), V=80 mL/min, wavelength 214 nm) to afford Example 13 (8.2 mg, yield 2%) as a white solid. LCMS $[M+1]^+$=452.9. NMR (400 MHz, DMSO-$d_6$) δ 7.95 (d, J=7.2 Hz, 1H), 7.46 (s, 1H), 3.07-3.03 (m, 1H), 1.20 (d, J=7.2 Hz, 6H).

Example 15: General Procedure for Synthesis of Compound Example 15

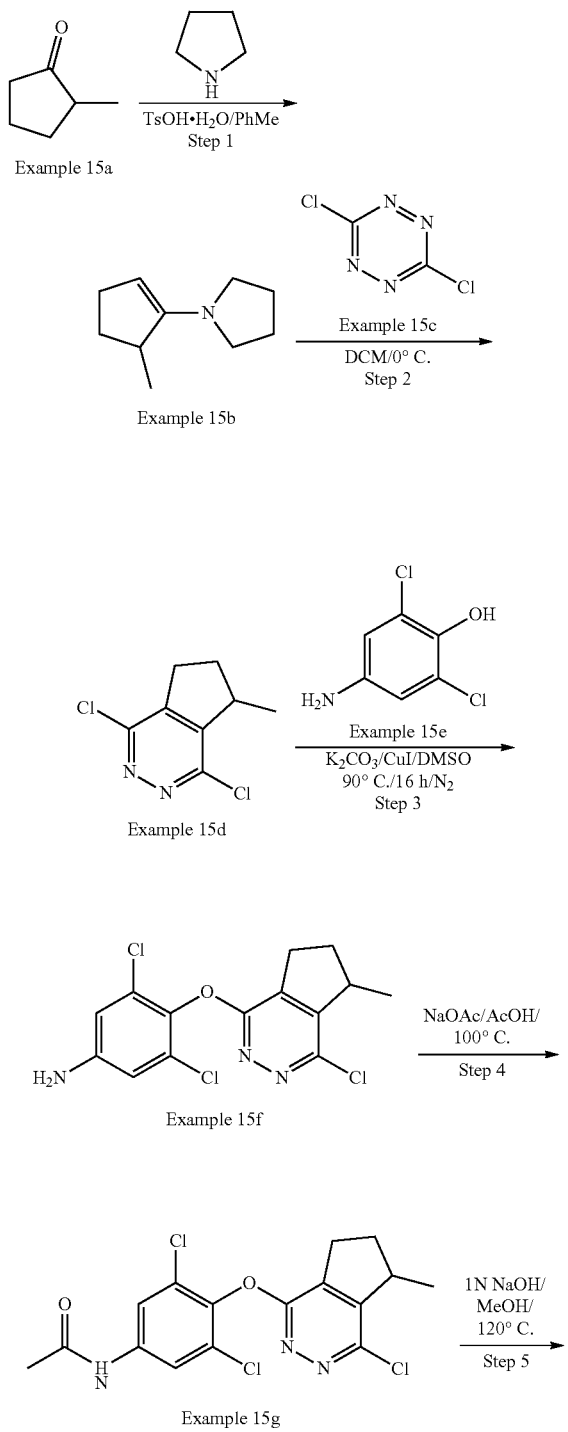

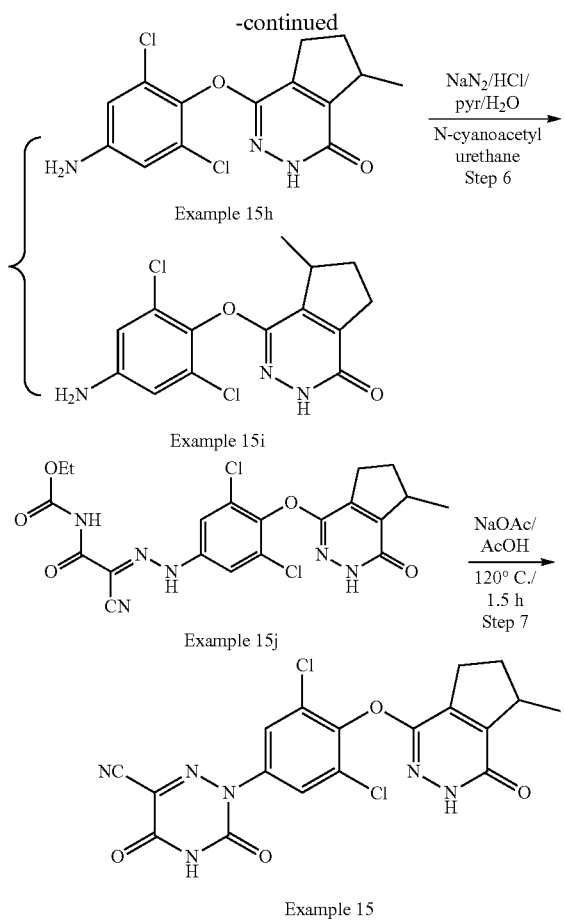

Example 15

Step 1: Example 15b

A mixture of Example 15a (6.0 g, 61.22 mmol), pyrrolidine (6.53 g, 91.84 mmol) and TsOH·H₂O (1.16 g, 6.12 mmol) in PhMe (70 mL) was refluxed at 130° C. with Dean-Stark for 16 h. The color of the solution turned black from colorless. The reaction mixture was cooled to room temperature and concentrated to afford the crude product Example 15b (6.0 g, yield 65%) as black oil, which was used for the next step without further purification.

Step 2: Example 15d

To an orange solution of Example 15c (2.8 g, 18.54 mmol) in DCM (100 mL) was added slowly Example 15b (5.6 g, 37.08 mmol) at 0° C. with ice-bath. After addition, the reaction mixture was stirred for 15 min at 0° C. The color of the reaction turned brown. The reaction mixture was purified by column chromatography (silica gel, Petroleum Ether/EtOAc=1/0~5/1) to afford Example 15d (3.08 g, yield 82%) as a yellow solid. LCMS [M+1]⁺=202.9.

Step 3: Example 15f

To a suspension of Example 15d (3.08 g, 15.25 mmol), Example 15e (1.81 g, 10.17 mmol) and K₂CO₃ (2.62 g, 19.01 mmol) in DMSO (60 mL) was added CuI (969 mg, 5.08 mmol) at room temperature under N₂. The reaction mixture was heated to 90° C. and stirred for 16 h under N₂. The reaction mixture was cooled to room temperature and poured into ice-water (100 mL), which was then diluted with EtOAc (50 mL), filtered and the filter cake was washed with EtOAc/H₂O (V/V=1/1, 50 mL 3). The filtrate was separated and the aqueous layer was extracted with EtOAc (50 mL*2). The combined organic layer was washed with brine (100 mL*2), dried over Na₂SO₄, filtered and concentrated to afford the crude product, which was purified by column chromatography (silica gel, Petroleum Ether/EtOAc=3/1) to afford Example 15f (1.9 g, yield 54%) as a yellow solid. LCMS [M+1]⁺=345.9.

Step 4: Example 15g

A solution of Example 15f (500 mg, 1.45 mmol) and NaOAc (416 mg, 5.08 mmol) in AcOH (5 mL) was heated to 100° C. and stirred for 16 h. The reaction mixture was cooled to room temperature and concentrated under reduced pressure. The residue was dissolved in H₂O (10 mL) and made to basic pH=8 with sat. NaHCO₃, and then extracted with EtOAc (20 mL*2). The aqueous layer was acidified with 6N HCl and extracted with EtOAc (20 mL). The combined organic layer was concentrated to afford the crude product Example 15g (533 mg, crude), which was used for the next step without further purification.

Step 5: Example 15h

To a solution of Example 15g (533 mg, 1.45 mmol) in MeOH (15 mL) was added 1N NaOH (50 mL) and then the reaction mixture was heated to 120° C. and stirred for 16 h. The reaction mixture was cooled to room temperature and concentrated under reduced pressure. The residue dissolved in H₂O (30 mL) and extracted with EtOAc (20 mL*2). The organic layer was concentrated and purified by prep-TLC (Petroleum Ether/EtOAc=1/2, Rf=0.5) to afford a mixture of products, which was further purified by column chromatography (silica gel, Petroleum Ether/EtOAc=1/1(peak1)~1/2 (peak2)) to afford product Example 15h (227 mg, yield 48%, LCMS: peak1, Rf=1.669 min) and Example 15i (89 mg, yield 19%, LCMS: peak2, Rf=1.659 min) as a yellow solid. LCMS [M+1]⁺=325.9

¹H NMR for Example 15h (400 MHz, DMSO-d₆) δ 11.98 (s, 1H), 6.58 (s, 2H), 5.60 (s, 2H), 3.01-2.92 (m, 1H), 2.88-2.79 (m, 1H), 2.40-2.30 (m, 1H), 1.74-1.65 (m, 1H), 1.30-1.20 (m, 4H). ¹H NMR for Example 15i (400 MHz, DMSO-d₆) δ 12.01 (s, 1H), 6.66 (s, 2H), 5.60 (s, 2H), 2.84-2.77 (m, 1H), 2.72-2.69 (m, 1H), 2.39-2.29 (m, 1H), 1.75-1.69 (m, 1H), 1.34-1.29 (m, 4H).

Step 6: Example 15j

To a solution of Example 15h (220 mg, 0.674 mmol) in H₂O (11.2 mL) was treated with conc. HCl (5.6 mL). The reaction mixture was cooled to 0° C. and then treated with a solution of NaNO₂ (58.6 mg, 0.85 mmol) in H₂O (0.4 mL) followed by a H₂O (0.4 mL) rinse. The reaction mixture was stirred at 0° C. for 30 min to give solution A. In a separate flask equipped with a magnetic stirred were added N-cyanoacetyl urethane (116 mg, 0.74 mmol), H₂O (18.8 mL) and pyridine (5.6 mL). The reaction mixture was cooled to 0° C. and the solution A was poured into the second reaction mixture. An orange precipitate formed and the suspension was stirred at 0° C. for 30 min. The reaction mixture was extracted with EtOAc (15 mL*3) and the combined organic layer was washed with brine (15 mL), concentrated to afford the crude product Example 15j (473 mg, crude) as an orange solid, which was used for the next step without further purification. LCMS [M+1]$^+$=492.9.

Step 7: Example 15

A suspension of Example 15j (473 mg, 0.96 mmol) and NaOAc (393 mg, 4.79 mmol) in AcOH (10 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (60%/40%) 10 min and to A/B (30%/70%) 35 min, Rt of Peak: 23.1 min (58% of B), V=80 mL/min, wavelength 214 nm) to afford Example 15 (106 mg, yield 25%) as a white solid. LCMS [M+1]$^+$=446.9. $^1$H NMR (400 MHz, DMSO-d$_6$) δ 12.09 (s, 1H), 7.78 (s, 2H), 3.08-3.00 (m, 1H), 2.95-2.87 (m, 1H), 2.41-2.36 (m, 1H), 1.74-1.72 (m, 1H), 1.27-1.25 (d, J=8.0 Hz, 3H), (s, 1H), 2.82 (dt, J=14.0, 7.5 Hz, 4H), 2.06-1.99 (m, 2H), 1.19 (d, J=6.9 Hz, 6H).

Example 16: General Procedure for Synthesis of Compound Example 16

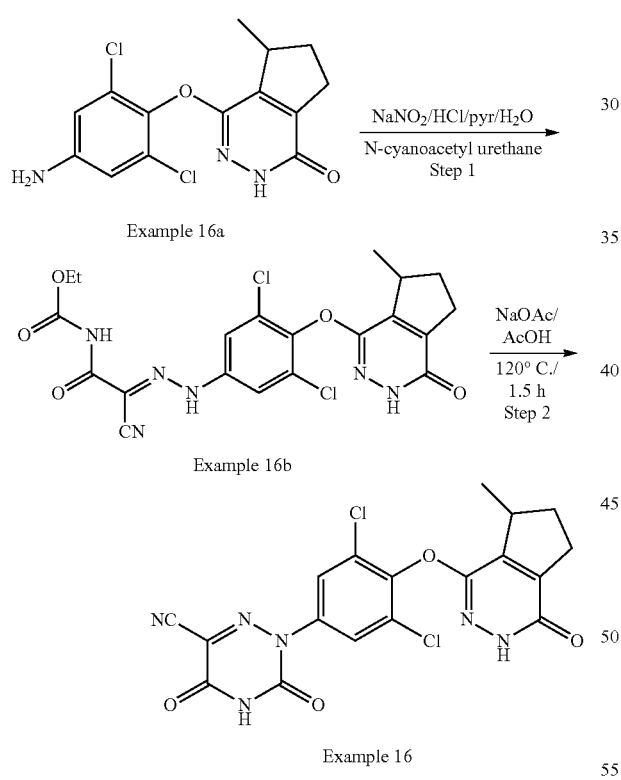

Step 1: Example 16b

To a solution of Example 16a (85 mg, 0.26 mmol, from Example 15i) in H$_2$O (5.6 mL) was treated with con. HCl (2.8 mL). The reaction mixture was cooled to 0° C. and then treated with a solution of NaNO$_2$ (22.6 mg, 0.33 mmol) in H$_2$O (0.2 mL) followed by a H$_2$O (0.2 mL) rinse. The reaction mixture was stirred at 0° C. for 30 min to give solution A. In a separate flask equipped with a magnetic stirred were added N-cyanoacetyl urethane (45 mg, 0.29 mmol), H$_2$O (9.4 mL) and pyridine (2.8 mL). The reaction mixture was cooled to 0° C. and the solution A was poured into the reaction mixture. An orange precipitate formed and the suspension was stirred at 0° C. for 30 min. The reaction mixture was extracted with EtOAc (15 mL*3) and the combined organic layer was washed with brine (15 mL), concentrated to afford the crude product Example 16b (300 mg, yield 100%) as an orange solid, which was used for the next step without further purification. LCMS [M+1]$^+$=492.9

Step 2: Example 16

A suspension of Example 16b (300 mg, 0.61 mmol) and NaOAc (249 mg, 3.04 mmol) in AcOH (6 mL) was heated to 120° C. and stirred for 1.5 h. The reaction mixture was cooled to ambient temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 16 (39.8 mg, yield 15%) as a white solid. LCMS [M+1]$^+$=446.9. $^1$H NMR (400 MHz, DMSO-d$_6$) δ13.25 (bs, 1H), 12.13 (s, 1H), 7.78 (s, 2H), 3.49 (s, 1H), 2.90-2.81 (m, 1H), 2.76-2.68 (m, 1H), 2.43-2.34 (m, 1H), 1.78-1.72 (m, 1H), 1.38-1.36 (d, J=8.0 Hz, 3H).

Example 17: General Procedure for Synthesis of Compound Example 17

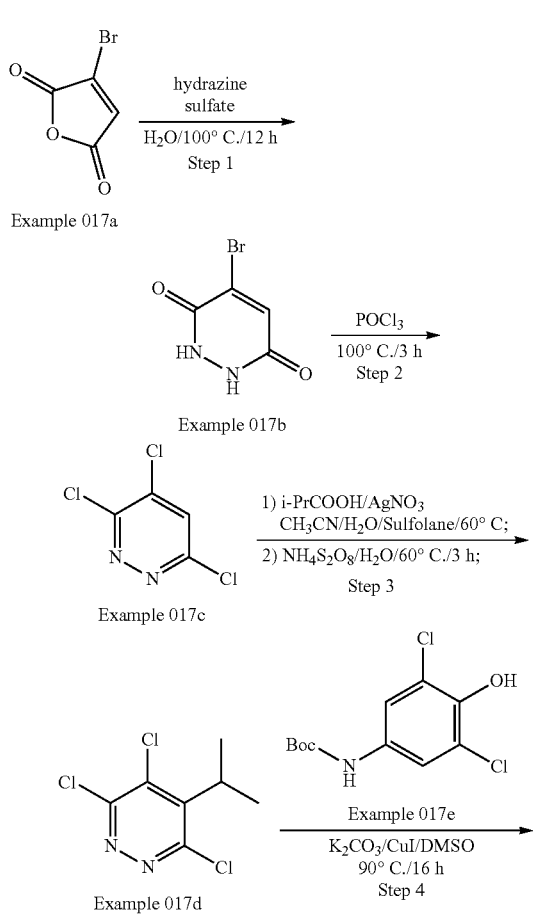

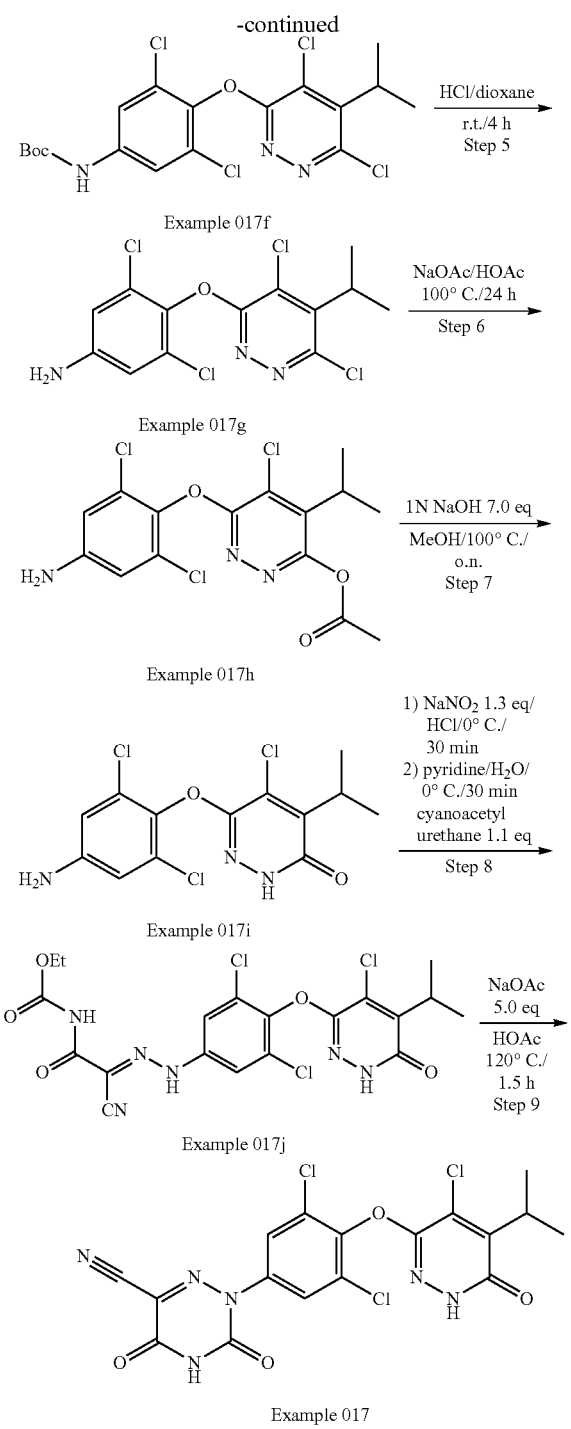

concentrated, which was purified by column chromatography (silica gel, Petroleum Ether/EtOAc=5/0~5/1) to afford Example 17c (6.6 g, yield 86%) as a yellow solid. LCMS [M+1]$^+$=182.9/184.9/186.9

Step 3: Example 17d

To a solution of Example 17c (2.59 g, 14.31 mmol) in CH$_3$CN/sulfolane/H$_2$O (8 mL/25 mL/20 mL) were added silver nitrate (1.22 g, 7.16 mol) and isobutyric acid (1.35 g, 14.31 mmol). Then sulphuric acid (con., 4 mL) in water (18 mL) was added at 50° C. in one portion. After addition, ammonium persulphate (4.34 g, 19.03 mmol) in water (20 mL) was added drop wised while maintaining the temperature between 50-60° C. over 3 h. After addition, the reaction mixture was cooled to 30° C., and basified with solid sodium carbonate to pH=9~10. The mixture was extracted with EtOAc (40 mL*3), and the combined organic phase was washed with brine (30 mL), dried over sodium sulphate, and filtered. The filtrate was concentrated in vacuo to give Example 17d (900 mg, yield 30%) as a light yellow solid. LCMS [M+1]$^+$=224.9/226.9

Step 4: Example 17f

A mixture of Example 017d (900 mg, 4 mmol), Example 17e (741.3 mg, 2.67 mmol) and potassium carbonate (686 mg, 5 mmol) in dimethyl sulfoxide (15 mL) was degassed, then copper iodide (253 mg, 1.33 mol) was added, and the reaction mixture was stirred at 90° C. for 16 h. The mixture was cooled to ambient temperature, and the mixture poured into ice water (50 mL), and extracted by EtOAc (50*3 mL). The combined organic layer was washed with brine (50 mL), dried over sodium sulphate, and filtered. The filtrate was concentrated in vacuo, and the residue was purified by column chromatography (silica gel, Petroleum Ether/EtOAc=5/1) to give Example 17f (600 mg, yield 62%) as a light brown solid.
LCMS [M+1−100]$^+$=365.9/367.8/369.8

Step 5: Example 17g

Example 17f (900 mg, 19.26 mmol) was dissolved in 4N HCl/dioxane (20 mL) and stirred at r.t. for 4 h. After completion, the mixture was concentrated in vacuo to give the crude product Example 17g (600 mg, crude yield 100%) as a yellow solid. LCMS [M+1]$^+$=365.8/367.9/369.8

Step 6: Example 17h

To a solution of Example 17g (1.0 g, 2.72 mmol) in HOAc (30 mL) was added NaOAc (782 mg, 9.54 mmol). The mixture was stirred at 100° C. for 24 h. The solvent was evaporated and the residue was diluted with H$_2$O (40 mL), which was made basic to pH=9 by the addition of 1N NaOH (aq.). The mixture was extracted with EtOAc (40 mL*2). The combined organic phase was washed with brine, dried over Na$_2$SO$_4$, filtrated and the filtrate was concentrated under reduced pressure to give Example 017b (crude), which was used in next step without purification. LCMS [M+1]$^+$=389.9

Step 7: Example 17i

To a solution of Example 17h (crude, 2.72 mmol) in MeOH (19 mL) was added 1N NaOH (19 mL). The mixture was stirred at 100° C. for 24 h. The reaction mixture was Step 1: Example 17b To a solution of hydrazine sulfate (6.3 g, 48.59 mmol) in water (90 mL) was added Example 17a (8.6 g, 48.59 mmol), which was heated to 100° C. for 12 h. After completion, the reaction mixture was filtered and dried to give Example 17b (8 g, yield 86%) as a white solid.

Step 2: Example 17c

Example 017b (8 g, 0.042 mol) in POCl$_3$ (80 mL) was heated to 100° C. for 3 h. The reaction mixture was then extracted with EtOAc (30 mL*2). The combined organic phase was washed with brine, dried over Na$_2$SO$_4$, filtrated and the filtrate was concentrated under reduced pressure. The residue was purified by column chromatography (silica gel, Petroleum Ether/EtOAc=2/1) to give Example 0171 (380 mg, yield 40%) as a yellow solid. LCMS [M+1]$^+$=347.9

$^1$H NMR (400 MHz, DMSO-d$_6$) δ 13.06 (s, 1H), 6.66 (s, 2H), 5.63 (s, 2H), 3.10-3.00 (m, 1H), 1.14 (d, J=6.8 Hz, 6H).

Step 8: Example 17j

A suspension of Example 17i (100 mg, 0.29 mmol) in con. HCl/H$_2$O (2 mL/4 mL) was cooled to 0° C. and then was treated with a solution of NaNO$_2$ (26 mg, 0.37 mmol) in H$_2$O (0.2 mL). The mixture was stirred at 0° C. for 0.5 h. The resulting mixture was added to a solution of N-cyanoacetyl urethane (49 mg, 0.32 mmol) in pyridine/H$_2$O (2 mL/6 mL) at 0° C. The suspension was stirred at 0° C. for 0.5 h. The reaction mixture was extracted with EtOAc (20 mL*2). The combined organic phase was washed with brine, dried over Na$_2$SO$_4$, filtrated and the filtrate was concentrated under reduced pressure to give Example 17j (crude) as a yellow solid, which was used in the next step without purification.

Step 9: Example 17

To a solution of Example 17j (crude, 0.29 mmol) in HOAc (3 mL) was added NaOAc (118 mg, 1.44 mmol). The mixture was stirred at 120° C. for 1.5 h. The solvent was evaporated. The residue was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.8 min (58% of B), V=80 mL/min, wavelength 214 nm) to give Example 17 (37 mg, yield 27%) as a yellow solid. LCMS [M+1]$^+$=468.8. $^1$H NMR (400 MHz, DMSO-d$_6$) δ 13.27 (s, 1H), 7.77 (s, 2H), 3.17-3.07 (m, 1H), 1.20 (d, J=7.2 Hz, 6H).

Example 19: General Procedure for Synthesis of Compound Example 19

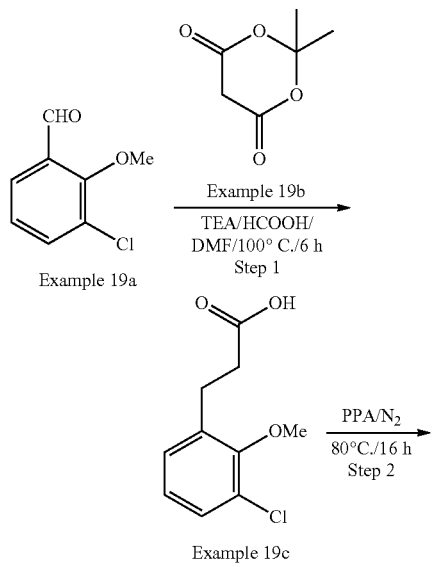

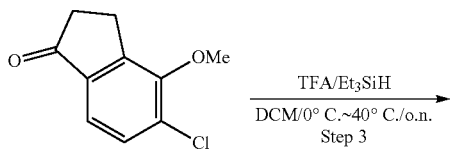

Example 19d

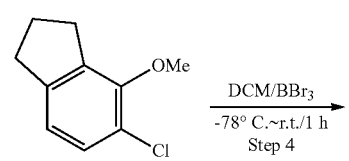

Example 19e

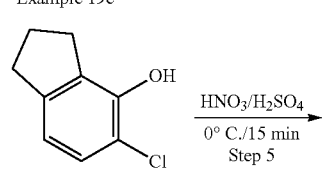

Example 19f

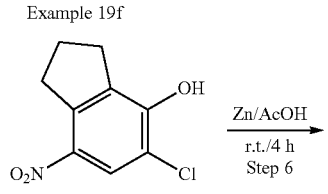

Example 19g

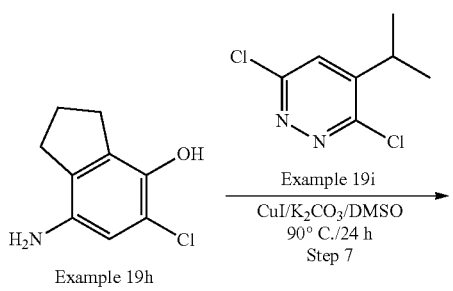

Example 19h

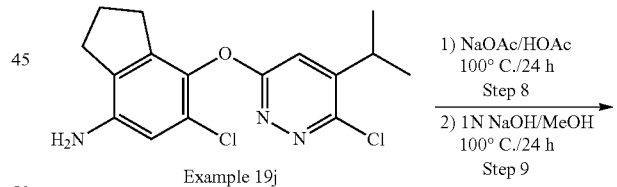

Example 19j

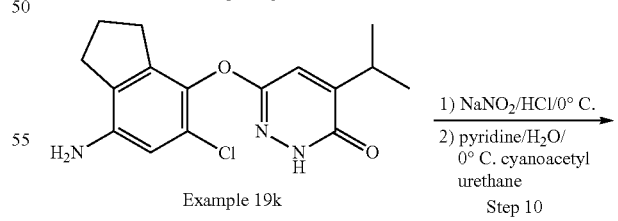

Example 19k

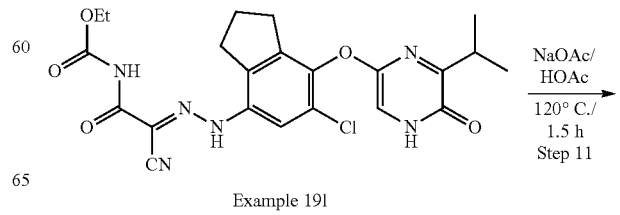

Example 19l

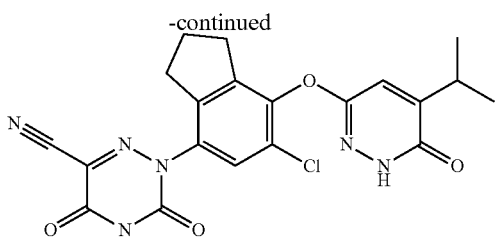

Example 19

Step 1: Example 19c

TEA (21.3 g, 154.8 mmol) was added slowly to HCOOH (22.7 g, 493 mmol) at 0° C. Then Example 19b (22.3 g, 154.8 mmol) was added, followed by a solution of Example 19a (24.0 g, 140.7 mmol) in DMF (500 mL). The reaction mixture was stirred at r.t. for 1 h and then stirred at 100° C. for 6 h. After cooling to room temperature, water was added and the reaction mixture was basified with NaOH (31V) to pH=9, exacted by EtOAc (200 mL*3), the aqueous layer was separated, and then acidified with saturated potassium hydrogen sulfate to pH-3. This aqueous layer was extracted with MTBE (200 mL), and the organic layer was separated, washed with brine, dried, filtered and concentrated under reduced pressure. The residue was purified by column chromatography (silica gel, Petroleum Ether/EtOAc=100/0~10/1) to afford Example 19c (15.3 g, yield 51%) as a white solid. LCMS [M+1]$^+$=215.6.

Step 2: Example 19d

A solution of Example 19c (15 g, 70.1 mmol) and PPA (166 g, 490 mmol) was stirred at 80° C. for 16 h. 200 mL of ice water was added to the mixture, and the resulting mixture was extracted with EtOAc (100 mL*3). The combined organic layer was washed with NaHCO$_3$ aqueous (pH=9) solution and brine, dried over Na$_2$SO$_4$, concentrated in vacuo. The residue was purified column chromatography (silica gel, Petroleum Ether/EtOAc=10/1~5/1) to afford Example 19d (10 g, yield 73%) as a yellow solid. LCMS [M+1]$^+$=197.6.
$^1$H NMR (400 MHz, CDCl$_3$) δ 7.44 (d, J=8.4 Hz, 1H), 7.39 (d, J=8.4 Hz, 1H), 3.96 (s, 3H), 3.18-3.14 (m, 2H), 2.73-2.69 (m, 2H).

Step 3: Example 19e

To a solution of Example 19d (1.9 g, 9.7 mmol) in DCM (20 mL) was added TFA (20 mL) at 0° C. Triethylsilane (5.7 g, 48.5 mmol) was added drop wise at the same temperature. The mixture was stirred at room temperature for 1 h and heated to 40° C. for overnight. The mixture was quenched by sat. NaHCO$_3$ at 0° C., extracted by EtOAc (100 mL*3) and the combine organic layer was washed with water, brine, dried over Na$_2$SO$_4$, concentrated under reduced pressure. The residue was purified by column chromatography (silica gel, Petroleum Ether 100%) to give Example 19e (1.35 g, yield 77%) as yellow oil. LCMS [M+1]$^+$=183.6.
$^1$H NMR (400 MHz, CDCl$_3$) δ 7.15 (d, J=7.8 Hz, 1H), 6.90 (d, J=7.8 Hz, 1H), 3.86 (s, 3H), 2.98 (t, J=7.4 Hz, 2H), 2.89 (t, J=7.4 Hz, 2H), 2.14-2.07 (m, 2H).

Step 4: Example 19f

To a solution of Example 19e (2.0 g, 11 mmol) in DCM (40 mL) was added BBr$_3$ (13.8 g, 55 mmol) dropwise at −78° C. At the end of addition, the reaction mixture was stirred at room temperature for 1 h. The mixture was quenched with ice-water, the organic phase was separated, and the aqueous layer was extracted with EtOAc (100 mL*3). The combine organic layer was washed with brine, dried over Na$_2$SO$_4$ and concentrated in vacuo. The residue was purified by column chromatography (silica gel, Petroleum Ether 100%) to afford Example 19f (1.6 g, yield 89%) as a white solid. LCMS [M+1]$^+$=169.6.

Step 5: Example 19g

To a solution of Example 19f (1.6 g, 9.4 mmol) in H$_2$SO$_4$ (50 mL) was added KNO$_3$ (1.0 g, 10.3 mmol) in H$_2$SO$_4$ (10 mL) at 0° C. The mixture was stirred at same temperature for 15 min. The reaction mixture was poured into ice-water and the resulting suspension was extracted with a portion of EtOAc (100 mL*3). The organic phase was washed with water, brine, and dried over Na$_2$SO$_4$. The organic layer was concentrated under reduced pressure, and the residue was purified by column chromatography (silica gel, Petroleum Ether/EtOAc=20/1~10/1) to afford Example 19g (1.3 g, yield 65%) as a yellow solid. LCMS [M+1]$^+$=214.6.

Step 6: Example 19h

To a solution of Example 19g (639 mg, 3 mmol) in AcOH (15 mL) was added zinc powder (975 mg, 15 mmol). The reaction mixture was stirred at room temperature for 4 h. The mixture was quenched by sat. NaHCO$_3$ at 0° C., and then extracted with EtOAc (100 mL*3). The organic phase was washed with water, brine, and dried over Na$_2$SO$_4$. The organic layer was concentrated under reduced pressure, which was purified by column chromatography (silica gel, Petroleum Ether/EtOAc=20/1~5/1) to afford Example 19h (500 mg, yield 90%) as a yellow solid. LCMS [M+1]$^+$=184.6.

Step 7: Example 19j

A solution of Example 19h (500 mg, 3.3 mmol) in anhydrous DMSO (15 mL) was treated with Example 19i (940 mg, 4.9 mmol) at room temperature under nitrogen, followed by anhydrous potassium carbonate (911 mg, 6.6 mmol) and copper(I) iodide (313.5 mg, 1.65 mmol). The reaction mixture was heated to 90° C. for 24 h. The reaction mixture was then cooled to room temperature and poured into water (50 mL). The solution was neutralized with hydrochloric acid (1N) to pH=8. The aqueous layer was diluted with EtOAc (50 mL), and the mixture was filtered over celite. The organic layer was separated and the celite was washed with EtOAc. The aqueous layer was extracted again with EtOAc (50 mL) and the combined organics were then washed with brine (40 mL), dried over magnesium sulfate, filtered and concentrated under vacuum. The residue was dissolved in DCM and purified by column chromatography (silica gel, Petroleum Ether/EtOAc=100/0~10/1) to afford Example 19j (740 mg, yield 80%) as a yellow solid. LCMS [M+1]$^+$=339.2.

Step 8 & Step 9: Example 19k

A mixture of glacial acetic acid (10 mL), sodium acetate (632 mg, 7.7 mmol) and Example 19j (740 mg, 2.2 mmol) was heated to 100° C. for 24 h. The reaction mixture was cooled to room temperature and concentrated in vacuo. The resulting residue was diluted with water (50 mL) and was basified with NaOH solution (UV) to pH=9. This suspension was extracted with EtOAc (50 mL), and the aqueous layer was acidified with concentrated hydrochloric acid to pH=5. The resulting mixture was extracted with EtOAc (50 mL), and the organic layers were combined, dried over magnesium sulfate, filtered and concentrated under vacuum. The resulting oil was diluted with methanol (10 mL) and treated with sodium hydroxide solution (1N, 10 mL, 10 mmol). The resulting mixture was heated to 120° C. for 24 h. After cooling to room temperature, the reaction mixture was concentrated under vacuum. The residue was diluted with water (50 mL) and extracted with EtOAc (50 mL). The organic layer was washed with hydrochloric acid solution (UV) to pH=5, followed by brine wash, which was then dried over magnesium sulfate, filtered and concentrated under vacuum. The residue was dissolved in DCM and purified by Prep-TLC (Petroleum ther/EtOAc=1/1) to afford Example 19k (92 mg, yield 13%) as a brown solid. LCMS [M+1]$^+$=320.8.

Step 10: Example 19l

A suspension of Example 19k (92 mg, 0.29 mmol) in H$_2$O (5 mL) was treated with conc. HCl (2 mL). The reaction mixture was cooled to 0° C. and then treated with a solution of NaNO$_2$ (25 mg, 0.37 mmol) in H$_2$O (1 mL). The reaction mixture was stirred at 0° C. for 30 min to give solution A. In a separated flask equipped with a magnetic stirred were added N-cyanoacetyl urethane (50 mg, 0.32 mmol), H$_2$O (8 mL) and pyridine (2 mL). The reaction mixture was cooled to 0° C. and the solution A was poured into the reaction mixture. An orange precipitate formed and the suspension was stirred at 0° C. for 30 min. The reaction mixture was extracted with EtOAc (10 mL*3) and the combined organic layer was washed with brine (10 mL), and concentrated to afford the crude product Example 19l (100 mg, yield 71%) as an orange solid, which was used for the next step without further purification. LCMS [M+1]$^+$=487.9.

Step 11: Example 19

A suspension of Example 19l (100 mg, 0.21 mmol) and NaOAc (85 mg, 1.05 mmol) in AcOH (5 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (60%/40%) 10 min and to A/B (30%/70%) 35 min, Rt of Peak: 23.1 min (58% of B), V=80 mL/min, wavelength 214 nm) to afford Example 19 (4.5 mg, yield 3%) as a white solid. LCMS [M+1]$^+$=441.8.
$^1$H NMR (400 MHz, DMSO-d$_6$) δ 13.10 (s, 1H), 12.11 (s, 1H), 7.45 (s, 1H), 7.34 (s, 1H), 3.03

Example 20: General Procedure for Synthesis of Compound Example 20

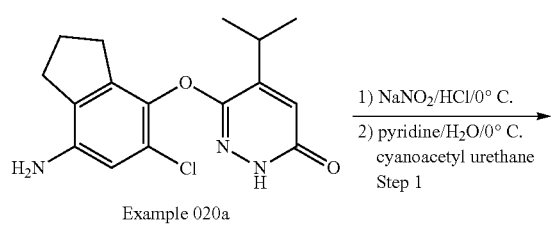

1) NaNO$_2$/HCl/0° C.
2) pyridine/H$_2$O/0° C. cyanoacetyl urethane
Step 1

Example 020a

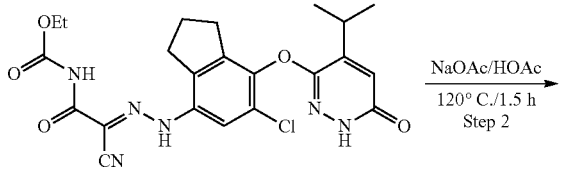

NaOAc/HOAc
120° C./1.5 h
Step 2

Example 020b

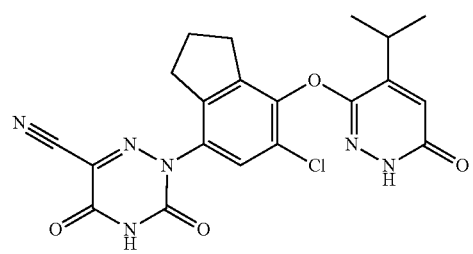

Example 020

Step 1: Example 20b

A suspension of Example 20a (78 mg, 025 mmol) in H$_2$O (5.0 mL) was treated with con. HCl (2 mL). The reaction mixture was cooled to 0° C. and then treated with a solution of NaNO$_2$ (22 mg, 0.31 mmol) in H$_2$O (1 mL) followed by a H$_2$O (1 mL) rinse. The reaction mixture was stirred at 0° C. for 30 min and a solution formed. In a separate flask equipped with a magnetic stirred were added N-cyanoacetyl urethane 43 mg, 0.275 mmol), H$_2$O (8 mL) and pyridine (2 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (10 mL*3) and the combined organic layer was washed with brine (10 mL), concentrated to afford the crude product Example 20b (92 mg, yield 71%) as an orange solid, which was used for the next step without further purification. LCMS [M+1]$^+$=487.9

Step 2: Example 20

A suspension of Example 20b (92 mg, 0.19 mmol) and NaOAc (78 mg, 0.95 mmol) in AcOH (5 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 20 (2.3 mg, yield 3%) as a white solid. LCMS [M+1]$^+$=441.8. $^1$H NMR (400 MHz, DMSO-d$_6$) δ 12.06 (s, 1H), 8.85 (s, 1H), 7.46 (s, 1H), 6.83 (s, 1H), 3.13-3.04 (m, 1H), 2.86-2.78 (m, 4H), 2.09-1.99 (m, 2H), 1.30 (d, J=6.8 Hz, 6H).

Example 22: General Procedure for Synthesis of Compound Example 22

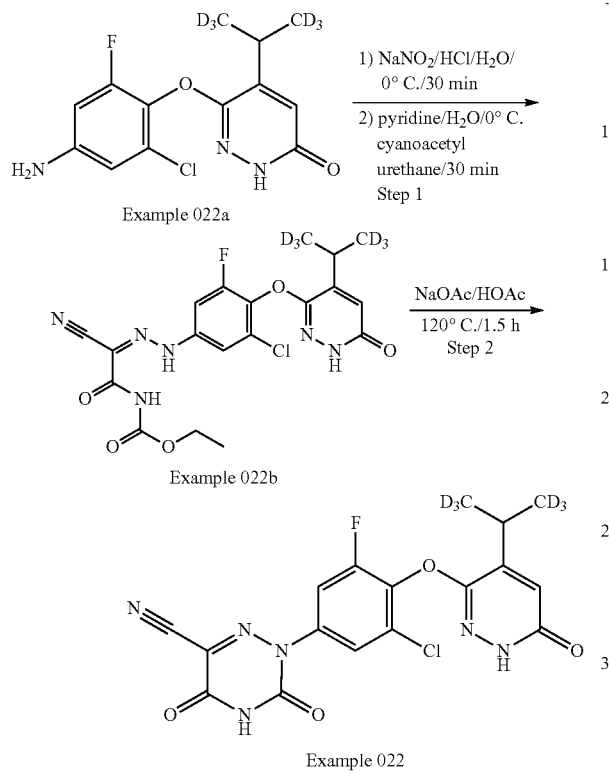

Step 1: Example 22b

A suspension of Example 22a (160 mg, 0.53 mmol) in H$_2$O (5.0 mL) was treated with con. HCl (2 mL). The reaction mixture was cooled to 0° C. and then treated with a solution of NaNO$_2$ (46 mg, 0.67 mmol) in H$_2$O (1 mL) followed by a H$_2$O (1 mL) rinse. The reaction mixture was stirred at 0° C. for 30 min and a solution formed. In a separate flask equipped with a magnetic stirred were added N-cyanoacetyl urethane (91 mg, 0.58 mmol), H$_2$O (8 mL) and pyridine (2 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (10 mL*3) and the combined organic layer was washed with brine (10 mL), concentrated to afford the crude product Example 22b (170 mg, yield 100%) as an orange solid, which was used for the next step without further purification. LCMS [M+1]$^+$=471.8

Step 7: Example 22

A suspension of Example 22b (170 mg, 0.34 mmol) and NaOAc (140 mg, 1.7 mmol) in AcOH (5 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 22 (31 mg, yield 21%) as a white solid. LCMS [M+1]$^+$=425.8. $^1$H NMR (400 MHz, DMSO-d$_6$) δ 13.25 (s, 1H), 12.20 (s, 1H), 7.67-7.64 (m, 2H), 6.87 (s, 1H), 3.05 (s, 1H).

Example 23: General Procedure for Synthesis of Compound Example 23

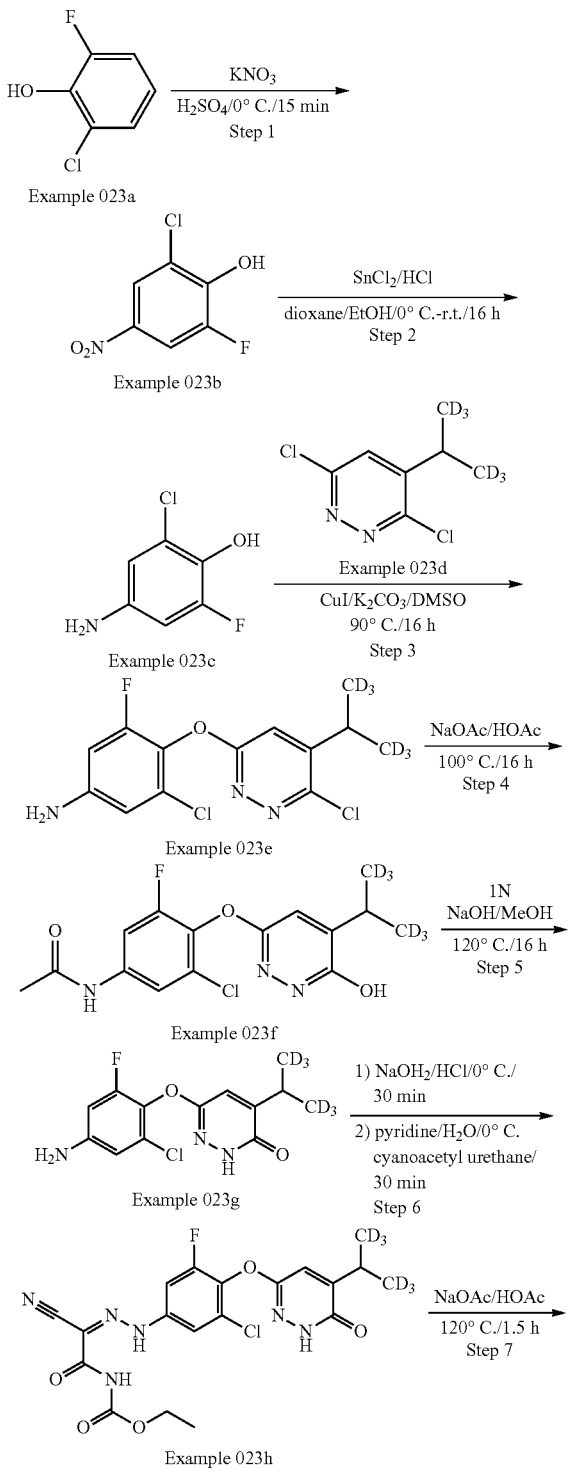

-continued

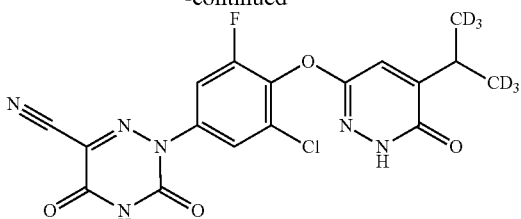

Example 023

Step 1: Example 23b

To a solution of Example 23a (5.0 g, 34.2 mmol) in $H_2SO_4$ (50 mL) was added $KNO_3$ (3.76 g, 37.6 mmol) in $H_2SO_4$ (10 mL) at 0° C. The mixture was stirred at same temperature for 15 min. The reaction mixture was poured into ice-water and the resulting suspension was extracted with a portion of EtOAc. The organic phase was washed with water, brine, dried over $Na_2SO_4$, and filtered. The filtrate was concentrated under reduced pressure, and the residue was purified by column chromatography (silica gel, Petroleum Ether/EtOAc=20/1~10/1) to afford Example 23b (4.0 g, yield 61%) as a yellow solid. LCMS $[M+1]^+=192.5$

Step 2: Example 23c

To a solution of Example 23b (3.5 g, 18.4 mmol) in 1,4-dioxane/EtOH (15 mL/30 mL) at 0° C. was dropwise added a solution of $SnCl_2 \cdot H_2O$ (18.7 g, 82.8 mmol) in con·HCl (18 mL). After addition, the mixture was allowed to stirred from 0° C. to room temperature for 16 h. Water (100 mL) was added, the mixture was adjusted by sat·$NaHCO_3$ (aq.) to pH=6~7, and then extracted by EtOAc (100 mL). The organic layer were dried over $Na_2SO_4$, filtered and concentrated, which was then treated with (DCM/MeOH=10/1, 100 mL*2), filtered and concentrated to give Example 23c (2.0 g, yield 67%) as a yellow solid.
LCMS $[M+1]^+=162.5$

Step 3: Example 23e

A solution of Example 23c (650 mg, 4.04 mmol) in anhydrous dimethyl sulfoxide (20 mL) under $N_2$ at room temperature were treated with Example 23d (1.2 mg, 6.1 mmol), anhydrous potassium carbonate (1.1 g, 8.08 mmol) and copper (I) iodide (384 mg, 2.02 mmol). The reaction mixture was heated to 90° C. for 16 h, and cooled to room temperature, which was then poured onto water (50 mL). The solution was brought to pH=8 with 1N aqueous hydrochloric acid solution. The aqueous layer was diluted with EtOAc (50 mL), and the two phases were filtered over celite. The organic layer was separated and the celite was washed with EtOAc. The aqueous layer was extracted again with EtOAc (50 mL). The combined organics were then washed with brine (40 mL), dried with magnesium sulfate, filtered and concentrated under vacuum. The residue was dissolved in DCM and purified by column chromatography (silica gel, Petroleum Ether/EtOAc=100/0~10/1) to afford Example 23e (990 mg, yield 76%) as a yellow solid. LCMS $[M+1]^+=323.1$

Step 4~5: Example 23g

A mixture of glacial acetic acid (15 mL), sodium acetate (890 mg, 10.85 mmol) and Example 23e (990 mg, 3.1 mmol) was heated to 100° C. for 16 h. The reaction mixture was cooled to room temperature and was concentrated. The residue was diluted with water (50 mL) and made basic to pH=9 by the addition of 1N aqueous sodium hydroxide solution. This suspension was extracted with EtOAc (50 mL). The aqueous layer was acidified to pH=5 by the addition of conc. HCl, and then extracted with EtOAc (50 mL). The organic layers were combined, dried with magnesium sulfate, filtered and concentrated under vacuum to give Example 23f (990 mg, yield 100%), which was then diluted with methanol (10 mL) and treated with 1N aqueous sodium hydroxide solution (10 mL, 10 mmol). The resulting mixture was heated to 120° C. for 16 h, cooled to room temperature and concentrated under vacuum. The residue was diluted with water (50 mL) and extracted with EtOAc (50 mL). The organic layer was washed with 1 N aqueous hydrochloric acid solution (to pH=5) and brine, dried with magnesium sulfate, filtered and concentrated under vacuum. The residue was dissolved in DCM and purified by column chromatography (silica gel, Petroleum Ether/EtOAc=3/1~1/1) to afford Example 23g (460 mg, yield 54%) as a brown solid. LCMS $[M+1]^+=304.7$

Step 6: Example 23h

A suspension of Example 23g (100 mg, 0.33 mmol) in $H_2O$ (5.0 mL) was treated with con. HCl (2 mL). The reaction mixture was cooled to 0° C. and then treated with a solution of $NaNO_2$ (29 mg, 0.42 mmol) in $H_2O$ (1 mL) followed by a $H_2O$ (1 mL) rinse. The reaction mixture was stirred at 0° C. for 30 min and a solution formed. In a separate flask equipped with a magnetic stirred were added N-cyanoacetyl urethane (57 mg, 0.36 mmol), $H_2O$ (8 mL) and pyridine (2 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (10 mL*3) and the combined organic layer was washed with brine (10 mL), concentrated to afford the crude product Example 23h (170 mg, crude) as an orange solid, which was used for the next step without further purification. LCMS $[M+1]^+=471.8$

Step 7: Example 23

A suspension of Example 023h (170 mg, 0.37 mmol) and NaOAc (153 mg, 1.86 mmol) in AcOH (5 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A ($H_2O$)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 23 (62 mg, yield 41%) as a white solid. LCMS $[M+1]^+=425.8$. $^1$H NMR (400 MHz, DMSO-$d_6$) δ 13.25 (s, 1H), 12.25 (s, 1H), 7.68-7.61 (m, 2H), 7.43 (s, 1H), 3.01 (s, 1H).

Example 24: General Procedure for Synthesis of Compound Example 24

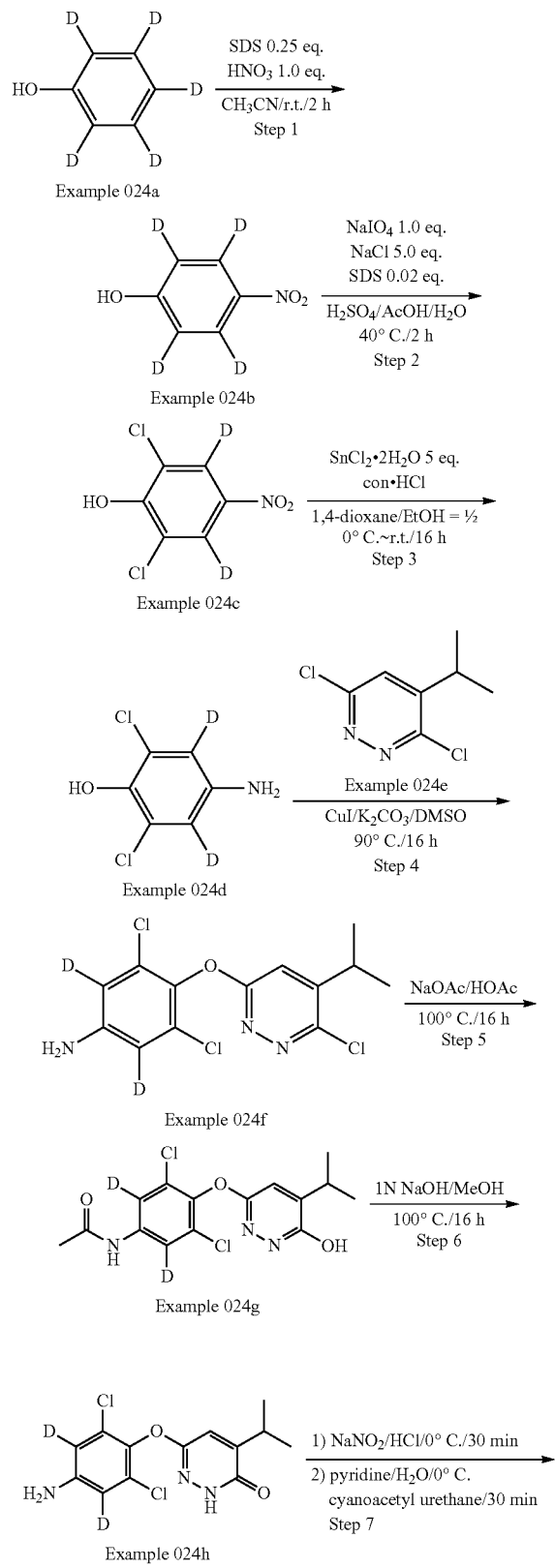

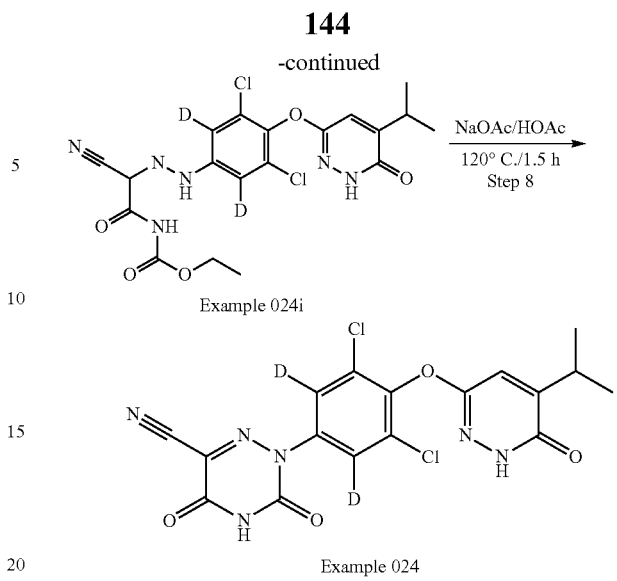

Step 1: Example 24b

HNO$_3$ (65%, 4.9 g, 50.5 mmol) was added to a solution of Example 24a (5.0 g, 50.5 mmol) in CH$_3$CN (200 mL), followed by the addition of SDS (3.6 g, 12.6 mmol) in CH$_3$CN (50 mL), and the reaction was stirred at room temperature for 2 h. The mixture was concentrated, diluted with DCM (200 mL), and washed with water. The organic layer was separated, dried over Na$_2$SO$_4$, filtered and concentrated, which was purified by column chromatography (silica gel, Petroleum Ether/EtOAc=5/1~3/1) to give Example 24b (3.1 g, yield 43%) as a orange solid. LCMS [M+1]$^+$=144.1

Step 2: Example 24c

SDS (97 mg, 0.38 mmol), NaCl (5.6 g, 97.2 mmol) and con·H$_2$SO$_4$ (2 mL) were added to a solution of Example 24b (2.8 g, 19.4 mmol) in AcOH (20 mL) at 40° C., followed by dropwise addition of aqueous solution of NaIO$_4$ (4.2 g, 19.4 mmol) in water (14 mL). The resulting mixture was stirred at 40° C. for 2 h and cooled to room temperature, which was then poured into water (100 mL), and extracted by EtOAc (100 mL*2). The combined organic layer were dried over Na$_2$SO$_4$, filtered and concentrated, which was purified by column chromatography (silica gel, Petroleum Ether/EtOAc=10/1) to give Example 24c (1.9 g, yield 46%) as a yellow solid. LCMS [M+1]$^+$=211.0

Step 3: Example 24d

To a solution of Example 24c (1.9 g, 13.2 mmol) in 1,4-dioxane/EtOH (22 mL/44 mL) at 0° C. was dropwise added a solution of SnCl$_2$·H$_2$O (13.4 g, 59.4 mmol) in con·HCl (5 mL). After addition, the mixture was allowed to stirred from 0° C. to room temperature for 16 h. Water (100 mL) was added, and the mixture was adjusted by sat·NaHCO$_3$ (aq.) to pH=6~7, and then extracted by EtOAc (100 mL). The organic layer were dried over Na$_2$SO$_4$, filtered and concentrated, and the residue was treated with (DCM/MeOH=10/1, 100 mL*2), filtered and concentrated to give Example 24c (1.35 g, yield 83%) as a black solid. LCMS [M+1]$^+$=181.0

Step 4: Example 24f

A solution of Example 24d (700 mg, 3.89 mmol) in anhydrous dimethyl sulfoxide (15 mL) under $N_2$ at room temperature were treated with Example 24e (891 mg, 4.67 mmol), anhydrous potassium carbonate (1.08 g, 7.77 mmol) and copper (I) iodide (149 mg, 0.78 mmol). The reaction mixture was heated to 90° C. for 16 h. The reaction mixture was then cooled to room temperature and poured onto water (50 mL). The solution was brought to pH=8 with 1N aqueous hydrochloric acid solution. The aqueous layer was diluted with EtOAc (50 mL), and the two phases were filtered over celite. The organic layer was separated and the celite was washed with EtOAc. The aqueous layer was extracted again with EtOAc (50 mL). The combined organics were then washed with brine (40 mL), dried with magnesium sulfate, filtered and concentrated under vacuum. The resulting residue was dissolved in DCM and purified by column chromatography (silica gel, Petroleum Ether/EtOAc=100/0~10/1) to afford Example 24f (570 mg, yield 44%) as a yellow solid. LCMS $[M+1]^+=335.6$

Step 5~6: Example 24h

A mixture of glacial acetic acid (10 mL), sodium acetate (490 mg, 5.97 mmol) and Example 24f (570 mg, 1.71 mmol) was heated to 100° C. for 16 h. The reaction mixture was cooled to room temperature and concentrated. The residue was diluted with water (50 mL) and made basic to pH=9 by the addition of 1N aqueous sodium hydroxide solution. This suspension was extracted with EtOAc (50 mL). The aqueous layer was acidified to pH=5 by the addition of concentrated hydrochloric acid, and then extracted with EtOAc (50 mL). The organic layers were combined, dried with magnesium sulfate, filtered and concentrated under vacuum to give Example 24g (570 mg, crude), which was diluted with methanol (10 mL) and treated with 1N aqueous sodium hydroxide solution (10 mL, 10 mmol). The reaction mixture was heated to 100° C. for 16 h. The reaction mixture was cooled to room temperature and concentrated under vacuum. The residue was diluted with water (50 mL) and extracted with EtOAc (50 mL). The organic layer was washed with 1N aqueous hydrochloric acid solution (to pH=5) and brine, dried with magnesium sulfate, filtered and concentrated under vacuum. The residue was dissolved in DCM and purified by column chromatography (silica gel, Petroleum Ether/EtOAc=3/1~1/1) to afford Example 24h (200 mg, yield 37%) as a brown solid. LCMS $[M+1]^+=317.6$. $^1$H NMR (400 MHz, $CDCl_3$) δ 9.35 (s, 1H), 7.08 (s, 1H), 3.25-3.18 (m, 1H), 1.28 (d, J=6.8 Hz, 6H).

Step 7: Example 24i

A suspension of Example 24h (100 mg, 0.32 mmol) in $H_2O$ (5.0 mL) was treated with con. HCl (2 mL). The reaction mixture was cooled to 0° C. and then treated with a solution of $NaNO_2$ (28 mg, 0.40 mmol) in $H_2O$ (1 mL) followed by a $H_2O$ (1 mL) rinse. The reaction mixture was stirred at 0° C. for 30 min and a solution formed. In a separate flask equipped with a magnetic stirred were added N-cyanoacetyl urethane (54.6 mg, 0.35 mmol), $H_2O$ (8 mL) and pyridine (2 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (10 mL*3) and the combined organic layer was washed with brine (10 mL), concentrated to afford the crude product Example 24i (110 mg, yield 72%) as an orange solid, which was used for the next step without further purification. LCMS $[M+1]^+=484.3$

Step 8: Example 24

A suspension of Example 24i (110 mg, 0.23 mmol) and NaOAc (95 mg, 1.15 mmol) in AcOH (5 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A ($H_2O$)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 24 (21.5 mg, yield 22%) as a white solid. LCMS $[M+1]^+=438.2$ $^1$H NMR (400 MHz, DMSO-$d_6$) δ 13.27 (s, 1H), 12.23 (s, 1H), 7.44 (s, 1H), 3.10-2.99 (m, 1H), 1.20 (d, J=6.8 Hz, 6H).

Example 25: General Procedure for Synthesis of Compound Example 25

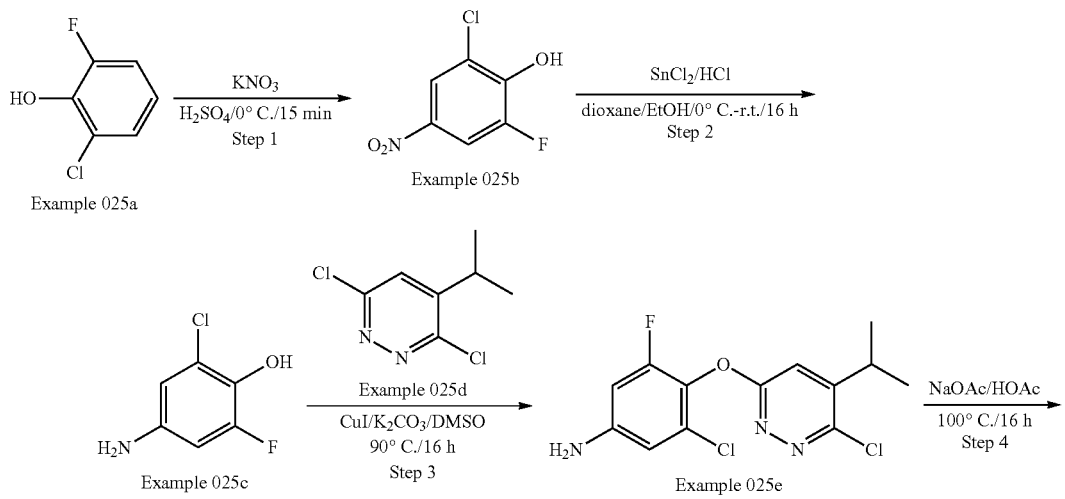

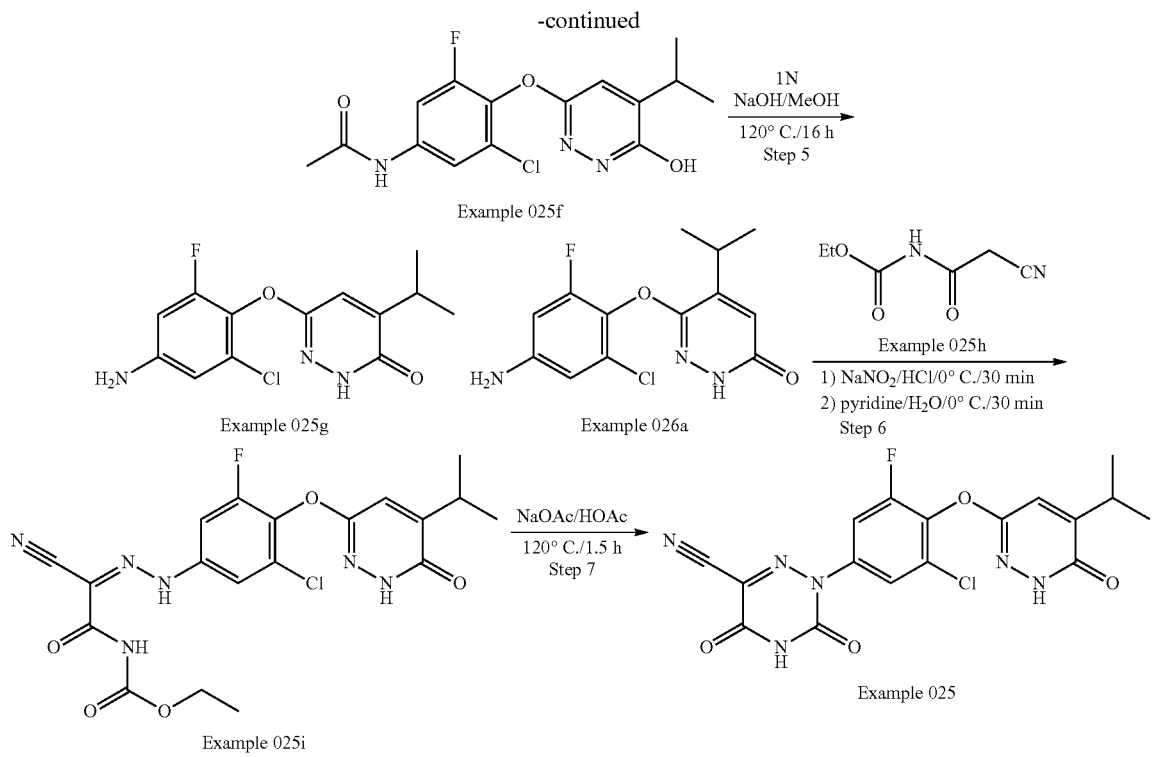

Step 1: Example 25b

To a solution of Example 25a (5.0 g, 34.2 mmol) in H₂SO₄ (30 mL) was added KNO₃ (3.5 g, 34.2 mmol) (dissolved in 30 mL of H₂SO₄) at 0° C. and stirred for 15 min. The reaction was poured to ice water and extracted by EtOAc (200 mL*3). The combined organic layer was dried over anhydrous sodium sulfate and concentrated under reduced pressure. The residue was purified by column chromatography (silica gel, Petroleum Ether/EtOAc=10/1) to give the product Example 25b (4.0 g, yield 61%) as a yellow solid. LCMS [M−18+1]⁺=174.1

Step 2: Example 25c

To a solution of Example 25b (3.5 g, 18.4 mmol) in dioxane/EtOH (15 mL/30 mL) was added SnCl₂ (15.7 g, 82.5 mmol, dissolved in concentrated HCl) at 0° C., which was stirred from 0° C. to r.t. for 16 h. The reaction was adjusted pH to 8 by NaHCO₃ aqueous solution and extracted by EtOAc (200 mL*3). The combined organic layer was dried over anhydrous sodium sulfate and concentrated to give the product Example 25c (2.0 g, crude yield 67%) as a yellow solid.

Step 3: Example 25e

To a solution of Example 25c (2.0 g, 12.4 mmol), Example 25d (2.8 g, 14.9 mmol), CuI (1.2 g, 6.2 mmol) and K₂CO₃ (3.4 g, 24.8 mol) in DMSO (40 mL) was stirred at 90° C. under N₂ for 16 h. The mixture was diluted with water and extracted by EtOAc (200 mL*3). The combined organic layer was dried over anhydrous sodium sulfate and concentrated under reduced pressure. The residue was purified by column chromatography (silica gel, Petroleum Ether/EtOAc=3/1) to give the product Example 25e (2.3 g, yield 58%) as brown oil.

Step 4: Example 25f

To a solution of Example 25e (2.3 g, 7.3 mmol) and NaOAc (2 g, 25.5 mmol) in HOAc (70 mL) was stirred at 100° C. for 16 h. The reaction was concentrated and adjusted pH to 10 by 1N NaOH aqueous solution. The mixture was extracted by EtOAc (200 mL*3) and concentrated to give the product Example 25f (2.6 g, crude) as brown oil.

Step 5: Example 25g

A solution of Example 25f (2.6 g, 7.3 mmol) in 1N NaOH (aq)/MeOH (70 mL/70 mL) was stirred at 120° C. for 16 h. The reaction was extracted by EtOAc (200 mL*3). The combined organic layer was dried over anhydrous sodium sulfate and concentrated under reduced pressure. The residue was purified by column chromatography (silica gel, Petroleum Ether/EtOAc=3/1) to give the product Example 25g (1.1 g, yield 52%) as a brown solid. LCMS [M+1]⁺=298.0

Step 6: Example 25i

To a solution of Example 25g (200 mg, 0.67 mmol) in 6N HCl (6 mL) was added NaNO₂ (58 mg, 0.84 mmol) (dissolved in 3 mL of H₂O) at 0° C. and stirred for 30 min. At the same time Example 25h (115 mg, 0.73 mmol) dissolved in pyridine/H₂O (2 mL/8 mL) was cooled to 0° C. and added Example 25g solution slowly, which was stirred for 30 min. The mixture was diluted with water, extracted by EtOAc (100 mL*2) and concentrated to give the product Example 25i (300 mg, yield 96%) as a yellow solid.

Step 7: Example 25

To a solution of Example 25i (300 mg, 0.64 mmol) and NaOAc (262 mg, 3.2 mmol) in HOAc (5 mL) was stirred at 120° C. for 1.5 h. The reaction was concentrated and purified by prep-HPLC (by Ultimate XB-C18, 50*250 mm, 10 μm, Mobile Phase: A (H₂O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the product Example 25 (60 mg, yield 22%) as a white solid. LCMS [M+1]⁺=419.0

NMR (400 MHz, DMSO-$d_6$) δ 13.25 (s, 1H), 12.25 (s, 1H), 7.67-7.62 (m, 2H), 7.43 (s, 1H), 3.08-3.01 (m, 1H), 1.19 (d, J=6.8 Hz, 6H).

Example 26: General Procedure for Synthesis of Compound Example 26

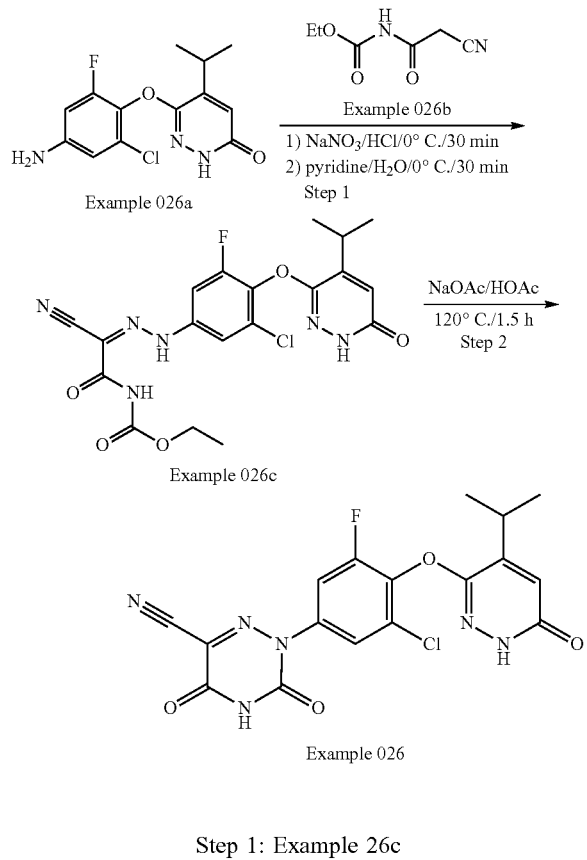

Step 1: Example 26c

To a solution of Example 26a (200 mg, 0.67 mmol) in 6N HCl (6 mL) was added NaNO₂ (58 mg, 0.84 mmol) (dissolved in 3 mL H₂O) at 0° C. and stirred for 30 min. At the same time Example 26b (115 mg, 0.73 mmol) dissolved in pyridine/H₂O (2 mL/8 mL) was cooled to 0° C. and added Example 26a solution slowly, stirring for 30 min. The mixture was diluted with water, extracted by EtOAc (100 mL*2) and concentrated to give the product Example 26c (300 mg, yield 96%) as a yellow solid. LCMS [M+1]⁺=465.1

Step 2: Example 26

A solution of Example 26c (300 mg, 0.64 mmol) and NaOAc (262 mg, 3.2 mmol) in HOAc (5 mL) was stirred at 120° C. for 1.5 h. The reaction was concentrated and purified by prep-HPLC (by Ultimate XB-C18, 50*250 mm, 10 μm, Mobile Phase: A (H₂O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the product Example 26 (49 mg, yield 18%) as a yellow solid. LCMS [M+1]⁺=419.0

¹H NMR (400 MHz, DMSO-$d_6$) δ 13.26 (s, 1H), 12.20 (m, 1H), 7.68-7.64 (m, 2H), 6.88 (s, 1H), 3.13-3.05 (m, 1H), 1.30 (d, J=6.8 Hz, 6H).

Example 27: General Procedure for Synthesis of Compound Example 27

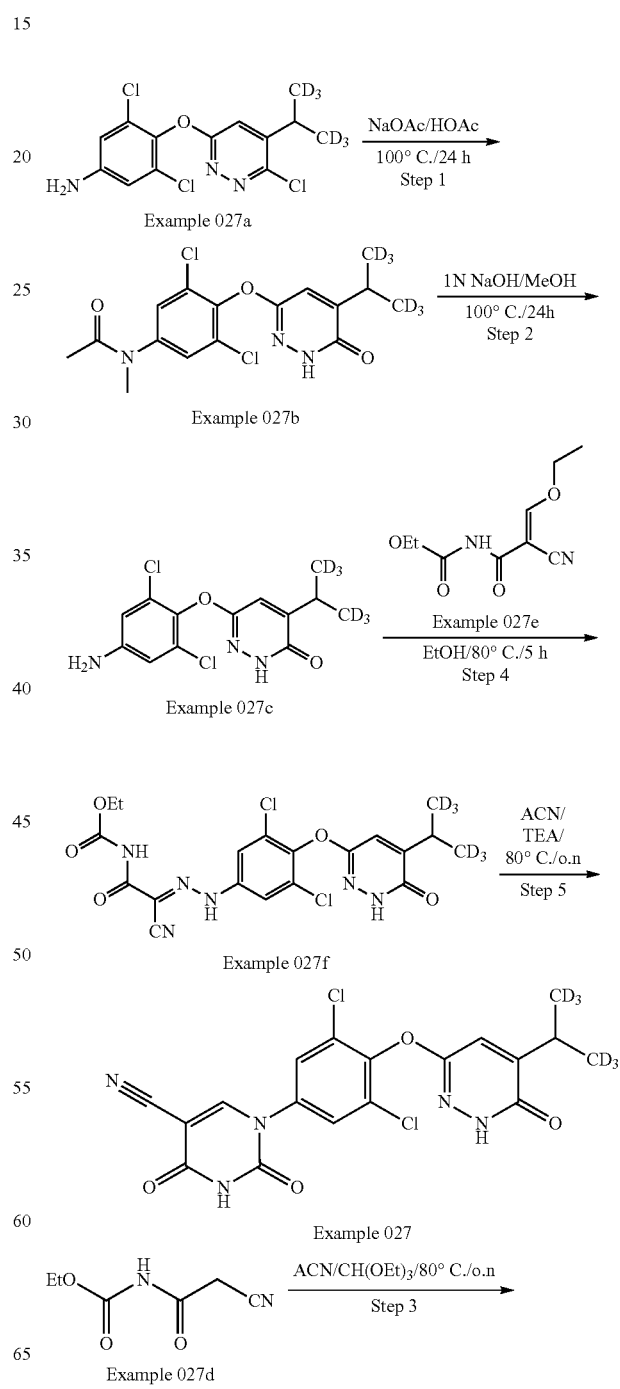

-continued

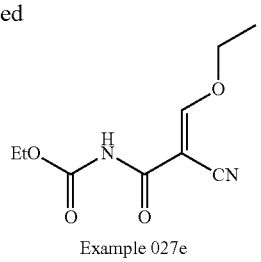

Example 027e

Step 1: Example 27b

A mixture of glacial acetic acid (20 ml), sodium acetate (3.1 g, 38 mmol) and Example 27a (2.5 g, 7.6 mmol) was heated to 100° C. for 24 h. The reaction mixture was cooled to room temperature, stirred for 2 days, and then concentrated. The residue was diluted with water (50 mL) and made basic to pH=9 by the addition of 1N aqueous sodium hydroxide solution. This suspension was extracted with EtOAc (50 mL). The aqueous layer was acidified to pH=5 by the addition of concentrated hydrochloric acid, which was then extracted with EtOAc (50 mL). The organic layers were combined, dried with magnesium sulfate, filtered and concentrated under vacuum to give Example 27b (12.8 g, crude) as black solid, which was used for the next step without purification. LCMS [M+1]$^+$=362.1

Step 2: Example 27c

The Example 27b (12.8 g crude, 35.5 mmol) was diluted with methanol (10 mL) and treated with 2N aqueous sodium hydroxide solution (100 mL). The reaction mixture was heated to 120° C. for 24 h. The reaction mixture was cooled to room temperature and concentrated under vacuum. The residue was diluted with water (50 mL) and extracted with EtOAc (50 mL). The organic layer was washed with 1 N aqueous hydrochloric acid solution (to pH=5), and brine, dried with magnesium sulfate, filtered and concentrated under vacuum. The residue was dissolved in DCM and purified by prep-TLC (Petroleum Ether/EtOAc=1/1) to afford Example 27c (2.0 g, yield 82% of two steps) as a white solid. LCMS [M+1]$^+$=320.1. $^1$H NMR (400 MHz, DMSO-d$_6$) δ 12.10 (s, 1H), 7.26 (d, J=1.0 Hz, 1H), 6.66 (s, 2H), 5.60 (s, 2H), 2.98 (s, 1H).

Step 3: Example 27e

To a solution of Example 27d (15.6 g, 100 mmol) in ACN (200 mL) was added CH(OEt)$_3$ (45.8 g, 300 mmol) under a nitrogen atmosphere. The mixture was heated to 80° C. for 4 h. After the reaction was complete, the reaction mixture was cooled down and concentrated under reduced pressure. The crude product was purified by column chromatography (silica gel, Petroleum Ether/EtOAc=10/1) to afford Example 27e (19.0 g, yield 90%) as a yellow solid. LCMS [M+1]$^+$=213.2

Step 4: Example 27f

Example 27c (100 mg, 0.32 mmol) and Example 27e (133 mg, 0.64 mmol) were dissolved in EtOH (4 mL) and stirred at 80° C. for 5 h. The mixture was concentrated under reduced pressure to give Example 27b (250 mg, crude) as a yellow solid which was used for the next step without purification.

Step 5: Example 27

Example 27f (250 mg crude, 0.51 mmol) and TEA (100 mg, 1.0 mmol) were dissolved in ACN (5 mL). The mixture was heated at 80° C. for overnight. The mixture was concentrated under reduced pressure and purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give Example 27 (1.5 mg, yield 1% for 2 steps) as a white solid. LCMS [M+1]$^+$=440.1. $^1$H NMR (400 MHz, DMSO-d$_6$) δ 12.22 (s, 1H), 8.62 (s, 1H), 7.78 (s, 2H), 7.42 (d, J=1.2 Hz, 1H), 3.01 (s, 1H).

Example 28: General Procedure for Synthesis of Compound Example 28

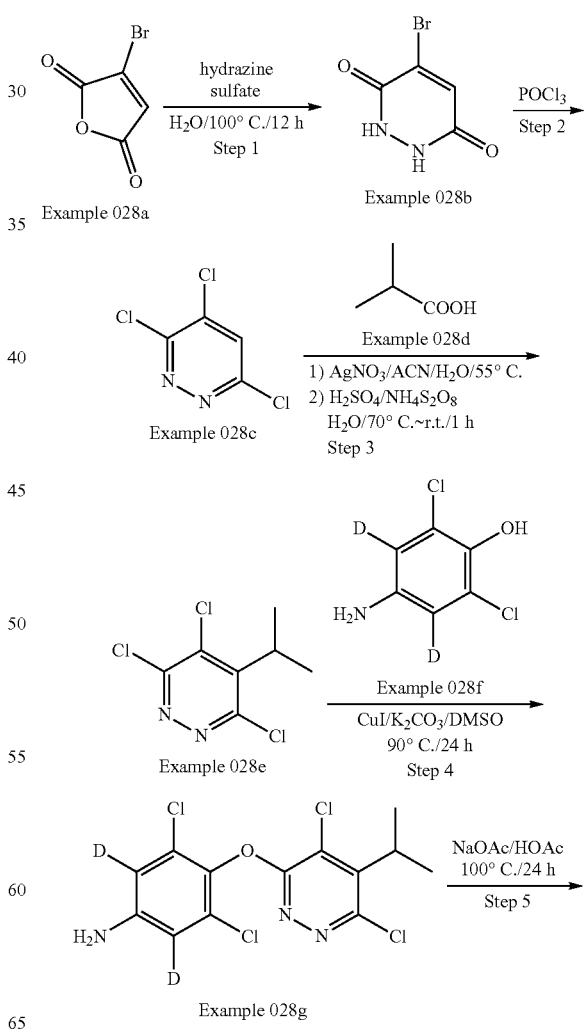

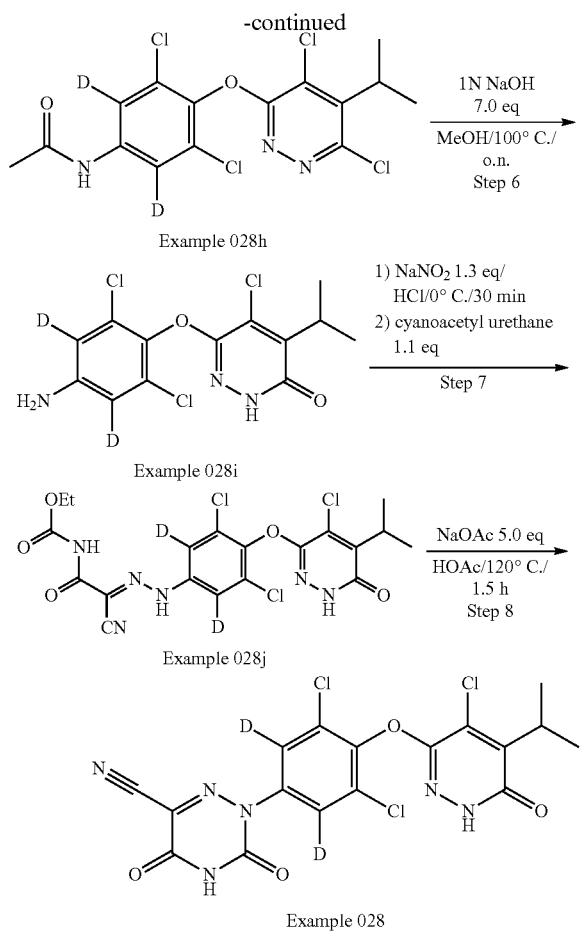

Step 1: Example 28b

To a solution of hydrazine sulfate (6.3 g, 48.59 mmol) in water (90 mL) was added Example 28a (8.6 g, 48.59 mmol), which was heated to reflux for 18 h. The mixture was filtered and dried to give Example 28b (8.0 g, yield 86%) as a white solid.

Step 2: Example 28c

Example 28b (8.0 g, 0.042 mol) in POCl$_3$ (80 mL) was heated to 100° C. for 3 h. The mixture was concentrated, and the residue was purified by column chromatography (silica gel, Petroleum Ether/EtOAc=1/0~5/1) to afford Example 28c (6.6 g, yield 86%) as a yellow solid. LCMS [M+1]$^+$=182.9/184.9/186.9

Step 3: Example 28e

A solution of Example 28c (6.6 g, 0.036 mol) in water (100 mL), was treated with isobutyric acid (9.5 g, 0.11 mol) at room temperature, followed by silver nitrate (4.3 g, 0.025 mol). The reaction mixture was heated to 55° C., and a solution of concentrated sulfuric acid (23.3 g, 0.24 mol) in water (100 mL) was added in one portion, followed a solution of ammonium persulfate (44.3 g, 0.19 mol) in water (100 mL). The reaction mixture was heated to 70° C. for 30 min and then cooled to room temperature and stirred for 2 h. The mixture was extracted with EtOAc (100 mL*2), and the combined organic phase was a washed with water, brine, dried over Na$_2$SO$_4$, and filtered. The filtrate was concentrated under vacuum, and the residue was purified by column chromatography (silica gel, Petroleum Ether/EtOAc=10/1~5/1) to afford Example 28e (4.5 g, yield 55%) as yellow oil. LCMS [M+1]$^+$=225.0/227.0

Step 4: Example 28g

A solution of Example 28e (750 mg, 3.33 mmol) in anhydrous dimethyl sulfoxide (10 mL) under nitrogen at room temperature were treated with Example 28f (500 mg, 2.78 mmol), anhydrous potassium carbonate (767 mg, 5.56 mmol) and copper (I) iodide (54 mg, 0.28 mmol). The reaction mixture was heated to 90° C. for 24 h. The reaction mixture was then cooled to room temperature and poured into water (50 mL), which was extracted with EtOAc (50 mL*2). The combined organic layer was washed with brine (40 mL), dried over Na$_2$SO$_4$, and filtered. The filtrate was concentrated under vacuum, and the residue was purified by column chromatography (silica gel, Petroleum Ether/EtOAc=100/0~5/1) to afford Example 28g (410 mg, yield 40%) as a yellow solid. LCMS [M+1]$^+$=368.0/370.0

Step 5: Example 28h

To a solution of Example 28g (410 mg, 1.11 mmol) in HOAc (10 mL) was added NaOAc (319 mg, 3.89 mmol). The mixture was stirred at 100° C. overnight and then concentrated. The residue was diluted with H$_2$O (40 mL) and made basic to pH=9 by the addition of 1N NaOH. The mixture was extracted with EtOAc (40 mL*2). The combined organic phase was washed with brine, dried over Na$_2$SO$_4$, filtered and the filtrate was concentrated under reduced pressure to give Example 28h (430 mg, yield 100%), which was used in next step without further purification. LCMS [M+1]$^+$=392.0

Step 6: Example 28i

To a solution of Example 28h (430 mg, 1.1 mmol) in MeOH (3 mL) was added 1N NaOH (10 mL). The mixture was stirred at 100° C. overnight. The reaction mixture was extracted with EtOAc (30 mL*2). The combined organic phase was washed with brine, dried over Na$_2$SO$_4$, filtrated and the filtrate was concentrated under reduced pressure. The residue was purified by column chromatography (silica gel, Petroleum Ether/EtOAc=2/1) to give Example 28i (210 mg, yield 54%) as a yellow solid. LCMS [M+1]$^+$=350.0

Step 7: Example 28j

A suspension of Example 28i (85 mg, 0.24 mmol) in con·HCl/H$_2$O (2 mL/4 mL) was cooled to 0° C. and then treated with a solution of NaNO$_2$ (21 mg, 0.31 mmol) in H$_2$O (0.3 mL). The mixture was stirred at 0° C. for 0.5 h. The resulting mixture was added to a solution of cyanoacetyl urethane (41 mg, 0.26 mmol) in pyridine/H$_2$O (2 mL/6 mL) at 0° C. The suspension was stirred at 0° C. for 0.5 h. The reaction mixture was extracted with EtOAc (20 mL*2). The combined organic phase was washed with brine, dried over Na$_2$SO$_4$, filtrated and the filtrate was concentrated under reduced pressure to give Example 28j (85 mg, yield 68%) as a yellow solid, which was used in next step.

Step 8: Example 28

To a solution of Example 28j (92 mg, 0.18 mmol) in HOAc (1 mL) was added NaOAc (73 mg, 0.89 mmol). The mixture was stirred at 120° C. for 0.5 h and then concentrated. The residue was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give Example 28 (28 mg, yield 29%) as a yellow solid.

LCMS [M+1]$^+$=471.0/473.0. NMR (400 MHz, DMSO-d$_6$) δ 13.27 (s, 1H), 7.78 (s, 1H), 3.15-3.10 (m, 1H), 1.20 (d, J=6.8 Hz, 6H).

Example 29: General Procedure for Synthesis of Compound Example 29

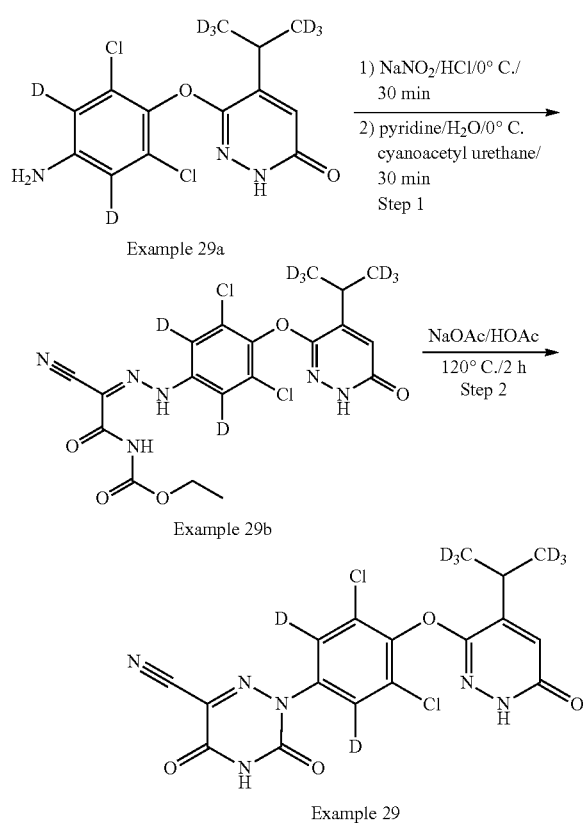

Step 1: Example 29b

A suspension of Example 29a (100 mg, 0.31 mmol) in H$_2$O (5 mL) was treated with con·HCl (2.5 mL). The reaction mixture was cooled to 0° C. and then treated with a solution of NaNO$_2$ (27 mg, 0.39 mmol) in H$_2$O (1 mL) under the surface of the reaction mixture. The reaction mixture was stirred at 0° C. for 30 min and a solution formed. In a separate flask equipped with a magnetic stirred were added N-cyanoacetyl urethane (53 mg, 0.34 mmol), H$_2$O (8 mL) and pyridine (2.5 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (30 mL*2) and the combined organic layers were washed with brine (20 mL), concentrated to afford the crude product Example 29b (145 mg, yield 96%) as a brown solid, which was used for the next step without further purification. LCMS [M+1]$^+$=489.0

Step 2: Example 29

A suspension of Example 29b (145 mg, 0.30 mmol) and NaOAc (122 mg, 1.48 mmol) in AcOH (5 mL) was heated to 120° C. and stirred for 2 h. The reaction mixture was cooled to room temperature and concentrated in reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the desired product Example 29 (15.1 mg, yield 12%, D=91.0% by HNMR) as a white solid. LCMS [M+1]$^+$=443.0. $^1$H NMR (400 MHz, DMSO-d$_6$) δ 13.26 (s, 1H), 12.18 (s, 1H), 6.88 (s, 1H), 3.06 (s, 1H).

Example 30: General Procedure for Synthesis of Compound Example 30

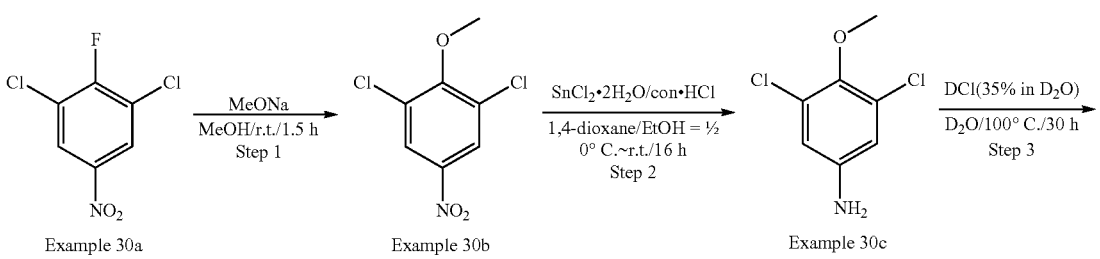

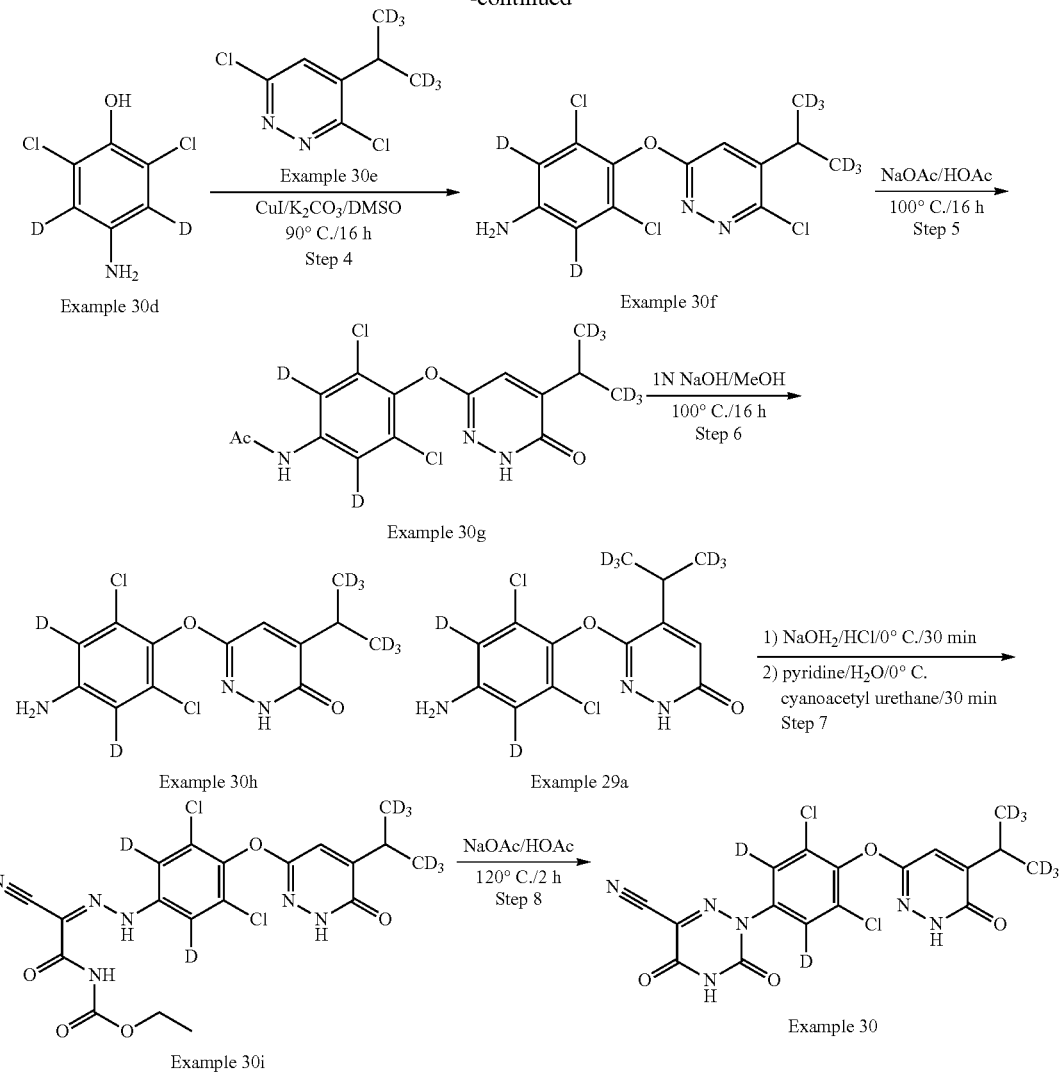

Step 1: Example 30b

A mixture of Example 30a (2.1 g, 10 mmol) in MeOH (25 mL) was slowly added NaOMe (810 mg, 15 mmol) at 0° C. The reaction mixture was stirred at r.t. for 1.5 h. Water (50 mL) was added, and the mixture was extracted with EtOAc (100 mL*2). The combined organic layers were washed by brine (50 mL), separated, dried over $Na_2SO_4$ and filtered. The solvent was removed in reduced pressure to give the desired product Example 30b (2.18 g, yield 98%) as a white solid. $^1$H NMR (400 MHz, $CDCl_3$) δ 8.21 (s, 2H), 4.01 (s, 3H).

Step 2: Example 30c

To a solution of Example 30b (2.18 g, 9.8 mmol) in 1,4-dioxane/EtOH (15 mL/30 mL) at 0° C. was slowly added a solution of $SnCl_2 \cdot 2H_2O$ (5.5 g, 24.5 mmol) in con·HCl (2 mL). The mixture was stirred from 0° C. to r.t. for 16 h. The reaction was re-cooled to 0° C., carefully neutralized with aqueous $NaHCO_3$ solution, and filtered. The solid was washed by MeOH and the filtrate was extracted with EtOAc (50 mL*3). The combined organic layers were dried over $Na_2SO_4$, filtered and concentrated, which was purified by column chromatography (silica gel, Petroleum Ether/EtOAc=88/12) to give the desired product Example 30c (1.7 g, yield 90%) as a yellowish solid. LCMS [M+1]$^+$=192.0

Step 3: Example 30d

To a solution of Example 30c (1.0 g, 5.21 mmol) in $D_2O$ (10 mL) was added DCl (20 mL, 35% in $D_2O$). The reaction mixture was stirred at 100° C. for 30 h. The mixture was concentrated in reduced pressure to give the crude desired product Example 30d (1.0 g, yield 100%, D>98% by HNMR) as a brown solid, which was used for the next step directly. LCMS [M+1]$^+$=180.0 $^1$H NMR (400 MHz, MeOD) δ 3.91 (s, 3H).

Step 4: Example 30f

A solution of Example 30d (609 mg, 3.38 mmol) in anhydrous DMSO (9 mL) at room temperature were treated with Example 30e (700 mg, 3.55 mmol), anhydrous potassium carbonate (1.2 g, 8.46 mmol) and copper (I) iodide (130 mg, 0.68 mmol). The reaction mixture was heated to 90° C. for 16 h under nitrogen atmosphere. The reaction mixture was then cooled to room temperature and poured into water (50 mL). The solution was brought to pH=8 with 1N aqueous hydrochloric acid solution. The aqueous layer was extracted with EtOAc (50 mL*3), The combined organics were then washed with brine (100 mL), dried over $Na_2SO_4$, filtered and concentrated under vacuum. The resulting residue was purified by column chromatography (silica gel, 14% EtOAc in Petroleum Ether) to afford the desired product Example 30f (566 mg, yield 49%) as brown oil. LCMS $[M+1]^+$=340.1

Step 5: Example 30g

A mixture of glacial acetic acid (15 mL), sodium acetate (478 mg, 5.83 mmol) and Example 30f (566 mg, 1.66 mmol) was heated to 100° C. for 16 h. The reaction mixture was cooled to room temperature, and then concentrated. The residue was diluted with water (50 mL) and made basic to pH=9 by the addition of 1N aqueous sodium hydroxide solution. This suspension was extracted with EtOAc (50 mL*3). The organic layers were combined, dried over $Na_2SO_4$, filtered and concentrated under vacuum to give the desired product Example 30g (582 mg, yield 96%) as a gray solid. LCMS $[M+1]^+$=364.1

Step 6: Example 30h

Example 30g (582 mg, 1.60 mmol) was diluted with methanol (30 mL) and treated with 1N aqueous sodium hydroxide solution (30 mL). The reaction mixture was heated to 100° C. for 16 h. The reaction mixture was cooled to room temperature and concentrated under vacuum. The residue was diluted with water (50 mL) and extracted with EtOAc (50 mL*2). The organic layer was washed with 1 N aqueous hydrochloric acid solution and brine, dried over $Na_2SO_4$, filtered and concentrated. The residue was purified by column chromatography (silica gel, Petroleum Ether/EtOAc=70/30) to afford the desired product Example 30h (240 mg, yield 47%) & (silica gel, Petroleum Ether/EtOAc=64/36) to afford Example 29a (100 mg, yield 20%) both as a gray solid. LCMS $[M+1]^+$=322.0 Example 30h: $^1$H NMR (400 MHz, DMSO-$d_6$) δ 12.10 (s, 1H), 7.25 (d, J=1.2 Hz, 1H), 5.59 (s, 2H), 2.98 (s, 1H). Example 29a: $^1$H NMR (400 MHz, DMSO-$d_6$) δ 12.05 (s, 1H), 6.77 (s, 1H), 5.60 (s, 2H), 3.00 (s, 1H).

Step 7: Example 30i

A suspension of Example 30h (120 mg, 037 mmol) in $H_2O$ (5 mL) was treated with con. HCl (2.5 mL). The reaction mixture was cooled to 0° C. and then treated with a solution of $NaNO_2$ (33 mg, 0.47 mmol) in $H_2O$ (1 mL). The reaction mixture was stirred at 0° C. for 30 min and a solution formed. In a separate flask equipped with a magnetic stirred were added N-cyanoacetyl urethane (64 mg, 0.41 mmol), $H_2O$ (8 mL) and pyridine (2.5 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (30 mL*2) and the combined organic layer was washed with brine (10 mL), concentrated to afford the crude product Example 30i (149 mg, yield 82%) as a brown solid, which was used for the next step without further purification. LCMS $[M+1]^+$=489.0

Step 8: Example 30

A suspension of Example 30i (149 mg, 0.30 mmol) and NaOAc (125 mg, 1.52 mmol) in AcOH (5 mL) was heated to 120° C. and stirred for 2 h. The reaction mixture was cooled to room temperature and concentrated under reduced pressure, which was purified by prep-HPLC (by Ultimate XB-C18, 50*250 mm, 10 μm, Mobile Phase: A ($H_2O$)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the desired product Example 30 (28.6 mg, yield 21%, D=90% by HNMR) as a white solid. LCMS $[M+1]^+$=443.0. NMR (400 MHz, DMSO-$d_6$) δ 13.26 (s, 1H), 12.22 (s, 1H), 7.43 (s, 1H), 3.01 (s, 1H).

Example 31: General Procedure for Synthesis of Compound Example 31

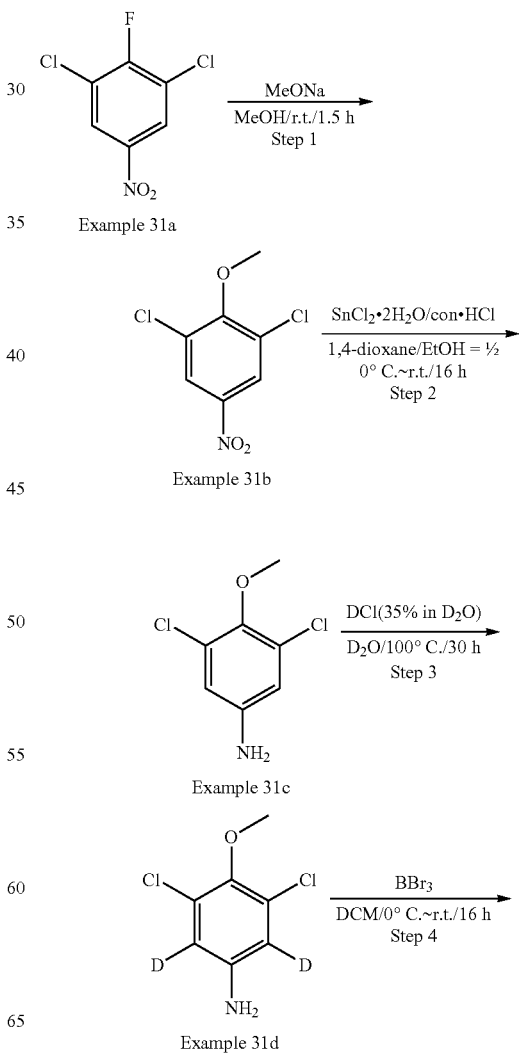

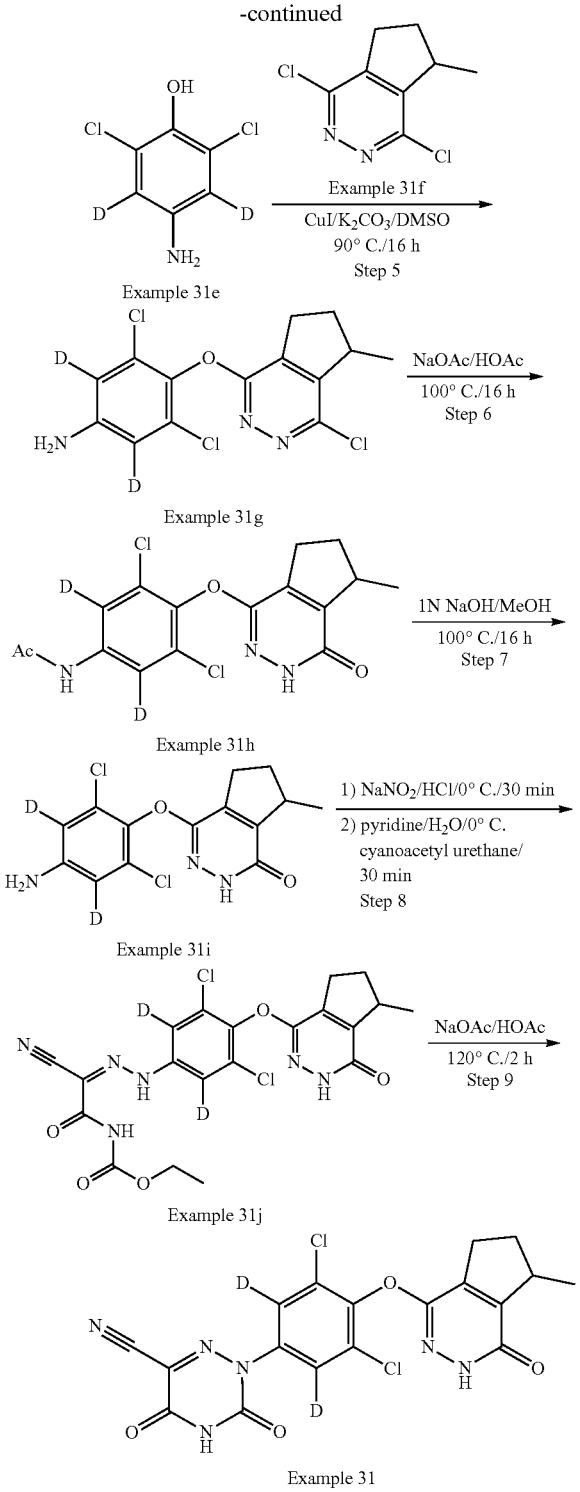

and filtered. The filtrate was concentrated under reduced pressure to give the desired product Example 31b (50 g, yield 95%) as a light yellow solid. $^1$H NMR (400 MHz, CDCl$_3$) δ 8.21 (s, 2H), 4.01 (s, 3H).

Step 2: Example 31c

To a solution of Example 31b (50 g, 225.2 mmol) in 1,4-dioxane/EtOH (250 mL/500 mL) at 0° C. was slowly added a solution of SnCl$_2$.2H$_2$O (152.7 g, 675.7 mmol) in con·HCl (50 mL). The mixture was stirred from 0° C. to r.t. for 16 h. The reaction was re-cooled to 0° C., carefully neutralized with aqueous NaHCO$_3$ solution, and filtered. The filtered cake was washed by MeOH (20 mL) and the filtrate extracted with EtOAc (1 L*3). The combined organic layers were dried over Na$_2$SO$_4$, filtered and concentrated to give the crude product, which was purified by column chromatography (silica gel, Petroleum Ether/EtOAc=10/1) to give the desired product Example 31c (38 g, yield 88%) as a yellowish solid. LCMS [M+1]$^+$=192.0

Step 3: Example 31d

To a solution of Example 31c (5.0 g, 26.0 mmol) in D$_2$O (40 mL) was added DCl (80 mL, 35% in D$_2$O). The reaction mixture was stirred at 100° C. for 30 h. The mixture was concentrated in reduced pressure to give the crude desired product Example 31d (5.0 g, yield 99%, D>=99%) as a pink solid which was used for the next step directly. LCMS [M+1]$^+$=194.0
$^1$H NMR (400 MHz, MeOD) δ 3.91 (s, 3H).

Step 4: Example 31e

To a solution of Example 31d (5.0 g, 25.8 mmol) in dry DCM (120 mL) was added BBr$_3$ (19.4 g, 77.3 mmol) slowly at 0° C. After addition, the reaction was allowed to stir from 0° C. to r.t. for 16 h. The reaction was cooled to 0° C., and quenched by adding MeOH dropwise until bubbling ceased. The mixture was concentrated, triturated with DCM/MeOH (v/v=15/1, 80 mL) and stirred at r.t. for 30 min, which was a then filtered and the solid was washed by DCM. The solid was collected and dried to give the desired product Example 31e (4.2 g, yield 91%) as a brick-red solid. LCMS [M+1]$^+$=180.0

Step 5: Example 31g

A solution of Example 31e (400 mg, 2.22 mmol) in anhydrous DMSO (6 mL) at room temperature were treated with Example 31f (541 mg, 2.67 mmol), anhydrous potassium carbonate (920 mg, 6.67 mmol) and copper (I) iodide (85 mg, 0.44 mmol). The reaction mixture was heated to 90° C. for 16 h under nitrogen atmosphere. The reaction mixture was then cooled to room temperature and poured into water (50 mL). The solution was brought to pH=8 with 1N aqueous hydrochloric acid solution. The aqueous layer was extracted with EtOAc (50 mL*3), The combined organics were then washed with brine (100 mL), dried over Na$_2$SO$_4$, filtered and concentrated under vacuum. The residue was purified by column chromatography (silica gel, 36% EtOAc in Petroleum Ether) to afford the desired product Example 31g (440 mg, yield 57%) as brown oil. LCMS [M+1]$^+$=346.0

Step 6: Example 31h

A mixture of glacial acetic acid (10 mL), sodium acetate (365 mg, 4.45 mmol) and Example 31g (440 mg, 1.27

Step 1: Example 31b

A mixture of Example 31a (50 g, 238.1 mmol) in MeOH (600 mL) was slowly added NaOMe (19.3 g, 357.1 mmol) at 0° C. The reaction mixture was stirred at r.t. for 1.5 h. Water (500 mL) was added, and the mixture was extracted with EtOAc (500 mL*3). The combined organic layers were washed by brine (500 mL), separated, dried over Na$_2$SO$_4$ mmol) was heated to 100° C. for 16 h. The reaction mixture was cooled to room temperature, and then concentrated. The residue was diluted with water (50 mL) and was made basic to pH=9 by the addition of 1N aqueous sodium hydroxide solution. This suspension was extracted with EtOAc (50 mL*3). The organic layer were combined, dried over Na$_2$SO$_4$, filtered and concentrated under vacuum to give the desired product Example 31h (450 mg, 95.7%) as brown oil. LCMS [M+1]$^+$=370.0

Step 7: Example 31i

Example 31h (450 mg, 1.22 mmol) was diluted with methanol (30 mL) and treated with 1N aqueous sodium hydroxide solution (30 mL). The reaction mixture was heated to 100° C. for 16 h. The reaction mixture was cooled to room temperature and concentrated under vacuum. The residue was diluted with water (50 mL) and extracted with EtOAc (50 mL*3). The organic layer was washed with 1 N aqueous hydrochloric acid solution and brine, dried over Na$_2$SO$_4$, filtered and concentrated. The residue was purified by column chromatography (silica gel, Petroleum Ether/EtOAc=70/30) to afford the desired product Example 31i (110 mg, yield 28%) as a yellow solid. LCMS [M+1]$^+$=328.0 $^1$H NMR (400 MHz, DMSO-d$_6$) δ 11.98 (s, 1H), 5.59 (s, 2H), 3.01-2.79 (m, 2H), 2.39-2.30 (m, 1H), 1.73-1.64 (m, 1H), 1.33-1.25 (m, 1H), 1.24 (d, J=6.8 Hz, 3H).

Step 8: Example 31j

A suspension of Example 31i (95 mg, 0.29 mmol) in H$_2$O (5 mL) was treated with con. HCl (2.5 mL). The reaction mixture was cooled to 0° C. and then treated with a solution of NaNO$_2$ (25.2 mg, 0.36 mmol) in H$_2$O (1 mL). The reaction mixture was stirred at 0° C. for 30 min and a solution formed. In a separate flask equipped with a magnetic stirred were added N-cyanoacetyl urethane (50 mg, 0.32 mmol), H$_2$O (8 mL) and pyridine (2.5 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (50 mL*2) and the combined organic layer was washed with brine (10 mL), concentrated to afford the crude product Example 31j (143 mg, yield 100%) as an orange solid, which was used for the next step without further purification. LCMS [M+1]$^+$=495.0

Step 9: Example 31

A suspension of Example 31j (143 mg, 0.29 mmol) and NaOAc (83 mg, 1.01 mmol) in AcOH (5 mL) was heated to 120° C. and stirred for 2 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the desired product Example 31 (24.2 mg, yield 19%, D=93% by HNMR) as a white solid. LCMS [M+1]$^+$=449.0. $^1$H NMR (400 MHz, DMSO-d$_6$) δ 13.27 (s, 1H), 12.11 (s, 1H), 3.11-3.01 (m, 1H), 2.96-2.88 (m, 1H), 2.43-2.33 (m, 1H), 1.76-1.71 (m, 1H), 1.27 (d, J=7.2 Hz, 3H), 1.21-1.17 (m, 1H).

Example 32: General Procedure for Synthesis of Compound Example 32

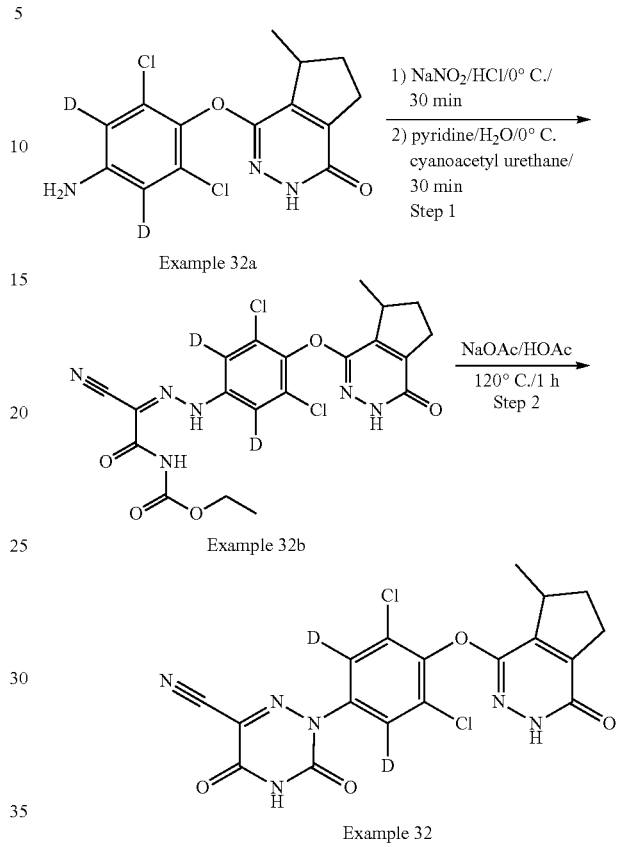

Step 1: Example 32b

A suspension of Example 32a (60 mg, 0.18 mmol) in H$_2$O (2 mL) was treated with con. HCl (1 mL). The reaction mixture was cooled to 0° C. and then treated with a solution of NaNO$_2$ (16 mg, 0.23 mmol) in H$_2$O (1 mL) under the surface of the reaction mixture. The reaction mixture was stirred at 0° C. for 30 min and a solution formed. In a separate flask equipped with a magnetic stirred were added N-cyanoacetyl urethane (31 mg, 0.20 mmol), H$_2$O (4 mL) and pyridine (1 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (30 mL*2) and the combined organic layers were washed with brine (20 mL), concentrated to afford the crude product Example 32b (90.5 mg, crude) as an orange solid, which was used for the next step without further purification. LCMS [M+1]$^+$=495.0

Step 2: Example 32

A suspension of Example 32b (90.5 mg, 0.18 mmol) and NaOAc (52.5 mg, 0.64 mmol) in AcOH (5 mL) was heated to 120° C. and stirred for 1 h. The reaction mixture was cooled to room temperature and concentrated in reduced pressure, which was purified by prep-HPLC (by Ultimate XB—C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the desired product Example 32 (18.1 mg, yield 22%, D=90% by HNMR) as a white solid. LCMS [M+1]$^+$=449.0. $^1$H NMR (400 MHz, DMSO-d$_6$) δ 12.12 (s, 1H), 7.43 (s, 1H), 3.52-3.46 (m, 1H), 2.90-2.81 (m, 1H), 2.76-2.68 (m, 1H), 2.43-2.33 (m, 1H), 1.79-1.71 (m, 1H), 1.37 (d, J=7.2 Hz, 3H).

Example 34: General Procedure for Synthesis of Compound Example 034

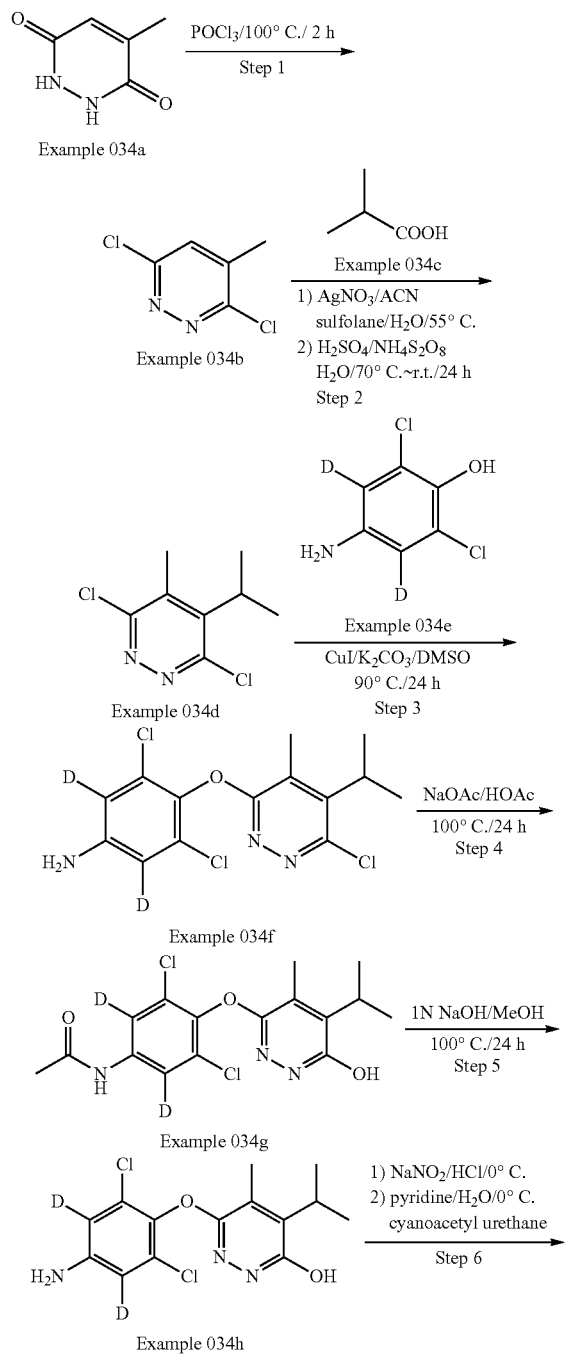

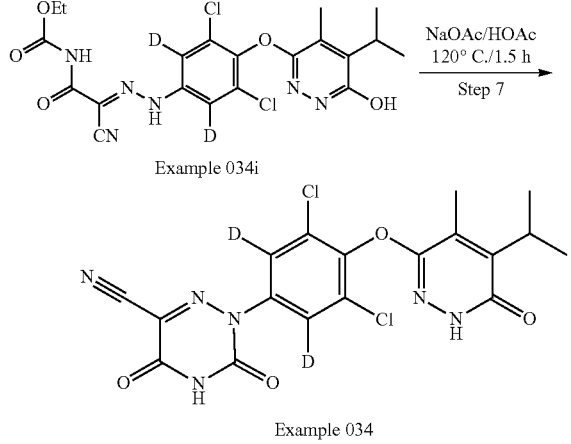

Step 1: Example 34b

Example 34a (6.0 g, 0.048 mol) in POCl$_3$ (40 mL) was heated to 100° C. for 3 h. The mixture was concentrated, and the residue was purified by column chromatography (silica gel, Petroleum Ether/EtOAc=1/0~5/1) to afford Example 34b (7.1 g, yield 91%) as a yellow solid. LCMS [M+1]$^+$=163.0

Step 2: Example 34d

A solution of Example 34b (6.8 g, 0.042 mol) in water (100 mL) was treated with isobutyric acid (11.0 g, 0.13 mol), followed by silver nitrate (5.0 g, 0.029 mol) at room temperature. The reaction mixture was heated to 55° C., and a solution of concentrated sulfuric acid (27.2 g, 0.28 mol) in water (100 mL) was added in one portion, followed by a solution of ammonium persulfate (51.7 g, 0.23 mol) in water (100 mL). The reaction mixture was heated to 70° C. for 30 min and then cooled to room temperature, stirring for 2 h. The reaction mixture was extracted with EtOAc (100 mL*2), and the combined organic phase was washed with water, brine, dried over Na$_2$SO$_4$, and filtered. The filtrate was concentrated under vacuum, and the residue was purified by column chromatography (silica gel, Petroleum Ether/EtOAc=10/1~5/1) to afford Example 34d (6.5 g, yield 76%) as yellow oil. LCMS [M+1]$^+$=205.0/207.0

Step 3: Example 34f

A solution of Example 34d (431 mg, 2.1 mmol) in anhydrous dimethyl sulfoxide (7 mL) under nitrogen at room temperature were treated with Example 34e (315 mg, 1.75 mmol), anhydrous potassium carbonate (483 mg, 3.5 mmol) and copper (I) iodide (35 mg, 0.18 mmol). The reaction mixture was heated to 90° C. for 24 h and then cooled to room temperature, which was poured into water (50 mL), and extracted with EtOAc (50 mL*2). The combined organic layer was washed with brine (40 mL), dried over Na$_2$SO$_4$, and filtered. The filtrate was concentrated under vacuum and the residue was purified by column chromatography (silica gel, Petroleum Ether/EtOAc=100/0~5/1) to afford Example 34f (160 mg, yield 22%) as a yellow solid. LCMS [M+1]$^+$=348.0/350.0

Step 4: Example 34g

To a solution of Example 34f (160 mg, 0.46 mmol) in HOAc (10 mL) was added NaOAc (132 mg, 1.61 mmol).

The mixture was stirred at 100° C. overnight and then concentrated. The residue was diluted with H₂O (40 mL) and made basic to pH=9 by the addition of 1N NaOH. The mixture was extracted with EtOAc (40 mL*2). The combined organic phase was washed with brine, dried over Na₂SO₄, filtrated and the filtrate was concentrated under reduced pressure to give Example 34g (50 mg, crude yield 29%), which was used in next step without further purification. LCMS [M+1]⁺=372.0

Step 5: Example 34h

To a solution of Example 34g (40 mg, 0.11 mmol) in MeOH (1 mL) was added 1N NaOH (3 mL). The mixture was stirred at 100° C. overnight. The reaction mixture was extracted with EtOAc (30 mL*2). The combined organic phase was washed with brine, dried over Na₂SO₄, filtrated and the filtrate was concentrated under reduced pressure to give Example 34h (50 mg, crude) as a yellow solid. LCMS [M+1]⁺=330.0

Step 6: Example 34i

A suspension of Example 34h (50 mg, 0.15 mmol) in con·HCl/H₂O (1 mL/2 mL) was cooled to 0° C. and then treated with a solution of NaNO₂ (13 mg, 0.19 mmol) in H₂O (0.5 mL). The mixture was stirred at 0° C. for 0.5 h. The resulting mixture was added to a solution of cyanoacetyl urethane (26 mg, 0.17 mmol) in pyridine/H₂O (1 mL/2 mL) at 0° C. The suspension was stirred at 0° C. for 0.5 h. The reaction mixture was extracted with EtOAc (20 mL*2). The combined organic phase was washed with brine, dried over Na₂SO₄, filtrated and the filtrate was concentrated under reduced pressure to give Example 34i (32 mg, crude yield 43%) as a yellow solid, which was used in next step without purification.

Step 7: Example 34

To a solution of Example 34i (32 mg, 0.064 mmol) in HOAc (0.3 mL) was added NaOAc (26 mg, 0.32 mmol). The mixture was stirred at 120° C. for 0.5 h and then concentrated. The residue was purified by prep-HPLC (by Ultimate XB-C18, 50*250 mm, 10 μm, Mobile Phase: A (H₂O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give Example 34 (3 mg, yield 10%) as a yellow solid. LCMS [M+1]⁺=452.0 ¹H NMR (400 MHz, DMSO-d₆) δ 2.33 (s, 3H), 2.31 (d, J=3.0 Hz, 1H), 1.30 (d, J=6.8 Hz, 6H).

Example 35: General Procedure for Synthesis of Compound Example 35

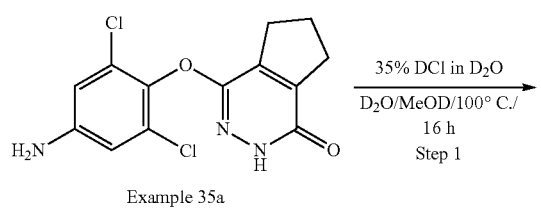

Example 35a

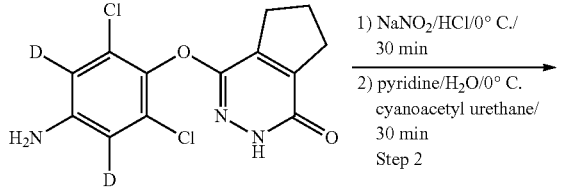

Example 35b

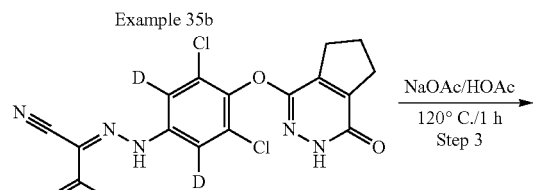

Example 35c

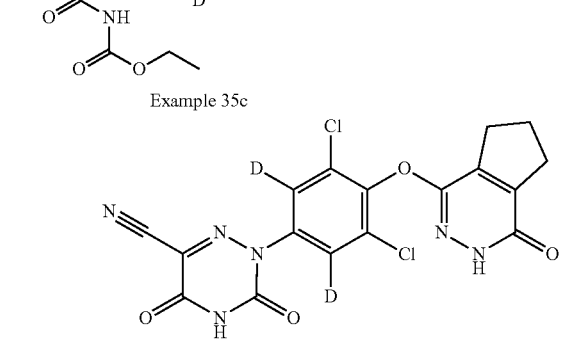

Example 35

Step 1: Example 35b

To a solution of Example 35a (157 mg, 0.5 mmol) in D₂O (1 mL) was added DCl (2 mL, 35% in D₂O) and MeOD (5 mL). The mixture was stirred at 100° C. for 16 h. The mixture was concentrated in reduced pressure to give the desired product Example 35b (158 mg, crude) as a yellow solid. LCMS [M+1]⁺=314.0. ¹H NMR (400 MHz, DMSO-d₆) δ 12.02 (s, 1H), 6.39 (s, 2H), 2.96 (t, J=7.6 Hz, 2H), 2.77 (t, J=7.6 Hz, 2H), 2.12 (p, J=7.4 Hz, 2H).

Step 2: Example 35c

A suspension of Example 35b (158 mg, 0.5 mmol) in H₂O (5 mL) was treated with con. HCl (2.5 mL). The reaction mixture was cooled to 0° C. and then treated with a solution of NaNO₂ (43.7 mg, 0.63 mmol) in H₂O (1 mL) under the surface of the reaction mixture. The reaction mixture was stirred at 0° C. for 30 min and a solution formed. In a separate flask equipped with a magnetic stirred were added N-cyanoacetyl urethane (86.4 mg, 0.55 mmol), H₂O (8 mL) and pyridine (2.5 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (50 mL*2) and the combined organic layers were washed with brine (30 mL), concentrated to afford the crude product Example 35c (240 mg, yield 99%) as a brown solid, which was used for the next step without further purification. LCMS [M+1]⁺=481.0

Step 3: Example 35

A suspension of Example 35c (240 mg, 0.50 mmol) and NaOAc (143 mg, 1.75 mmol) in AcOH (5 mL) was heated to 120° C. and stirred for 2 h. The reaction mixture was cooled to room temperature and concentrated in reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the desired product Example 35 (38.0 mg, yield 18%, D=96% by HNMR) as a white solid. LCMS [M+1]$^+$=435.0. $^1$H NMR (400 MHz, DMSO-d$_6$) δ 13.26 (s, 1H), 12.12 (s, 1H), 3.01 (t, J=7.6 Hz, 2H), 2.79 (t, J=7.6 Hz, 2H), 2.15 (p, J=7.6 Hz, 2H).

Example 38: General Procedure for Synthesis of Compound Example 38 then heated to 120° C. and stirred for 16 h. The reaction mixture was cooled to room temperature and concentrated under reduced pressure. The residue dissolved in H$_2$O (20 mL) and extracted with EtOAc (20 mL*2). The organic layer was concentrated and purified by column chromatography (silica gel, Petroleum Ether/EtOAc=5/1~1/1) to afford product Example 38c (137 mg, yield 48%) as a yellow solid. LCMS [M+1]$^+$=325.9

Step 3: Example 38d

Example 38c (135 mg) was further separated by chiral SFC to afford Example 38d (peak 1: 40.9 mg, yield 40%) as a white solid and Example 38e (peak 2: 92.1 mg, yield 70%) as a white solid. (The absolute structures were unknown, which were randomly assigned.) Chiral SFC conditions

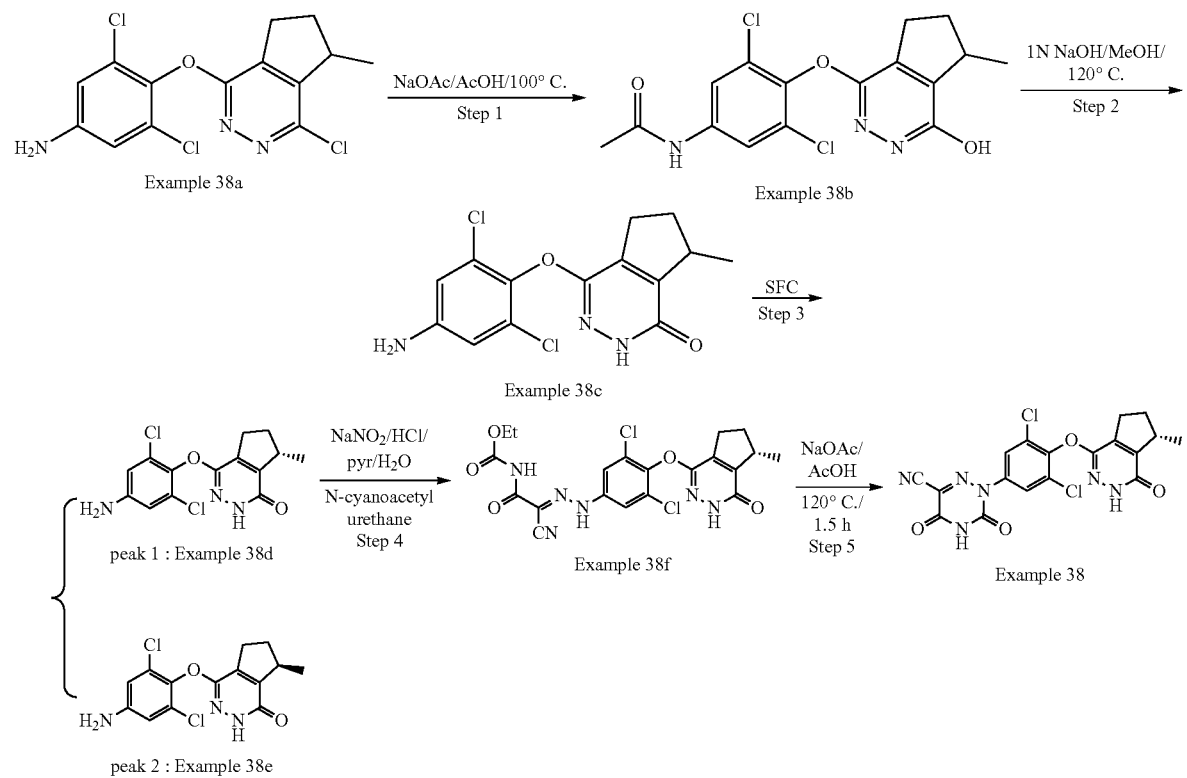

Step 1: Example 38b

A solution of Example 38a (313 mg, 0.91 mmol, example 15f) and NaOAc (261 mg, 3.18 mmol) in AcOH (8 mL) was heated to 100° C. and stirred for 16 h. The reaction mixture was cooled to room temperature and concentrated under reduced pressure. The residue dissolved in H$_2$O (20 mL) and made to basic pH=8 with sat·NaHCO$_3$ (30 mL), which was then extracted with EtOAc (20 mL*2). The aqueous layer was acidified with 6N HCl and extracted with EtOAc (20 mL). The combined organic layer was concentrated to afford the crude product Example 38b (320 mg, crude), which was used for the next step without further purification.

Step 2: Example 38c

To a solution of Example 38b (320 mg, 0.87 mmol) in MeOH (20 mL) was added 1N NaOH (20 mL), which was

| Column: | CHIRALPAK IC(IC00CD-TB016) |
|---|---|
| Column size: | 0.46 cm I.D. × 15 cm L |
| Injection: | 4.0 ul |
| Mobile phase: | Hexane/EtOH = 90/10(V/V) |
| Flow rate: | 1.0 ml/min |
| Wave length: | UV 214 nm |
| Temperature: | 35° C. |
| HPLC equipment: | Shimadzu LC-20AD    CP-HPLC-08 |

Step 4: Example 38f

To a solution of Example 38d (40.9 mg, 0.13 mmol) in H$_2$O (3 mL) was treated with conc. HCl (1.5 mL). The reaction mixture was cooled to 0° C. and then treated with a solution of NaNO$_2$ (11 mg, 0.16 mmol) in H$_2$O (1 mL) under the surface of the reaction mixture followed by a H$_2$O (1 mL) rinse. The reaction mixture was stirred at 0° C. for 30 min to give solution A. In a separate flask equipped with a magnetic stirred were added N-cyanoacetyl urethane (21.5 mg, 0.14 mmol), H$_2$O (5 mL) and pyridine (1.5 mL). The reaction mixture was cooled to 0° C. and the solution A was poured into the second reaction mixture. An orange precipitate formed and the suspension was stirred at 0° C. for 30 min. The reaction mixture was extracted with EtOAc (20 mL*3) and the combined organic layer was washed with brine (20 mL), concentrated to afford the crude product Example 38f (53 mg, crude) as an orange solid, which was used for the next step without further purification. LCMS [M+1]$^+$=492.9.

Step 5: Example 38

A suspension of Example 38f (53 mg, 0.11 mmol) and NaOAc (44 mg, 0.54 mmol) in AcOH (3 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 38 (19.7 mg, yield 40%) as a white solid. LCMS [M+1]$^+$=446.9. $^1$H NMR (400 MHz, DMSO-d$_6$) δ 13.26 (s, 1H), 12.09 (s, 1H), 7.76 (s, 2H), 3.06-2.97 (m, 1H), 2.95-2.86 (m, 1H), 2.40-2.34 (m, 1H), 1.76-1.66 (m, 1H), 1.24 (d, J=6.8 Hz, 3H).

Example 41: General Procedure for Synthesis of Compound Example 41

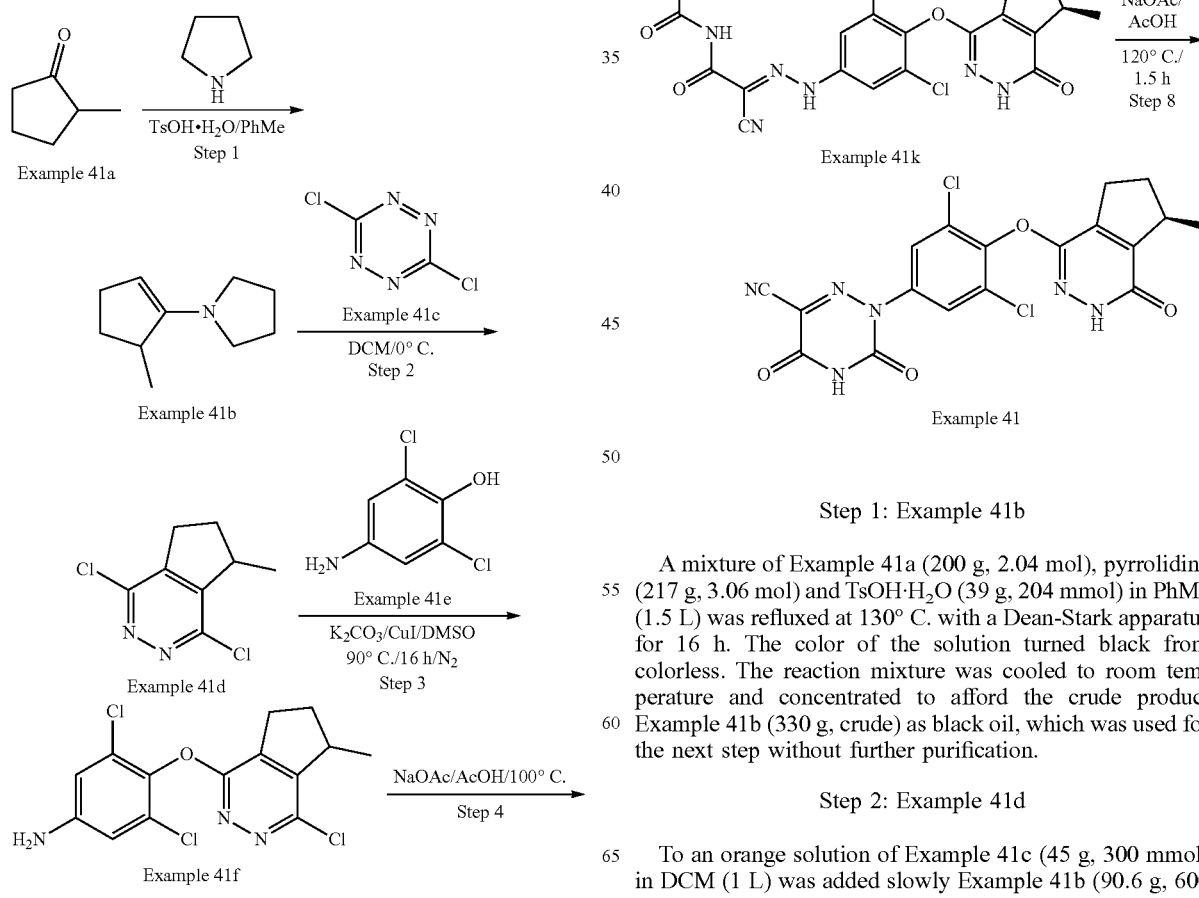

Step 1: Example 41b

A mixture of Example 41a (200 g, 2.04 mol), pyrrolidine (217 g, 3.06 mol) and TsOH·H$_2$O (39 g, 204 mmol) in PhMe (1.5 L) was refluxed at 130° C. with a Dean-Stark apparatus for 16 h. The color of the solution turned black from colorless. The reaction mixture was cooled to room temperature and concentrated to afford the crude product Example 41b (330 g, crude) as black oil, which was used for the next step without further purification.

Step 2: Example 41d

To an orange solution of Example 41c (45 g, 300 mmol) in DCM (1 L) was added slowly Example 41b (90.6 g, 600 mmol) at 0° C. with ice-bath. After addition, the reaction mixture was stirred for 15 min at 0° C. The color of the reaction turned brown. 1N HCl (100 mL) was added slowly at 0° C., and the resulting mixture was extracted with EtOAc (200 mL*3). The organic layer was washed with water, brine, dried over Na$_2$SO$_4$, and concentrated under reduced pressure. The residue was purified by column chromatography (silica gel, Petroleum Ether/EtOAc=1/0~10/1) to afford the product Example 41d (34.3 g, yield 57%) as a yellow solid. LCMS [M+1]$^+$=202.9.

Step 3: Example 41f

To a suspension of Example 41d (39.2 g, 193.1 mmol), Example 41e (29 g, 148.5 mmol) and K$_2$CO$_3$ (41 g, 297 mmol) in DMSO (400 mL) was added CuI (14 g, 74.3 mmol) at room temperature under N$_2$. The reaction mixture was heated to 90° C. and stirred for 16 h under N$_2$. The reaction mixture was cooled to room temperature, poured into ice-water (300 mL), diluted with EtOAc (300 mL), and filtered. The filtered cake was washed with EtOAc/H$_2$O (V/V=1/1, 500 mL*3). The organic was separated and the aqueous layer was extracted with EtOAc (500 mL*2). The combined organic layer was washed with brine (500 mL*2), dried over Na$_2$SO$_4$, filtered and concentrated. The residue was purified by column chromatography (silica gel, Petroleum Ether/EtOAc=10/1~3/1) to afford the product Example 41f (50.5 g, yield 90%) as a brown solid. LCMS [M+1]$^+$=345.9.

Step 4: Example 41g

A solution of Example 41f (50.5 g, 146.8 mmol) and NaOAc (60 g, 734 mmol) in AcOH (500 mL) was heated to 100° C. and stirred for 16 h. The reaction mixture was cooled to room temperature and concentrated under reduced pressure. The residue dissolved in H$_2$O (100 mL), made to basic pH=8 with sat·NaHCO$_3$ (300 mL), and extracted with EtOAc (200 mL*2). The aqueous layer was acidified with 6N HCl and extracted with EtOAc (200 mL). The combined organic layer was concentrated to afford the crude product Example 41g (51 g, crude), which was used for the next step without further purification.

Step 5: Example 41h

To a solution of Example 41g (51 g, 135.9 mmol) in MeOH (250 mL) was added 1N NaOH (250 mL) and then the reaction mixture was heated to 120° C. and stirred for 16 h. The reaction mixture was cooled to room temperature and concentrated under reduced pressure. The residue was dissolved in H$_2$O (200 mL) and extracted with EtOAc (200 mL*2). The organic layer was concentrated and purified by column chromatography (Petroleum Ether/EtOAc=5/1~1/1) to afford Example 41h (8.9 g, yield 21%) as a yellow solid. LCMS [M+1]$^+$=325.9

Step 6: Example 41i

Example 41h (8.9 g) was further separated by chiral SFC to afford Example 41i (peak 1: 3.57 g, yield 40%) as a white solid and Example 41j (peak 2: 3.65 g, yield 41%) as a white solid. (The absolute structures were unknown, which were randomly assigned.) Chiral SFC condition

| Column: | CHIRALPAK IC-3(IC3SCA-TG001) |
|---|---|
| Column size: | 0.46 cm I.D. × 15 cm L |
| Injection: | 0.5 ul |
| Mobile phase: | (M100NH4OH0.1)/CO2 = 30/70(V/V) |
| Flow rate: | 2.0 ml/min |
| Wave length: | UV 214 nm |
| Temperature: | 35° C. |

Step 7: Example 41k

To a solution of Example 41j (3.65 g, 11.3 mmol) in H$_2$O (140 mL) was treated with conc. HCl (70 mL). The reaction mixture was cooled to 0° C. and then treated with a solution of NaNO$_2$ (1.1 g, 14.7 mmol) in H$_2$O (10 mL) followed by a H$_2$O (10 mL) rinse. The reaction mixture was stirred at 0° C. for 30 min to give solution A. In a separate flask equipped with a magnetic stirred were added N-cyanoacetyl urethane (2 g, 12.4 mmol), H$_2$O (220 mL) and pyridine (70 mL). The reaction mixture was cooled to 0° C. and the solution A was poured into the second reaction mixture. An orange precipitate formed and the suspension was stirred at 0° C. for 30 min. The reaction mixture was extracted with EtOAc (200 mL*3) and the combined organic layer was washed with brine (200 mL), concentrated to afford the crude product Example 41k (5.5 g, crude) as an orange solid, which was used for the next step without further purification. LCMS [M+1]$^+$=492.9.

Step 8: Example 41

A suspension of Example 41k (5.5 g, 11.2 mmol) and NaOAc (4.6 g, 56 mmol) in AcOH (50 mL) was heated to 120° C. and stirred for 1.5 h. The reaction mixture was cooled to room temperature and concentrated under reduced pressure, which was purified by column chromatography (silica gel, Petroleum Ether/EtOAc=1/0~0/1, then EtOAc/MeOH=1/0~10/1, 0.1% TEA) to afford Example 41 (1.27 g, yield 50% for 2 steps) as a white solid. LCMS [M+1]$^+$=446.9. $^1$H NMR (400 MHz, DMSO-d$_6$) δ 13.26 (s, 1H), 12.09 (s, 1H), 7.77 (s, 2H), 3.06-2.99 (m, 1H), 2.94-2.85 (m, 1H), 2.42-2.32 (m, 1H), 1.76-1.67 (m, 1H), 1.24 (d, J=7.2 Hz, 3H).

Example 42: General Procedure for Synthesis of Compound Example 42

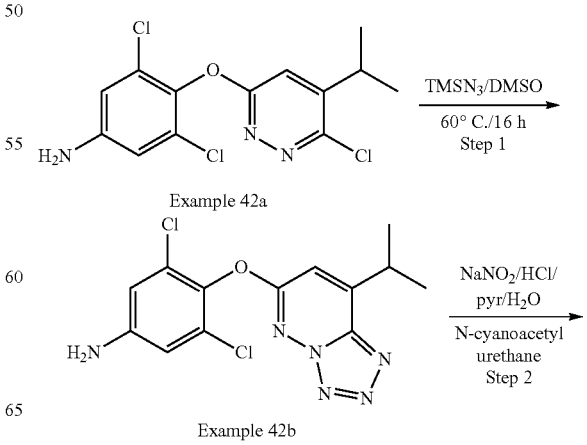

Example 42a

Example 42b

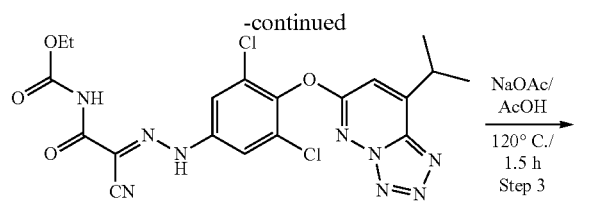

Example 42c

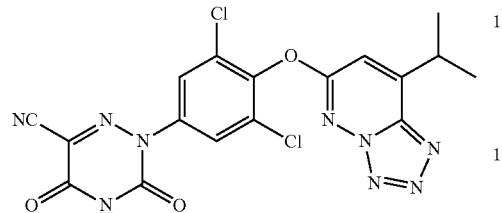

Example 42

Step 1: Example 42b

To a solution of Example 42a (332.6 mg, 1.0 mmol) in DMSO (5 mL) was added TMSN$_3$ (130 mg, 1.21 mmol). The reaction was heated to 60° C. and stirred for 16 h. The reaction was diluted with water and extracted with EtOAc (50 mL*3). The organic layer was washed with water, brine, dried over Na$_2$SO$_4$ and concentrated under reduced pressure. The residue was purified by column chromatography (silica gel, Petroleum Ether/EtOAc=10/1~4/1) to afford the product Example 42b (200 mg, yield 59%) as a yellow solid.

LCMS [M+1]$^+$=340.9.

Step 2: Example 42c

To a solution of Example 42b (200 mg, 0.59 mmol) in H$_2$O (10 mL) was treated with conc. HCl (5 mL). The reaction mixture was cooled to 0° C. and then treated with a solution of NaNO$_2$ (52 mg, 0.75 mmol) in H$_2$O (1 mL) followed by a H$_2$O (5 mL) rinse. The reaction mixture was stirred at 0° C. for 30 min to give solution A. In a separate flask equipped with a magnetic stirred were added N-cyanoacetyl urethane (102 mg, 0.65 mmol), H$_2$O (15 mL) and pyridine (5 mL). The reaction mixture was cooled to 0° C. and the solution A was poured into the second reaction mixture. An orange precipitate formed and the suspension was stirred at 0° C. for 30 min. The reaction mixture was extracted with EtOAc (20 mL*3) and the combined organic layer was washed with brine (20 mL), and concentrated to afford the crude product Example 42c (327 mg, crude) as an orange solid, which was used for the next step without further purification. LCMS [M+1]$^+$=507.9

Step 3: Example 42

A suspension of Example 42c (327 mg, 0.65 mmol) and NaOAc (265 mg, 3.3 mmol) in AcOH (5 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 42 (124 mg, yield 40%) as a white solid. LCMS [M+1]$^+$=459.9

$^1$H NMR (400 MHz, DMSO-d$_6$) δ 13.31 (s, 1H), 7.89 (s, 2H), 7.88 (s, 1H), 3.60-3.53 (m, 1H), 1.46 (d, J=6.8 Hz, 6H).

Example 43: General Procedure for Synthesis of Compound Example 43

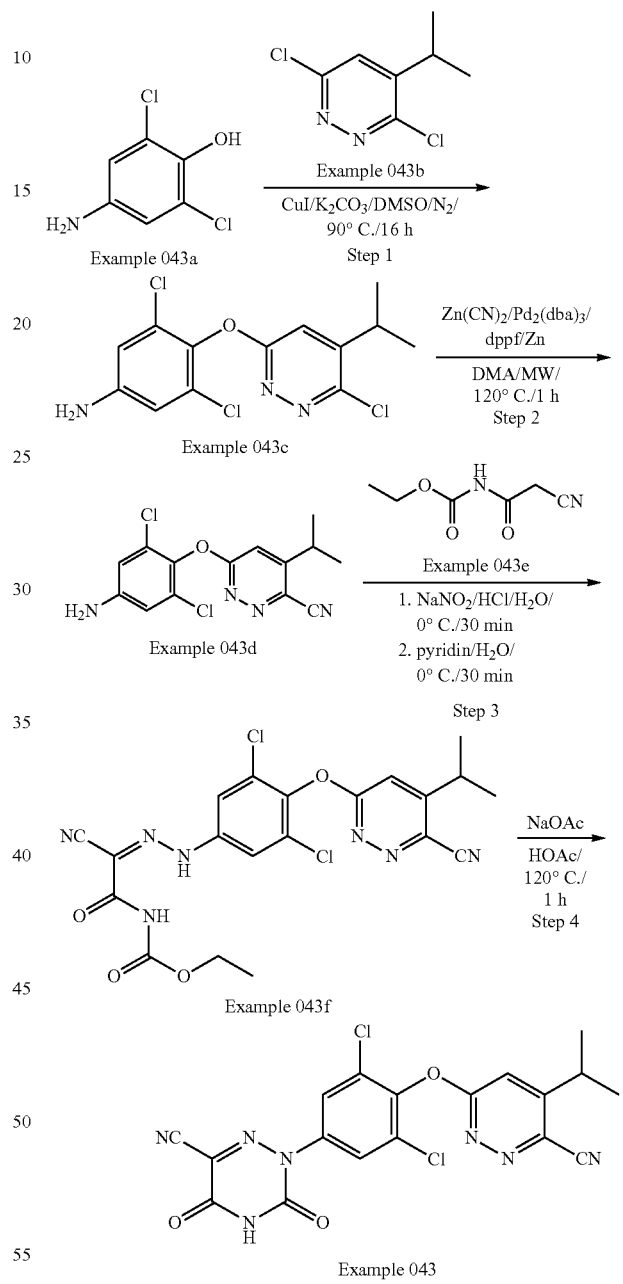

Step 1: Example 43c

To a solution of Example 43a (29.5 g, 165.7 mmol), Example 43b (38 g, 198.9 mmol), CuI (15.7 g, 82.8 mmol) and K$_2$CO$_3$ (45.7 g, 331.4 mmol) in DMSO was replaced with N$_2$ for 3 times and stirred at 90° C. under N$_2$ for 16 h. The reaction was diluted with water and extracted with EtOAc (500 mL*3). The combined organic layer was dried over anhydrous sodium sulfate and concentrated under reduced pressure. The residue was purified by column chromatography (silica gel, Petroleum Ether/EtOAc=5/1) to give the product Example 43c (35 g, yield 63%) as a brown solid. LCMS [M+1]$^+$=332.0

Step 2: Example 43d

To a solution of Example 43c (332 mg, 1 mmol), Zn(CN)$_2$ (117 mg, 1 mmol), Pd$_2$(dba)$_3$ (92 mg, 0.1 mmol), dppf (55 mg, 0.1 mmol) and Zn (16 mg, 0.25 mmol) in DMA (5 mL) was stirred at 120° C. under N$_2$ by microwave reaction for 1 h. The reaction was diluted with water and extracted by EtOAc (30 mL*3). The combined organic layer was dried over anhydrous sodium sulfate and concentrated to give the product Example 43d (300 mg, yield 93%) as a yellow solid. LCMS [M+1]$^+$=323.0

Step 3: Example 43f

To a solution of Example 043d (200 mg, 0.62 mmol) in 4N HCl (9 mL) was added NaNO$_2$ (54 mg, 0.78 mmol) at 0° C. and stirred for 30 min. At the same time a solution of Example 43e (106 mg, 0.68 mmol) in pyridine/H$_2$O (3 mL/9 mL) was cooled to 0° C. and added the Example 043d solution slowly. The mixture was stirred at 0° C. for 30 min. The reaction was diluted with water and extracted by EtOAc (30 mL*3). The combined organic layer was dried over anhydrous sodium sulfate and concentrated to give the product Example 43f (250 mg, yield 82%) as a yellow solid.

Step 4: Example 43

To a solution of Example 43f (250 mg, 0.5 mmol) and NaOAc (205 mg, 2.5 mmol) in HOAc (5 mL) was stirred at 120° C. for 1 h. The mixture was concentrated and purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the Example 43 (41 mg, yield 18%) as a yellow solid. LCMS [M+1]$^+$=444.1

$^1$H NMR (400 MHz, DMSO-d$_6$) δ 13.28 (s, 1H), 8.06 (s, 1H), 7.84 (s, 2H), 3.24-3.17 (m, 1H), 1.33 (d, J=7.6 Hz, 6H).

Example 44: General Procedure for Synthesis of Compound Example 044

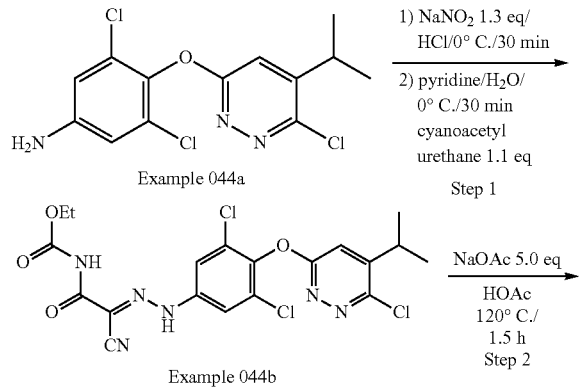

Example 044a

Example 044b

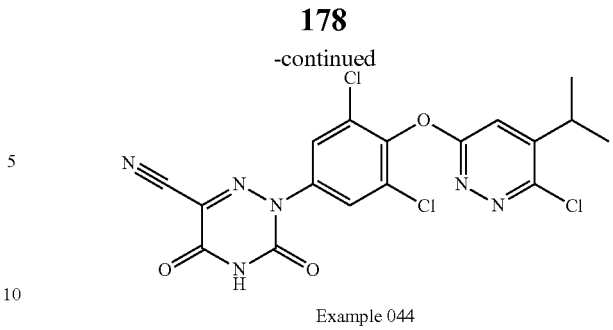

Example 044

Step 1: Example 44b

A suspension of Example 44a (1 g, 3.02 mmol) in con·HCl/H$_2$O (10 mL/20 mL) was cooled to 0° C. and then treated with a solution of NaNO$_2$ (270 mg, 3.8 mmol) in H$_2$O (2 mL). The mixture was stirred at 0° C. for 0.5 h. The resulting mixture was added to a solution of cyanoacetyl urethane (600 mg, 3.8 mmol) in pyridine/H$_2$O (10 mL/35 mL) at 0° C. The suspension was stirred at 0° C. for 0.5 h. The reaction mixture was extracted with EtOAc (20 mL*2). The combined organic phase was washed with brine, dried over Na$_2$SO$_4$, filtrated and the filtrate was concentrated under reduced pressure to give Example 044b (1.5 g crude) as yellow oil, which was used in next step.

Step 2: Example 44

To a solution of Example 44b (crude, 3.02 mmol) in HOAc (20 mL) was added NaOAc (1.24 g, 15 mmol). The mixture was stirred at 120° C. for 1.5 h and concentrated. The residue was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give Example 44 (15 mg, yield 10%) as a yellow solid. LCMS [M+1]$^+$=453.0

$^1$H NMR (400 MHz, CDCl$_3$) δ 8.99 (s, 1H), 7.65 (s, 2H), 7.27 (s, 1H), 3.29-3.26 (m, 1H), 1.37 (d, J=6.8 Hz, 6H).

Example 47: General Procedure for Synthesis of Compound Example 047

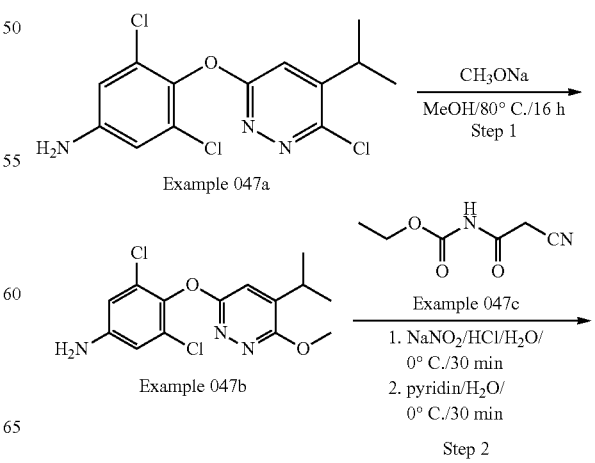

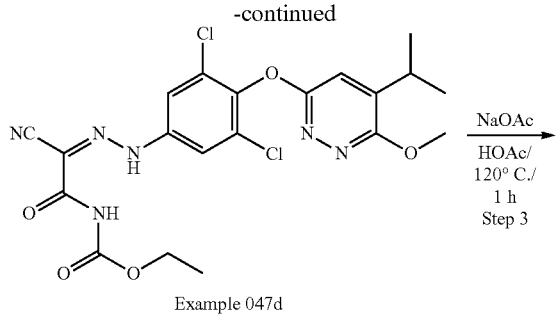

Example 047d

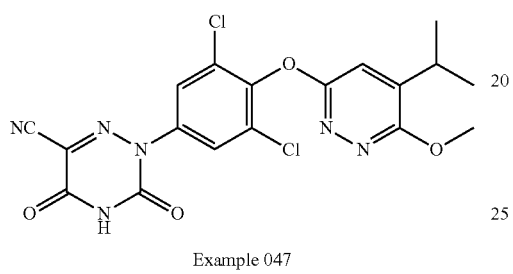

Example 047

Step 1: Example 47b

To a solution of Example 47a (332 mg, 1 mmol) and MeONa (60 mg, 1.1 mmol) in MeOH (10 mL) was stirred at 80° C. for 16 h. The reaction was concentrated and purified by column chromatography (silica gel, Petroleum Ether/EtOAc=5/1) to give the product Example 47b (100 mg, yield 30%) as a white solid. LCMS [M+1]$^+$=328.1

Step 2: Example 047d

To a solution of Example 47b (100 mg, 0.3 mmol) in 4N HCl (6 mL) was added NaNO$_2$ (26 mg, 0.38 mmol) at 0° C. and stirred for 30 min. At the same time a solution of Example 047c (51 mg, 0.33 mmol) in pyridine/H$_2$O (2 mL/6 mL) was cooled to 0° C. and added the Example 47b solution slowly. The mixture was stirred at 0° C. for 30 min. The reaction was diluted with water and extracted by EtOAc (100 mL*3). The combined organic layer was dried over anhydrous sodium sulfate and concentrated to give the product Example 47d (100 mg, yield 67%) as a yellow solid.

Step 3: Example 47

To a solution of Example 47d (100 mg, 0.2 mmol) and NaOAc (49 mg, 0.6 mmol) in HOAc (2 mL) was stirred at 120° C. for 1 h. The mixture was concentrated and purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give the Example 47 (19 mg, yield 21%) as a yellow solid. LCMS [M+1]$^+$=449.0

$^1$H NMR (400 MHz, DMSO-d$_6$) δ 13.25 (s, 1H), 7.77 (s, 2H), 7.55 (s, 1H), 3.95 (s, 3H), 3.10-3.03 (m, 1H), 1.23 (d, J=6.8 Hz, 6H).

Example 48: General Procedure for Synthesis of Compound Example 48

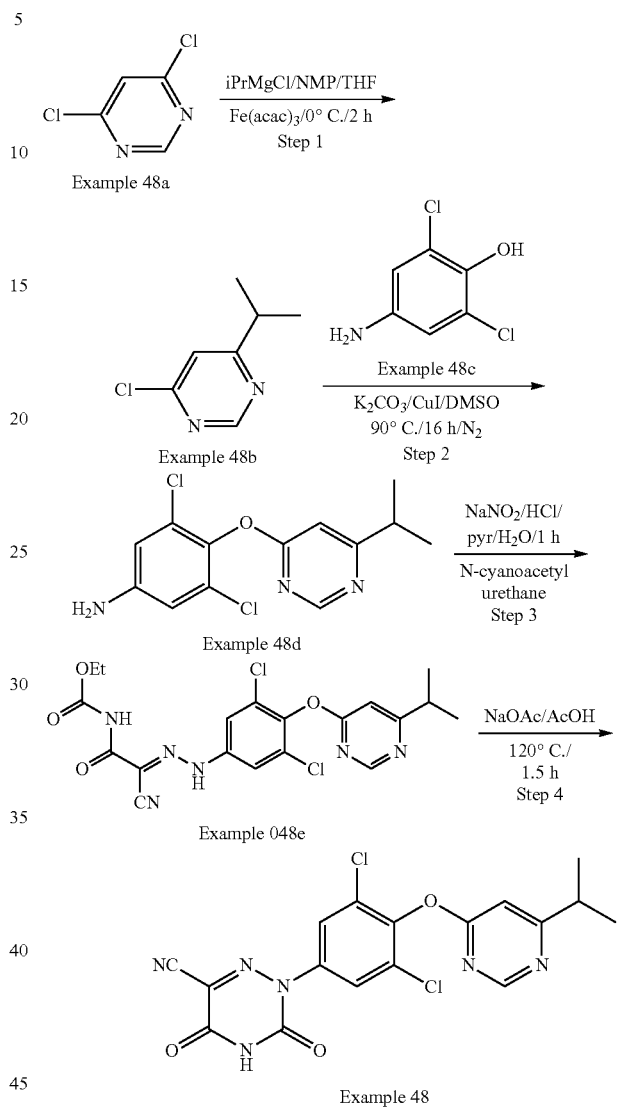

Step 1: Example 48b

To a mixture of Example 48a (1.5 g, 10 mmol) in NMP (5 mL) were added Tetrahydrofuran (50 mL), and Fe(acac)$_3$ (353 mg, 1.0 mmol). The solution was cooled to 0° C. and i-PrMgCl (10 mL, 2N) was added slowly at 0° C. The solution was stirred at 0° C. for 2 h, which was then extracted with EtOAc (50 mL*3), washed with brine, dried over Na$_2$SO$_4$, and filtered. The filtrate was concentrated, and the residue was purified by column chromatography (silica gel, Petroleum Ether/EtOAc=1/0~20/1) to give Example 48b (400 mg, yield 25%) as yellow oil. LCMS [M+1]$^+$=156.9

Step 2: Example 48d

To a suspension of Example 48b (400 mg, 2.56 mmol), Example 48c (456 mg, 2.56 mmol) and K$_2$CO$_3$ (706 mg, 5.12 mmol) in DMSO (20 mL) was added CuI (243 mg, 1.28 mmol) at room temperature under N₂. The reaction mixture was heated to 90° C. and stirred for 16 h under N₂. The reaction mixture was cooled to room temperature, poured into ice-water (100 mL), diluted with EtOAc (100 mL), and filtered. The filtered cake was washed with EtOAc/H₂O (V/V=1/1, 200 mL*3). The aqueous layer was extracted with EtOAc (100 mL*2). The combined organic layer was washed with brine (100 mL*2), dried over Na₂SO₄, and filtered. The filtrate was concentrated, and the residue was purified by column chromatography (Petroleum Ether/EtOAc=10/1~5/1) to afford the product Example 48d (600 mg, yield 79%) as a yellow solid. LCMS [M+1]⁺=298.9

Step 3: Example 48e

To a solution of Example 48d (600 mg, 2 mmol) in H₂O (30 mL) was treated with conc. HCl (20 mL). The reaction mixture was cooled to 0° C. and then treated with a solution of NaNO₂ (200 mg, 2.5 mmol) in H₂O (1 mL) followed by a H₂O (1 mL) rinse. The reaction mixture was stirred at 0° C. for 30 min to give solution A. In a separate flask equipped with a magnetic stirred were added N-cyanoacetyl urethane (350 mg, 2.2 mmol), H₂O (50 mL) and pyridine (20 mL). The reaction mixture was cooled to 0° C. and the solution A was poured into the second reaction mixture. An orange precipitate formed and the suspension was stirred at 0° C. for 30 min. The reaction mixture was extracted with EtOAc (100 mL*3) and the combined organic layer was washed with brine (100 mL), concentrated to afford the crude product Example 48e (960 mg, crude) as an orange solid, which was used for the next step without further purification. LCMS [M+1]⁺=465.9

Step 4: Example 48

A suspension of Example 48e (960 mg, 2 mmol) and NaOAc (1.6 g, 20 mmol) in AcOH (20 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H₂O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 48 (152 mg, yield 18%) as a white solid. LCMS [M+1]⁺=418.9. ¹H NMR (400 MHz, DMSO-d₆) δ 13.27 (s, 1H), 8.66 (s, 1H), 7.79 (s, 2H), 7.35 (s, 1H), 3.08-3.01 (m, 1H), 1.26 (d, J=6.8 Hz, 6H).

Example 50: General Procedure for Synthesis of Compound Example 50

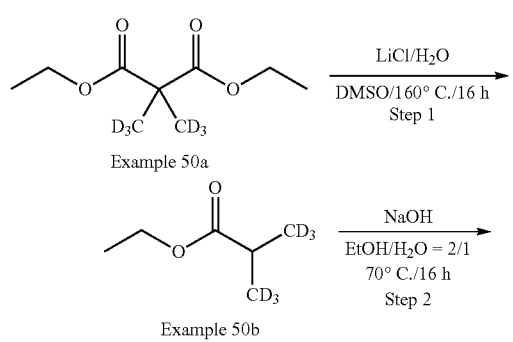

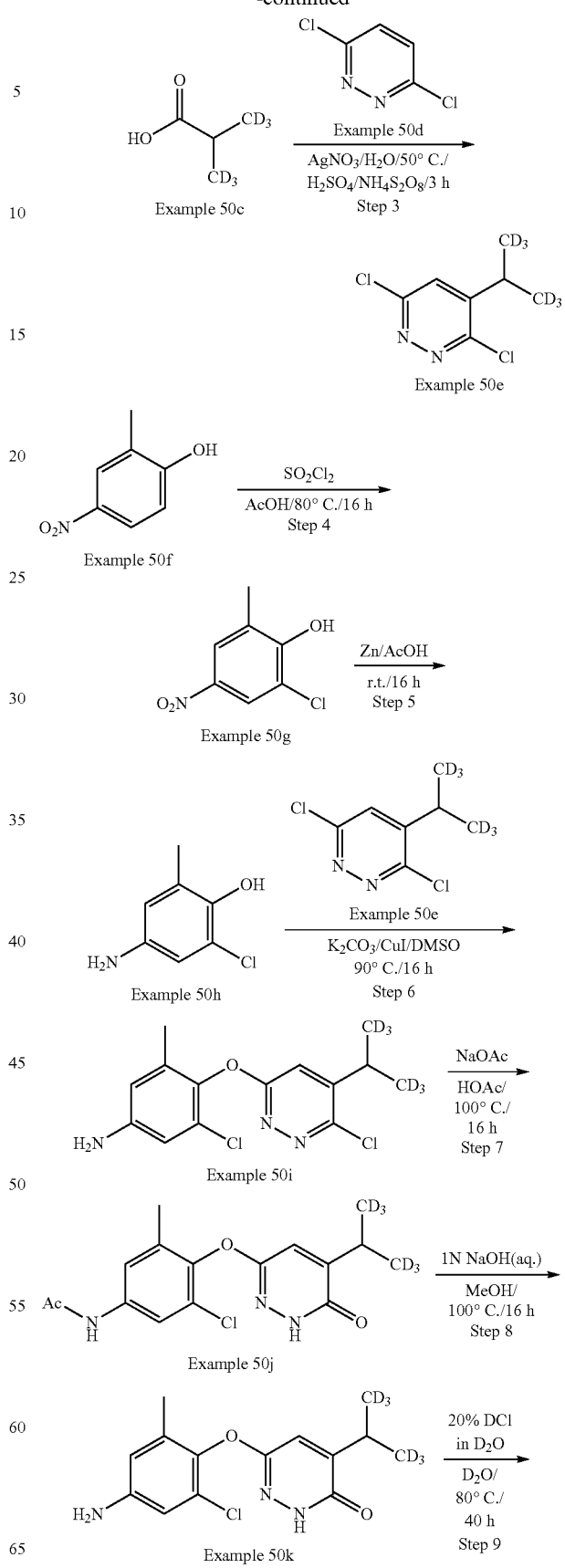

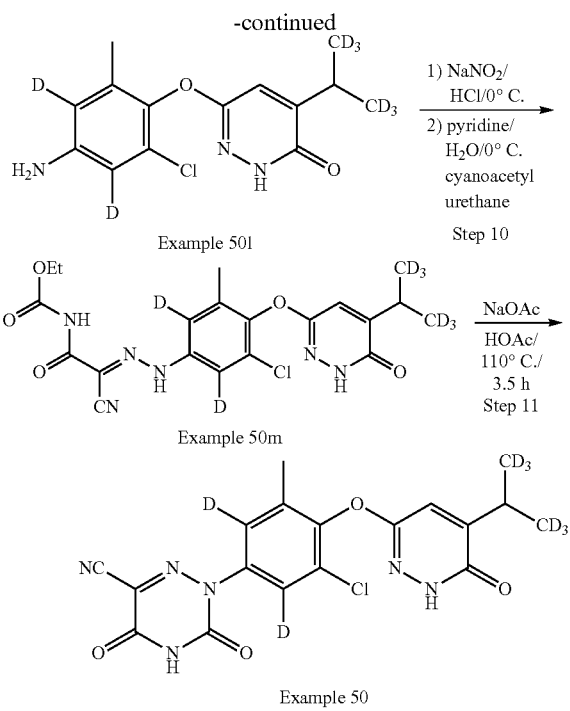

Example 50

Step 1: Example 50b

To a solution of Example 50a (50.0 g, 257.7 mmol) in DMSO (300 mL) was added LiCl (16.4 g, 386.6 mmol) and H$_2$O (2.3 g, 128.9 mmol). The reaction mixture was stirred at 160° C. under nitrogen atmosphere for 16 h. The reaction was cooled to r.t. and directly distilled (condition: atmospheric pressure; oil bath: 150° C.; inner temperature: 100° C.) to give the crude desired product Example 50b (34 g, crude) as a colorless liquid.

Step 2: Example 50c

Example 50b (34 g, 278.7 mmol) was dissolved in EtOH (200 mL) and H$_2$O (100 mL) and NaOH (22.3 g, 557.4 mmol) was added. The mixture was stirred at 70° C. for 16 h. EtOH was removed under reduced pressure and the residue was acidified by 6N HCl to pH=3~4, and extracted by DCM/MeOH (v/v=20/1, 200 mL*3). The combined organic layers were dried over Na$_2$SO$_4$, filtered and concentrated to give the desired product Example 50c (18 g, yield 69%) as a dark-brown liquid.

Step 3: Example 50e

A solution of Example 50d (28.5 g, 191.5 mmol) in water (180 mL) at room temperature, the reaction mixture was treated with Example 50c (18 g, 191.5 mmol), followed by silver nitrate (16.3 g, 95.7 mmol). The reaction mixture was heated to 50° C. A solution of sulfuric acid (conc. 56.3 g, 574.5 mmol) in water (180 mL) was added in one portion, followed by the drop wised addition of a solution of ammonium persulfate (131.0 g, 574.5 mmol) in water (180 mL). The reaction mixture was heated to 60° C. for 3 h. At this time, the reaction mixture was cooled to 0° C. and basified with solid NaHCO$_3$ to bring the reaction to pH=8. The reaction mixture was diluted with water (300 mL), and extracted with EtOAc (300 mL*3). The combined organics were washed with water (300 mL*2) and brine (400 mL), dried over magnesium sulfate, filtered and the filtrate was concentrated under vacuum. The residue was purified by column chromatography (silica gel, Petroleum Ether, then Petroleum Ether/EtOAc=20/1) to afford the desired product Example 50e (20 g, yield 53%) as yellowish oil. LCMS [M+1]$^+$=197.1

Step 4: Example 50g

To a solution of Example 50f (20.0 g, 130.7 mmol) in AcOH (600 mL) was added SO$_2$Cl$_2$ (35.3 g, 261.4 mmol), the mixture was stirred at 70° C. for 16 h under nitrogen atmosphere. Excess AcOH was removed in vacuo, followed by adding water slowly at 0° C. with stirring. The precipitate was collected by filtration. The solid was dried under vacuum, treated with mixed solution (300 mL, Petroleum Ether/EtOAc=20/1), stirred for 30 min and filtered to give the pure desired product Example 50g (19.5 g, yield 80%) as a yellow solid.
LCMS [M+1]$^+$=188.0

Step 5: Example 50h

To a solution of Example 50g (19.5 g, 104.3 mmol) in AcOH (400 mL) was added zinc powder (40.7 g, 625.6 mmol) at r.t. The mixture was allowed to stir at room temperature for 16 h. The reaction mixture was diluted with MeOH and filtered. The filtrate was washed by MeOH and the most AcOH was concentrated. The residue was poured into ice/water and large amount precipitate was formed, which was stirred for 10 min and filtered. The solid was collected and triturated in MeOH, filtered and dried to give the desired product Example 50h (13.0 g, yield 79%) as a white solid. LCMS [M+1]$^+$=158.0

Step 6: Example 50i

A solution of Example 50h (16.0 g, 101.5 mmol) in anhydrous DMSO (300 mL) at room temperature were treated with Example 50e (20.0 g, 101.5 mmol), anhydrous potassium carbonate (28.0 g, 203.0 mmol) and copper (I) iodide (3.9 g, 20.3 mmol). The reaction mixture was heated to 90° C. for 16 h under nitrogen atmosphere. The reaction mixture was then cooled to room temperature and poured into water (200 mL). The solution was brought to pH=8 with a hydrochloric acid (UV). The aqueous layer was extracted with EtOAc (500 mL*3). The combined organics were then washed with brine (500 mL), dried over magnesium sulfate, filtered and the filtrate was concentrated under vacuum. The residue was purified by column chromatography (silica gel, 27% EtOAc in Petroleum Ether) to afford the desired product Example 50i (26.5 g, yield 82%) as a black solid. LCMS [M+1]$^+$=318.0

Step 7: Example 50j

A mixture of glacial acetic acid (400 mL), sodium acetate (24.0 g, 291.7 mmol) and Example 50i (26.5 g, 83.3 mmol) was heated to 100° C. for 16 h. The reaction mixture was cooled to room temperature, and then concentrated. The residue was diluted with water (50 mL) and basified to pH=9 with NaOH (11V) solution. This suspension was extracted with EtOAc (500 mL*3). The organic layers were combined, dried with magnesium sulfate, filtered and the filtrate was concentrated under vacuum to give the crude product Example 50j (22.6 g, yield 80%) as black oil, which was used for the next step directly. LCMS [M+1]⁺=342.0

Step 8: Example 50k

Example 50j (22.6 g, 66.3 mmol) was diluted with methanol (200 mL) and treated with NaOH (UV, 400 mL). The reaction mixture was heated to 100° C. for 16 h. The reaction mixture was cooled to room temperature and concentrated under vacuum. The residue was diluted with water (300 mL) and extracted with EtOAc (500 mL*2). The EtOAc layer was washed with water and brine, dried over magnesium sulfate, filtered and the filtrate was concentrated under vacuum. The residue was purified by column chromatography (silica gel, Petroleum Ether/EtOAc=4/1) to afford the desired product Example 50k (7.0 g, 35.4%) as a brown solid. LCMS [M+1]⁺=300.0

Step 9: Example 50l

To a solution of Example 50k (7.0 g, 23.3 mmol) in $D_2O$ (40 mL) and MeOD (92 mL) was added DCl (184 mL, 20% in $D_2O$). The reaction mixture was stirred at 80° C. for 40 h. The mixture was concentrated in reduced pressure to give the crude desired product Example 50l (7.0 g, crude) as a pink solid, which was used for the next step directly. LCMS [M+1]⁺=302.0

Step 10: Example 50m

A suspension of Example 50l (7.0 g, 23.2 mmol) in $H_2O$ (280 mL) was treated with HCl (con., 140 mL). The reaction mixture was cooled to 0° C. and then treated with a solution of $NaNO_2$ (2.0 g, 29.2 mmol) in $H_2O$ (10 mL) followed by a $H_2O$ (10 mL) rinse. The reaction mixture was stirred at 0° C. for 30 min and a solution formed. In a separate flask equipped with a magnetic stirred were added N-cyanoacetyl urethane (4.0 g, 25.5 mmol), $H_2O$ (450 mL) and pyridine (140 mL). The reaction mixture was cooled to 0° C. and the solution from the first reaction was poured into the second reaction mixture. An orange precipitate formed and the suspension was stirred at 0° C. for 30 min. The reaction mixture was extracted with EtOAc (300 mL*3) and the combined organic layer was washed with brine (300 mL), dried over $Na_2SO_4$, filtered and concentrated to afford the crude product Example 50m (11.02 g, crude) as an orange solid, which was used for the next step without further purification. LCMS [M+1]⁺=469.0

Step 11: Example 50

A suspension of Example 50m (11.02 g, 23.5 mmol) and NaOAc (5.8 g, 70.5 mmol) in AcOH (600 mL) was heated to 110° C. and stirred for 3.5 h. The reaction mixture was cooled to room temperature and concentrated under reduced pressure. The residue was poured into ice/water, and stirred for 30 min. The solid was washed by water and MeCN, and then collected, which was then triturated in MeCN (50 mL) for 30 min, filtered, followed by a mixed solution of DCM/MeOH (v/v=10/1, 80 mL) trituration for another 30 min. The product was collected by filtration and dried to afford Example 50 (5.0 g, yield 51%, D=~99% by HNMR) as an orange solid. LCMS [M+1]⁺=423.0. ¹H NMR (400 MHz, DMSO-$d_6$) δ 13.13 (s, 1H), 12.11 (s, 1H), 7.35 (s, 1H), 2.98 (s, 1H), 2.21 (s, 3H).

Example 51: General Procedure for Synthesis of Compound Example 51

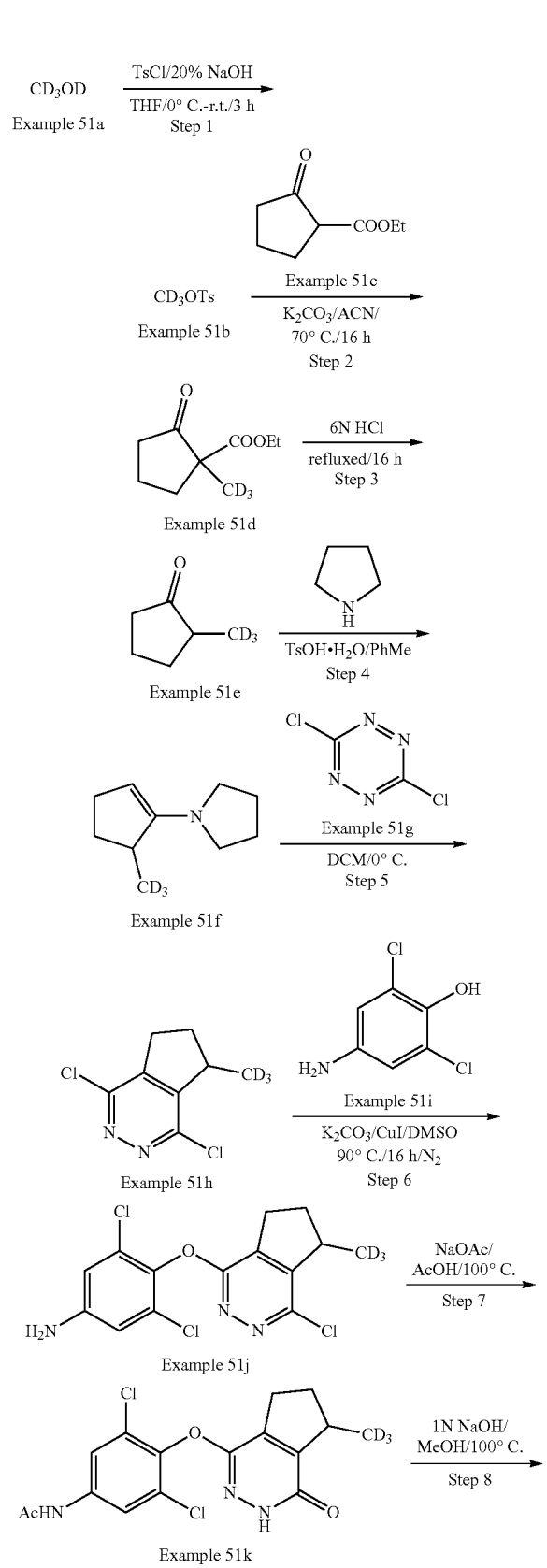

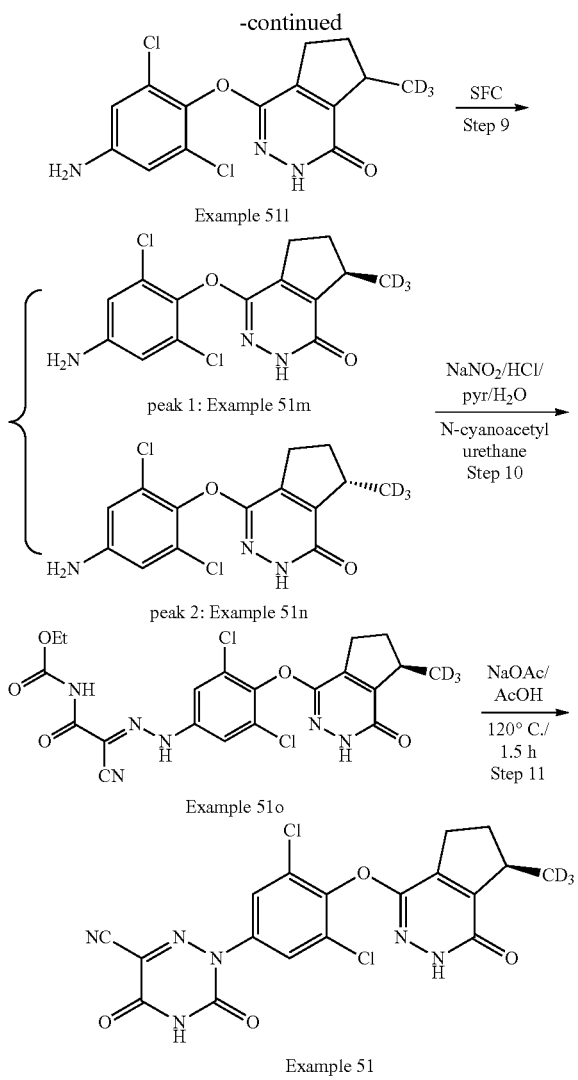

Step 3: Example 51e

To a solution of Example 51d (150 g, 867 mmol) in 6N HCl (300 mL) was stirred at reflux for 16 h. The reaction was diluted with water (500 mL) and extracted by DCM (300 mL*3). The combined organic layer was washed with brine, dried $Na_2SO_4$, and concentrated under reduce. The residue was purified by distillation to give the product Example 51e (62 g, 71%) as colorless oil. NMR (400 MHz, $CDCl_3$) δ 2.27-2.12 (m, 2H), 2.07-1.99 (m, 2H), 1.97-1.88 (m, 1H), 1.77-1.67 (m, 1H), 1.48-1.36 (m, 1H).

Step 4: Example 51f

A mixture of Example 51d (62 g, 613.9 mmol), pyrrolidine (65 g, 921 mmol) and TsOH·$H_2O$ (11.7 g, 61.4 mmol) in PhMe (300 mL) was refluxed at 130° C. with a Dean-Stark apparatus for 16 h. The color of the solution turned black from colorless. The reaction mixture was cooled to room temperature and concentrated to afford the crude product Example 51f (110 g, yield 100%) as black oil, which was used for the next step without further purification.

Step 5: Example 51h

To an orange solution of Example 51f (53 g, 350.6 mmol) in DCM (1.5 L) was added slowly Example 51g (108 g, 701.3 mmol) at 0° C. with ice-bath. After addition, the reaction mixture was stirred for 15 min at 0° C. The color of the reaction turned brown. 3N HCl (200 mL) was added slowly at 0° C., followed by EtOAc. The organic layer was washed with water, brine, dried over $Na_2SO_4$, and concentrated under reduced pressure. The residue was purified by column chromatography (silica gel, Petroleum Ether/EtOAc=1/0~30/1) to afford the product Example 51h (20 g, yield 27%) as a yellow solid. LCMS $[M+1]^+$=205.9.

Step 6: Example 51j

To a suspension of Example 51h (5 g, 24.3 mmol), Example 51i (4.3 g, 24.3 mmol) and $K_2CO_3$ (6.7 g, 48.6 mmol) in DMSO (120 mL) was added CuI (2.3 g, 12.2 mmol) at room temperature under $N_2$. The reaction mixture was heated to 90° C. and stirred for 16 h under $N_2$. The reaction mixture was cooled to room temperature and poured into ice-water (100 mL), which was then diluted with EtOAc (100 mL), and filtered. The filtered cake was washed with EtOAc/$H_2O$ (V/V=1/1, 100 mL*3). The aqueous layer was extracted with EtOAc (100 mL*2). The combined organic layer was washed with brine (100 mL*2), dried over $Na_2SO_4$, filtered and concentrated, which was purified by column chromatography (silica gel, Petroleum Ether/EtOAc=10/1~5/1) to afford the product Example 51j (4.6 g, yield 55%) as a brown solid. LCMS $[M+1]^+$=347.9.

Step 7: Example 51k

A solution of Example 51j (4.6 g, 13.3 mmol) and NaOAc (5.4 g, 66.3 mmol) in AcOH (80 mL) was heated to 100° C. and stirred for 16 h. The reaction mixture was cooled to room temperature and concentrated under reduced pressure. The residue was dissolved in $H_2O$ (100 mL), made to basic pH=8 with sat·$NaHCO_3$ (100 mL), and extracted with EtOAc (100 mL*2). The aqueous layer was acidified with 6N HCl and extracted with EtOAc (100 mL). The combined Step 1: Example 51b To a solution of Example 51a (140 g, 3.89 mol) and TsCl (665 g, 3.5 mol) in THF (1.4 L) was added 20% NaOH (aq) (1.4 L) under 20° C., the mixture was stirred at r.t. for 3 h. The reaction was extracted by EtOAc (1 L*3). The combined organic layer was washed with brine, dried $Na_2SO_4$, and concentrated to give the product Example 51b (538 g, yield 81%) as colorless oil. LCMS $[M+1]^+$=190.0

Step 2: Example 51d

To a solution of Example 51b (538 g, 2.85 mol), Example 51c (296.4 g, 1.9 mol) and $K_2CO_3$ (522 g, 3.78 mol) in ACN (3 L) was stirred at 70° C. for 16 h. The reaction was filtered and concentrated, the residue was purified by column chromatography (silica gel, Petroleum Ether/EtOAc=20/1) to give the product Example 51d (150 g, yield 46%) as yellow oil (NOTE: very weak UV spot is desired; strong UV spot is incorrect). LCMS $[M+1]^+$=174.1. $^1$H NMR (400 MHz, $CDCl_3$) δ 4.14 (m, 2H), 2.52-2.41 (m, 2H), 2.34-2.24 (m, 1H), 2.08-2.00 (m, 1H), 1.95-1.81 (m, 2H), 1.23 (t, J=7.2 Hz, 3H).

organic layer was concentrated to afford the crude product Example 51k (5 g, crude), which was used for the next step without further purification.

Step 8: Example 51l

To a solution of Example 51k (5 g, 13.5 mmol) in MeOH (70 mL) was added 1N NaOH (70 mL) and then the reaction mixture was heated to 120° C. and stirred for 16 h. The reaction mixture was cooled to room temperature and concentrated under reduced pressure. The residue was dissolved in H$_2$O (100 mL) and extracted with EtOAc (100 mL*2). The organic layer was concentrated and purified by column chromatography (silica gel, Petroleum Ether/EtOAc=10/1~3/2) to afford product Example 51l (1.7 g, yield 39%) as a yellow solid. LCMS [M+1]$^+$=328.9

Step 9: Example 51m

Example 51l (1.7 g) was further separated by chiral SFC to afford Example 51m (peak 1: 0.787 g, yield 46%) as a brown solid and Example 51n (peak 2: 0.922 g, yield 54%) as a brown solid. (NOTE: The absolute structures were unknown and the drawn structures were randomly assigned) Chiral SFC condition:

| | |
|---|---|
| Column: | CHIRALPAK IB N-5(IBN5CD-VD005) |
| Column size: | 0.46 cm I.D. × 15 cm L |
| Injection: | 20.0 ul |
| Mobile phase: | EtOAc/DCM/DEA = 80/20/0.1(V/V/V) |
| Flow rate: | 1.0 ml/min |
| Wave length: | UV 214 nm |
| Temperature: | 35° C. |
| HPLC equipment: | Shimadzu LC-20AT    CP-HPLC-07 |

Step 10: Example 51o

To a solution of Example 51m (98.7 mg, 0.3 mmol) in H$_2$O (3 mL) was treated with con. HCl (2 mL). The reaction mixture was cooled to 0° C. and then treated with a solution of NaNO$_2$ (26 mg, 0.38 mmol) in H$_2$O (1 mL) followed by a H$_2$O (5 mL) rinse. The reaction mixture was stirred at 0° C. for 30 min to give solution A. In a separate flask equipped with a magnetic stirred were added N-cyanoacetyl urethane (51.5 mg, 0.33 mmol), H$_2$O (5 mL) and pyridine (2 mL). The reaction mixture was cooled to 0° C. and the solution A was poured into the second reaction mixture. An orange precipitate formed and the suspension was stirred at 0° C. for 30 min. The reaction mixture was extracted with EtOAc (20 mL*3) and the combined organic layer was washed with brine (20 mL), concentrated to afford the crude product Example 51k (153 mg, crude) as an orange solid, which was used for the next step without further purification. LCMS [M+1]$^+$=495.9.

Step 8: Example 51

A suspension of Example 51o (153 mg, 0.31 mmol) and NaOAc (126 mg, 1.55 mmol) in AcOH (5 mL) was heated to 110° C. and stirred for 2.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 51 (32 mg, yield 23% for 2 steps) as a white solid. LCMS [M+1]$^+$=449.9. $^1$HNMR (400 MHz, DMSO-d$_6$) δ 12.09 (s, 1H), 7.76 (s, 2H), 3.26-3.23 (m, 1H), 3.08-2.97 (m, 1H), 2.95-2.85 (m, 1H), 2.40-2.34 (m, 1H), 1.76-1.67 (m, 1H).

Example 52: General Procedure for Synthesis of Compound Example 52

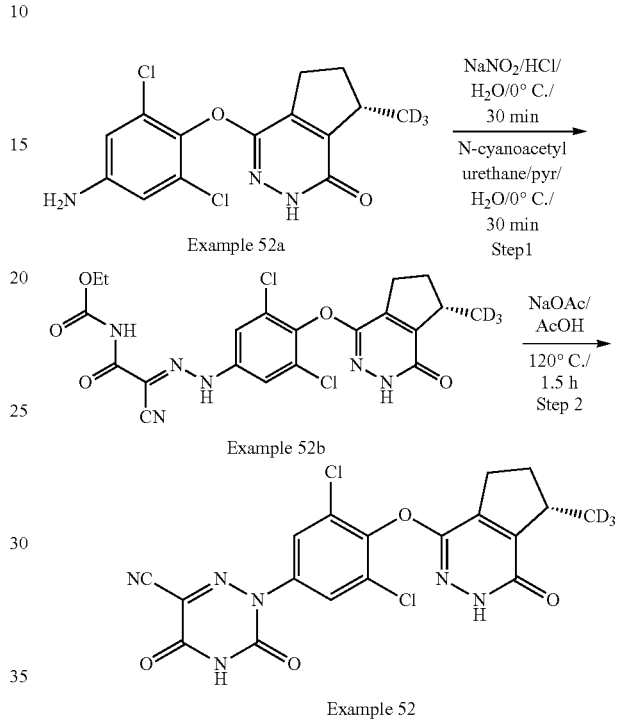

Step 1: Example 52b

To a solution of Example 52a/51h (98.7 mg, 0.3 mmol) in H$_2$O (3 mL) was treated with con. HCl (2 mL). The reaction mixture was cooled to 0° C. and then treated with a solution of NaNO$_2$ (26 mg, 0.38 mmol) in H$_2$O (1 mL) followed by a H$_2$O (2 mL) rinse. The reaction mixture was stirred at 0° C. for 30 min to give solution A. In a separate flask equipped with a magnetic stirred were added N-cyanoacetyl urethane (51.5 mg, 0.33 mmol), H$_2$O (5 mL) and pyridine (2 mL). The reaction mixture was cooled to 0° C. and the solution A was poured into the second reaction mixture. An orange precipitate formed and the suspension was stirred at 0° C. for 30 min. The reaction mixture was extracted with EtOAc (20 mL*3) and the combined organic layer was washed with brine (20 mL), concentrated to afford the crude product Example 52b (125 mg, crude) as an orange solid, which was used for the next step without further purification. LCMS [M+1]$^+$=495.9.

Step 2: Example 52

A suspension of Example 52b (125 mg, 0.25 mmol) and NaOAc (103 mg, 1.25 mmol) in AcOH (5 mL) was heated to 120° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford Example 52 (61 mg, yield 54%) as a yellow solid. LCMS [M+1]$^+$=449.9.

$^1$H NMR (400 MHz, DMSO-d$_6$) δ 12.07 (s, 1H), 7.76 (s, 2H), 3.27-3.23 (m, 1H), 3.07-3.00 (m, 1H), 2.94-2.85 (m, 1H), 2.41-2.32 (m, 1H), 1.71 (m, 1H).

Example 53: General Procedure for Synthesis of Compound Example 53

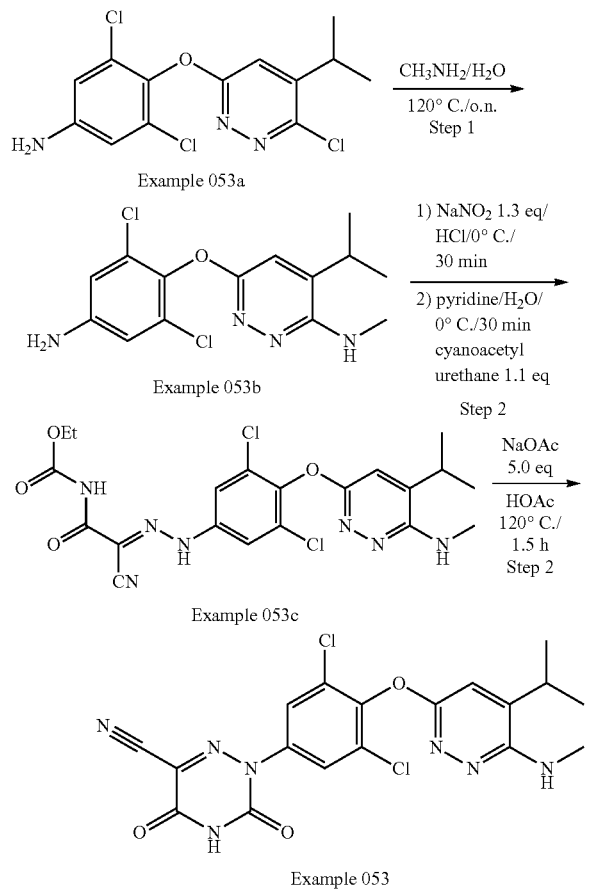

Step 1: Example 53b

A suspension of Example 53a (5 g, 15 mmol) in CH$_3$NH$_2$/H$_2$O (20 mL) in a sealed tube was heated to 120° C. for overnight. The reaction mixture was extracted with EtOAc (60 mL*2). The combined organic phase was washed with brine, dried over Na$_2$SO$_4$, filtrated and the filtrate was concentrated under reduced pressure. The residue was purified by column chromatography (silica gel, DCM/EtOAc=0~100% with 0.1% TEA) to get crude product Example 53b (1 g, yield 20%) as a brown solid, which was used in the next step without purification. LCMS [M+1]$^+$=327.0

Step 2: Example 53b

A suspension of Example 53a (1 g, 3.05 mmol) in con·HCl/H$_2$O (5 mL/10 mL) was cooled to 0° C. and then treated with a solution of NaNO$_2$ (265 mg, 3.84 mmol) in H$_2$O (2 mL). The mixture was stirred at 0° C. for 0.5 h. The resulting mixture was added to a solution of cyanoacetyl urethane (600 mg, 3.84 mmol) in pyridine/H$_2$O (10 mL/20 mL) at 0° C. The resulting suspension was stirred at 0° C. for 0.5 h. The reaction mixture was extracted with EtOAc (40 mL*2). The combined organic phase was washed with brine, dried over Na$_2$SO$_4$, filtrated and the filtrate was concentrated under reduced pressure to give Example 53b (1.5 g crude yield 99%) as yellow oil, which was used in the next step. LCMS [M+1]$^+$=494.1/496.1

Step 3: Example 53

To a solution of Example 53b (1.5 g, 3.05 mmol) in HOAc (20 mL) was added NaOAc (1.24 g, 15 mmol). The mixture was stirred at 120° C. for 1.5 h and concentrated. The 1/3 of residue was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to give Example 53 (24.7 mg, yield 6%) as a yellow solid. LCMS [M+1]$^+$=448.0. NMR (400 MHz, DMSO-d$_6$) δ 13.26 (s, 1H), 7.74 (s, 2H), 7.20 (s, 1H), 6.48-6.32 (m, 1H), 2.95-2.87 (m, 1H), 2.80 (d, J=4.4 Hz, 3H), 1.20 (d, J=6.8 Hz, 6H).

Example 56: General Procedure for Synthesis of Compound Example 56

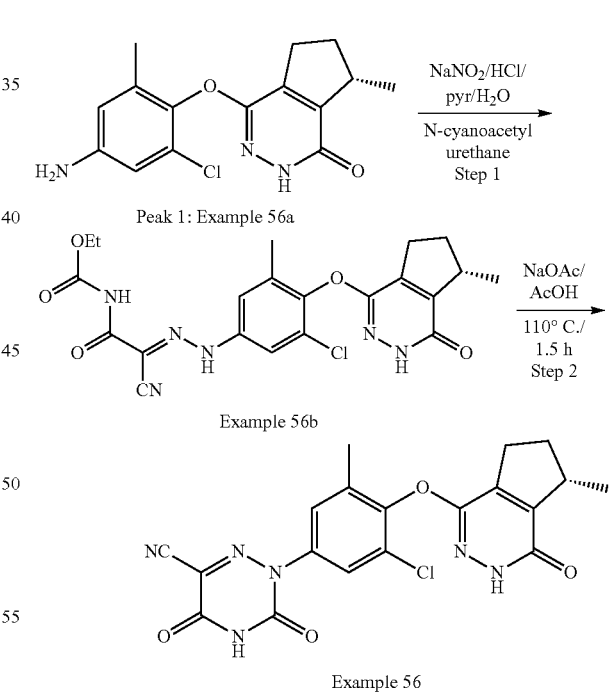

Step 1: Example 56b

To a solution of Example 56a (251.9 mg, 0.82 mmol, from Example 57f) in H$_2$O (7 mL) was treated with conc. HCl (5 mL). The reaction mixture was cooled to 0° C. and then treated with a solution of NaNO$_2$ (71.6 mg, 1.04 mmol) in H$_2$O (5 mL) followed by a H$_2$O (1 mL) rinse. The reaction mixture was stirred at 0° C. for 30 min to give solution A. In a separate flask equipped with a magnetic stirred were added N-cyanoacetyl urethane (141 mg, 0.91 mmol), H$_2$O (10 mL) and pyridine (5 mL). The reaction mixture was cooled to 0° C. and the first solution was poured into the second reaction mixture. An orange precipitate formed and the suspension was stirred at 0° C. for 30 min. The reaction mixture was extracted with EtOAc (30 mL*3) and the combined organic layer was washed with brine (100 mL), dried over Na$_2$SO$_4$, filtered and concentrated to afford the crude product Example 56b (368 mg, crude) as orange solid, which was used for the next step without further purification. LCMS [M+1]$^+$=472.9.

Step 2: Example 56

A suspension of Example 56b (368 mg, 0.78 mmol) and NaOAc (223 mg, 2.72 mmol) in AcOH (12 mL) was heated to 110° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford the desired product Example 56 (97 mg, yield 29%) as a yellow solid. LCMS [M+1]$^+$=426.9. $^1$H NMR (400 MHz, DMSO-d$_6$) δ 13.10 (s, 1H), 11.98 (s, 1H), 7.55 (d, J=2.4 Hz, 1H), 7.42 (d, J=2.4 Hz, 1H), 3.27-3.24 (m, 1H), 3.06-2.98 (m, 1H), 2.94-2.86 (m, 1H), 2.41-2.32 (m, 1H), 1.75-1.67 (m, 1H), 1.24 (d, J=7.2 Hz, 3H).

Example 57: General Procedure for Synthesis of Compound Example 57

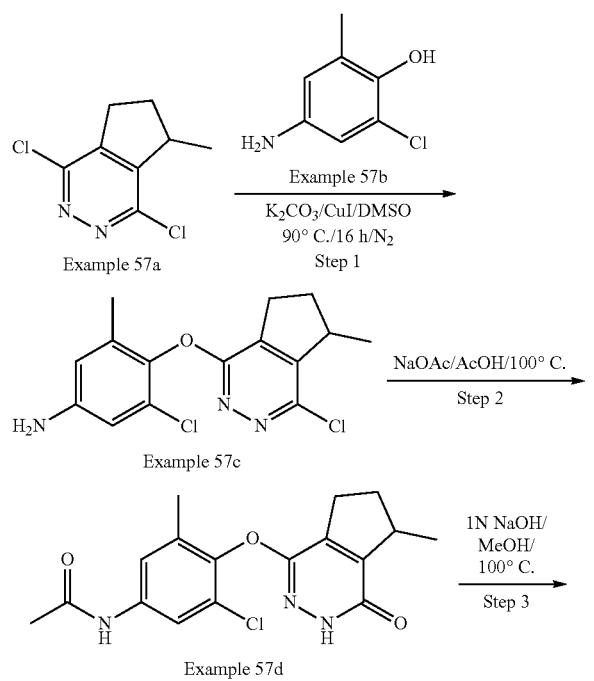

Step 1: Example 57c

To a suspension of Example 57a (2.5 g, 12.26 mmol), Example 57b (1.9 g, 12.26 mmol) and K$_2$CO$_3$ (3.4 g, 24.52 mmol) in DMSO (100 mL) was added CuI (1.16 g, 6.13 mmol) at room temperature under N$_2$. The reaction mixture was heated to 90° C. and stirred for 16 h under N$_2$. The reaction mixture was cooled to room temperature and poured into ice-water (100 mL) and diluted with EtOAc (100 mL), filtered and the filter cake was washed with EtOAc/H$_2$O (V/V=1/1, 100 mL*3). The aqueous layer was extracted with EtOAc (100 mL*2). The combined organic layer was washed with brine (100 mL*2), dried over Na$_2$SO$_4$, filtered and concentrated to afford the crude product, which was purified by column chromatography (silica gel, Petroleum Ether/EtOAc=10/1~3/1) to afford the product Example 57c (1.2 g, yield 31%) as a yellow solid. LCMS [M+1]$^+$=324.9.

Step 2: Example 57d

A solution of Example 57d (1.1 g, 3.4 mmol) and NaOAc (1.4 g, 17 mmol) in AcOH (20 mL) was heated to 100° C.

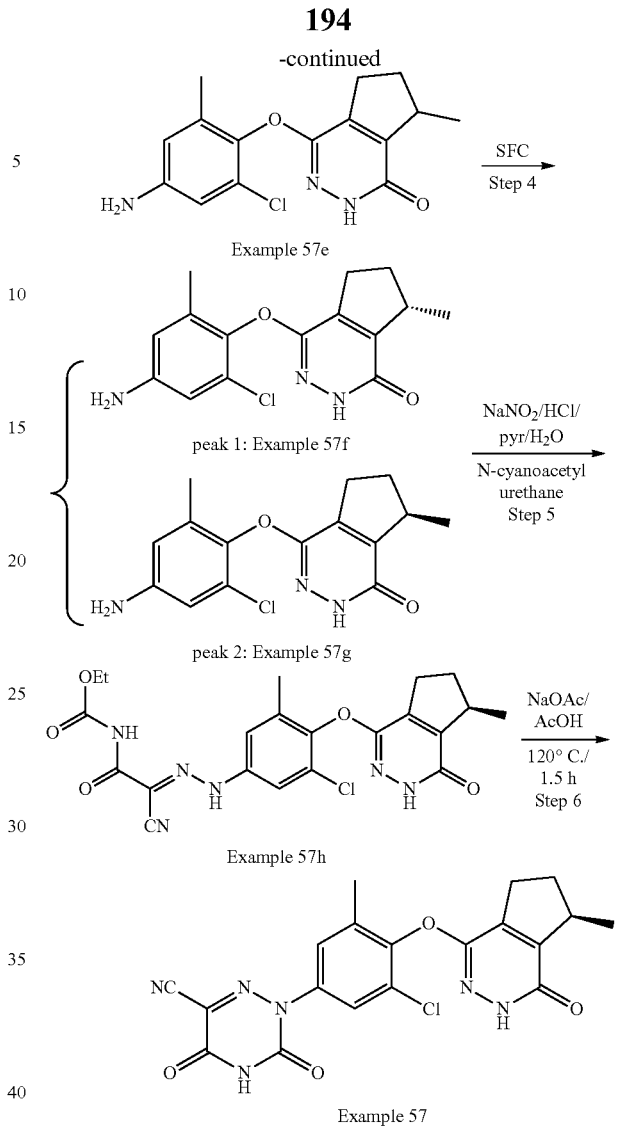

and stirred for 16 h. The reaction mixture was cooled to room temperature and concentrated under reduced pressure. The residue was dissolved in H$_2$O (100 mL), made to basic pH=8 with sat·NaHCO$_3$ (100 mL) and extracted with EtOAc (100 mL*2). The aqueous layer was acidified with 6N HCl and extracted with EtOAc (100 mL). The combined organic layer was concentrated to afford the crude product Example 57d (1.5 g, crude), which was used for the next step without further purification.

Step 3: Example 57e

To a solution of Example 57d (1.5 g, 4.4 mmol) in MeOH (20 mL) was added 1N NaOH (40 mL) and then the reaction mixture was heated to 100° C. and stirred for 16 h. The reaction mixture was cooled to room temperature and concentrated under reduced pressure. The residue was dissolved in H$_2$O (100 mL) and extracted with EtOAc (100 mL*2). The organic layer was concentrated and purified by Prep-TLC (Petroleum Ether/EtOAc=1/2, Rf=0.5), followed by column chromatography purification (silica gel, Petroleum Ether/EtOAc=5/1~1/1) to afford product Example 57e (500 mg, yield 39%) as a yellow solid.
LCMS [M+1]$^+$=305.9

Step 4: Example 57g

Example 57e (500 mg) was further separated by chiral SFC to afford Example 57f (peak 1: 260 mg, yield 50%) as a white solid and Example 57g (peak 2: 269.4 mg, yield 50%) as a yellow solid. Chiral SFC conditions:

| | | |
|---|---|---|
| Column: | CHIRALCELOD-H(ODH0CD-TC012) | |
| Column size: | 0.46 cm I.D. × 15 cm L | |
| Injection: | 2.0 ul | |
| Mobile phase: | Hexane/MeOH/EtOH = 50/40/10(V/V/V) | |
| Flow rate: | 1.0 ml/min | |
| Wave length: | UV 214 nm | |
| Temperature: | 35° C. | |
| HPLC equipment: | Shimadzu LC-20AT | CP-HPLC-09 |

Step 5: Example 57h

To a solution of Example 57g (269.4 mg, 0.883 mmol) in H$_2$O (7 mL) was treated with con. HCl (5 mL). The reaction mixture was cooled to 0° C. and then treated with a solution of NaNO$_2$ (80 mg, 1.11 mmol) in H$_2$O (5 mL) under the surface of the reaction mixture followed by a H$_2$O (1 mL) rinse. The reaction mixture was stirred at 0° C. for 30 min to give solution A. In a separate flask equipped with a magnetic stirred were added N-cyanoacetyl urethane (152 mg, 0.97 mmol), H$_2$O (10 mL) and pyridine (5 mL). The reaction mixture was cooled to 0° C. and the solution A was poured into the second reaction mixture. An orange precipitate formed and the suspension was stirred at 0° C. for 30 min. The reaction mixture was extracted with EtOAc (50 mL*3) and the combined organic layer was washed with brine (100 mL), concentrated to afford the crude product Example 57h (370 mg, crude) as an orange solid, which was used for the next step without further purification. LCMS [M+1]$^+$=472.9.

Step 6: Example 57

A suspension of Example 57h (370 mg, 0.78 mmol) and NaOAc (641 mg, 7.8 mmol) in AcOH (10 mL) was heated to 110° C. and stirred for 1.5 h. The reaction mixture was cooled to room temperature and concentrated under reduced pressure, which was purified by prep-HPLC (by Ultimate XB-C18, 50*250 mm, 10 μm, Mobile Phase: A (H$_2$O)/B (MeCN), Range of ratio:A/B (80%/20%) to A/B (52%/48%) 10 min and to A/B (32%/68%) 35 min, Rt of Peak: 23.6 min (58% of B), V=80 mL/min, wavelength 214 nm) to afford 105 mg crude as a yellow solid, which was further purified by trituration in DCM (3 mL) to afford Example 57 (68 mg, yield 20%) as a white solid. LCMS [M+1]$^+$=426.9.
$^1$H NMR (400 MHz, DMSO-d$_6$) δ 13.12 (s, 1H), 11.97 (s, 1H), 7.55-7.54 (m, 1H), 7.42-7.41 (m, 1H), 3.30-3.26 (m, 1H), 3.06-2.98 (m, 1H), 2.94-2.86 (m, 1H), 2.41-2.32 (m, 1H), 2.21 (s, 3H), 1.75-1.68 (m, 1H), 1.24 (d, J=7.2 Hz, 3H).

Example 58: General Procedure for Synthesis of Compound Example 58

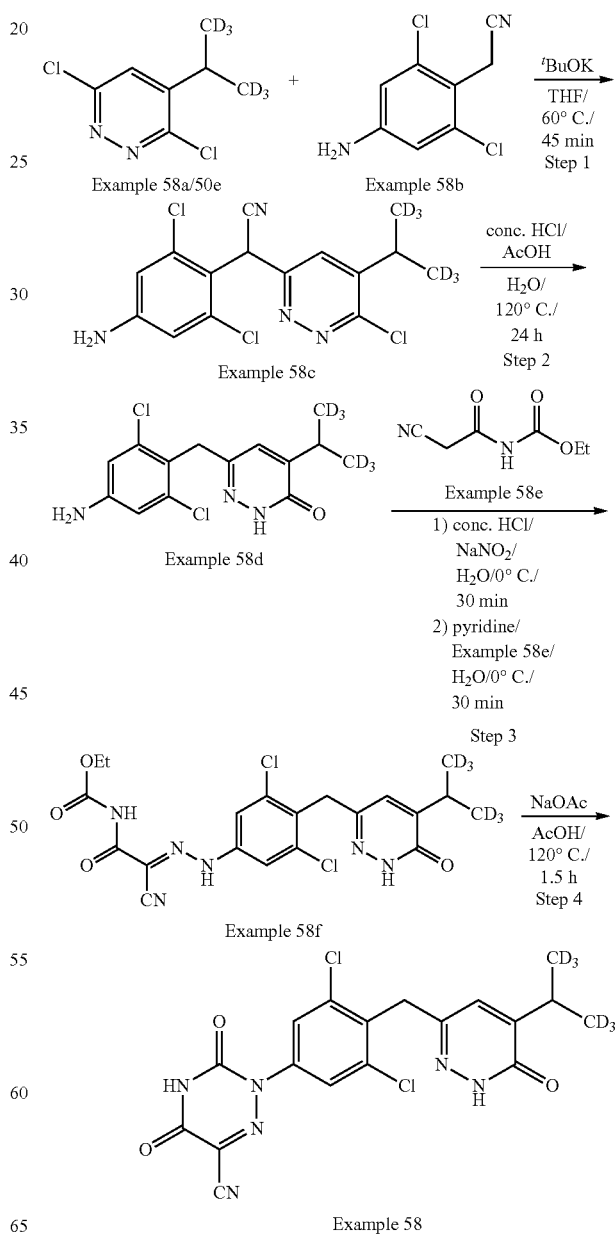

Step 1: Example 58c

A solution of Example 58a/50e (5.54 g, 29.0 mmol) in tetrahydrofuran (116 mL) in a 500 mL round bottom flask (caution: use an extra large flask) was treated with Example 58b (5.81 g, 28.9 mmol). The reaction flask was equipped with a cold water condenser and heated to 60° C. The flask was then raised out of the oil bath and potassium tert-butoxide (6.85 g, 58.0 mmol) was added. The mixture was heated to 60° C. for 45 min. The reaction mixture was cooled to room temperature, transferred to a separatory funnel, diluted with ethyl acetate (500 mL) and was washed with a saturated aqueous sodium chloride solution. The organic layer was separated, dried with magnesium sulfate, and was filtered. Silica gel was added to the filtrate and the solvent was concentrated under vacuum. The residue was purified by column chromatography (silica gel, 27% EtOAc in Petroleum Ether) to afford the desired product Example 58c (2.9 g, yield 52%) as a yellow solid. LCMS [M+1]=357.1.

Step 2: Example 58d

A mixture of Example 58c (6.98 g, 19.63 mmol), water (30 mL), concentrated hydrochloric acid (120 mL) and glacial acetic acid (30 mL) was heated to 120° C. for 24 h. The reaction mixture was cooled to room temperature and the mixture was poured onto water (250 mL). The pH was made neutral (pH=7) by the addition of a 4N aqueous sodium hydroxide solution. The suspension was placed in the freezer for 15 min and the resulting solids were filtered and washed with water and petroleum ether. The solids were collected and dissolved in hot ethyl acetate. The resulting mixture was purified by column chromatography using silica gel eluting with 40% ethyl acetate in hexanes to 50% ethyl acetate in hexanes containing 0.5% glacial acetic acid to afford the desired product Example 58d (4.65 g, yield 76%) as an off-white solid. LCMS [M+1]=314.1.

Step 3: Example 58f

A suspension of Example 58d (134 mg, 0.42 mmol) in water (5.6 mL) was treated with concentrated hydrochloric acid (2.8 mL). The reaction mixture was cooled to 0° C. and then was treated with a solution of sodium nitrate (36.5 mg, 0.529 mmol) in water (0.2 mL) under the surface of the reaction mixture followed by a water (0.2 mL) rinse. The reaction mixture was stirred at 0° C. for 30 min, and a solution formed. In a separate flask, equipped with a magnetic stirrer, was added N-cyanoacetylurethane Example 58e (73 mg, 0.46 mol), water (9.4 mL) and pyridine (2.8 mL). This reaction mixture was cooled to 0° C. and the solution from the first reaction was quickly filtered and poured into the second reaction mixture. An orange precipitate formed and the suspension was stirred at 0° C. for 30 min. The solid was filtered and rinsed with water followed by petroleum ether. The solid was dried in a vacuum oven overnight at 80° C. to afford to afford the desired product Example 58f (156 mg, 76%) as an orange solid. LCMS [M+1]=484.1.

Step 8: Example 58

A mixture of Example 58f (100 mg, 0.2 mmol) in glacial acetic acid (5 mL) was treated with sodium acetate (82.8 mg, 1.01 mmol) at room temperature. The reaction mixture was heated to 120° C. for 1.5 h. At this time, the reaction mixture was cooled to 0° C., diluted with water (10 mL), and stirred for 30 min. The reaction mixture was cooled to ambient temperature and concentrated under reduced pressure, which was purified by prep-HPLC (by Xbridge C18, 19 mm*250 mm, Mobile Phase: A (H$_2$O)/B (MeCN), gradient elution, 15 min) to afford the desired product Example 58 (30 mg, yield 34%) as a white solid. LCMS [M+1]=438.1. $^1$H NMR (400 MHz, DMSO-d6) δ 13.25 (br. s., 1H), 12.60 (s, 1H), 7.65 (s, 2H), 7.34 (s, 1H), 4.29 (s, 2H), 2.91-3.08 (m, 1H).

Example 59: General Procedure for Synthesis of Compound Example 59

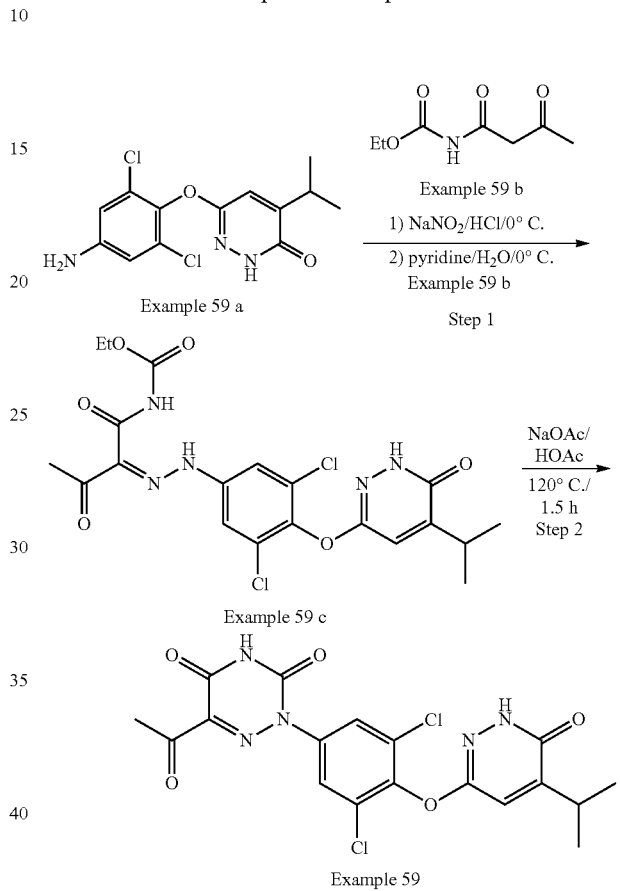

Step 1: Example 59c

A suspension of Example 59a (500 mg, 2 mmol) in H$_2$O (12 mL) was treated with HCl (conc., 6 mL). The reaction mixture was cooled to 0° C. and then added a solution of NaNO$_2$ (100 mg, 2 mmol) in H$_2$O (0.2 mL) followed by a rinsed with H$_2$O (0.2 mL). The reaction mixture was stirred at 0° C. for 30 min to give solution A. In a separate flask equipped with a magnetic stirrer were added Example 59b (300 mg, 2 mmol), H$_2$O (9.4 mL) and pyridine (6 mL). The reaction mixture was cooled to 0° C. and the solution A was dropped into the reaction mixture. An orange precipitate formed and the suspension was stirred at 0° C. for 30 min. The reaction mixture was extracted with EtOAc (10 mL*3), and the combined organic layer was washed with brine (10 mL), and concentrated to afford Example 59c (500 mg, crude) as an orange solid, which was used for next step without further purification. LC-MS [M+1]$^+$=498.1

Step 2: Example 59

A suspension of Example 59c (184 mg, 0.369 mmol) and NaOAc (152 mg, 1.845 mmol) in AcOH (10 mL) was heated to 120° C. and stirred for 1.5 h. The reaction mixture was cooled to room temperature and concentrated under reduced pressure. The residue was purified by prep-HPLC (by Xbridge C18, 19 mm*250 mm, Mobile Phase: A ($H_2O$)/B (MeCN), gradient elution, 15 min) to afford Example 59 (46.8 mg, yield 28%) as a white solid. LC-MS [M+1]$^+$=452.1. $^1$H NMR (400 MHz, $CDCl_3$) δ 11.58 (s, 1H), 10.90 (s, 1H), 7.57 (s, 2H), 7.18 (d, J=0.9 Hz, 1H), 3.32-3.23 (m, 1H), 2.60 (s, 3H), 1.31 (d, J=6.9 Hz, 6H).

Example A: THR Coactivator Recruitment Assay

Binding of compounds to the THRβ or THRα receptor causes a conformational change around helix 12 in the ligand binding domain, resulting in higher affinity for the coactivator peptide. The coactivator recruitment assay was performed using LanthaScreen™ TR-FRET TR coactivator assay kit (ThermoFisher). A 10-point 1:5 dilution series of Thyroid hormone T3 (top dose 500 nM), and 9-point 1:4 dilution series of test compounds (top dose 6,250 nM) was prepared in TR-FRET coregulator buffer C using liquid dispenser (Tecan D300e) in 2× of the final test concentration. THRβ-LBD (ligand binding domain) or THRα-LBD was added to test compounds at a final concentration of 2.5 nM followed by addition of a mixture of the fluorescein-coactivator peptide and terbium-conjugated anti-GST antibody. The diluted test compounds were mixed with the same volume of other reagents (10 μl:10 μl). After 2-hour incubation period at room temperature, the plate was read at wavelengths of 520 nm and 495 nm using Envison plate reader (PerkinElmer). The TR-FRET ratio of 520:495 was calculated and used to determine the $EC_{50}$ from a dose response curve of test compounds. Table 2 shows the activity of the compounds measured described above. Compounds with an activity designation of "A" provided an $EC_{50}$≤0.1 μM; Compounds with an activity designation of "B" provided an $EC_{50}$ of 0.1 μM–1 μM; Compounds with an activity designation of "C" provided an $EC_{50}$ of 1 μM–10 μM; Compounds with an activity designation of "D" provided an $EC_{50}$≥10 μM. In addition, the selectivity for each compound was normalized for the selectivity of T3 run in the same assay. The level of maximum activity was described as the percentage of the maximum activity of each compound relative to the maximum activity of 500 nM T3.

TABLE 2

In vitro binding activity of compounds

| Ex. | THRβ binding | THRβ Bmax % (vs T3) | THRα binding | THRα Bmax % (vs T3) | THRβ/α selectivity ratio |
|---|---|---|---|---|---|
| MGL-3196 | A | 54 | B | 49 | 10.2 |
| 1 | B | 80 | C | 88 | 11.9 |
| 2 | D | 27 | | | |
| 3 | D | 6 | | | |
| 4 | D | 0 | | | |
| 5 | B | 27 | | | |
| 6 | D | 0 | | | |
| 7 | A | 52 | B | 41 | 15.6 |
| 9 | B | 46 | D | 39 | |
| 10 | D | 1 | | | |
| 11 | D | 0 | | | |
| 12 | C | 35 | | | |
| 13 | C | 41 | | | |
| 15 | B | 38 | | | |
| 16 | D | 1 | | | |
| 17 | D | 0 | | | |
| 19 | D | 16 | | | |

TABLE 2-continued

In vitro binding activity of compounds

| Ex. | THRβ binding | THRβ Bmax % (vs T3) | THRα binding | THRα Bmax % (vs T3) | THRβ/α selectivity ratio |
|---|---|---|---|---|---|
| 20 | D | 6 | | | |
| 22 | D | 6 | | | |
| 23 | C | 24 | | | |
| 24 | B | 38 | | | |
| 25 | C | 28 | | | |
| 26 | D | 7 | | | |
| 29 | D | 8 | | | |
| 30 | A | 48 | B | 34 | 15.1 |
| 31 | B | 26 | | | |
| 32 | D | 12 | | | |
| 34 | D | 23 | | | |
| 38 | D | 6 | | | |
| 41 | A | 50 | B | 36 | 12.3 |
| 42 | B | 27 | D | 3 | |
| 43 | D | 7 | D | 3 | |
| 44 | D | 7 | D | 5 | |
| 47 | D | 10 | D | 4 | |
| 48 | B | 45 | B | 23 | 4.85 |
| 50 | B | 51 | C | 36 | 13.5 |
| 51 | A | 37 | B | 33 | 5 |
| 52 | B | 23 | B | 15 | 1 |
| 53 | B | 12 | D | 2 | |
| 56 | | | | | |
| 57 | A | 53 | C | 43 | 13.7 |
| 58 | A | 69 | B | 51 | 12.5 |

Example B: Cholesterol-Lowering Efficacy in Trans-Fat AMLN Diet-Induced Hypercholesterolemia Mouse Model C57BL/6cnc mice were fed with AMLN diet containing 40Kcal % Fat, 20Kcal % Fructose and 2% Cholesterol (Research Diets, D09100301) for 5 weeks to induce hypercholesterolemia. The cholesterol lowering efficacy of compounds disclosed herein were tested in two separate studies. In the first study, animals were administered MGL-3196 and Example 7 at 0.3, 1, 3 mg/kg by oral gavage or simply the vehicle (2% Klucel). In the second study, animals were administered orally with MGL-3196, Example 41, Example 30, and Example 50 at 1 and 3 mg/kg. Thyroid hormone T3 (0.1 mg/kg, intraperitoneal injection) was evaluated as a positive control in both studies. The treatment lasted two weeks with daily oral gavage. Blood samples were taken before the dosing on the first day and again at the end of study for detection of plasma cholesterol (TC), triglycerides (TG) and LDL-c. The ALT and AST levels were also measured to monitor the effects of MGL-3196 and Example 7 on liver function. At the end of study, the liver tissues were taken for measuring the hepatic TC and TG levels. The compound concentration was quantified in blood, liver and heart.

Figure 1D:
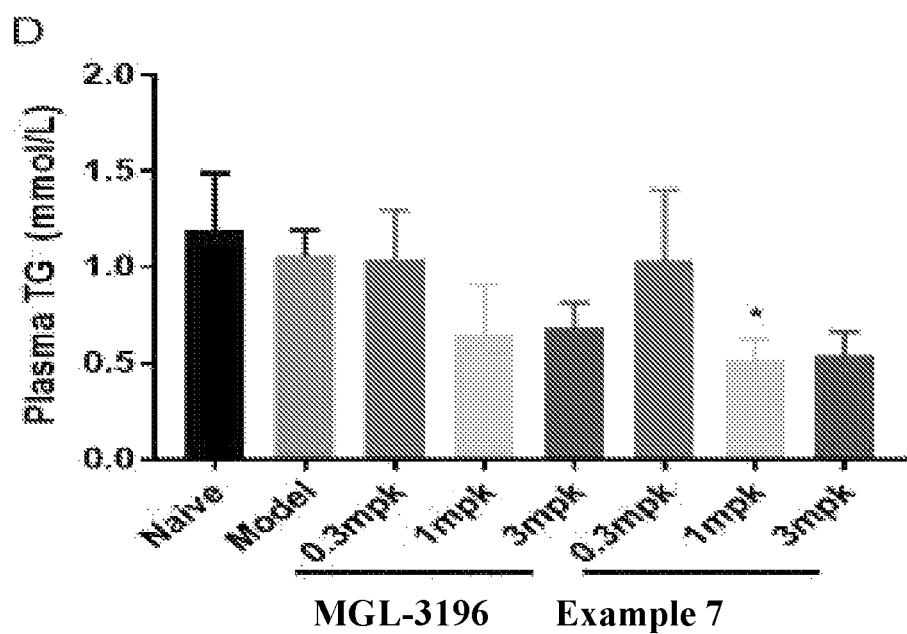
FIG. 1D shows the plasma triglyceride levels after administration of MGL-3196 and Example 7 in a trans-fat AMLN diet-induced hypercholesterolemia mouse model.
Figure 1E:
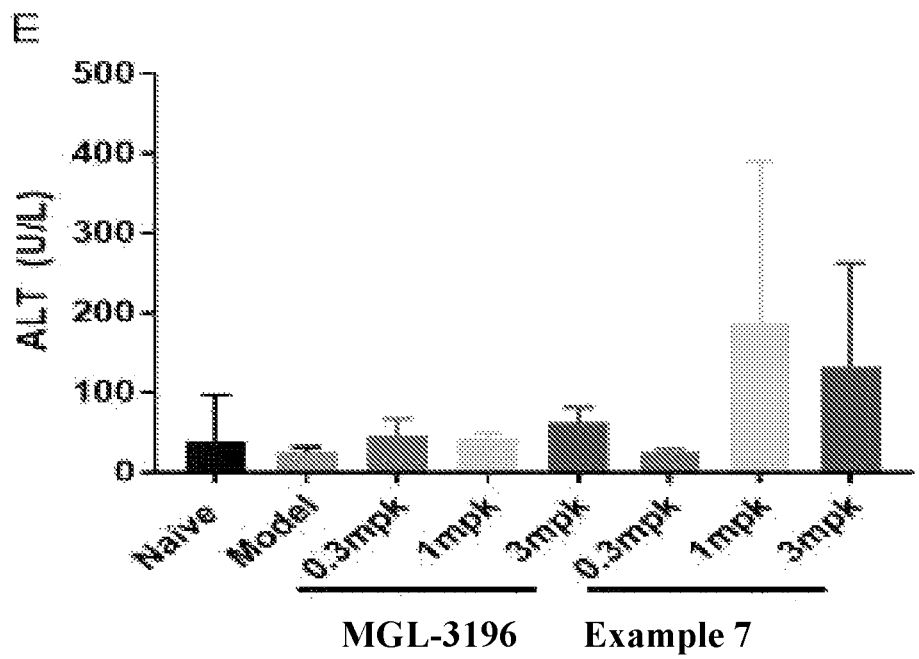
FIG. 1E shows the ALT (alanine transaminase) levels after administration of MGL-3196 and Example 7 in a trans-fat AMLN diet-induced hypercholesterolemia mouse model.
Figure 1F:
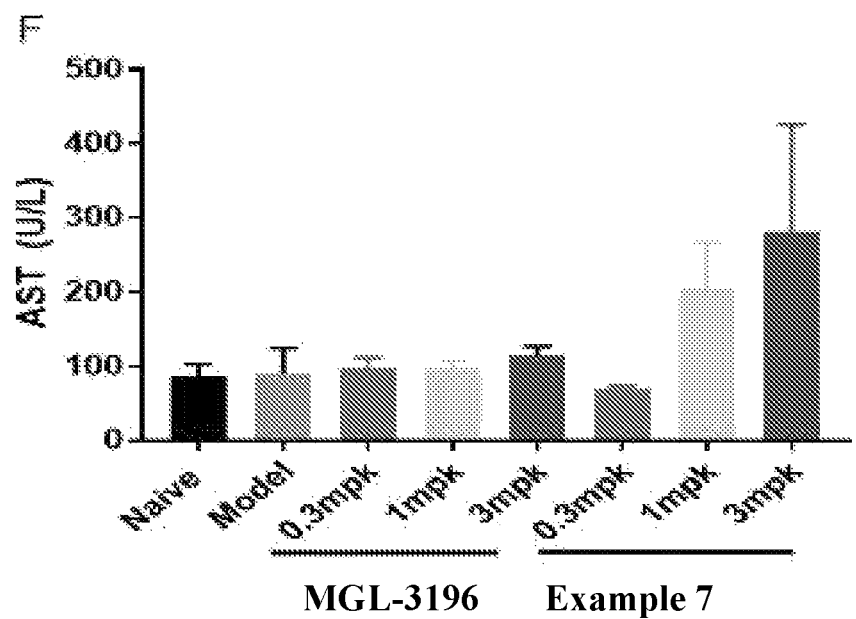
FIG. 1F shows the AST (aspartate transaminase) levels after administration of MGL-3196 and Example 7 in a trans-fat AMLN diet-induced hypercholesterolemia mouse model.
Figure 2A:
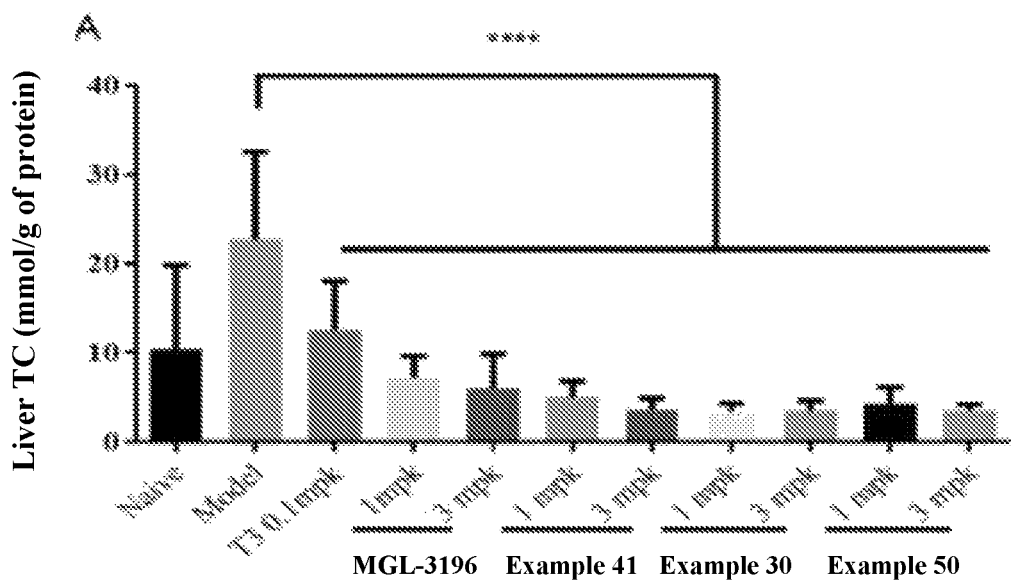
FIG. 2A shows the liver cholesterol levels after administration of MGL-3196, Example 41, Example 30, and Example 50 in a trans-fat AMLN diet-induced hypercholesterolemia mouse model.
Figure 2B:
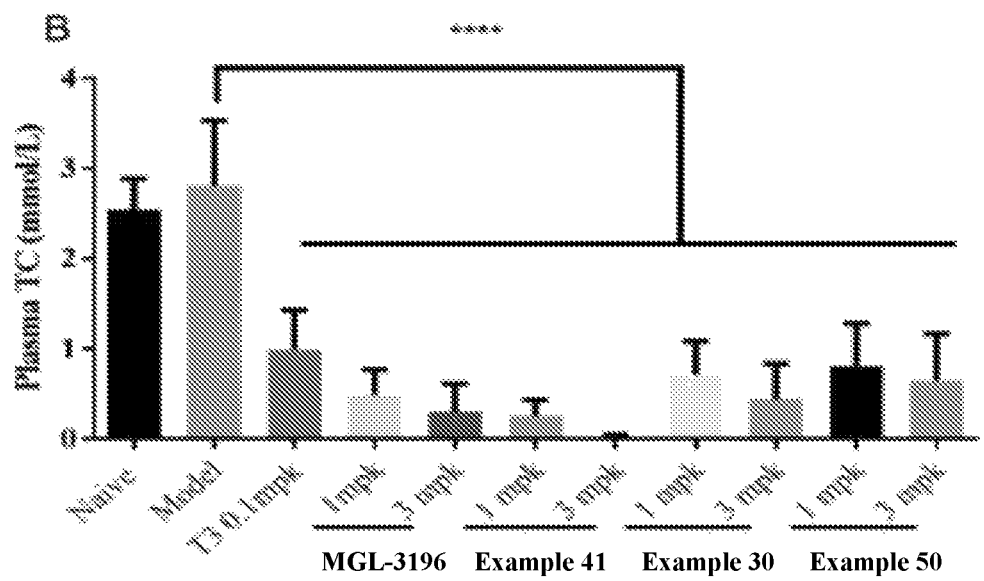
FIG. 2B shows the plasma cholesterol levels after administration of MGL-3196, Example 41, Example 30, and Example 50 in a trans-fat AMLN diet-induced hypercholesterolemia mouse model.
Figure 2C:
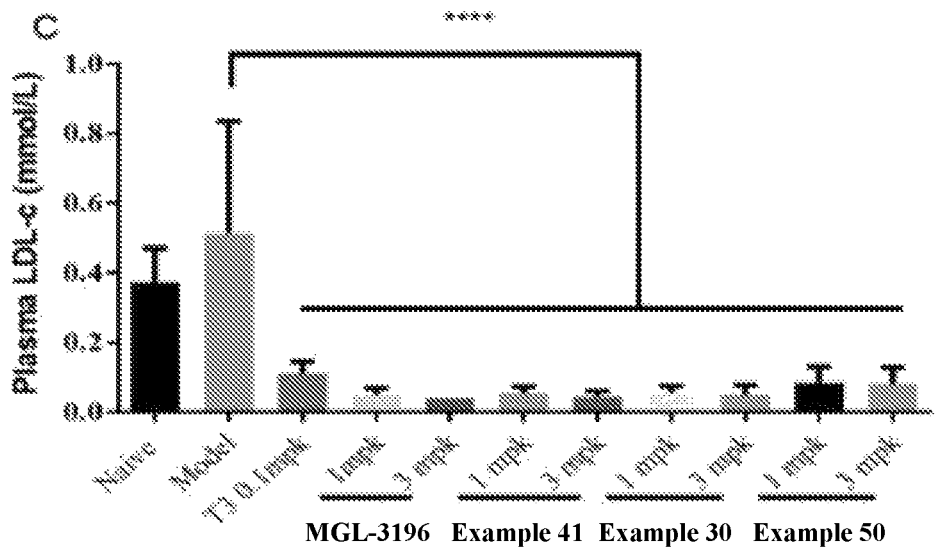
FIG. 2C shows the plasma LDL-c levels after administration of MGL-3196, Example 41, Example 30, and Example 50 in a trans-fat AMLN diet-induced hypercholesterolemia mouse model.
Figure 2D:
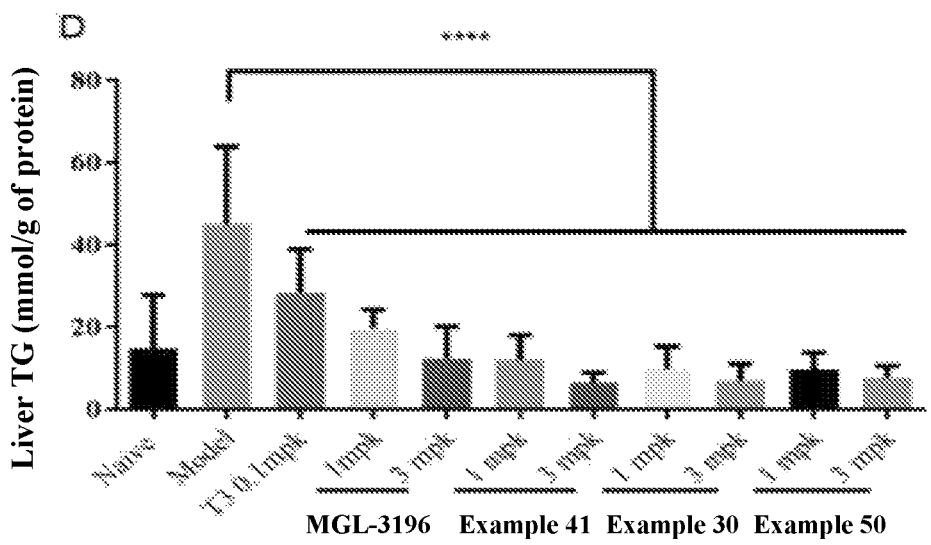
FIG. 2D shows the liver triglyceride levels after administration of MGL-3196, Example 41, Example 30, and Example 50 in a trans-fat AMLN diet-induced hypercholesterolemia mouse model.

Example 7, Example 41, Example 30, Example 50 all significantly reduced liver TC, plasma TC and LDL-c with efficacy comparable to or better than MGL-3196 at the same dose (FIG. 1A to FIG. 1F and FIG. 2A to FIG. 2D). Among these, Example 41 was the most effective in reducing the liver and plasma cholesterol (FIG. 2A and FIG. 2B). These compounds also reduced the triglyceride level in plasma and liver at dose of 1 mg/kg and above (FIG. 1D and FIG. 2D). More importantly, Example 7 had no effect on ALT and AST, but MGL-3196 increased ALT and AST at doses greater than 1 mg/kg (FIG. 1E and FIG. 1F). These results indicated that Example 7 has comparable efficacy to MGL-3196 in liver cholesterol reduction, but safer than MGL-3196 in liver function. Example 41 was more effective at lowing cholesterol than MGL-3196, while Example 30 and Example 50 had similar efficacy in reducing cholesterol. Significance analysis was compared with the model, *p<0.05, p<0.01, *p<0.001, ****p<0.0001 from one-way ANOVA. mpk: mg/kg.

Example C: Cholesterol-Lowering Efficacy in High Cholesterol Diet-Induced Hypercholesterolemia Mouse Model To further confirm the PD effects of compounds, another diet induced NAFLD mouse model was used. C57BL/6cnc mice were fed with the diet containing 1.5% cholesterol and 0.5% cholic acid (Research Diets, D12109C) for 2 weeks prior to the initiation of treatment. The cholesterol lowering efficacy of compounds disclosed herein was tested in two separate studies. In the first study, animals were administrated with MGL-3196 and Example 7 at 0.3, 1, 3 mg/kg or simply the vehicle (2% Klucel). In the second study, animals were administrated orally with MGL-3196, Example 41, Example 30, and Example 50 at 0.3, 1 and 3 mg/kg. Thyroid hormone T3 (0.1 mg/kg, intraperitoneal injection) was evaluated as a positive control in the second study. The treatment lasted two weeks with daily oral gavage. Blood samples were taken at the end of study for plasma cholesterol and LDL-c detection. At the end of study, the liver tissues were taken for measurement of the hepatic cholesterol levels. DIO1 is a THRβ target gene in liver, and its mRNA level reflects the activity of THRβ. Therefore, the expression of DIO1 was also quantitated in liver tissue by qPCR to examine the target engagement by these compounds. The compound concentration was quantified in blood, liver and heart.

Figure 3A:
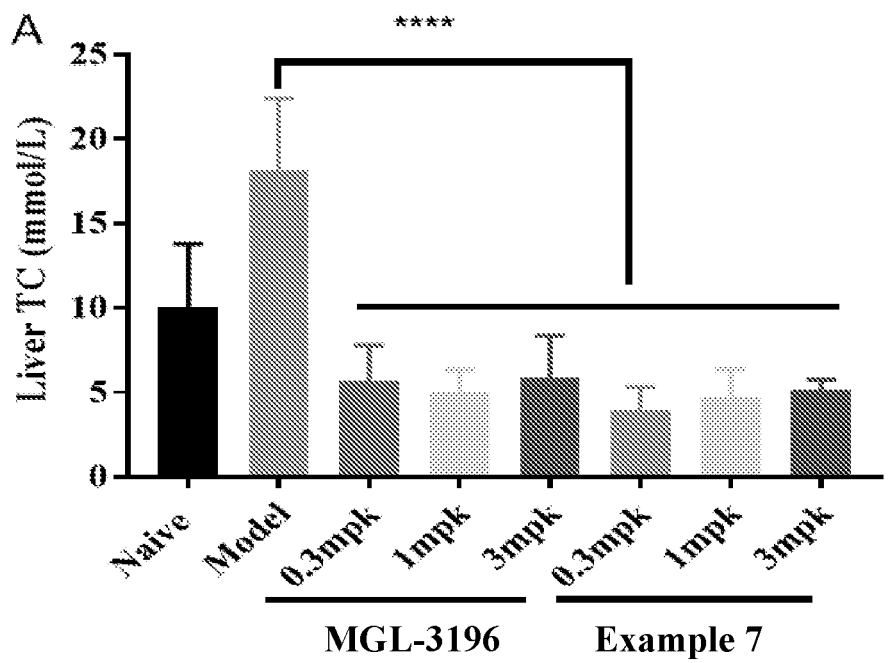
FIG. 3A shows the liver cholesterol levels after administration of MGL-3196 and Example 7 in a diet-induced hypercholesterolemia mouse model.
Figure 3B:
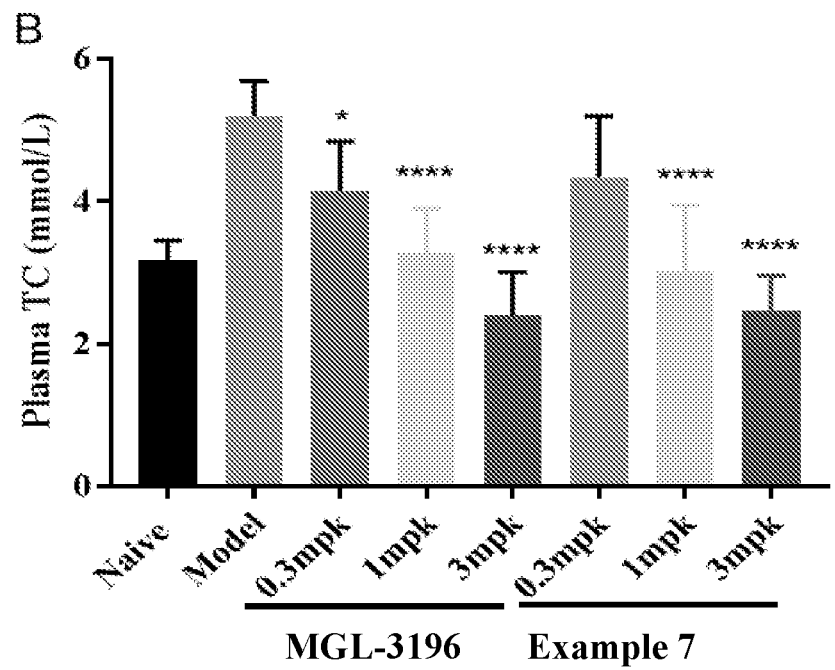
FIG. 3B shows the plasma cholesterol levels after administration of MGL-3196 and Example 7 in a high cholesterol diet-induced hypercholesterolemia mouse model.
Figure 3C:
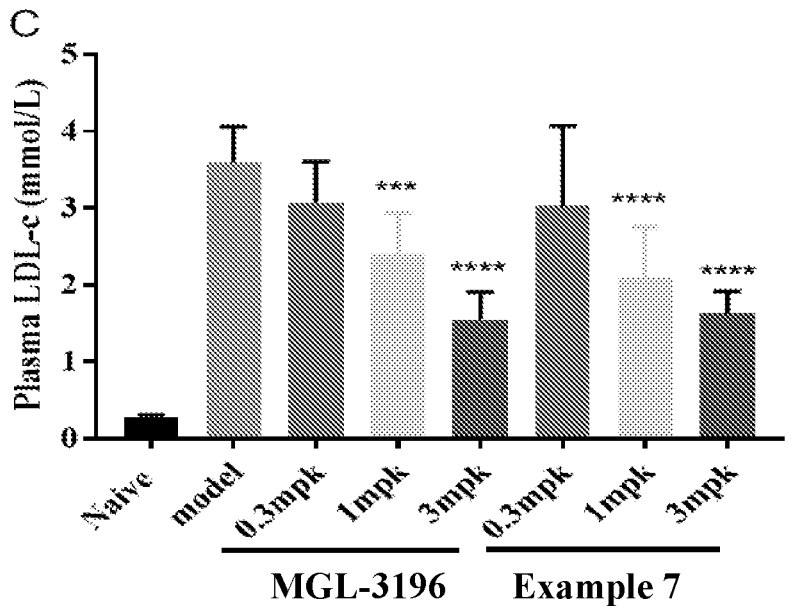
FIG. 3C shows the plasma LDL-c levels after administration of MGL-3196 and Example 7 in a diet-induced hypercholesterolemia mouse model.
Figure 3D:
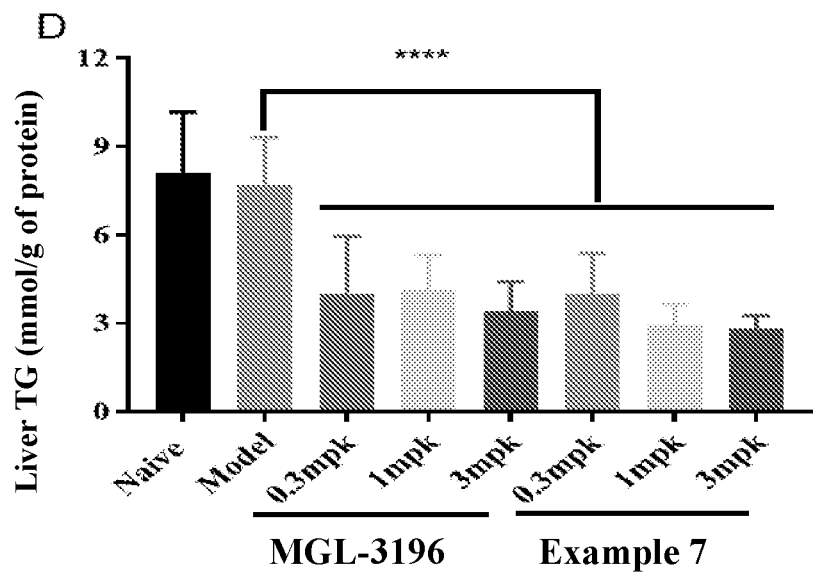
FIG. 3D shows the liver triglyceride levels after administration of MGL-3196 and Example 7 in a diet-induced hypercholesterolemia mouse model.
Figure 3E:
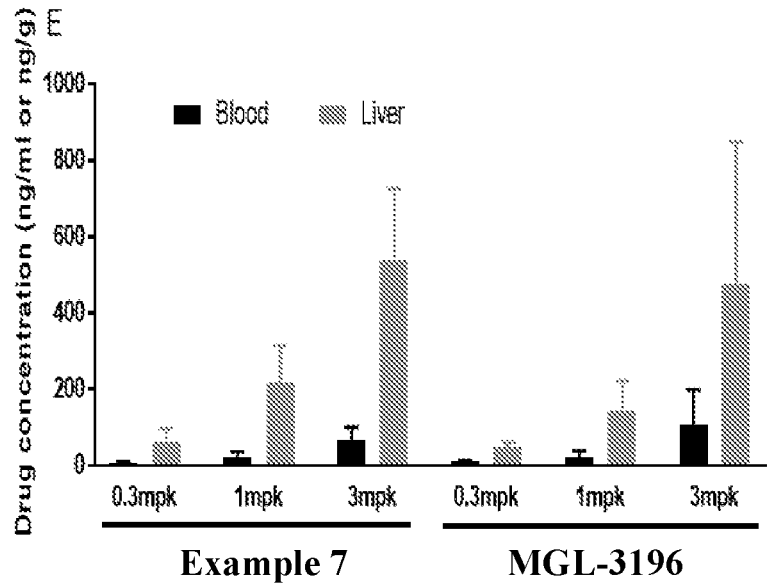
FIG. 3E shows the blood and liver compound distribution after administration of MGL-3196 and Example 7 in a diet-induced hypercholesterolemia mouse model.
Figure 3F:
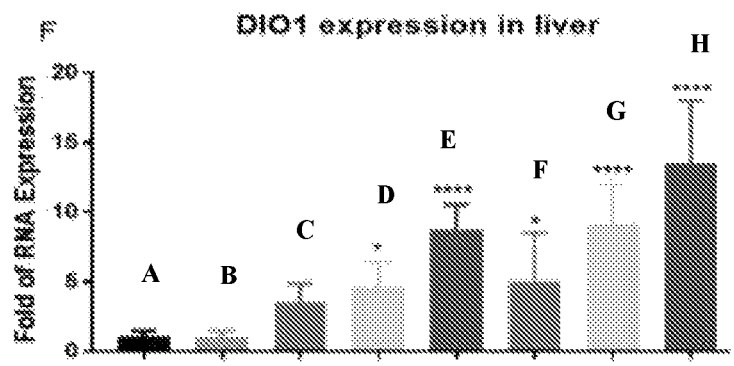
FIG. 3F shows the liver DIO1 expression after administration of MGL-3196 and Example 7 in a diet-induced hypercholesterolemia mouse model.
Figure 4A:
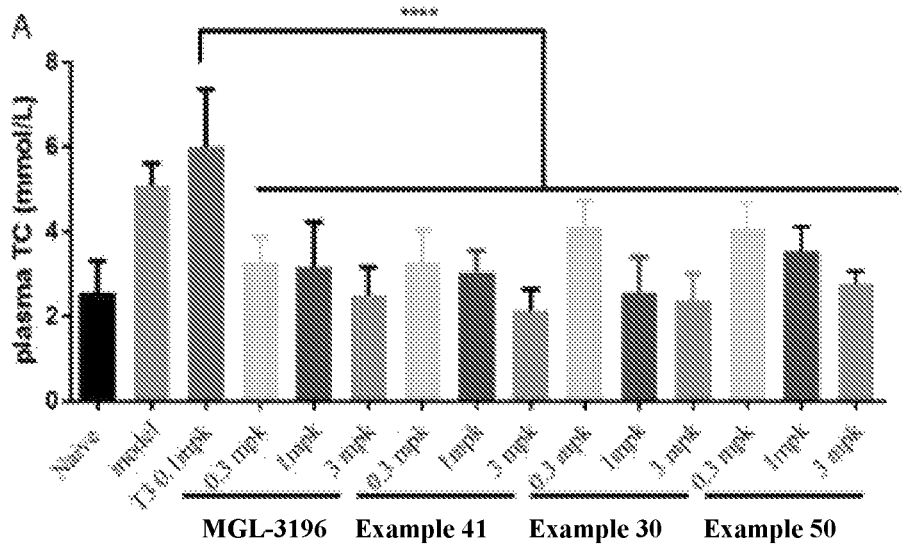
FIG. 4A shows the plasma cholesterol levels after administration of MGL-3196, Example 41, Example 30, and Example 50 in a high cholesterol diet-induced hypercholesterolemia mouse model.
Figure 4B:
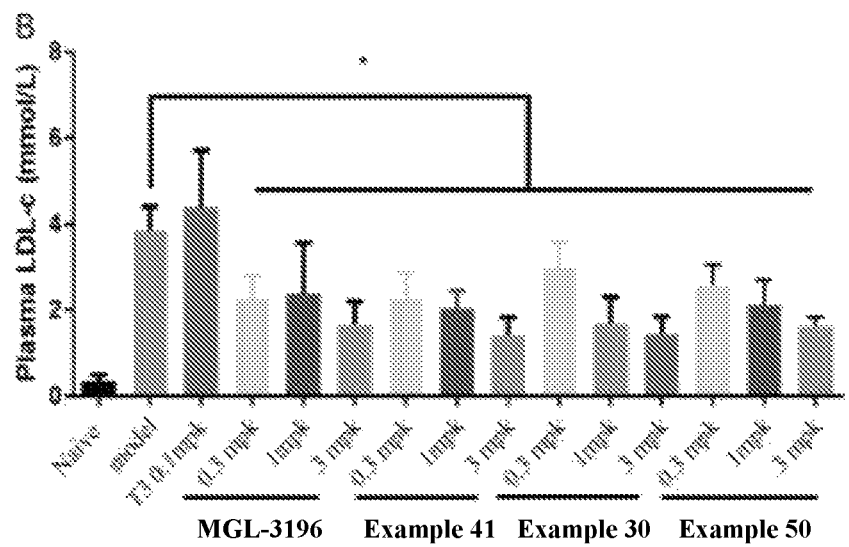
FIG. 4B shows the plasma LDL-c levels after administration of MGL-3196, Example 41, Example 30, and Example 50 in a diet-induced hypercholesterolemia mouse model.
Figure 4C:
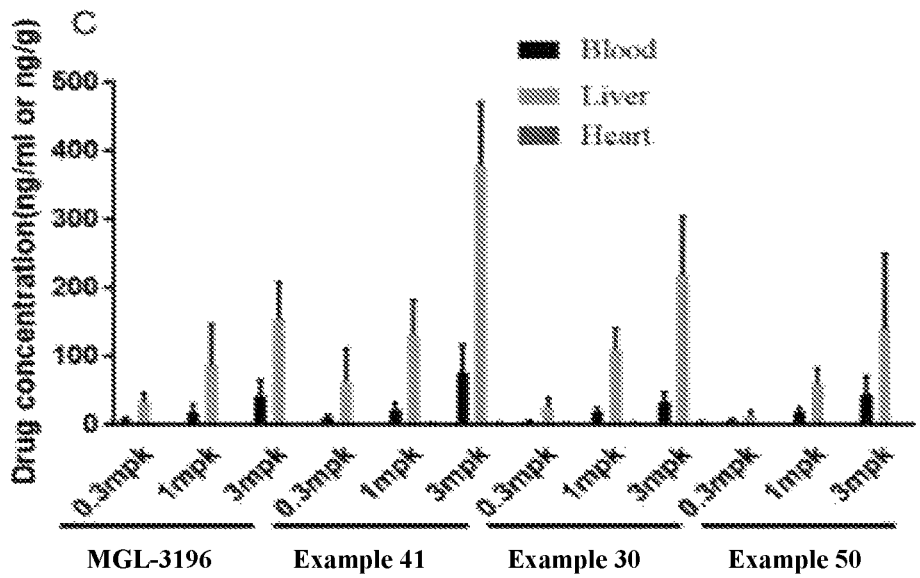
FIG. 4C shows the blood, liver, and heart compound distribution after administration of MGL-3196, Example 41, Example 30, and Example 50 in a diet-induced hypercholesterolemia mouse model.
Figure 4D:
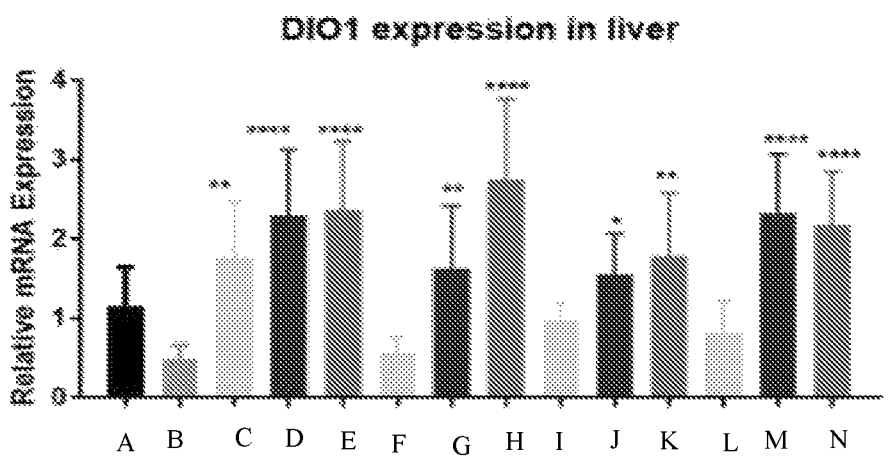
FIG. 4D shows the liver DIO1 expression after administration of MGL-3196, Example 41, Example 30, and Example 50 in a diet-induced hypercholesterolemia mouse model.

As MGL-3196, Example 7, Example 41, Example 30, and Example 50 reduced plasma TC and LDL-c after 2-week treatment (FIG. 3B, FIG. 3C, FIG. 4A, and FIG. 4B). The liver TC and TG were significantly decreased by Example 7 or MGL-3196 (FIG. 3A and FIG. 3D). Example 7, Example 41, Example 30 and Example 50 were as effective as MGL-3196 in reduce liver cholesterol. Example 7, Example 41, Example 30, Example 50 have similar blood and liver distribution, but not detectable in heart (FIG. 3E and FIG. 4C). The expression of DIO lin liver was dose-dependently upregulated by treatment of MGL-3196, Example 7, Example 41, Example 30 and Example 50 (FIG. 3F and FIG. 4D). These studies indicated these compounds lowered TC and LDL-c through activating THRβ. Significance analysis was compared with the model. *p<0.05, p<0.01, *p<0.001, ****p<0.0001 from one-way ANOVA. mpk: mg/kg Example D: Antifibrotic and Fat Reduction Efficacy in NASH Mouse Model C57BL/6cnc mice were fed with high-fat diet containing 60 kacl % fat and 0.1% methionine (no added choline) (Research Diets, A06071302) for 12 weeks to induce NASH model. After 12-week diet induction, the mice had increased plasma levels of TC, LDL-c, ALT, and fibrosis markers. Two studies were performed on this diet-induced NASH model with different compounds and treatment durations. In the first study, the mice were administrated with MGL-3196, Example 7 at 1 mg/kg or simply the vehicle (2% Klucel) every day by oral gavage for 12 weeks. In the second study, the mice were administrated with Example 7, Example 41 and Example 30 at 1 mg/kg or simply the vehicle (2% Klucel) every day by oral gavage for 6 weeks. Serum biochemistry was measured before dosing during study. At the end of the experiment, liver was collected to measure liver TC and TG. Livers were punched in 2 mm diameter and fixed, sectioned and stained with Sirius Red, and the fibrosis and steatosis were scored.

Figure 5A:
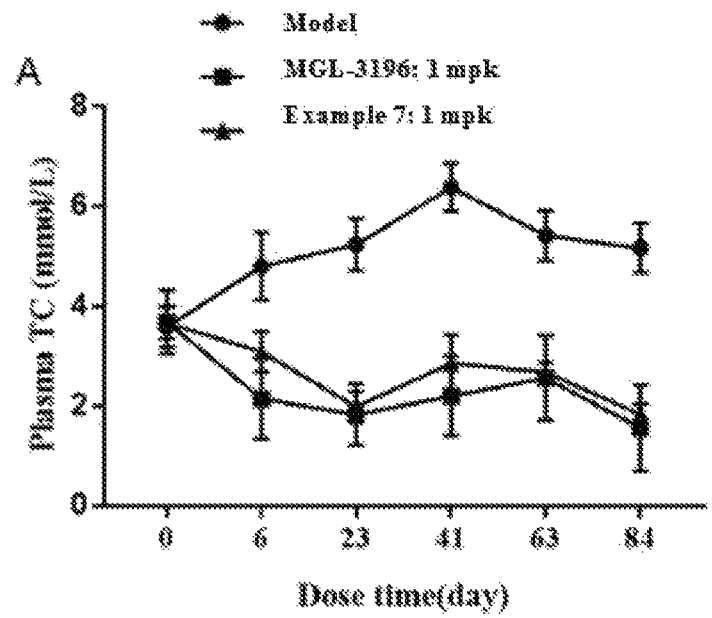
FIG. 5A shows the plasma cholesterol levels after administration of MGL-3196 and Example 7 in a NASH mouse model.
Figure 5B:
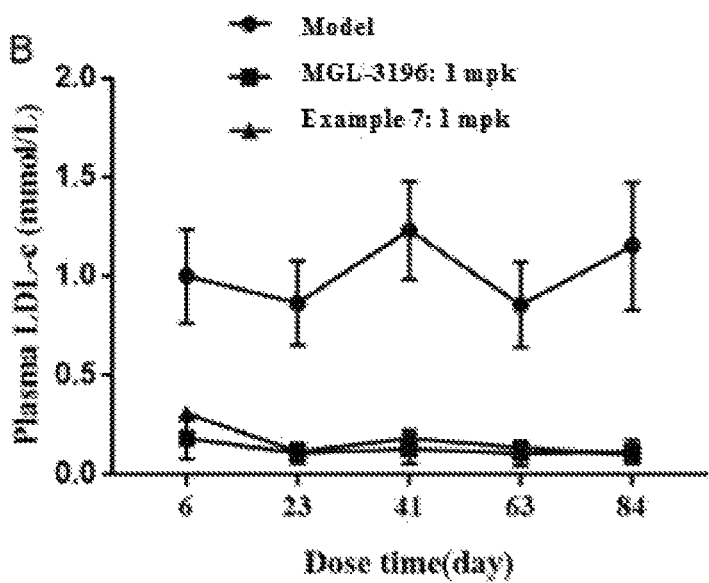
FIG. 5B shows the plasma LDL-c levels after administration of MGL-3196 and Example 7 in a NASH mouse model.
Figure 5C:
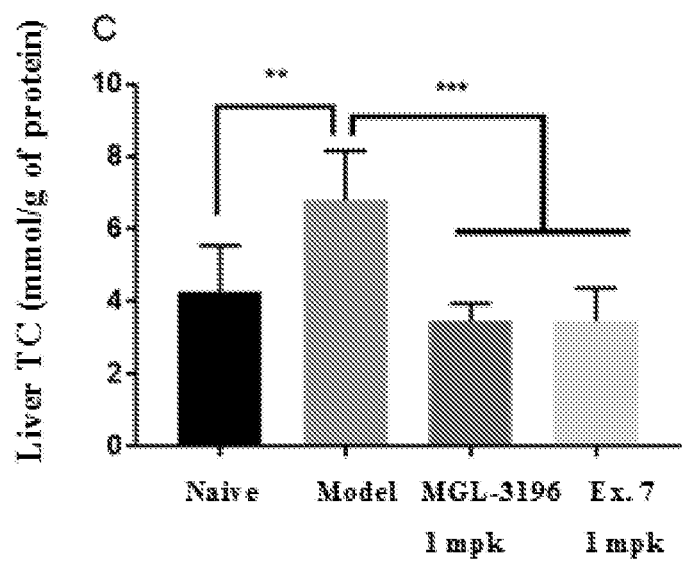
FIG. 5C shows the liver cholesterol levels after administration of MGL-3196 and Example 7 in a NASH mouse model.
Figure 5D:
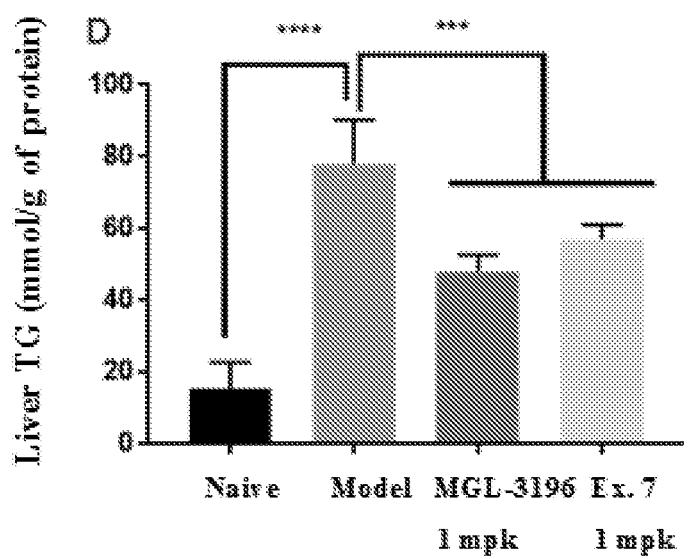
FIG. 5D shows the liver triglyceride levels after administration of MGL-3196 and Example 7 in a NASH mouse model.
Figure 5E:
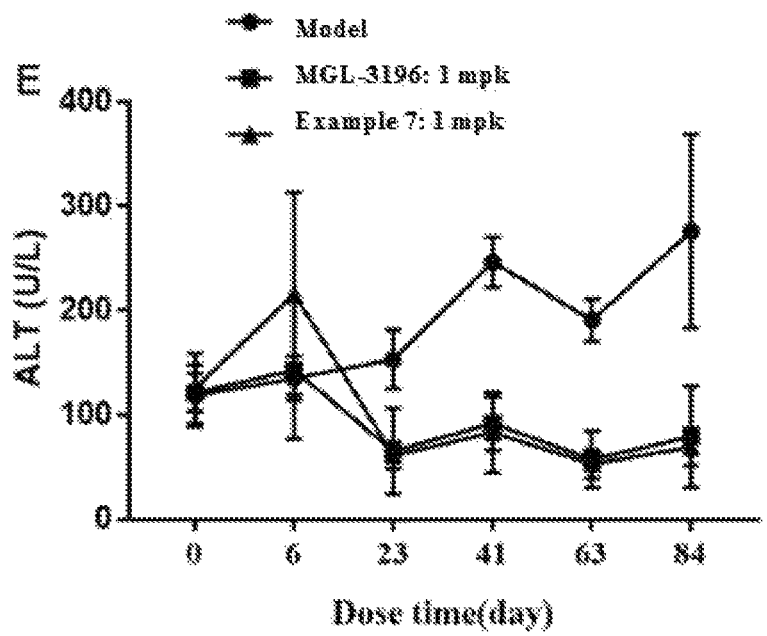
FIG. 5E shows the ALT (alanine transaminase) levels after administration of MGL-3196 and Example 7 in a NASH mouse model.
Figure 5F:
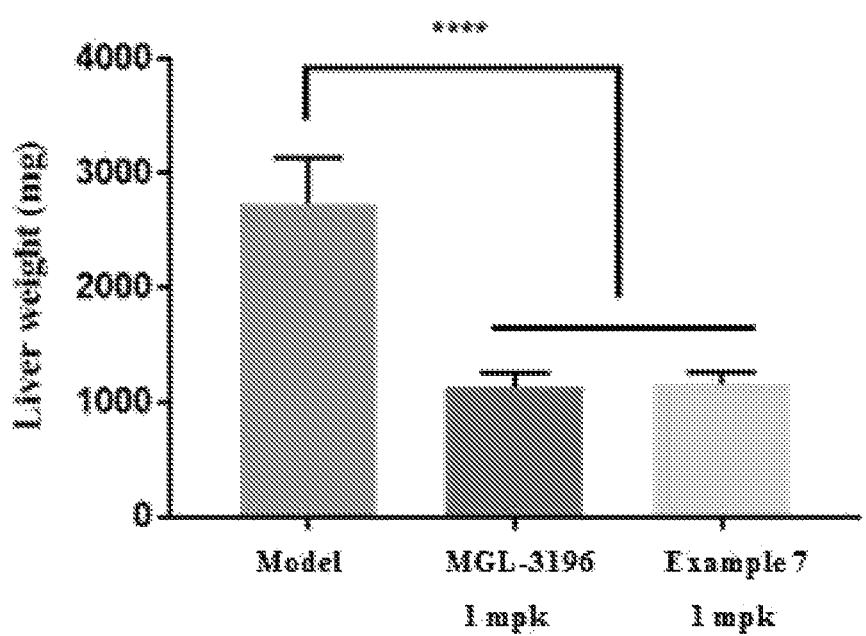
FIG. 5F shows the liver weight after administration of MGL-3196 and Example 7 in a NASH mouse model.
Figure 5G:
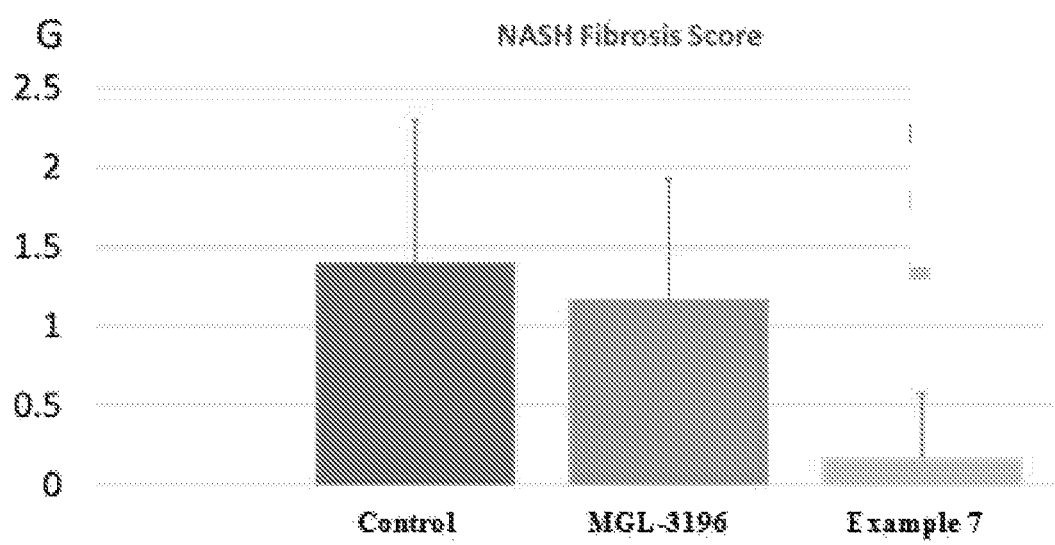
FIG. 5G shows the NASH fibrosis scores after administration of MGL-3196 and Example 7 in a NASH mouse model.

In the first NASH study of 12-week treatment of MGL-3196 or Example 7 at 1 mg/kg daily, the mice had reduced plasma TC level as early as 6 days after treatment. The TC level remained the trend of decrease until back to normal level (FIG. 5A). While the mice on vehicle continued to increase TC level until reach plateau. Similarly, plasma LDL-c level was reduced to normal range by treatment of MGL-3196 or Example 7 (FIG. 5B). The diet also induced increase of liver TC and TG at the end of study, but the treatments by MGL-3196 or Example 7 significantly decreased the liver TC and TG (FIG. 5C and FIG. 5D). While the diet deteriorated the liver function as indicated by increased ALT level and enlarged liver, the treatment ameliorated the liver function and reduced the ALT level and liver weight to normal range (FIG. 5E and FIG. 5F). MGL-3196 and Example 7 were equivalent in these activity, However, Example 7 was more efficient in improving fibrosis confirmed by histopathology. The liver tissue pathological measurement showed that the fibrosis score of Example 7 was much lower than that of control group and MGL-3196-treated group, indicating that Example 7 effectively relieved liver fibrosis (FIG. 5G). Significance analysis was compared with the model, *p<0.05, p<0.01, *p<0.001, ****p<0.0001 from one-way ANOVA. mpk: mg/kg.

Figure 6A:
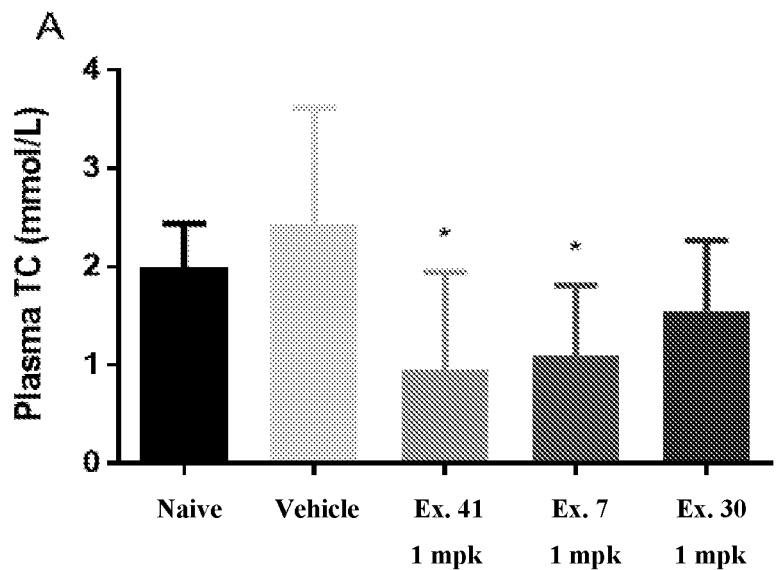
FIG. 6A shows the plasma cholesterol levels after administration of Example 7, Example 30, and Example 41 in a NASH mouse model.
Figure 6B:
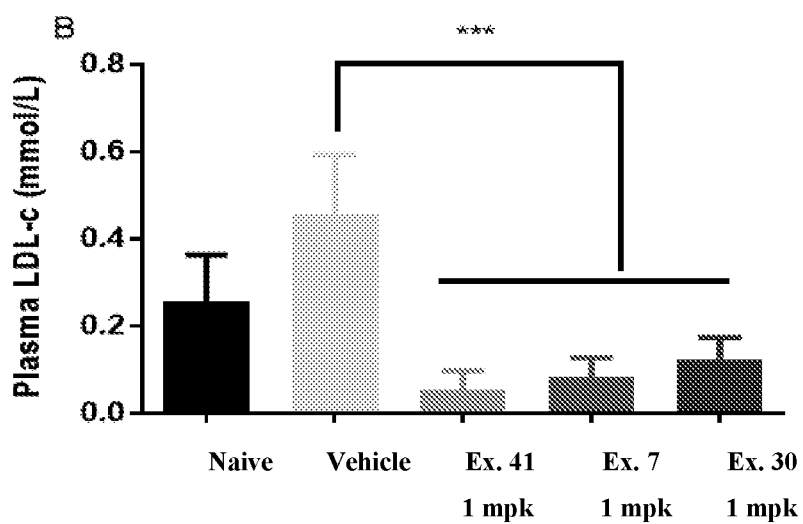
FIG. 6B shows the plasma LDL-c levels after administration of Example 7, Example 30, and Example 41 in a NASH mouse model.
Figure 6C:
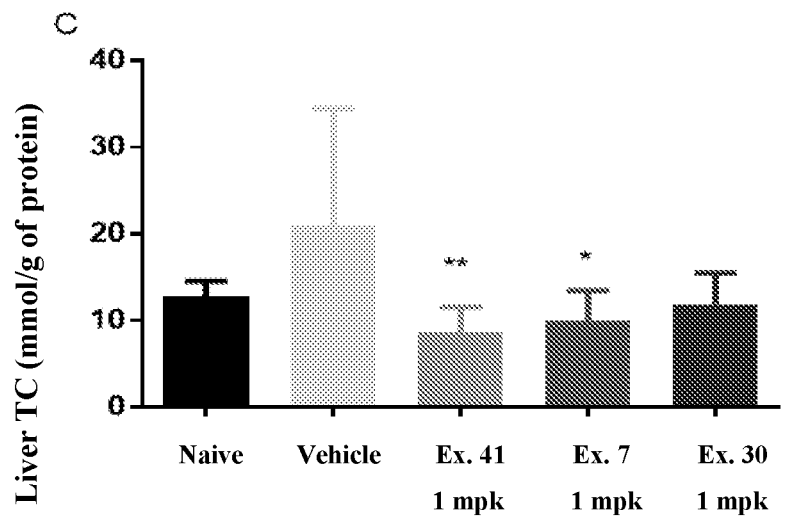
FIG. 6C shows the liver cholesterol levels after administration of Example 7, Example 30, and Example 41 in a NASH mouse model.
Figure 6D:
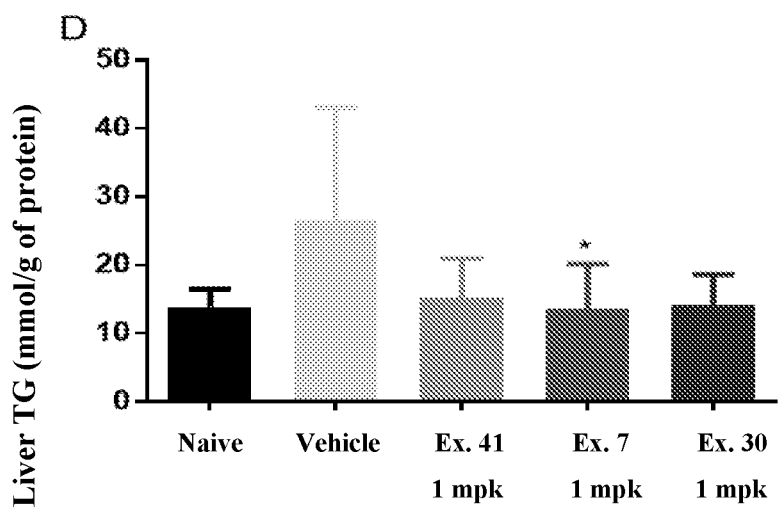
FIG. 6D shows the liver triglyceride levels after administration of Example 7, Example 30, and Example 41 in a NASH mouse model.
Figure 6E:
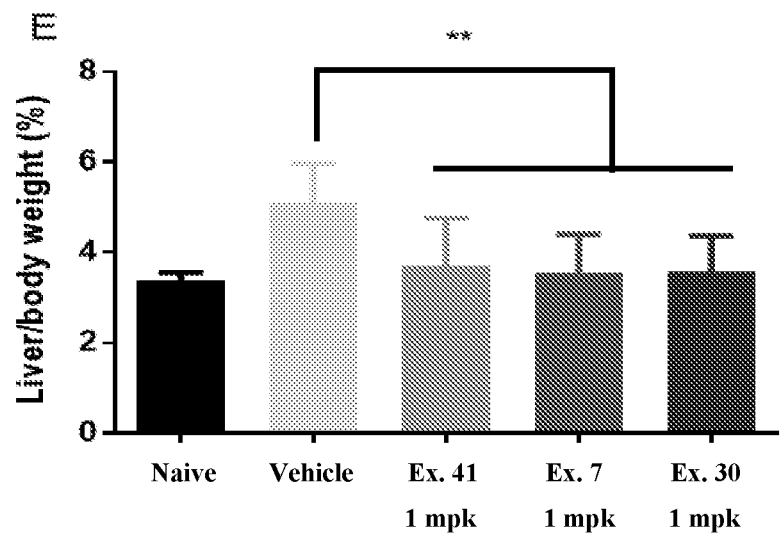
FIG. 6E shows the liver/body weight ratio (%) after administration of Example 7, Example 30, and Example 41 in a NASH mouse model.
Figure 6F:
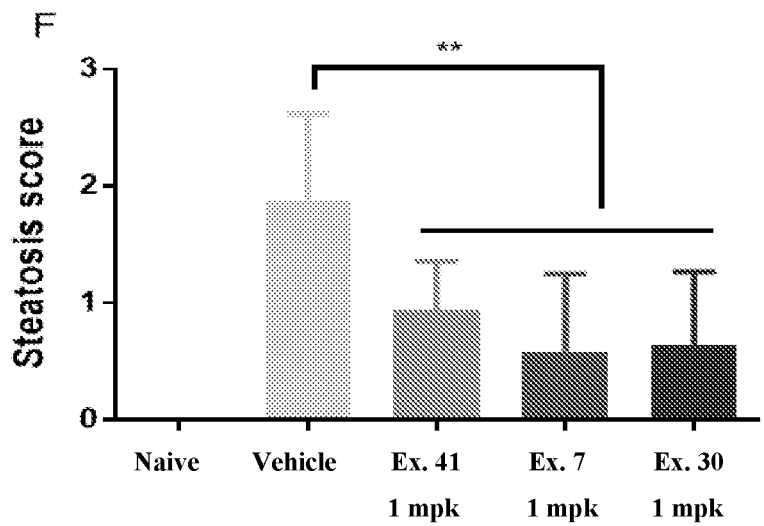
FIG. 6F shows the steatosis score after administration of Example 7, Example 30, and Example 41 in a NASH mouse model.

In the second NASH study of 6-week treatment of Example 41, Example 7 or Example 30 at 1 mg/kg daily, the mice had reduced plasma TC and LDL-c level (FIG. 6A and FIG. 6B). Similarly, the treatments by Example 41 or Example 7 significantly decreased the liver TC and TG (FIG. 6C and FIG. 6D). The treatments also restored the liver weight, comparable to the aged-matched naive mice (FIG. 6E). It was at least partially attributed to the capacity of compounds to reduce the liver fat as suggested by the reduced steatosis score in treated groups (FIG. 6F).

Figure 6G:
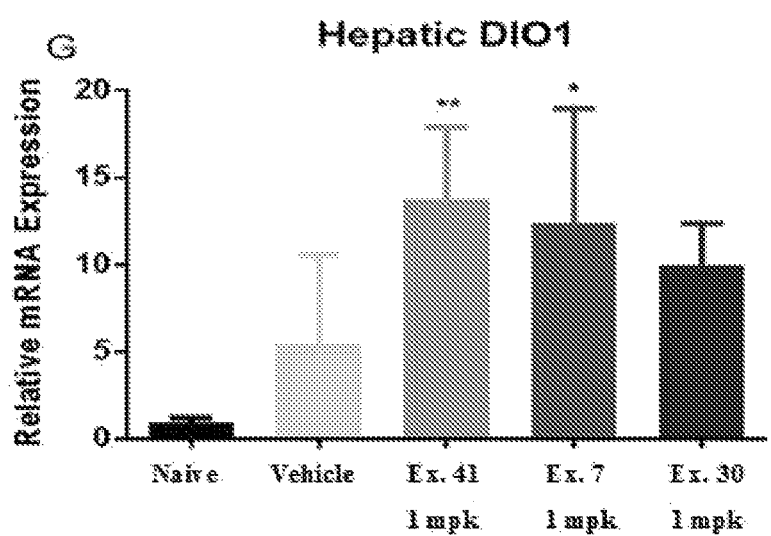
FIG. 6G shows the hepatic DIO1 expression after administration of Example 7, Example 30, and Example 41 in a NASH mouse model.

To check the target engagement, the expression of DIO1 in liver was examined at the end of study. The treatment of Example 41 and Example 7 significantly increased the expression of DIO1 (FIG. 6G), indicating THRβ activation by these compounds. Based on these data, Example 41 and Example 7 were equivalent in these activities, and Example 30 was less potent than them, since in some of examinations Example 30 failed to achieve statistical significance although a trend was aligned with Example 41 and Example 7.

Example E: Heart Safety Evaluation in Hypothyroid Rat

SD Rats underwent thyroidectomy and recovered for 10 days. T3 and T4 were tested to confirm the complete thyroidectomy. In one study, the heart rate was monitored for 1 hour after oral gavage of 100 mg/kg of MGL-3196, Example 7, Example 41, or Example 30. Note that the dose for these compounds was 100-fold higher than their therapeutic dose (1 mg/kg by oral gavage) in mouse models. For comparison, thyroid hormone T3 was also tested at 0.1 mg/kg with intraperitoneal injection. In another study, Thyroidectomized rats were administrated by intraperitoneal injection with 37.5 mg/kg of MGL-3196 and Example 7 or 0.1 mg/kg of T3. After 6 hours, the heart tissues were collected to quantitate the expression of α-MHC, a thyroid hormone responsive and THRα-target gene in heart.

Figure 7A:
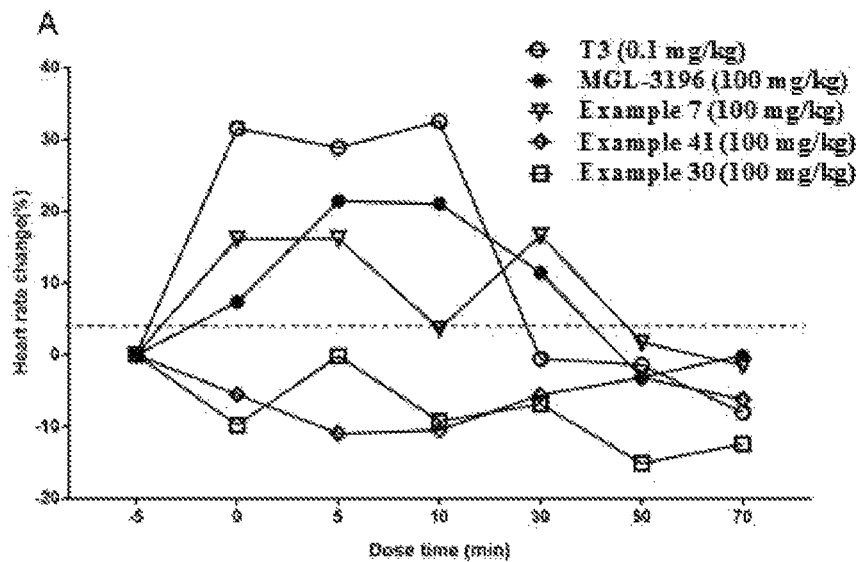
FIG. 7A shows the heart rate changes (%) after administration of T3, MGL-3196, Example 7, Example 41, or Example 30 in a hypothyroid Rat model.
Figure 7B:
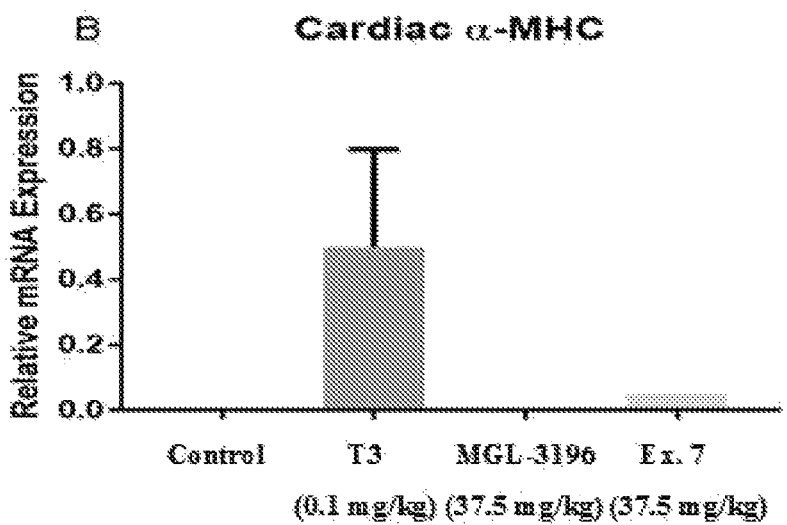
FIG. 7B shows the cardiac α-MHC expression after administration of T3, MGL-3196, and Example 7, in a hypothyroid Rat model.

Thyroidectomized rats were sensitive to thyroid, at 0.1 mg/kg, thyroid hormone T3 increased the heart rate by 30% for the first 30 minutes after intraperitoneal injection. In comparison, these rats were not sensitive to MGL-3196, Example 7, Example 41, or Example 30. At 100 mg/kg, Example 41 and Example 30 caused no heart rate change to the animals (10% change is normal noise in our assay), while MGL-3196 and Example 7, especially the latter, only mildly affected the heart rate (FIG. 7A). In the second study, the expression of cardiac α-MHC was responsive to T3, but not affected by the treatment of MGL-3196 and Example 7 at all (FIG. 7B), demonstrating that MGL-3196 and Example 7 would not activate THRα, which is the predominant receptor isoform expressed in heart.

Example F: CYP Inhibition in Human Liver Microsome

Test compounds were evaluated for CYP inhibition using human liver microsomes (HLM). Test compounds were 1:3 serially diluted starting at 50 µM to generate 7 different concentrations. After incubation of diluted test compounds with HLM, a substrate cocktail composed of phenacetin (10 uM), amodiaquine (2 uM), diclofenac (5 uM), s-mephenytoin (30 uM), dextromethorphan (5 uM), and midazolam (2 uM) was added to check the remaining CYP activity for CYP 1A2, 2C8, 2C9, 2C19, 2D6 and 3A4. The CYP activity was measured by detecting the peak area of individual metabolites of know CYP substrates using LC/MS/MS. A percentage of inhibition of CYP was calculated at each final concentration of test compound, through which an $IC_{50}$ was fitted to represent the inhibition potential.

TABLE 3

The $IC_{50}$ Values of test compounds in CYP isozymes 1A2, 2C8, 2C9, 2C19, 2D6 and 3A4.

| Compound Number | CYP450 inhibition IC50 (µM) | | | | | |
| --- | --- | --- | --- | --- | --- | --- |
|  | 1A2 | 2C8 | 2C9 | 2C19 | 2D6 | 3A4 |
| MGL-3196 | >50 | 4.31 | 18.8 | >50 | >50 | >50 |
| Example 7 | >50 | 7.56 | 30.7 | >50 | >50 | >50 |
| Example 41 | >50 | 3.08 | 15.6 | >50 | >50 | >50 |
| Example 30 | >50 | 4.24 | 22.1 | >50 | >50 | >50 |
| Example 50 | >50 | 4.19 | 41.4 | >50 | >50 | >50 |

Table 3 lists the $IC_{50}$ of each test compound in inhibition of CYP activity. These compounds did not inhibit 1A2, 2C19, 2D6, and 3A4 at the highest concentration, and mildly inhibited 2C9 with $IC_{50}$ less than 50 µM. Most of them had stronger inhibition on 2C8 with $IC_{50}$ around 4 uM, Interestingly, Example 7 had less inhibition on 2C8, its $IC_{50}$ is around 8 µM.

Example G: Synergistic Effect of Example 7 with Other NASH Compounds in Mouse Model There are other candidates being developed for inflammation, metabolism syndromes or NASH. These include glucagon-like peptide-1 (GLP-1) receptor agonist liraglutide, peroxisome proliferator-activated receptor-α and -δ (PPAR-α/δ) agonist elafibranor, and nuclear erythroid 2-related factor 2 (NRF2) activator bardoxolone methyl (CDDO-Me). These candidates target different proteins and pathways, therefore have different mechanisms of action related to steatosis, inflammation, and fibrosis. The potential of synergistic effect of Example 7 with liraglutide, Elafibranor, CDDO-Me was examined in a NASH mouse model.

C57BL/6cnc mice were fed with high-fat diet containing 60 kacl % fat and 0.1% methionine (no added choline) (Research Diets, A06071302) for 12 weeks to induce NASH model. After 12-week diet induction, the mice had increased plasma levels of TC, LDL-c, ALT, and fibrosis markers. The NASH animals were administrated with liraglutide (0.1 mg/kg, subcutaeous, daily), Elafibranor (10 mg/kg, oral, daily), CDDO-Me (0.65 mg/kg, IP, twice a week) alone or together with Example 7. An Example 7 alone group and a vehicle group were also set up for controls. To show the synergistic effect with other candidates, a suboptimal dose of Example 7 at 0.3 mg/kg (oral, daily) was used. After 2-week treatment, serum biochemistry was measured; liver was collected to measure liver TC and TG. Livers were punched in 2 mm diameter and fixed, sectioned and stained with Sirius Red, and the fibrosis and steatosis were scored.

Figure 8A:
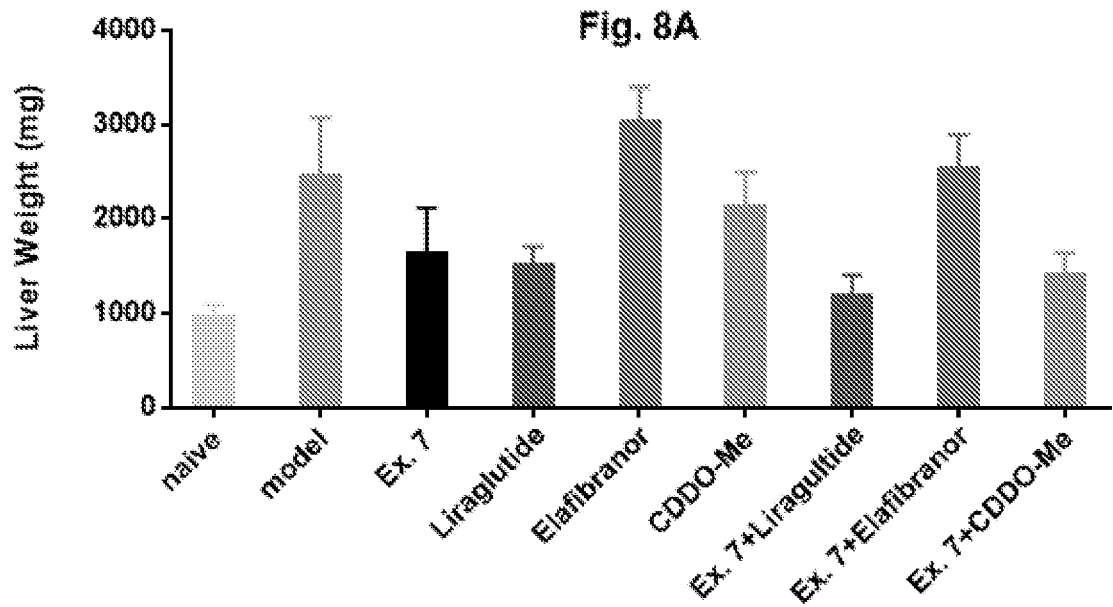
FIG. 8A shows the liver weight after administration of Example 7, liraglutide, elafibranor, CDDO-Me, Example 7+liraglutide, Example 7+elafibranor, and Example 7+CDDO-Me in a NASH mouse model.
Figure 8B:
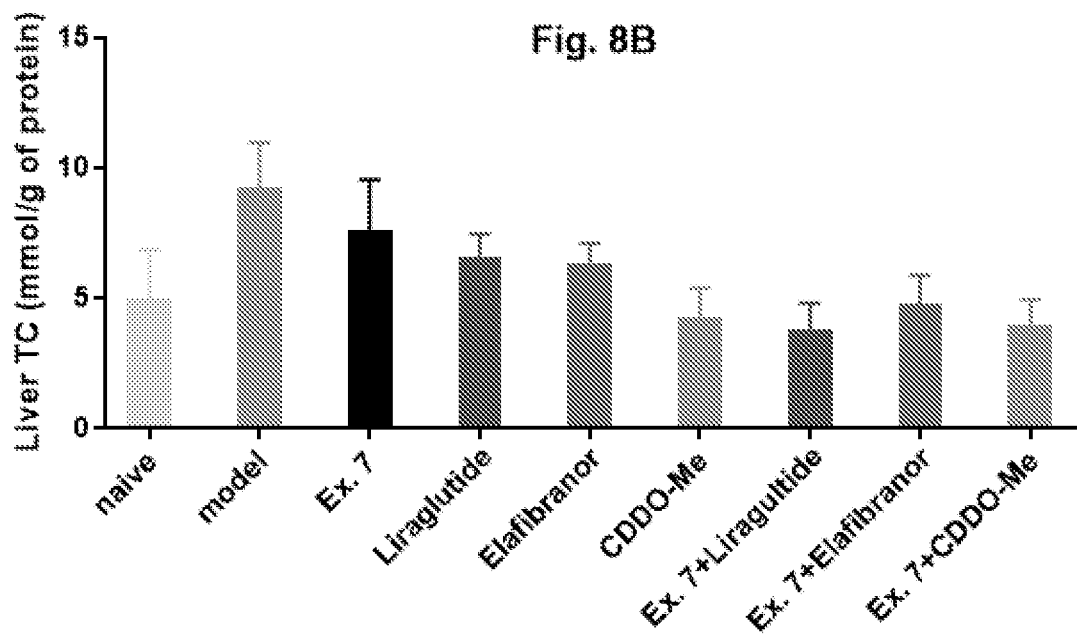
FIG. 8B shows the liver cholesterol levels after administration of Example 7, liraglutide, elafibranor, CDDO-Me, Example 7+liraglutide, Example 7+elafibranor, and Example 7+CDDO-Me in a NASH mouse model.
Figure 8C:
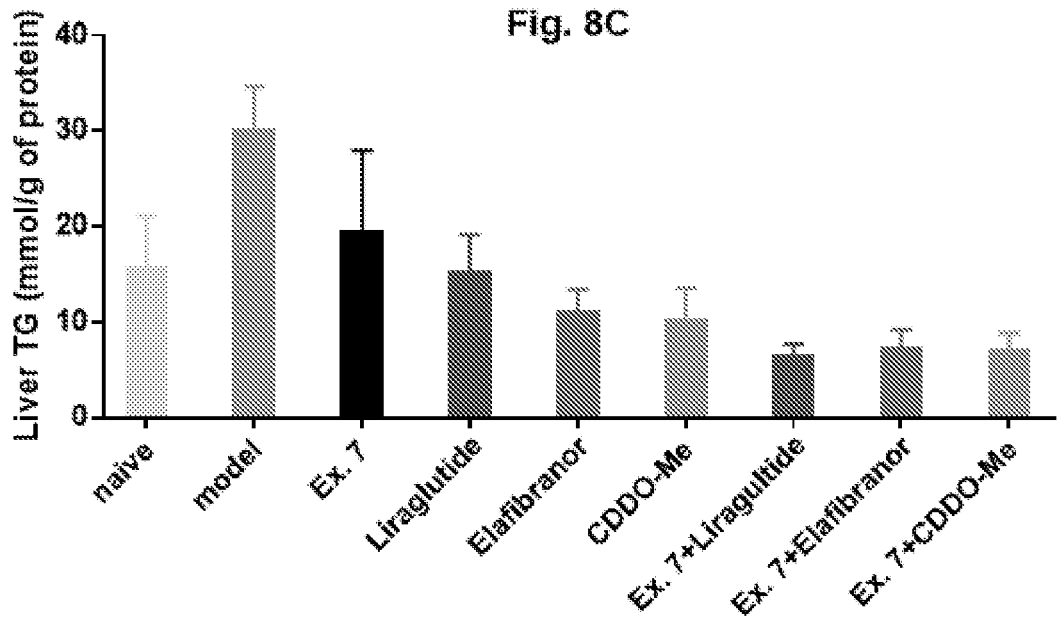
FIG. 8C shows the liver triglyceride levels after administration of Example 7, liraglutide, elafibranor, CDDO-Me, Example 7+liraglutide, Example 7+elafibranor, and Example 7+CDDO-Me in a NASH mouse model.
Figure 8D:
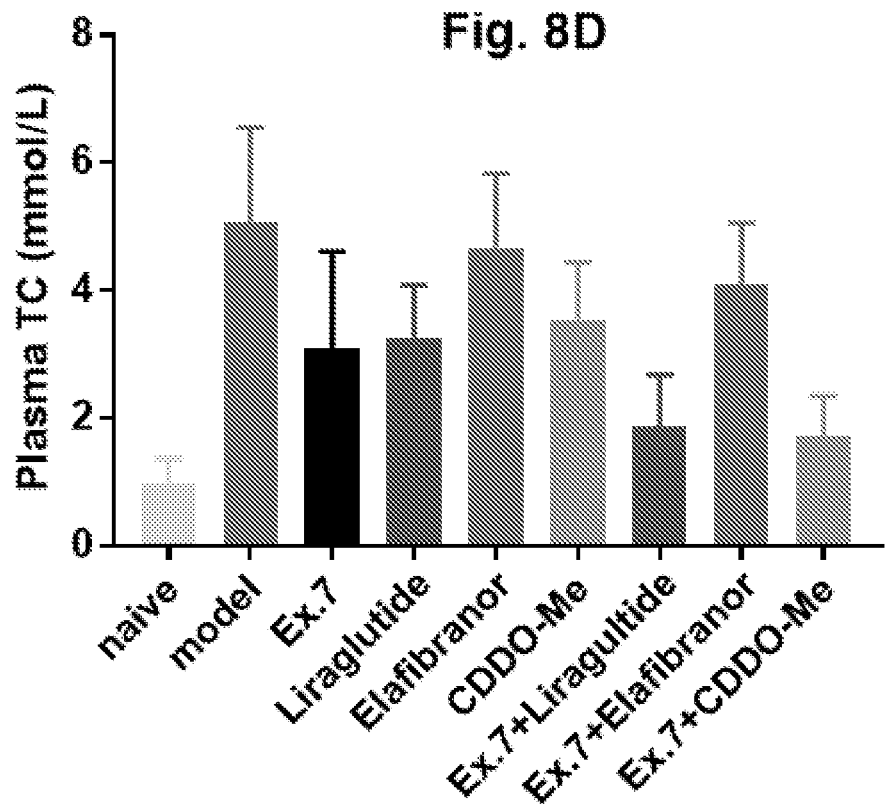
FIG. 8D shows the plasma cholesterol levels after administration of Example 7, liraglutide, elafibranor, CDDO-Me, Example 7+liraglutide, Example 7+elafibranor, and Example 7+CDDO-Me in a NASH mouse model.
Figure 8E:
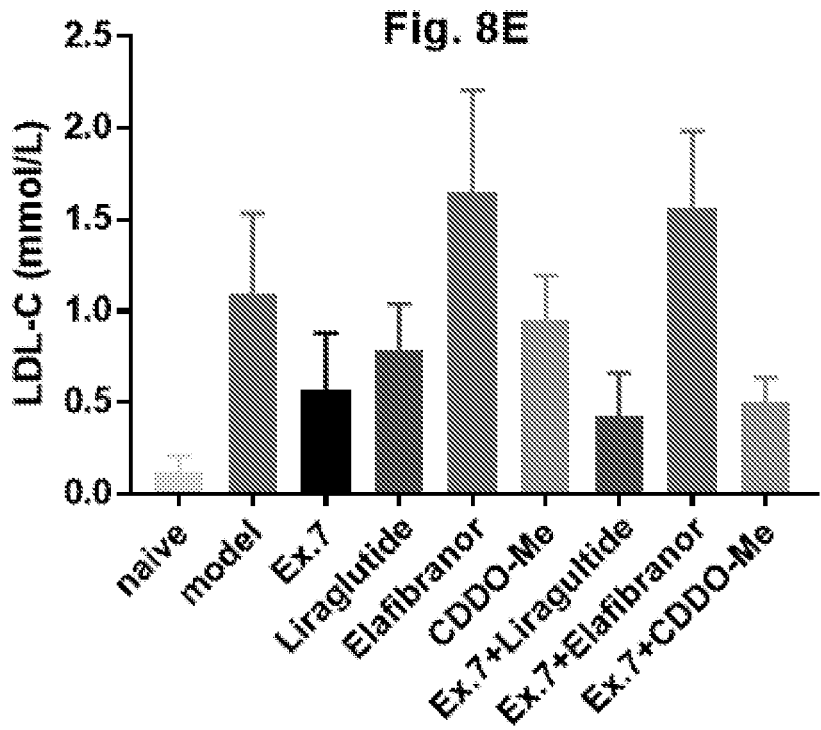
FIG. 8E shows the LDL-c levels after administration of Example 7, liraglutide, elafibranor, CDDO-Me, Example 7+liraglutide, Example 7+elafibranor, and Example 7+CDDO-Me in a NASH mouse model.
Figure 8F:
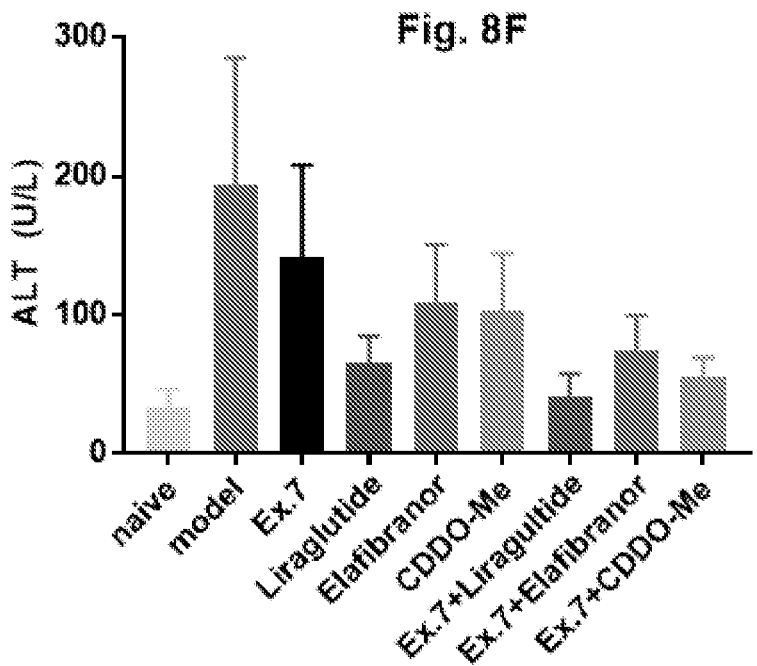
FIG. 8F shows the ALT (alanine transaminase) levels after administration of Example 7, liraglutide, elafibranor, CDDO-Me, Example 7+liraglutide, Example 7+elafibranor, and Example 7+CDDO-Me in a NASH mouse model.

Liver weight (FIG. 8A), liver TC (FIG. 8B), Liver TG (FIG. 8C), plasma TC (FIG. 8D), LDL-c (FIG. 8E), ALT (FIG. 8F), fibrosis (FIG. 8G), and steatosis (FIG. 8H) were examined in these animals. Liraglutide, Elafibranor, CDDO-Me reduced all or some of these parameters due to their unique mechanisms of action. There is a significantly synergistic effect of Example 7 with other candidates in reduction of liver and plasma lipids and improvement of liver conditions.

Example H: Pharmaceutical Compositions

Example H1: Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example H2: Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example H3: Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

The examples and embodiments described herein are for illustrative purposes only and in some embodiments, various modifications or changes are to be included within the purview of disclosure and scope of the appended claims.

What is claimed is:

1. A compound of Formula (IV), or a pharmaceutically acceptable salt, solvate, or stereoisomer thereof:

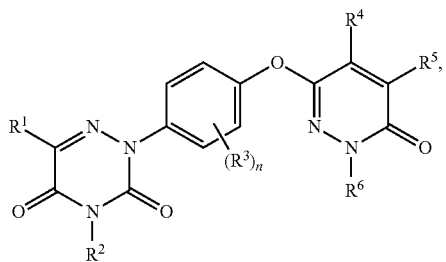

(IV)

wherein:
- $R^1$ is hydrogen, deuterium, halogen, —CN, —OH, —OR$^a$, —SH, —SR$^a$, —S(=O)R$^a$, —S(=O)$_2$R$_a$, —NO$_2$, —NR$^b$R$^c$, —NHS(=O)$_2$R$^a$, —S(=O)$_2$NR$_b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- $R^2$ is hydrogen, halogen, —CN, —OH, —OR$^a$, —S(=O)R$^a$, —S(=O)$_2$R$_a$, —S(=O)$_2$NR$^b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$_b$C(=O)R$^a$, —NR$^b$C(=O)OR$^b$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- $R^4$ and $R^5$ are taken together to form a cycloalkyl, heterocycloalkyl, aryl, or heteroaryl; wherein the cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, C$_1$-C$_6$deuteroalkyl, or C$_1$-C$_6$haloalkyl;
- $R^6$ is hydrogen, —CN, —OH, —OR$^a$, —S(=O)R$^a$, —S(=O)$_2$R$_a$, —S(=O)$_2$NR$_b$R$^c$, —C(=O)R$^a$, —OC(=O)R$^a$, —C(=O)OR$^b$, —C(=O)NR$^b$R$^c$, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OR$^a$, —NR$^b$R$^c$, —C(=O)R$^a$, —C(=O)OR$^b$, —C(=O)NR$^b$R$^c$, C$_1$-C$_6$alkyl, or C$_1$-C$_6$haloalkyl;
- n is 0-4;
- each $R^a$ is independently C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl; and
- each $R^b$ and $R^c$ are independently hydrogen, deuterium, C$_1$-C$_6$alkyl, C$_1$-C$_6$deuteroalkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl;
- or $R^b$ and $R^c$ are taken together with the nitrogen atom to which they are attached to form a heterocycloalkyl optionally substituted with one or more oxo, deuterium, halogen, —CN, —OH, —OMe, —NH$_2$, —C(=O)Me, —C(=O)OH, —C(=O)OMe, C$_1$-C$_6$alkyl, or C$_1$-C$_6$haloalkyl.

2. The compound of claim 1, or a pharmaceutically acceptable salt, solvate, or stereoisomer thereof, wherein:
$R^1$ is hydrogen or —CN.

3. The compound of claim 1, or a pharmaceutically acceptable salt, solvate, or stereoisomer thereof, wherein:
$R^2$ is hydrogen or C$_1$-C$_6$alkyl.

4. The compound of claim 1, or a pharmaceutically acceptable salt, solvate, or stereoisomer thereof, wherein:
n is 2-4 and each $R^3$ is independently hydrogen, deuterium, halogen, C$_1$-C$_6$alkyl, or C$_1$-C$_6$haloalkyl.

5. The compound of claim 1, or a pharmaceutically acceptable salt, solvate, or stereoisomer thereof, wherein:
$R^4$ and $R^5$ are taken together to form a cycloalkyl optionally substituted with one or more oxo, deuterium, halogen, —CN, —OH, —OMe, —NH$_2$, C$_1$-C$_6$alkyl, C$_1$-C$_6$deuteroalkyl, or C$_1$-C$_6$haloalkyl.

6. The compound of claim 1, or a pharmaceutically acceptable salt, solvate, or stereoisomer thereof, wherein:
$R^6$ is hydrogen or C$_1$-C$_6$alkyl.

7. The compound of claim 1, or a pharmaceutically acceptable salt, solvate, or stereoisomer thereof, wherein the compound is:

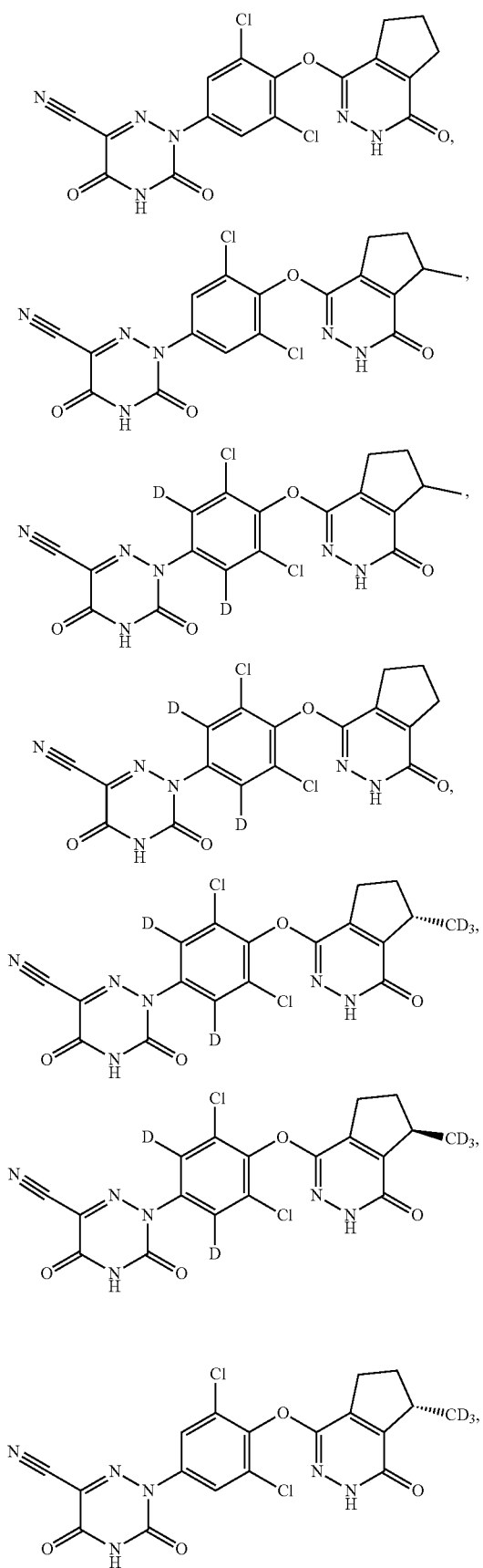

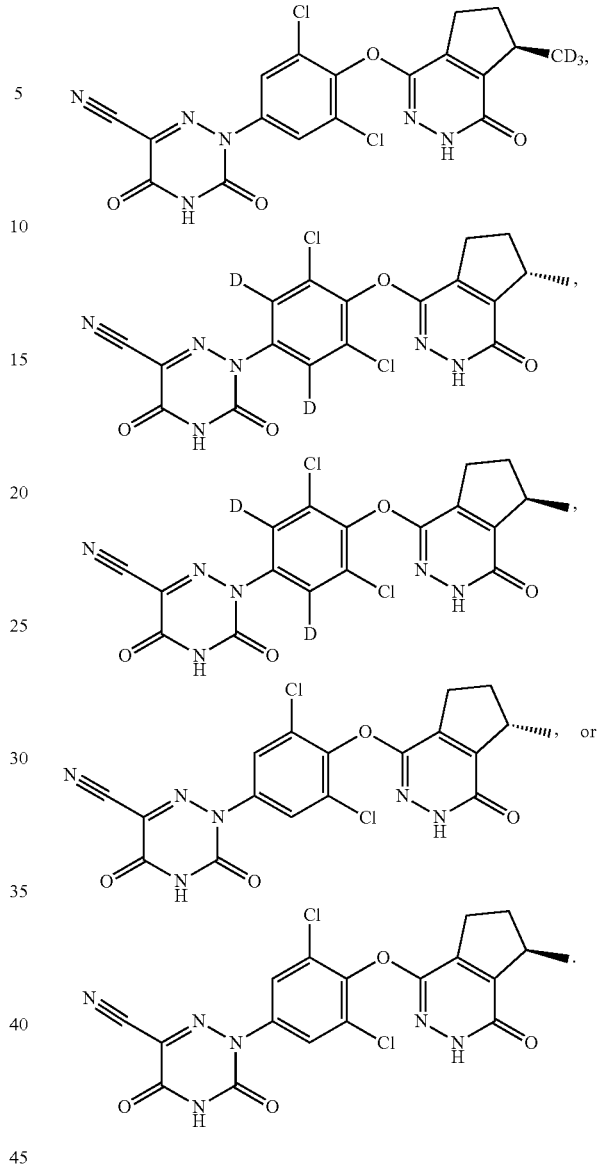

8. A pharmaceutical composition comprising a compound of claim 1, or a pharmaceutically acceptable salt, solvate, or stereoisomer thereof, and a pharmaceutically acceptable excipient.

9. A method of treating a metabolic disease in a subject, comprising administering to the subject a compound of claim 1, or a pharmaceutically acceptable salt, solvate, or stereoisomer thereof; wherein the metabolic disease is obesity, hyperlipidemia, hypercholesterolemia, diabetes, nonalcoholic steatohepatitis (NASH), atherosclerosis, a cardiovascular disease, hypothyroidism, or thyroid cancer.

10. The compound of claim 1, or a pharmaceutically acceptable salt, solvate, or stereoisomer thereof, wherein:
R$^4$ and R$^5$ are taken together to form a 5-membered cycloalkyl optionally substituted with one or more oxo, deuterium, halogen, —CN, —OH, —OMe, —NH$_2$, C$_1$-C$_6$alkyl, C$_1$-C$_6$deuteroalkyl, or C$_1$-C$_6$haloalkyl.

11. The compound of claim 1, or a pharmaceutically acceptable salt, solvate, or stereoisomer thereof, wherein:
R$^4$ and R$^5$ are taken together to form a 5-membered cycloalkyl optionally substituted with one or more C$_1$-C$_6$alkyl or C$_1$-C$_6$deuteroalkyl.

12. The compound of claim 11, or a pharmaceutically acceptable salt, solvate, or stereoisomer thereof, wherein:
$R^4$ and $R^5$ are taken together to form a 5-membered cycloalkyl substituted with one $C_1$-$C_6$alkyl.

13. The compound of claim 11, or a pharmaceutically acceptable salt, solvate, or stereoisomer thereof, wherein:
$R^4$ and $R^5$ are taken together to form a 5-membered cycloalkyl substituted with one $C_1$-$C_6$deuteroalkyl.

14. The compound of claim 1, or a pharmaceutically acceptable salt, solvate, or stereoisomer thereof, wherein:
$R^1$ is —CN.

15. The compound of claim 1, or a pharmaceutically acceptable salt, solvate, or stereoisomer thereof, wherein:
$R^2$ is hydrogen.

16. The compound of claim 1, or a pharmaceutically acceptable salt, solvate, or stereoisomer thereof, wherein:
each $R^3$ is independently hydrogen, halogen, $C_1$-$C_6$alkyl, or $C_1$-$C_6$haloalkyl.

17. The compound of claim 1, or a pharmaceutically acceptable salt, solvate, or stereoisomer thereof, wherein:
each $R^3$ is independently halogen.

18. The compound of claim 1, or a pharmaceutically acceptable salt, solvate, or stereoisomer thereof, wherein:
n is 2.

\* \* \* \* \*

UNITED STATES PATENT AND TRADEMARK OFFICE
CERTIFICATE OF CORRECTION

PATENT NO. : 11,964,964 B2  
APPLICATION NO. : 17/047358  
DATED : April 23, 2024  
INVENTOR(S) : Jin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 680 days.

Signed and Sealed this  
Eighth Day of October, 2024

Katherine Kelly Vidal  
*Director of the United States Patent and Trademark Office*